US009267142B2

(12) United States Patent
Pilpel et al.

(10) Patent No.: US 9,267,142 B2
(45) Date of Patent: Feb. 23, 2016

(54) RECOMBINANT PROTEIN PRODUCTION IN HETEROLOGOUS SYSTEMS

(75) Inventors: Yitzhak Pilpel, Rehovot (IL); Tamir Tuller, Rehovot (IL); Sivan Navon, Rehovot (IL); Menachem Rubinstein, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 504 days.

(21) Appl. No.: 13/582,472

(22) PCT Filed: Jan. 25, 2011

(86) PCT No.: PCT/IL2011/000082
§ 371 (c)(1),
(2), (4) Date: Sep. 4, 2012

(87) PCT Pub. No.: WO2011/111034
PCT Pub. Date: Sep. 15, 2011

(65) Prior Publication Data
US 2012/0329091 A1 Dec. 27, 2012

Related U.S. Application Data

(60) Provisional application No. 61/354,284, filed on Jun. 14, 2010, provisional application No. 61/311,444, filed on Mar. 8, 2010.

(51) Int. Cl.

| | | |
|---|---|---|
| *C07H 21/02* | (2006.01) | |
| *C12N 15/67* | (2006.01) | |
| *C07K 14/505* | (2006.01) | |
| *C07K 14/555* | (2006.01) | |
| *C07K 14/59* | (2006.01) | |
| *C07K 14/61* | (2006.01) | |
| *C07K 14/62* | (2006.01) | |
| *C07K 14/705* | (2006.01) | |
| *C07K 14/755* | (2006.01) | |
| *C12N 9/40* | (2006.01) | |
| *C12P 21/02* | (2006.01) | |
| *C12N 9/24* | (2006.01) | |

(52) U.S. Cl.
CPC .............. *C12N 15/67* (2013.01); *C07K 14/505* (2013.01); *C07K 14/555* (2013.01); *C07K 14/59* (2013.01); *C07K 14/61* (2013.01); *C07K 14/62* (2013.01); *C07K 14/705* (2013.01); *C07K 14/755* (2013.01); *C12N 9/2402* (2013.01); *C12N 9/2465* (2013.01); *C12P 21/02* (2013.01)

(58) Field of Classification Search
None
See application file for complete search history.

(56) References Cited

U.S. PATENT DOCUMENTS

2005/0177880 A1    8/2005    Martineau et al.

FOREIGN PATENT DOCUMENTS

WO    WO 2004/024915    3/2004

OTHER PUBLICATIONS

Communication Pursuant to Article 94(3) EPC Dated Jun. 30, 2014 From the European Patent Office Re. Application No. 11704680.5.
International Preliminary Report on Patentability Dated Sep. 20, 2012 From the International Bureau of WIPO Re. Application No. PCT/IL2011/000082.
International Search Report and the Written Opinion Dated May 24, 2011 From the International Searhcing Authority Re. Application No. PCT/IL2011/000082.
Allert et al. "Multifactorial Determinants of Protein Expression in Prokaryotic Open Reading Frames", Journal of Molecular Biology, XP027375330, 402(5): 905-918, Oct. 8, 2010. p. 914-915.
Huang et al. Analysis and Prediction of Translation Rate Based on Sequence and Functional Features of the mRNA, PLoS ONE, XP002633254, 6(1): e16036-1-e16036-8, Jan. 6, 2011.
Iida et al. "Strength of Translation Initiation Signal Sequence of mRNA as Studied by Quantification Method: Effect of Nucleotide Substitutions Upon Translation Efficiency in Rat Preproinsulin mRNA", Nucleic Acids Research, XP007918226, 24(17): 3313-3316, Sep. 1, 1996.
Ingolia et al. "Genome-Wide Analysis In Vivo of Translation With Nucleotide Resolution Using Ribosome Profiling", Science, XP002633253, 324(5924): 601-614, May 28, 2004.
Keum et al. "The Presence of a Common Downstream Box Enables the Simultaneous Expression of Multiple Proteins in an *E. coli* Extract", Biochemical and Biophysical Reseach Communications, BBRC, XP024924679, 350(3): 562-567, Nov. 24, 2006.
Mitarai et al. "Ribosome Collisions and Translation Efficiency: Optimization by Codon Usage and mRNA Destabilization", Journal of Molecular Biology, JMB, XP023906571, 382(1): 236-245, Sep. 26, 2008. Abstract, p. 237, 238, Right col., Table 1, p. 239, p. 243.
Rush et al. "Translation Enhancement by Optimized Downstream Box Sequences in *Escherichia coli* and *Mycobacterium smegmatis*", Biotechnology Letters, XP019231080, 27(3): 173-179, Feb. 1, 2005.
Tuller et al. "An Evolutionarily Conserved Mechanism for Controlling the Efficiency of Protein Translation", Cell, XP007918225, 141(2): 344-354, Apr. 16, 2010.
Tuller et al. "Translation Efficiency Is Determined by Both Codon Bias and Folding Energy", Proc. Natl. Acad. Sci. USA, PNAS, XP007918224, 107(8): 3645-3650, Feb. 23, 2010.
Voges et al. "Analyzing and Enhancing mRNA Translational Efficiency in an *Escherichia coli* In Vitro Expression System", Biochemical and Biophysical Research Communications, XP004505422, 318(2): 601-614, May 28, 2004.
Waldman et al. "Translation Efficiency in Humans: Tissue Specificity, Global Optimization and Differences Between Developmental Stages", Nucleic Acids Research, XP007918223, 38(9): 2964-2974, Jan. 21, 2010. Abstract, p. 2965, 2968-2969, 2971.
Zhang et al. "Generic Algorithm to Ptedict the Speed of Translational Elongation: Implications for Protein Biogenesis", PLoS ONE, XP007918248, 4(4): e5036-1-e5036-9, 2009.

*Primary Examiner* — Michele K Joike

(57) ABSTRACT

Isolated polynucleotides are disclosed which increase the efficiency of gene expression in a heterologous cell. The polynucleotide sequences which encode polypeptides are adapted such that the average rate of translation of the first at least about 30 amino acids is slower by at least two fold than the average rate of translation of the remaining amino acids of the polypeptide.

12 Claims, 94 Drawing Sheets
(91 of 94 Drawing Sheet(s) Filed in Color)

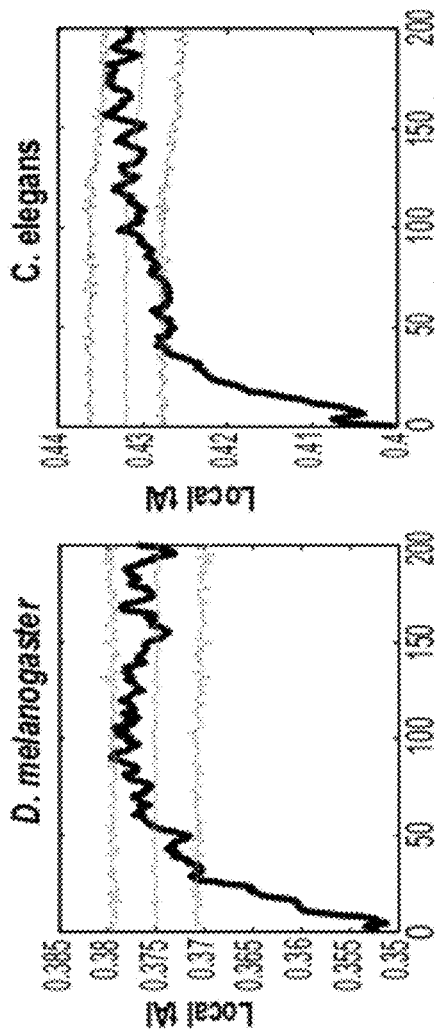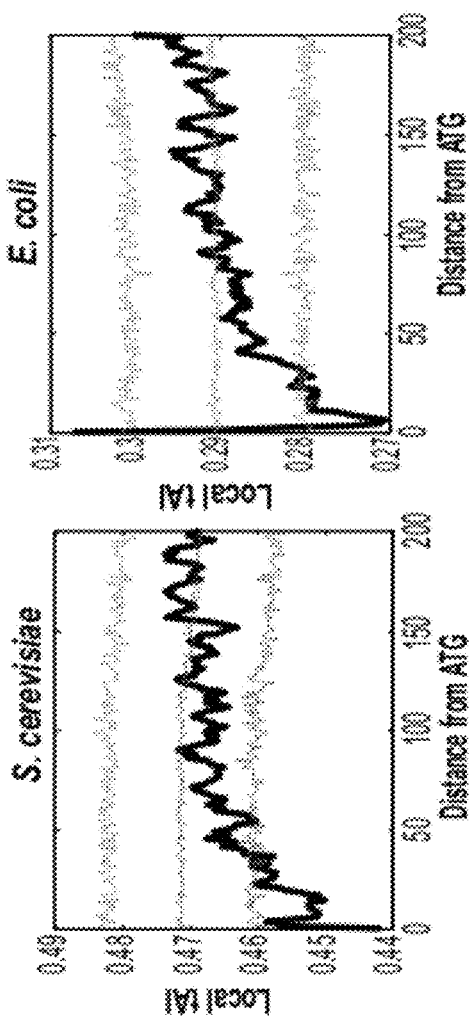
FIG. 2A  FIG. 2B  FIG. 2C  FIG. 2D

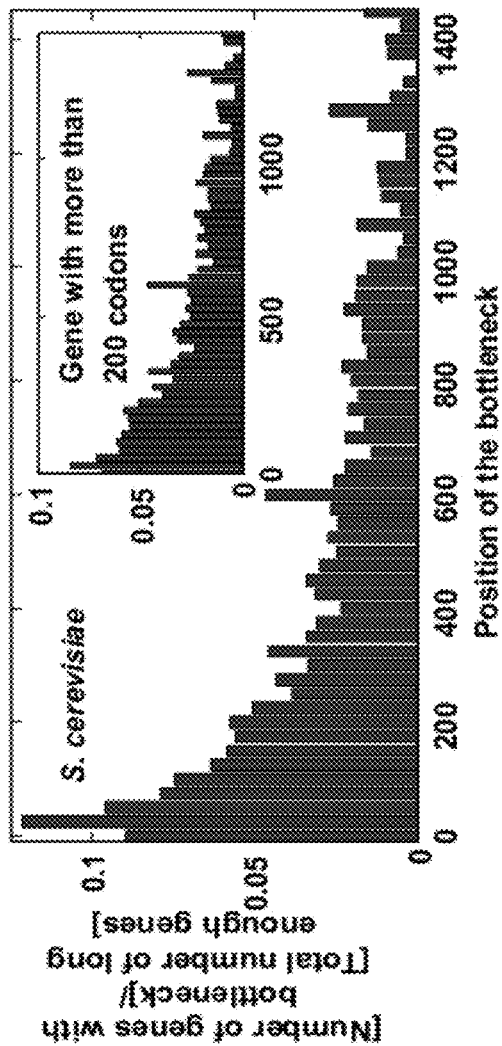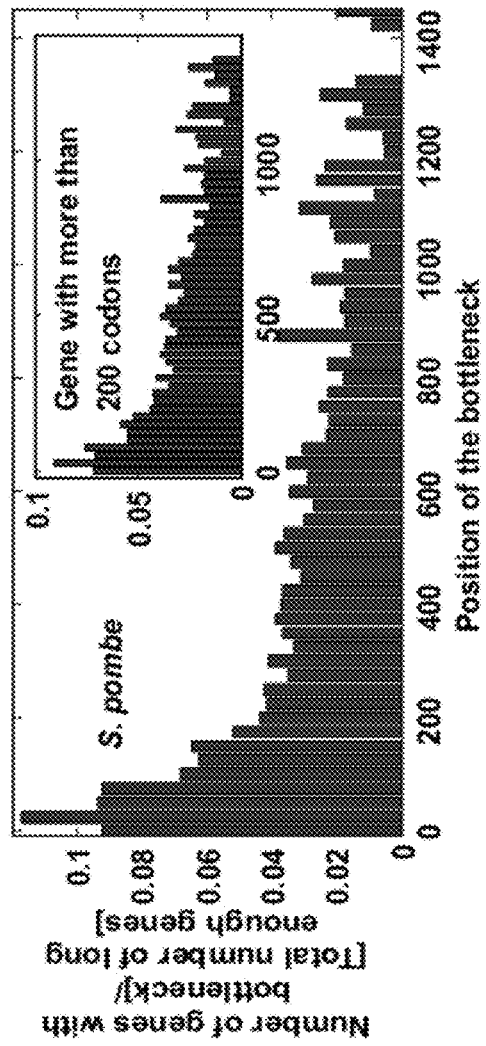
FIG. 3A
FIG. 3B

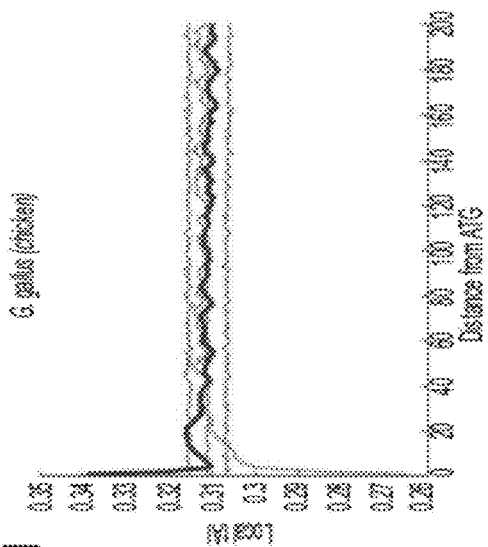
FIG. 7M
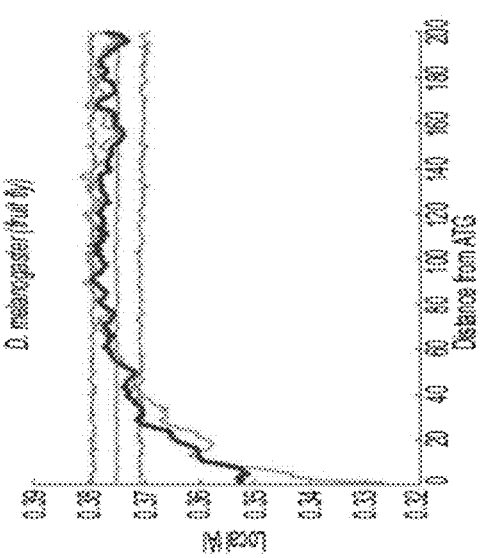
FIG. 7N
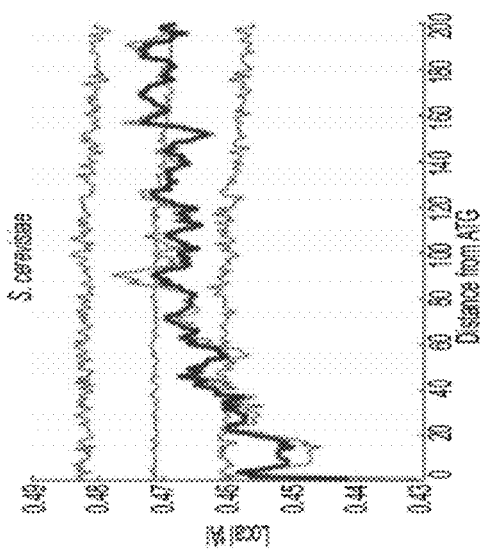
FIG. 7O
FIG. 7P

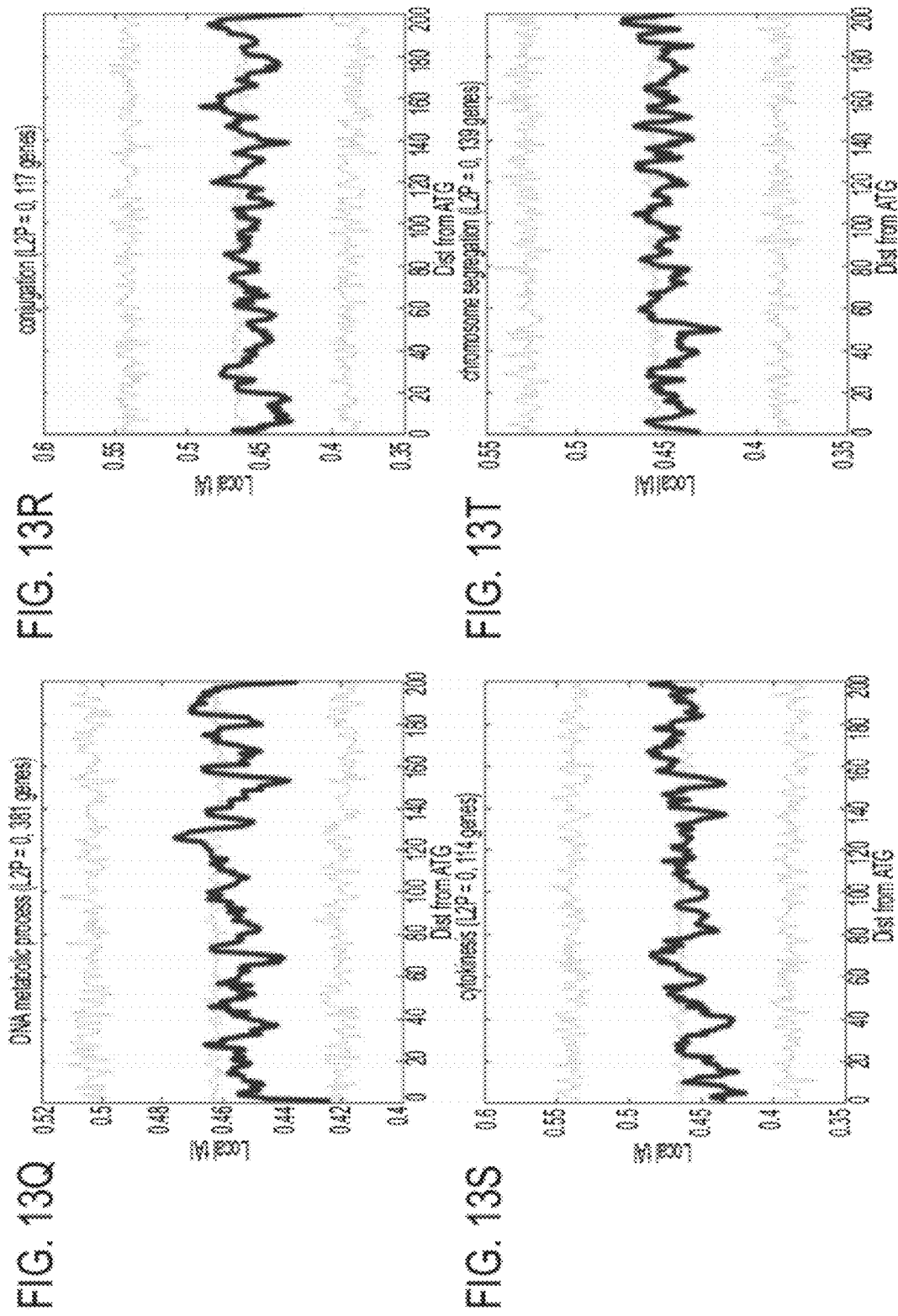

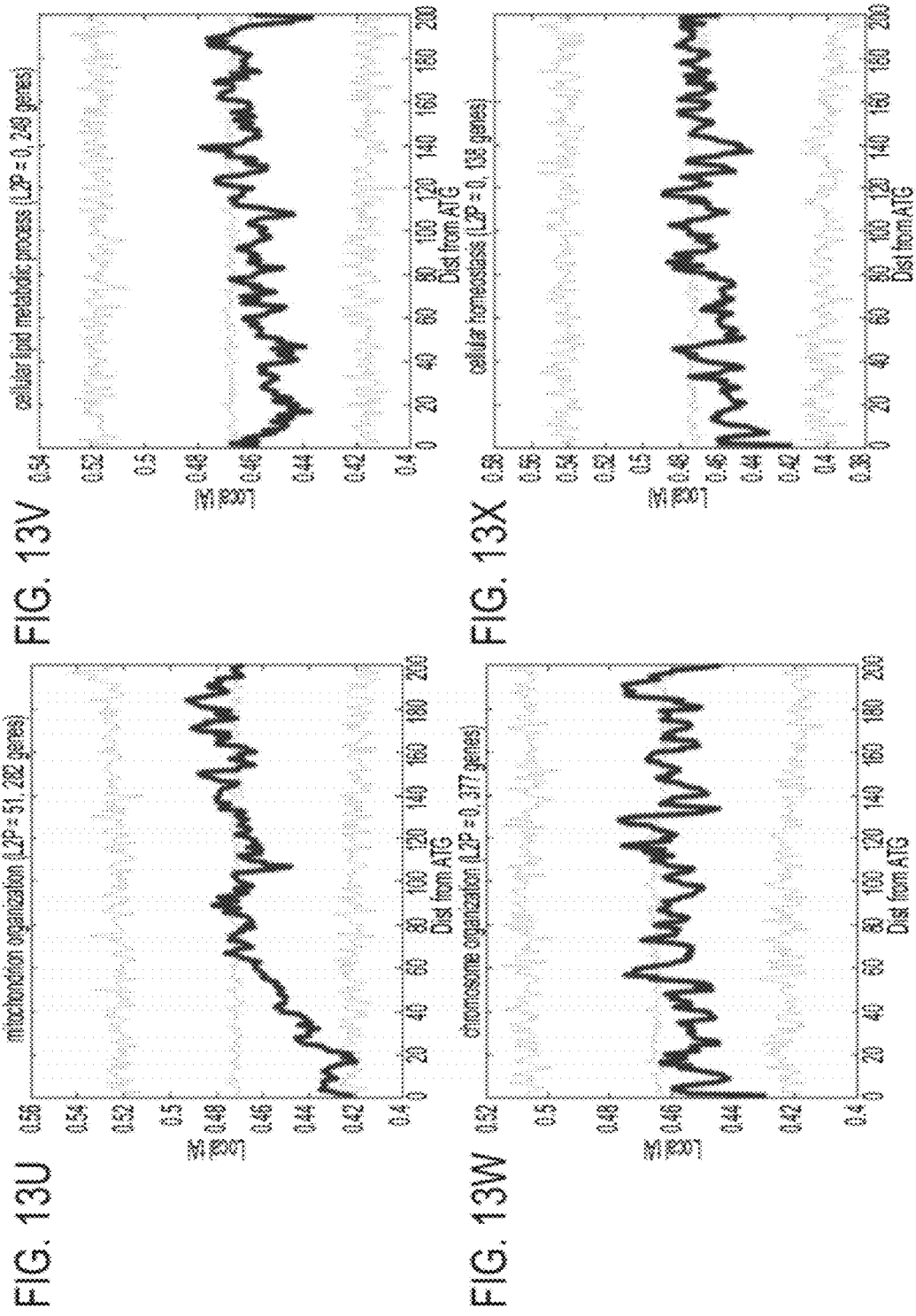

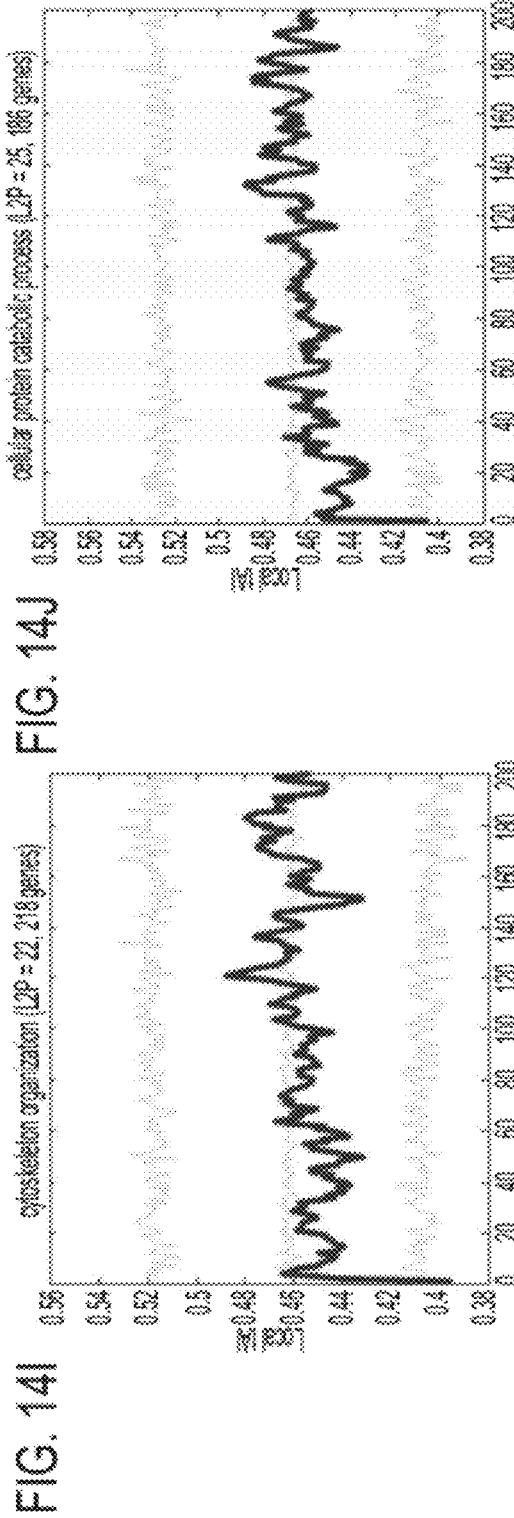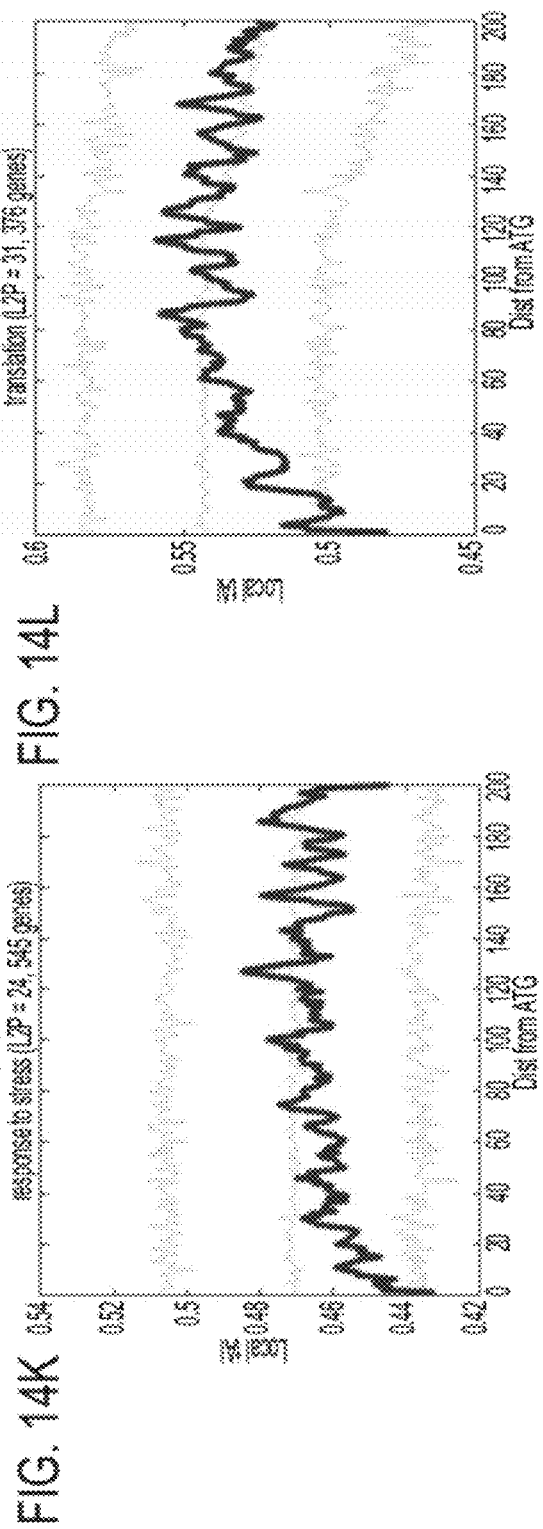
FIG. 14I  FIG. 14J  FIG. 14K  FIG. 14L

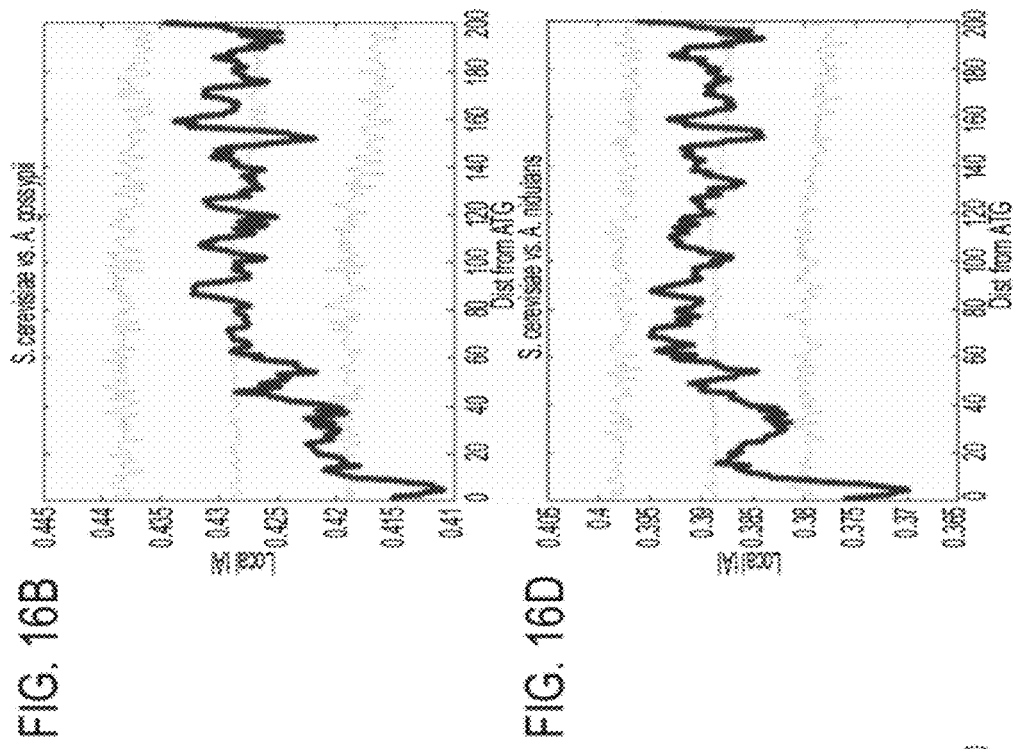
FIG. 16A  FIG. 16B
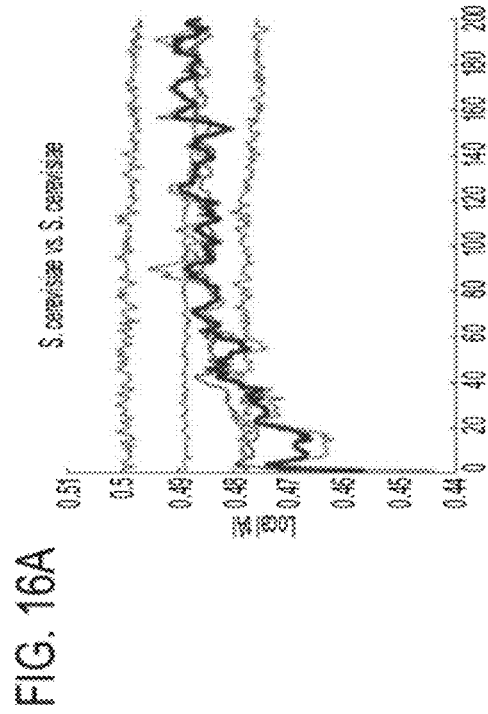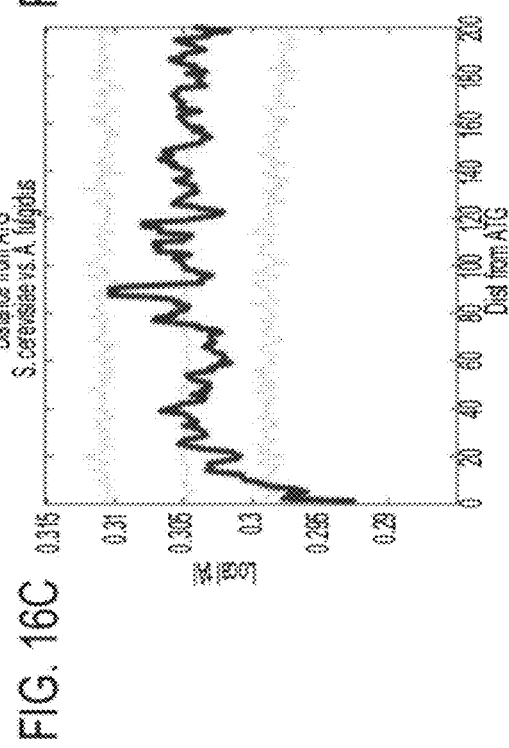
FIG. 16C  FIG. 16D

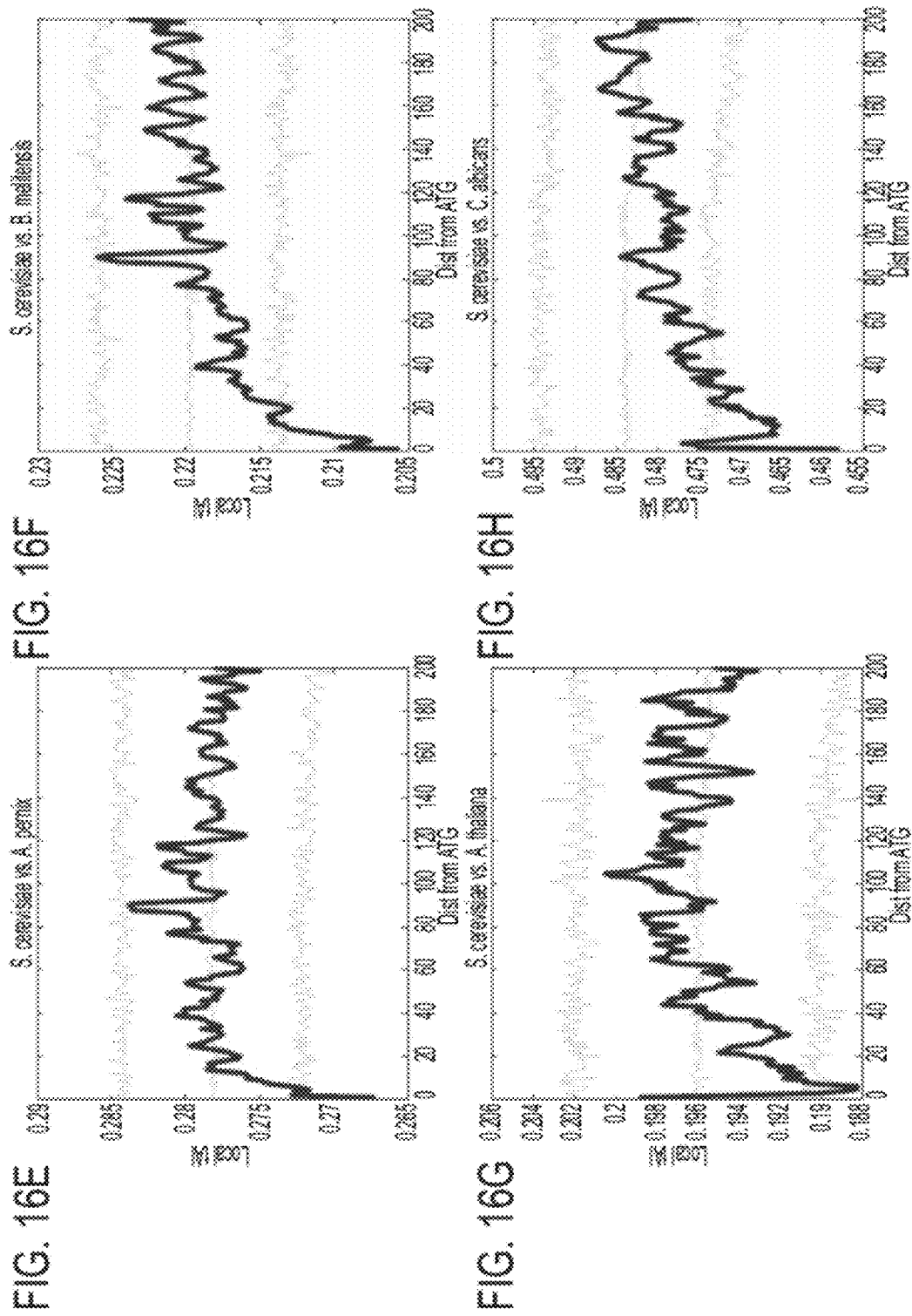

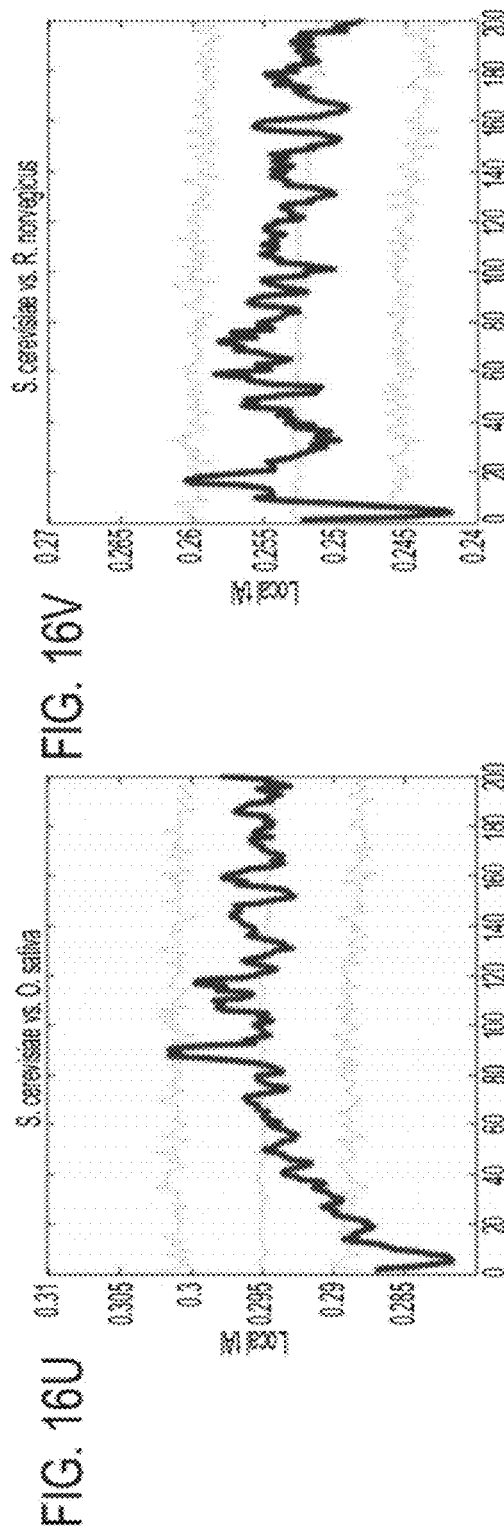
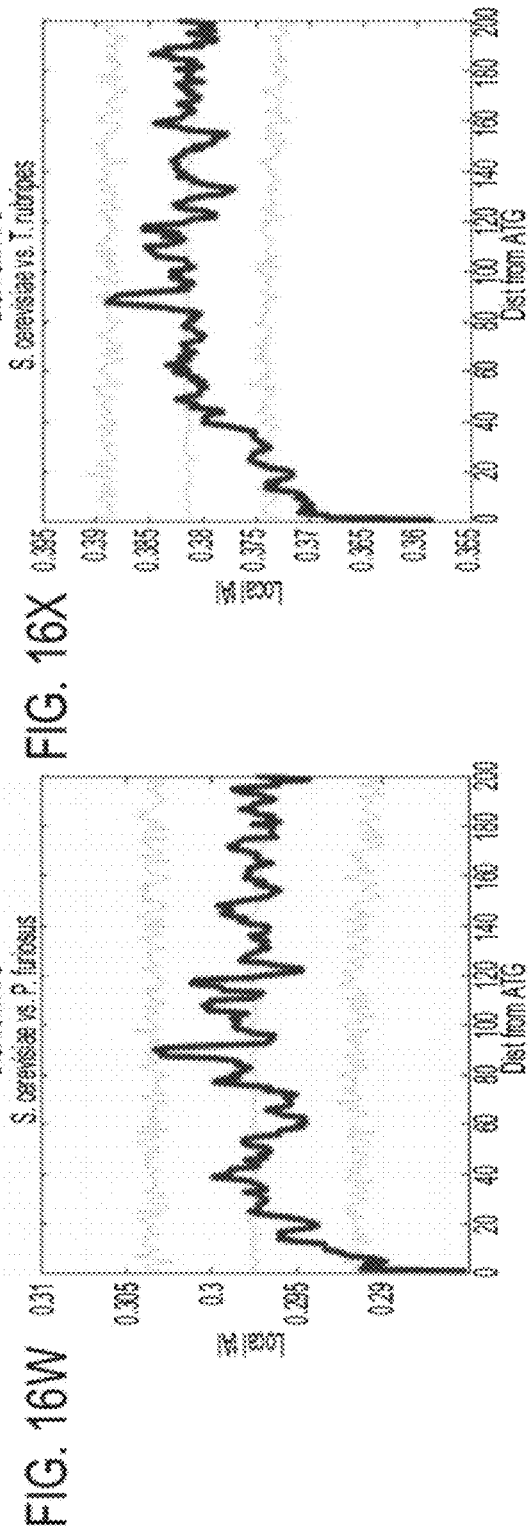
FIG. 16U
FIG. 16V
FIG. 16W
FIG. 16X

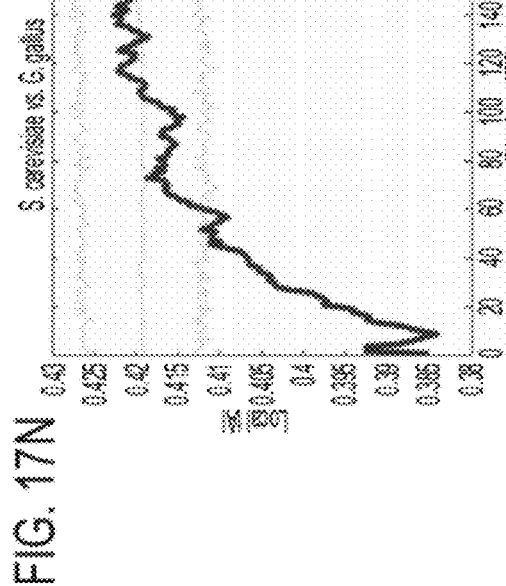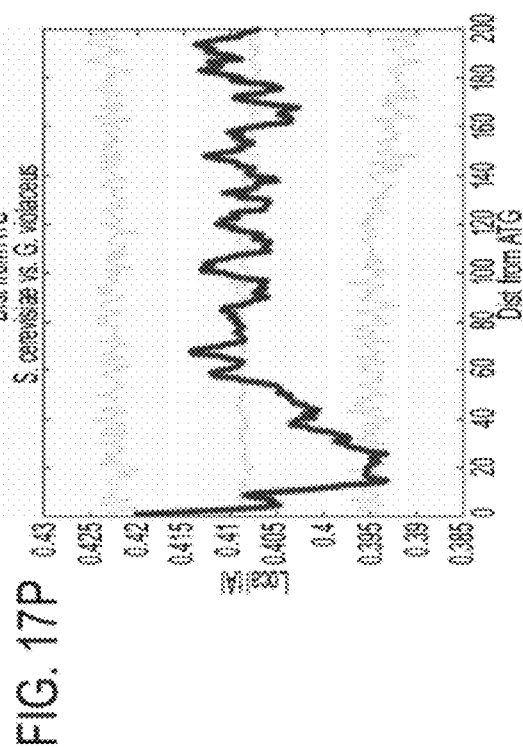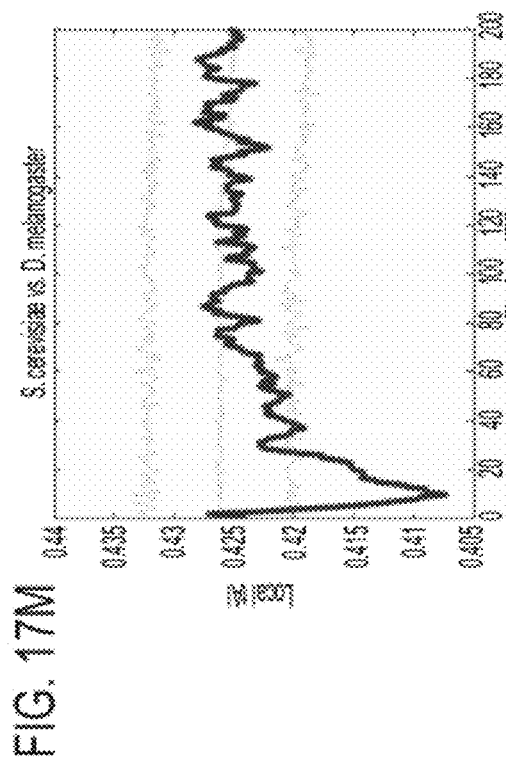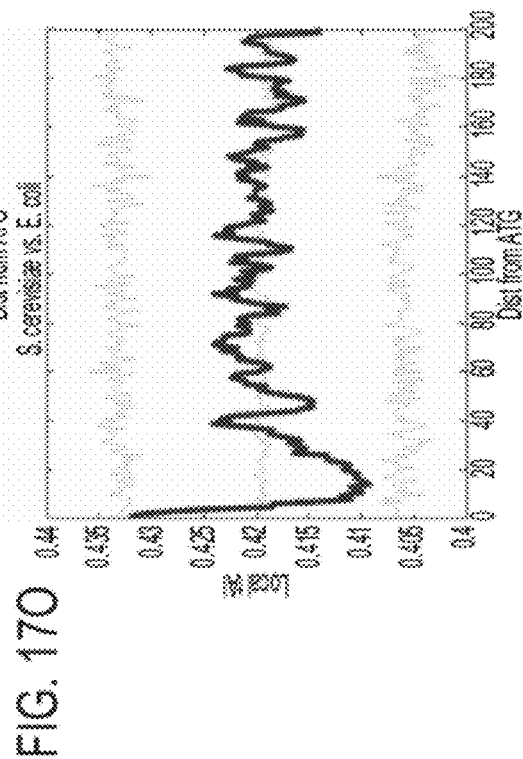
FIG. 17M   FIG. 17N
FIG. 17O   FIG. 17P

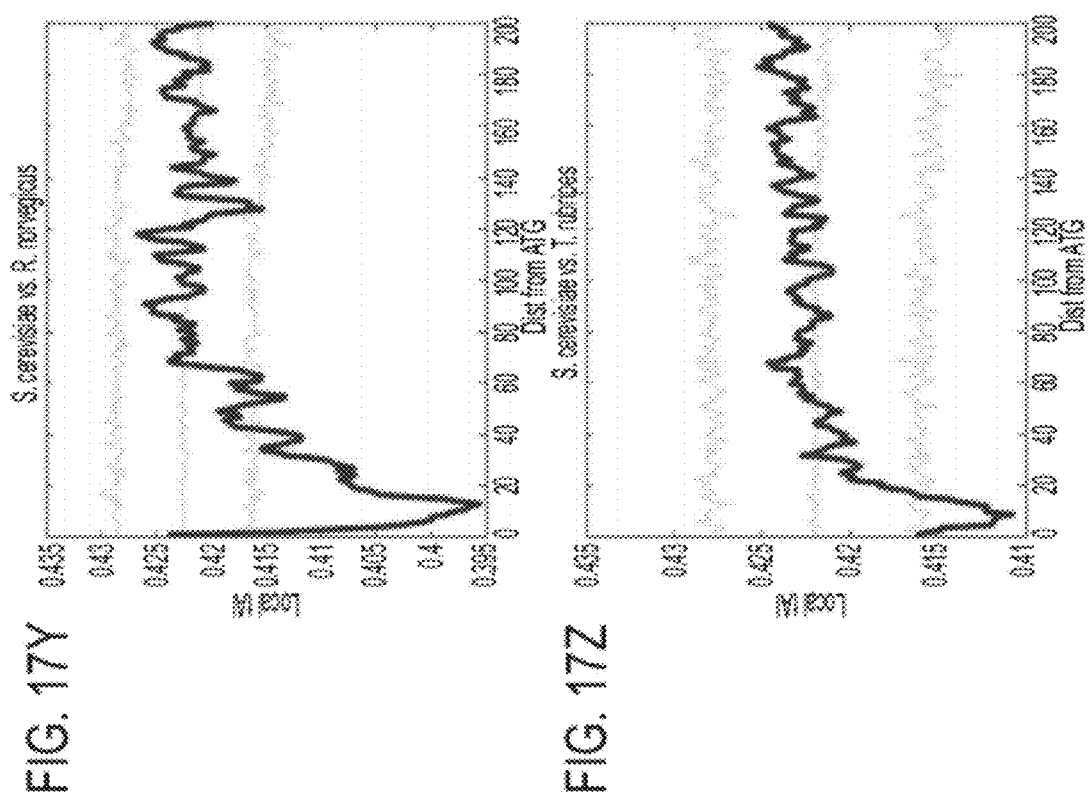

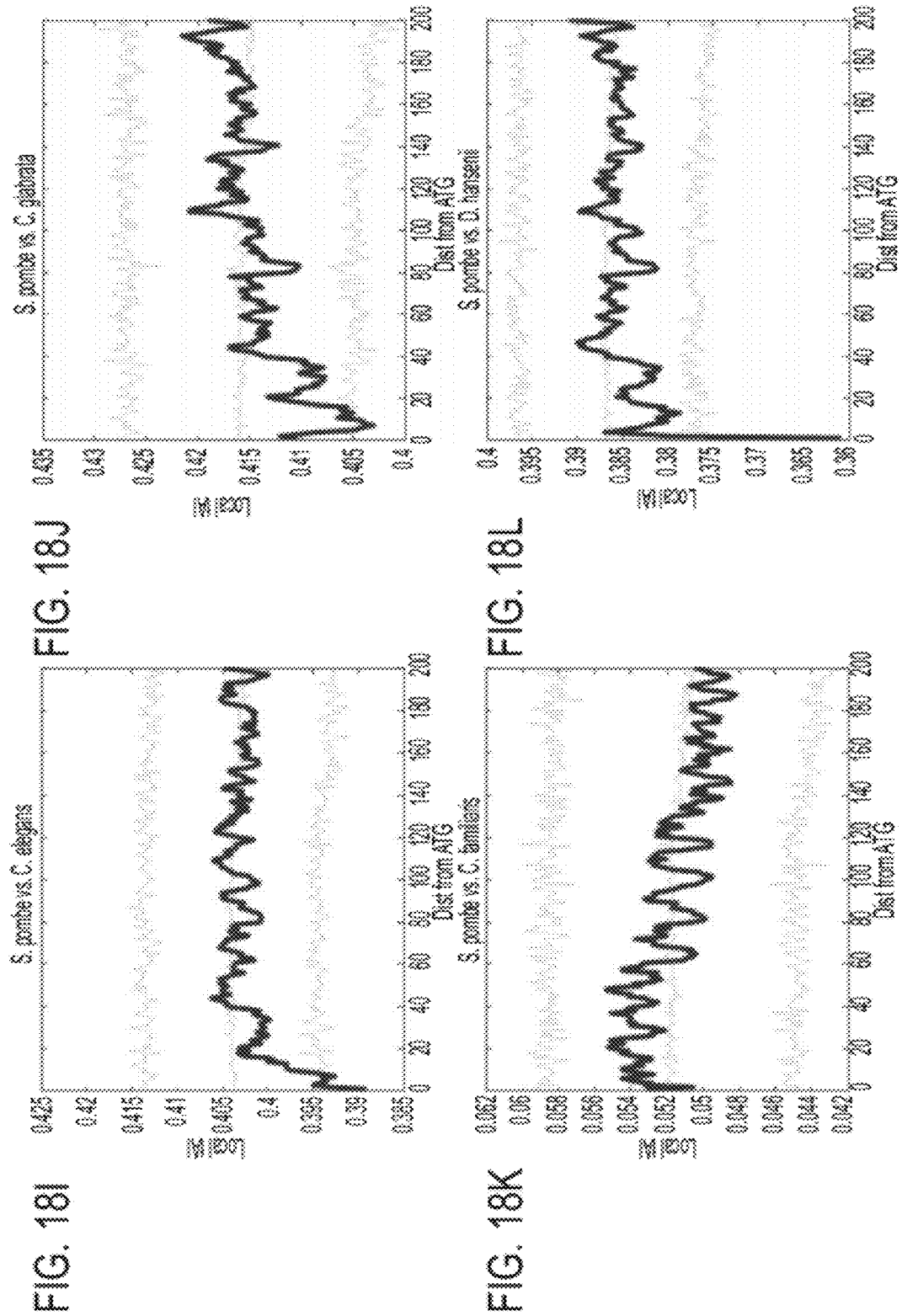

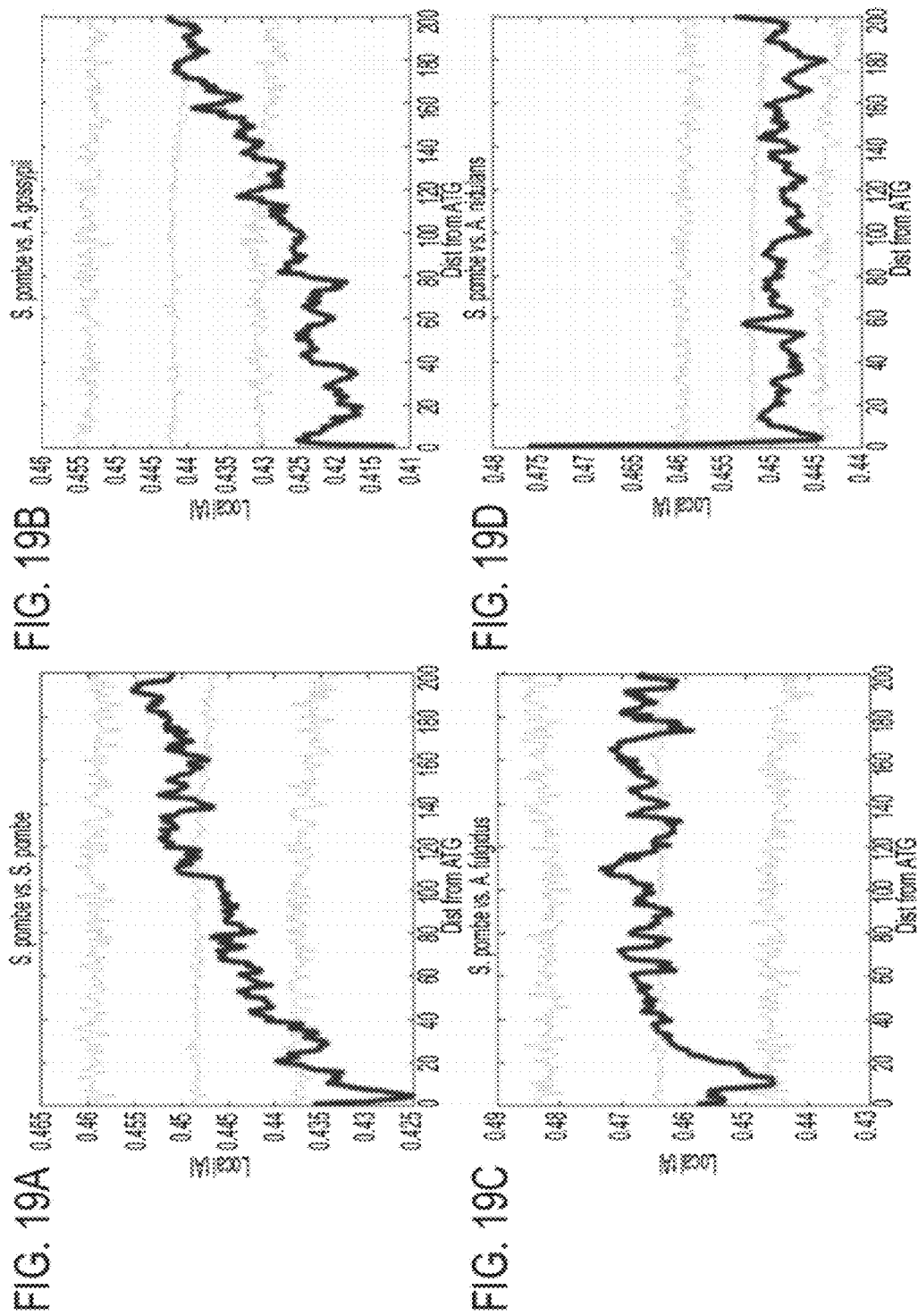

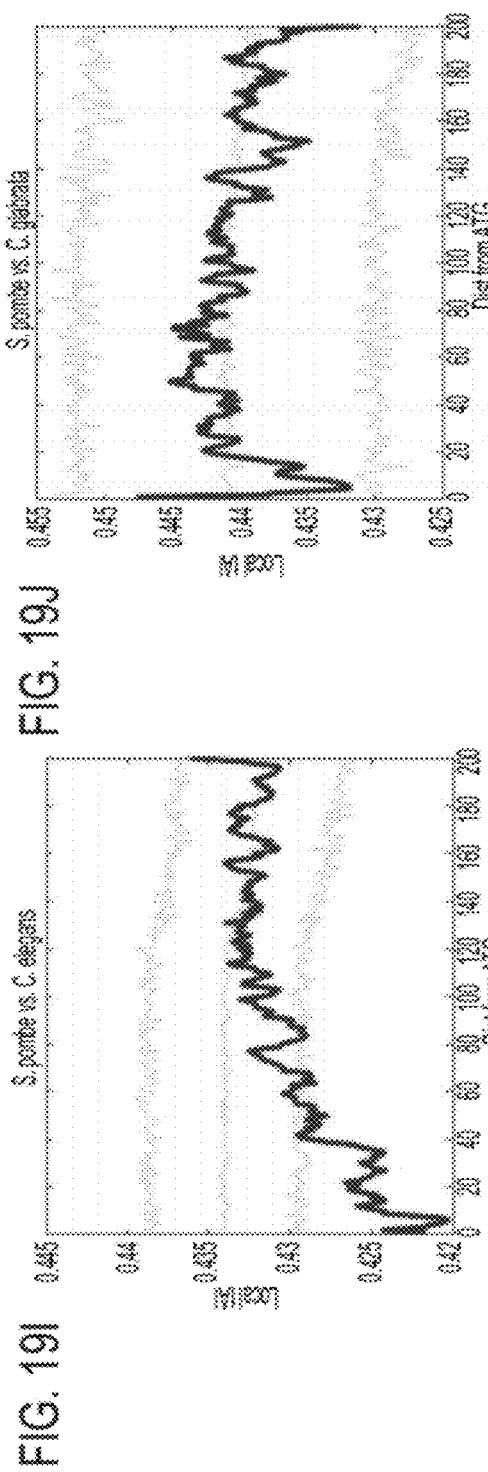
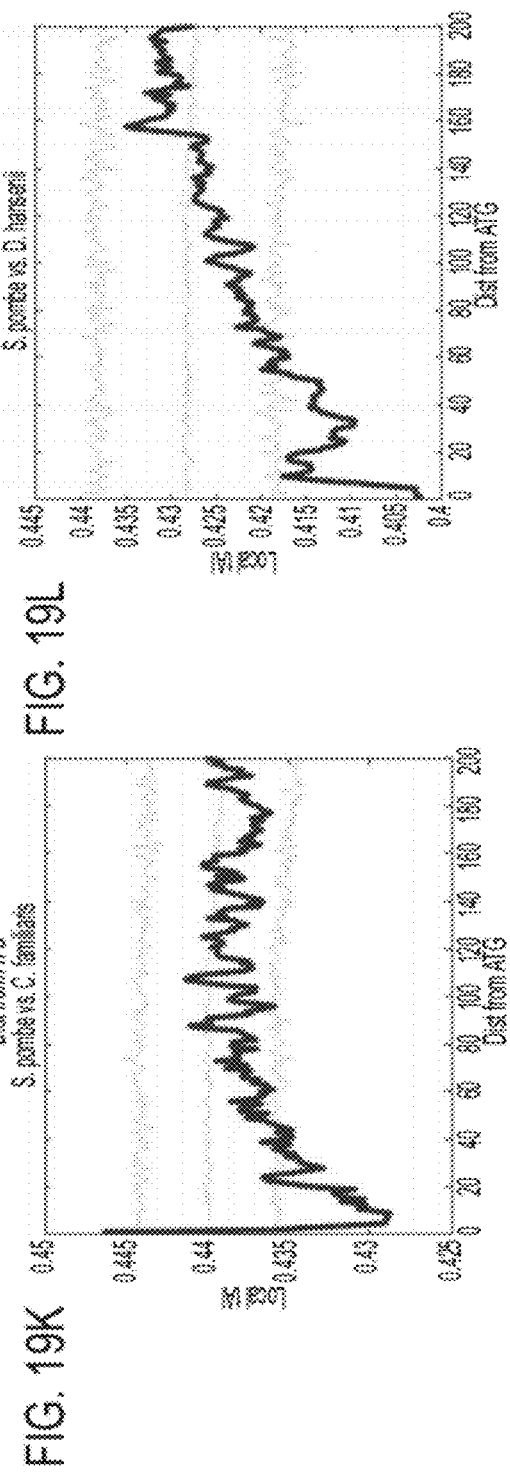
FIG. 19I  FIG. 19J
FIG. 19K  FIG. 19L

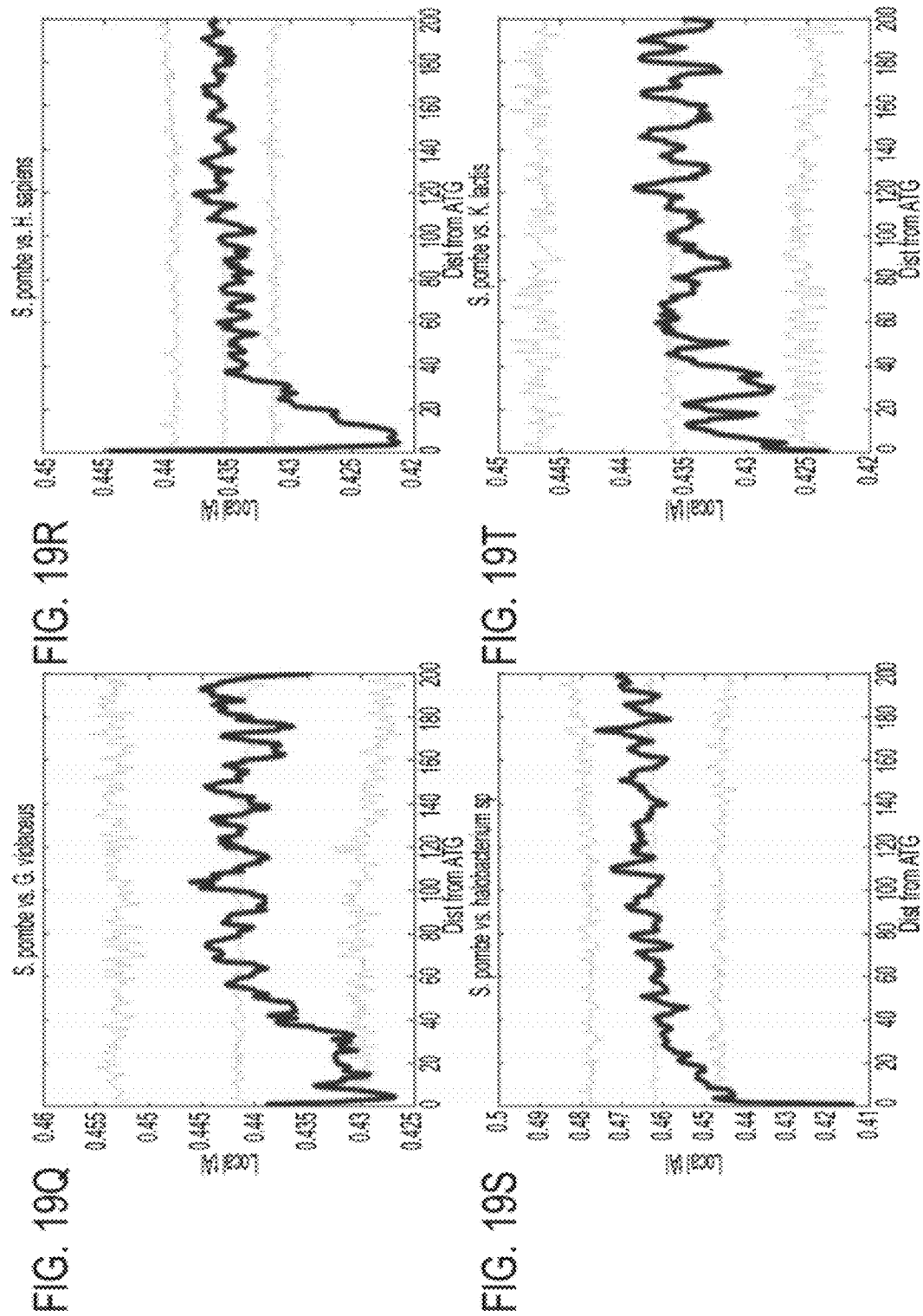

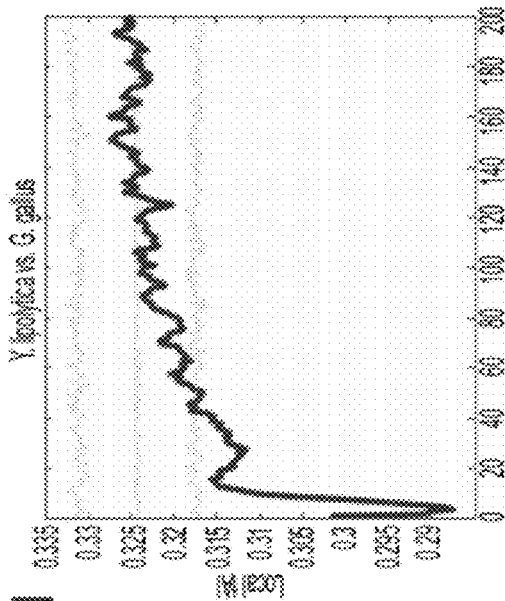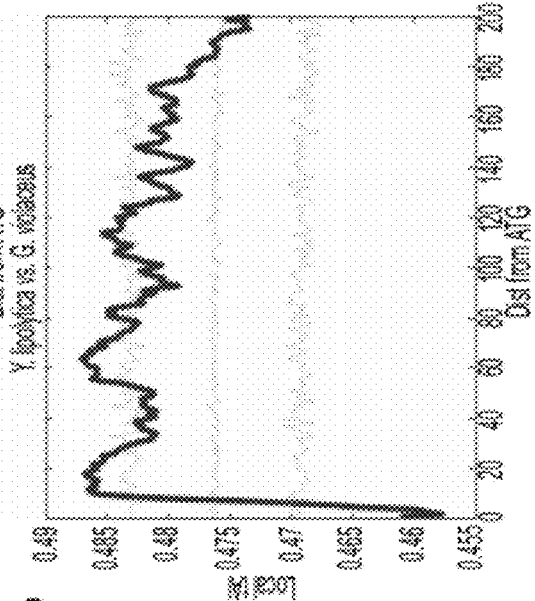
FIG. 20M  FIG. 20N
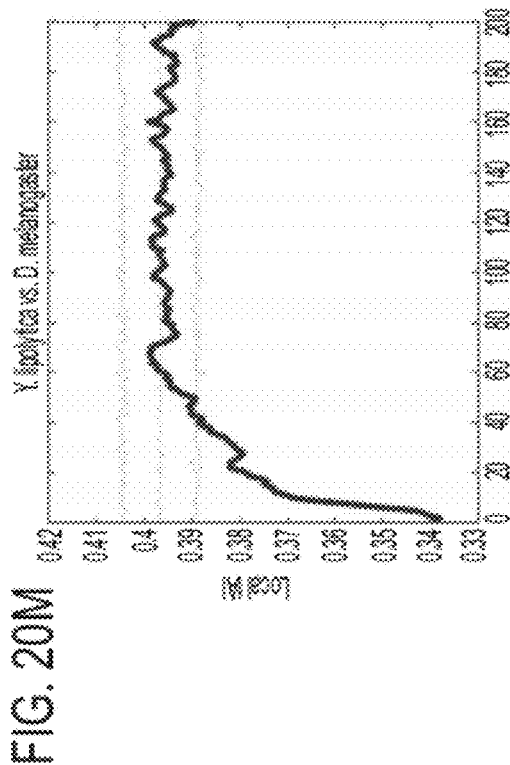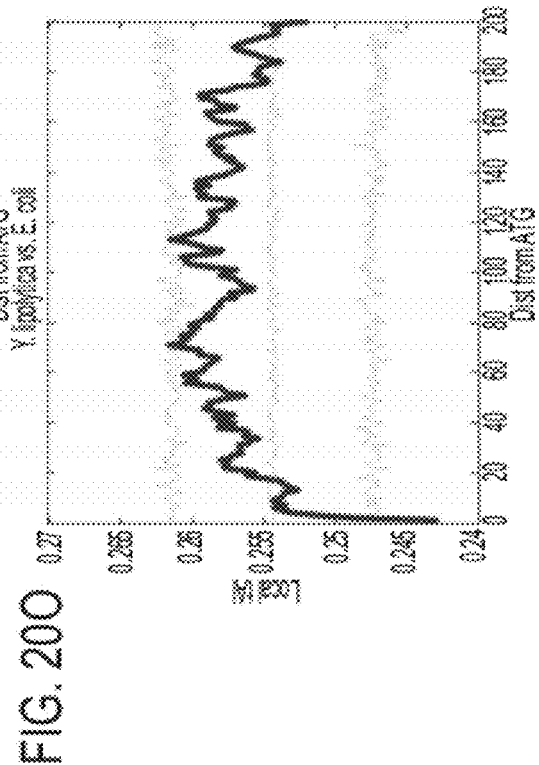
FIG. 20O  FIG. 20P

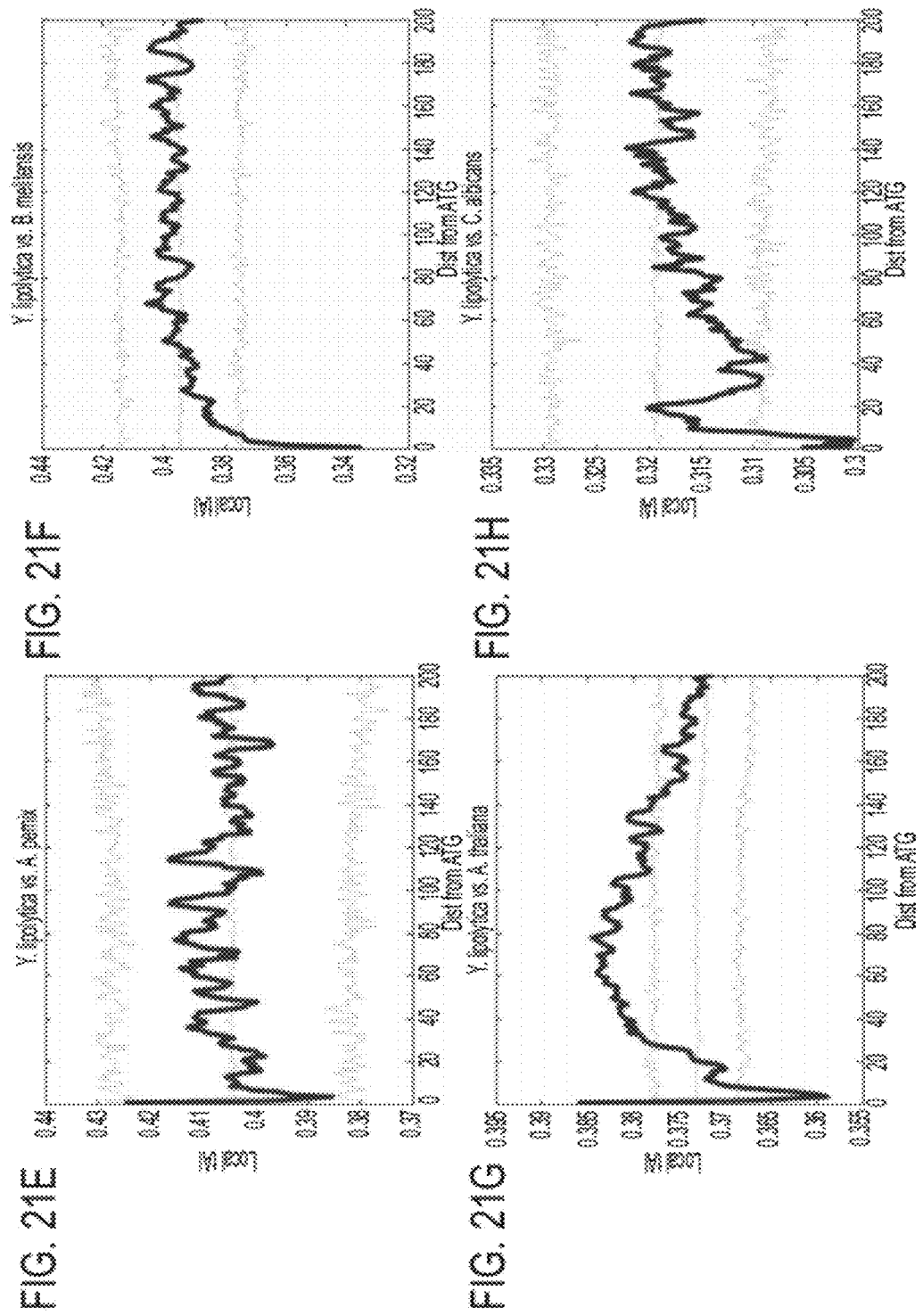

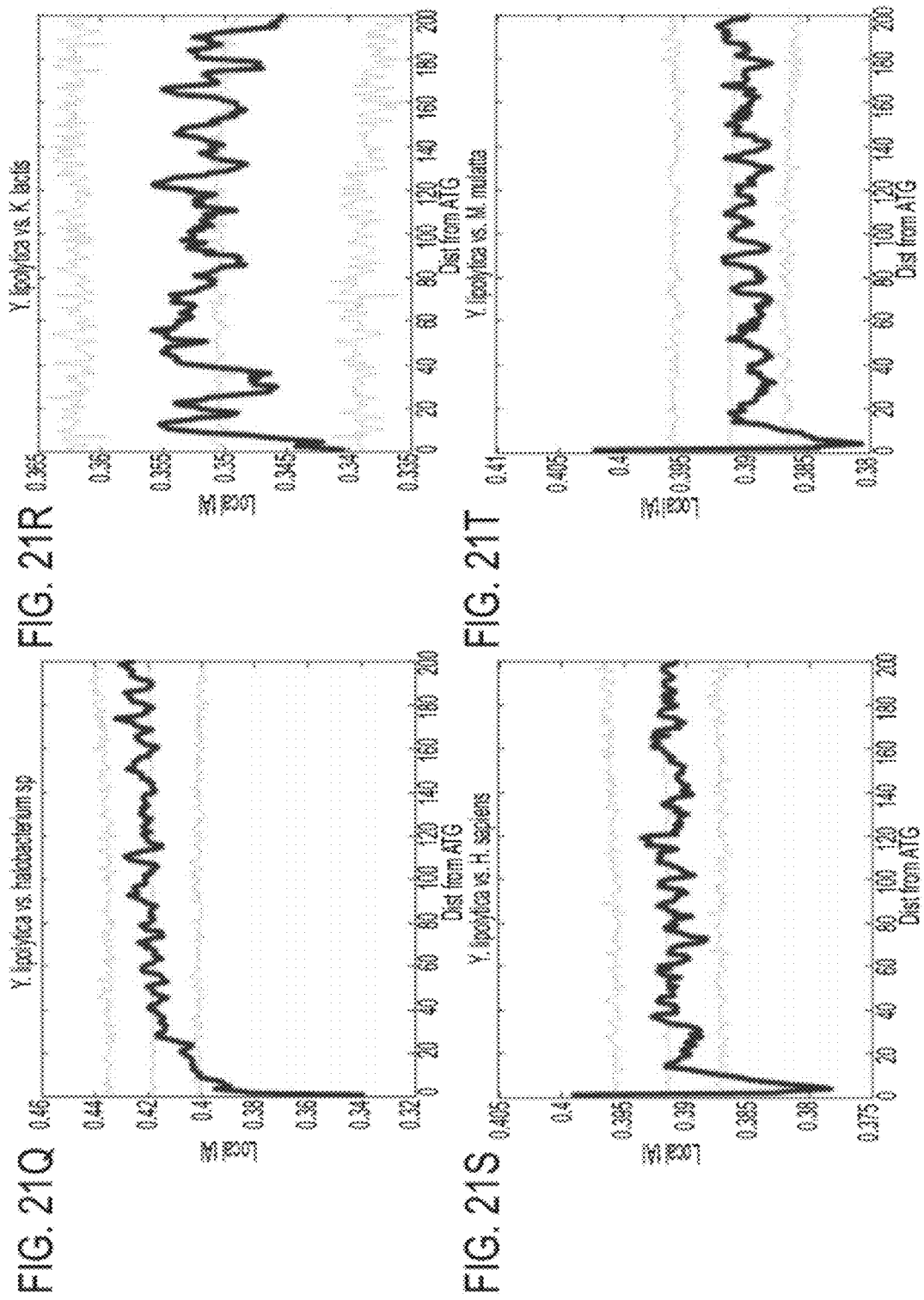

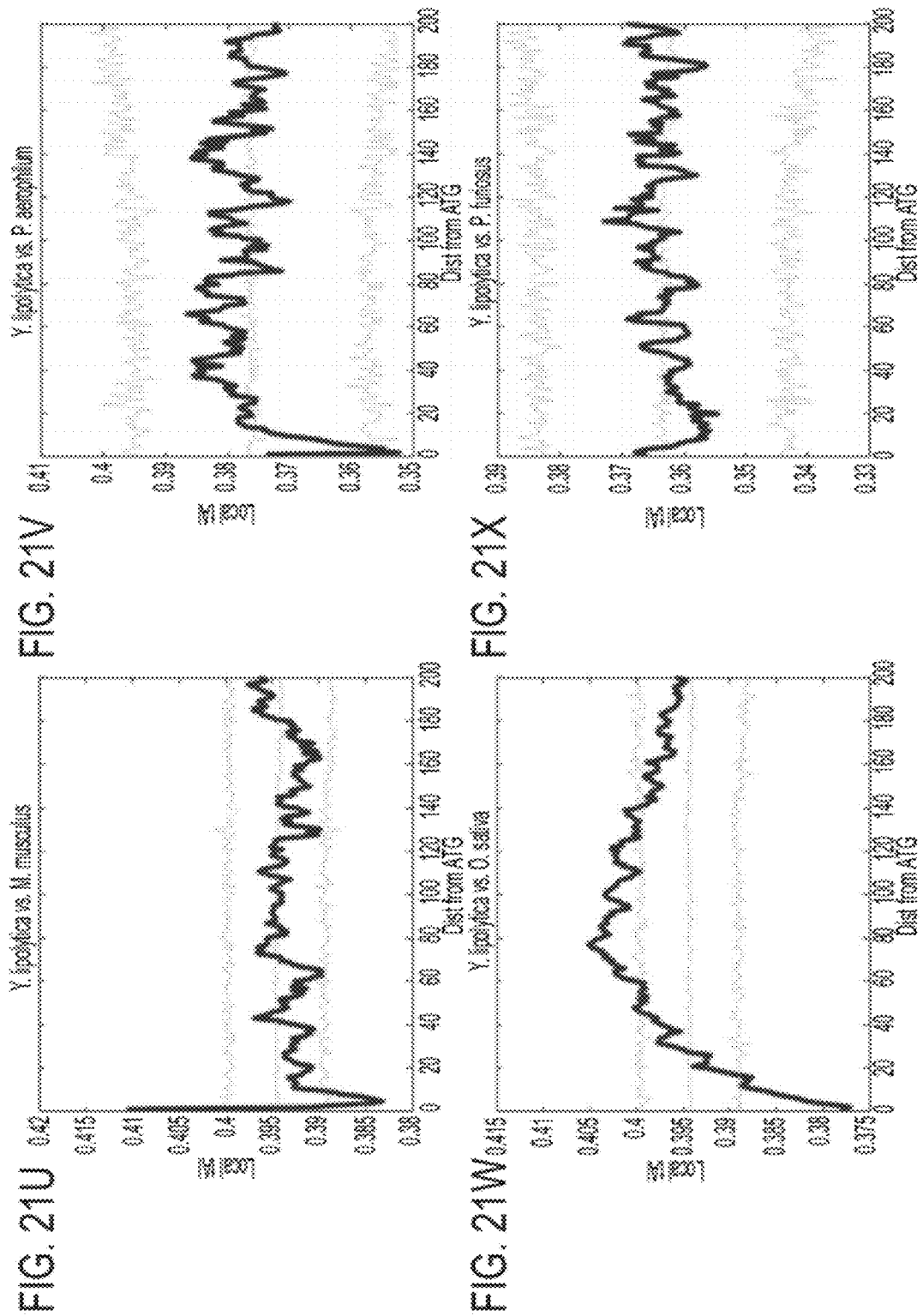

| Measure | Random 1 | Random 2 | Random 3 | Random 4 | Random 5 | Random 6 |
|---|---|---|---|---|---|---|
| RISS | 0.0045* | --- | 0.001* | 0.095* | --- | 0.095* |
| TSS | 0.2358 | --- | 0.2962 | 0.3511 | --- | 0.35 |
| IT | <0.000499* | --- | <0.000499* | 0.082* | --- | 0.093* |
| TT | 0.0255* | --- | 0.0270* | 0.086* | --- | 0.095* |
| RPM | 0.0065* | --- | 0.0095* | 0.086* | --- | 0.095* |
| CPS | 0.0280* | --- | 0.036* | 0.084* | --- | 0.093* |
| RCSS | 0.0255* | --- | 0.0255* | 0.086* | --- | 0.095* |
| RCTSS | 0.0255* | --- | 0.0255* | 0.086* | --- | 0.095* |
| CPSPR | <0.000499* | --- | <0.000499* | 0.082* | --- | 0.0893* |

FIG. 25A

| Measure | Random 1 | Random 2 |
|---|---|---|
| RISS | $P<0.01$ | $P<0.01$ |
| TSS | $P<0.01$ | $P<0.01$ |
| TT | $P<0.01$ | $P<0.01$ |
| TT | $P<0.01$ | $P<0.01$ |
| RPM | $P<0.01$ | $P<0.01$ |
| CPS | $P<0.01$ | $P<0.01$ |
| RCSS | $P<0.01$ | $P<0.01$ |
| RCTSS | $P<0.01$ | $P<0.01$ |
| CPSPR | $P<0.01$ | $P<0.01$ |

FIG. 25B

RECOMBINANT PROTEIN PRODUCTION IN HETEROLOGOUS SYSTEMS

RELATED APPLICATIONS

This application is a National Phase of PCT Patent Application No. PCT/IL2011/000082 having International filing date of Jan. 25, 2011, which claims the benefit of priority under 35 USC §119 (e) of U.S. Provisional Patent Application Nos. 61/311,444 filed on Mar. 8, 2010 and 61/354,284 filed on Jun. 14, 2010. The contents of the above applications are all incorporated by reference as if fully set forth herein in their entirety.

FIELD AND BACKGROUND OF THE INVENTION

The present invention, in some embodiments thereof, relates to recombinant protein production in heterologous systems.

Advances in genetic engineering have made possible the production of therapeutics and vaccines for human and animals in the form of recombinant proteins. These biotechnology-derived recombinant proteins form a new class of drugs for many ailments like genetic disorders, cancer, hypertension and AIDS for which there is no better treatment or cure. Unlike chemical drugs, biologicals are the body's own molecules and hence more compatible with biological systems. At present there are more than 100 biotechnology-derived therapeutics and vaccines approved by US FDA for medical use and over 1000 additional drugs and vaccines are in various phases of clinical trials. In addition, use of DNA, proteins and enzymes in diagnostics is increasing exponentially. Industrial uses of enzymes in food, textile, leather, detergent, medicinal chemistry sectors are also increasing rapidly.

The growing need of therapeutic and other applications of enzymes and proteins is presently met by heterologous synthesis of recombinant proteins.

Commonly used expression systems for heterologous protein production include *E. coli*, baculovirus, yeast, Chinese Hamster Ovary cells (CHO) and plants.

Efficiency of expression of recombinant proteins in heterologous systems depends on many factors, both on the transcriptional level and the translational level.

mRNA translation is controlled at multiple stages and by a diversity of mechanisms. A major part of the control is on the stage of initiation, where ribosomes are recruited and assembled on the mRNA, typically on the 5' un-translated region (UTR) (1). The elongation phase is governed by the mRNA secondary structure (2), and by the extent of adaptation of the coding sequence to the cellular tRNA pool (3, 4). The abundance of tRNAs that correspond to the different codons in a gene was suggested to determine the speed (5, 6) and accuracy (7) of translation. Thus, codons that are recognized by abundant or rare tRNAs will be respectively referred to here as codons with high and low efficiency (or as codons that are respectively highly or lowly adapted to the tRNA pool). It may be hypothesized that ribosomes will spend less time on high efficiency codons, explore less mismatched tRNAs and thus waste less GTP molecules when translating them, will be less likely to introduce a translation error on such codons and in addition may have lower probability of pre-mature drop off when translating them.

Indeed transcripts whose codons are biased towards the more abundant tRNAs were found to be more highly expressed (5, 8). In addition protein expression levels can be artificially increased by designed mutations that increased their codon-tRNA adaptation (9-12), pointing to a causal relationship between codon usage and expression level. Accordingly, the extent of adaptation between genes to the tRNA pool in different species was found to vary in evolution according to organisms' life style needs (5, 13).

SUMMARY OF THE INVENTION

According to an aspect of some embodiments of the present invention there is provided an isolated polynucleotide encoding a polypeptide of a species having a predetermined amino acid sequence, the polynucleotide having been modified so that the average rate of translation of the first at least about 30 amino acids is slower by at least two fold than the average rate of translation of the remaining amino acids of the polypeptide in cells of another species.

According to an aspect of some embodiments of the present invention there is provided an isolated polynucleotide encoding a polypeptide of a species having a predetermined amino acid sequence, the polynucleotide having been modified so as to generate codons forming a suitable ramp sequence at the 5' end of the polynucleotide for increasing translation efficiency of the polynucleotide in cells of another species.

According to an aspect of some embodiments of the present invention there is provided an expression construct comprising the polynucleotide of the present invention and a promoter suitable for expressing the polypeptide in the other species.

According to an aspect of some embodiments of the present invention there is provided a method of increasing the efficiency of gene expression in a heterologous cell, the method comprising adapting a sequence of a polynucleotide which encodes a polypeptide such that the average rate of translation of the first at least about 30 amino acids is slower by at least two fold than the average rate of translation of the remaining amino acids of the polypeptide, so as to generate a modified polynucleotide that is more efficiently expressed in the heterologous cell as compared to a non-modified polynucleotide.

According to an aspect of some embodiments of the present invention there is provided a method of generating a polypeptide, the method comprising:
  (a) inserting the isolated polynucleotide of the present invention into a cell, the cell being of the another species; and
  (b) culturing the cell under conditions that allows expression of the polypeptide, thereby generating the polypeptide.

According to some embodiments of the invention, the 5' end of the polynucleotide is modified.

According to some embodiments of the invention, the 3' end of the polynucleotide is non-modified.

According to some embodiments of the invention, the 3' end of the polynucleotide is modified.

According to some embodiments of the invention, the 5' end of the polynucleotide is non-modified.

According to some embodiments of the invention, the isolated polynucleotide comprises deoxyribonucleotides.

According to some embodiments of the invention, the isolated polynucleotide comprises ribonucleotides.

According to some embodiments of the invention, the ramp sequence comprises between about 30-50 codons.

According to some embodiments of the invention, the polypeptide of a species is a polypeptide of a human.

According to some embodiments of the invention, the cells of another species comprises cells of a species selected from the group consisting of a bacterial species, a fungal species, a plant species, an insect species and a mammalian species.

According to some embodiments of the invention, the cells of a bacterial species comprise E. coli cells.

According to some embodiments of the invention, the codon CAC is used to encode a histidine of a histidine tag of the polypeptide.

According to some embodiments of the invention, the cells of a mammalian species comprise Chinese hamster ovary (CHO) cells.

According to some embodiments of the invention, the cells of a fungal species comprise S. cerevisiae cells.

According to some embodiments of the invention, the polypeptide is selected from the group consisting of an antibody, insulin, interferon, growth hormone, erythropoietin, growth hormone, follicle stimulating hormone, factor VIII, low density lipoprotein receptor (LDLR) alpha, galactosidase A and glucocerebrosidase.

According to some embodiments of the invention, the polypeptide comprises a signal sequence.

According to some embodiments of the invention, the isolated polynucleotide comprises a sequence as set forth in SEQ ID NOs: 2-7.

According to some embodiments of the invention, the first at least 30 amino acids comprises no more than about 50 amino acids.

According to some embodiments of the invention, the polypeptide encoded by the gene is selected from the group consisting of an antibody, insulin, interferon, growth hormone, erythropoietin, growth hormone, follicle stimulating hormone, factor VIII, alpha galactosidase A and glucocerebrosidase.

According to some embodiments of the invention, the polypeptide comprises a signal sequence.

According to some embodiments of the invention, the modified polynucleotide comprises a sequence as set forth in SEQ ID NOs: 2-7.

According to some embodiments of the invention, the method further comprises purifying the polypeptide following the culturing.

According to some embodiments of the invention, the 3' end of the polynucleotide is non-modified.

According to some embodiments of the invention, the 3' end of the polynucleotide is modified.

According to some embodiments of the invention, the 5' end of the polynucleotide is non-modified.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
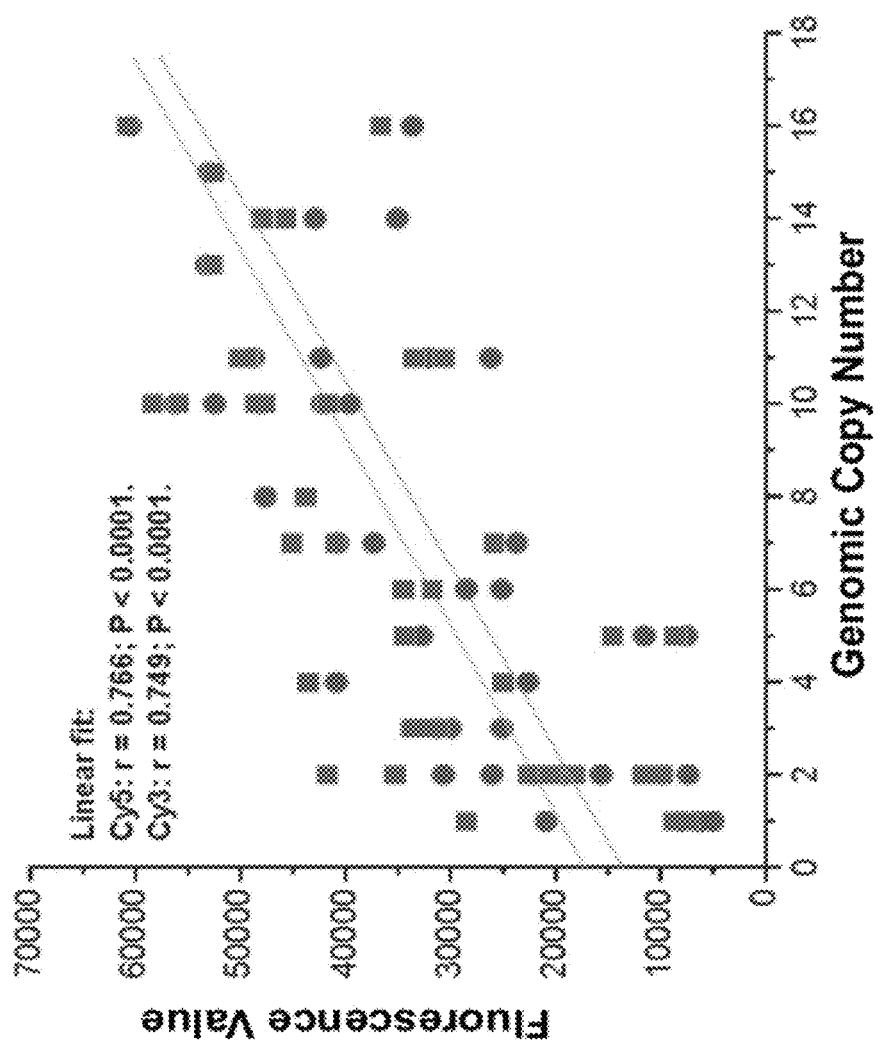
Figures 2E, 2F:
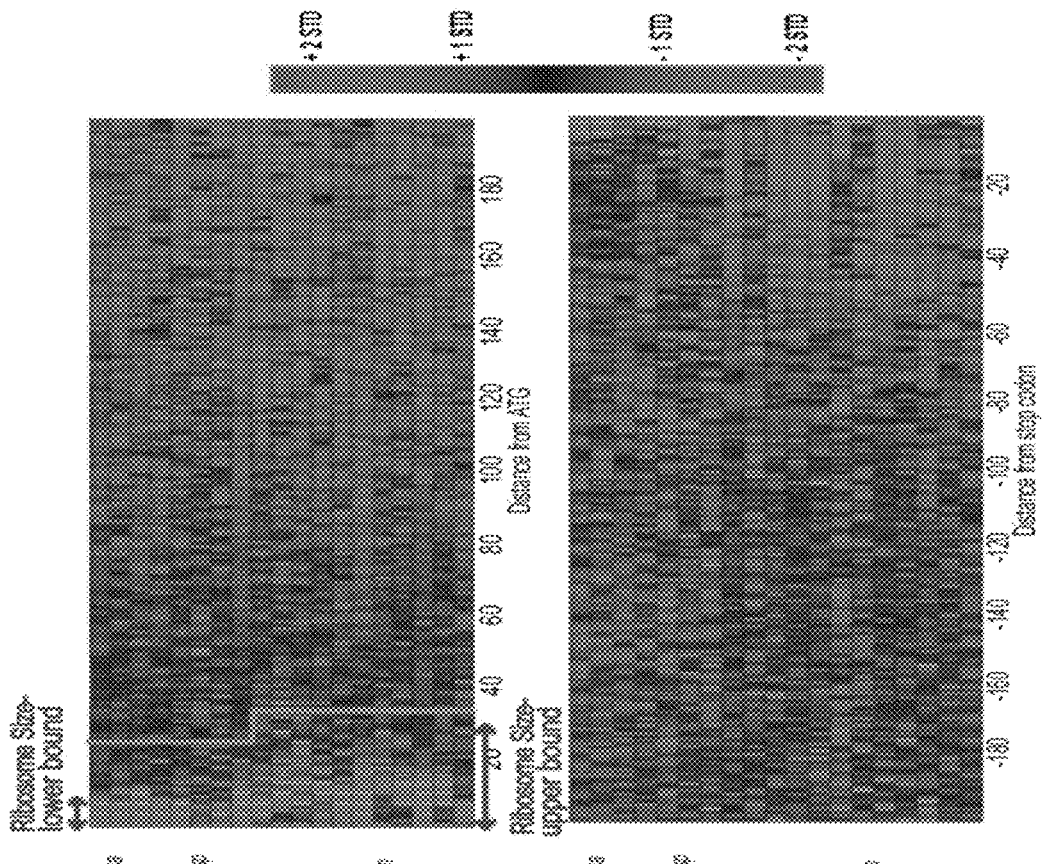

FIG. 1 is a graph illustrating the tRNA gene copy correlates with levels of tRNA genes in S. cerevisiae. tRNA gene copy numbers vs. the expression levels of tRNA genes in S. cerevisiae measured by a micro-array dedicated to the tRNAs in this species (Dittmar et al., 2004). tRNA levels were measured independently with two alternative dyes (cy5 and cy3), each producing similar correlations with the gene copy numbers. See also Tables 4-7 and FIGS. 10A-F.

FIGS. 2A-F illustrate selected genome-averaged translation efficiency profiles.

A.-D. Averaged translation efficiency profile (for the start line-up, see Methods) for the first 200 codons D. melanogaster (A.), S. cerevisiae (B.), C. elegans (C.), and E. coli (D.) Note the different span of values in each sub-plot. Each figure contains the averaged tAI profile (black) and the randomized profile +−3 standard deviations (grey; see details in the Methods).

E.-F. The translation efficiency profiles in various organisms for the start/end codon line-up (see Method). Each row describes the translation efficiency profile of a different organism and each pixel describes a codon. Green denote lower tAI whereas red denote higher tAI (see color bar on the right). The blue vertical line (A.) denotes the means of the length of the ramp (FIG. S2, Methods), in prokaryotes/eukaryotes; the ratio between the means of these regions in prokaryotes/eukaryotes (34.5/24=1.43) may correspond to a difference in the size of the footprinted region of the eukaryotic and prokaryotic ribosomes on transcripts. See also FIGS. 7-9 and 11A-C.

FIGS. 3A-B are graphs illustrating that bottlenecks in translation efficiency tend to be localized close to mRNAs 5' ends. A.-B. The distribution of the positions of the bottlenecks in S. cerevisiae (A.) and S. pombe (B.). For each bottleneck position, the number of genes with a bottleneck in that position was normalized by dividing it by the number of genes whose length extends beyond that position. The distribution is similar also when considering only genes with more than 200 codons (inset).

Figure 4A:
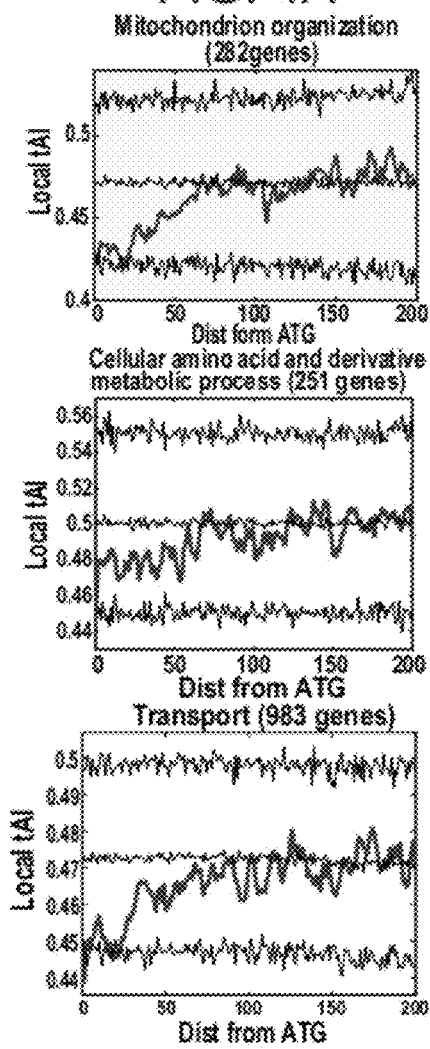
Figure 4B:
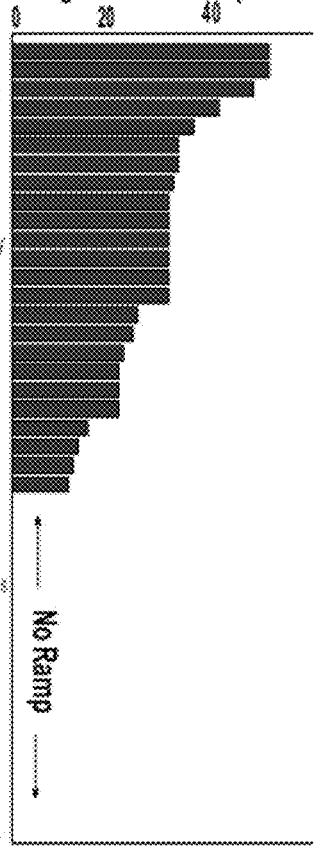
Figure 4C:
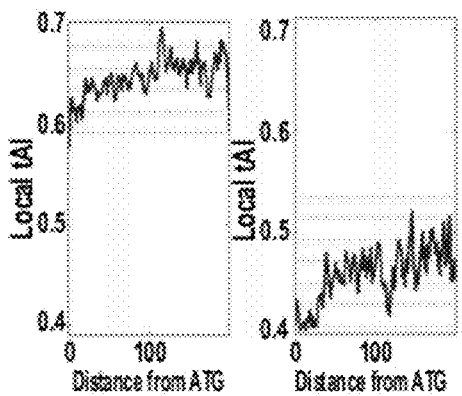
Figure 5A:
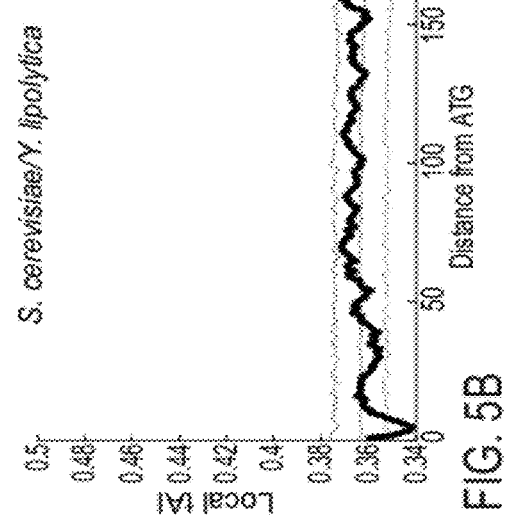
Figure 5B:
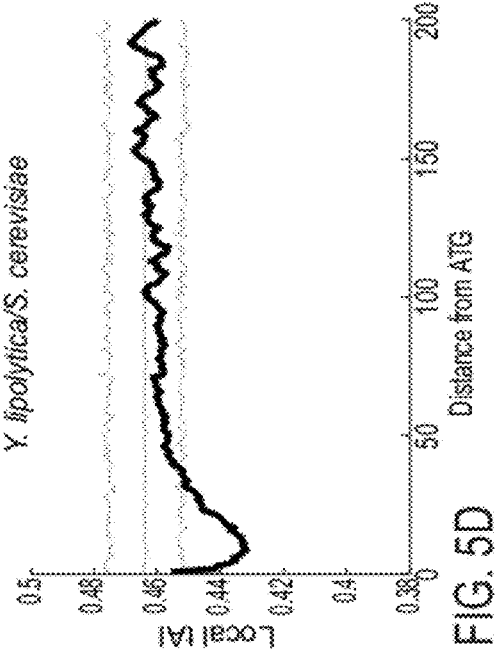
Figure 5C:
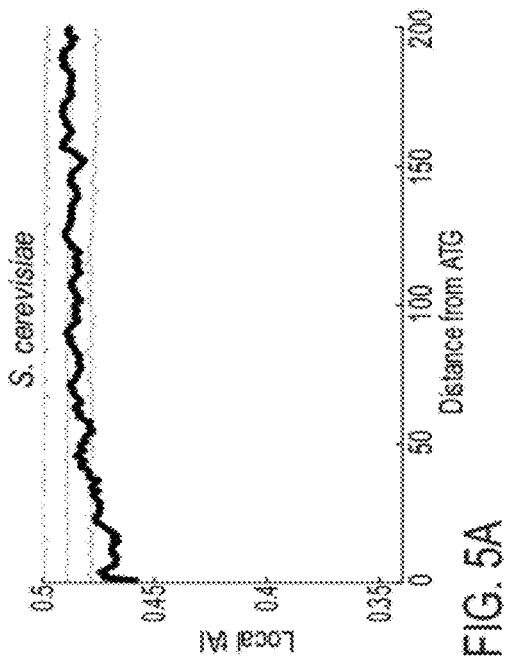
Figure 5D:
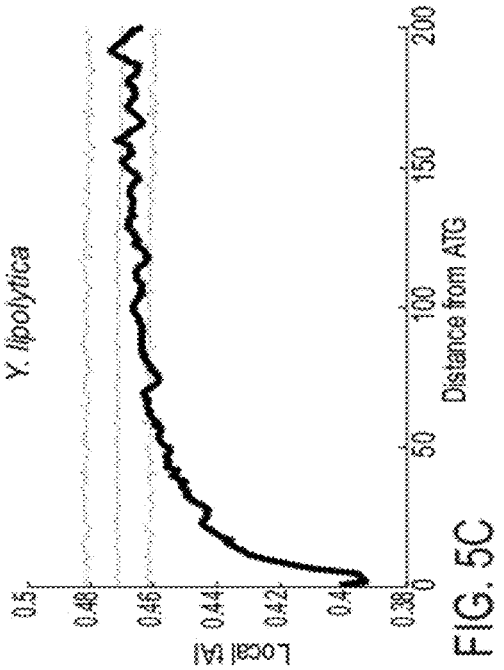

FIGS. 4A-C illustrate the profile of local translation efficiency of selected gene groups. A. The profile of local translation efficiency of three GO slim (Gene ontology: tool for the unification of biology. Nat. Genet. May 2000; 25(1):25-9) categories that have a ramp. B. The length of the ramp of all the GO slim categories. C. The profile of local translation efficiency of cytosolic ribosomal proteins (left) and mitochondrial ribosomal proteins (right). See also FIGS. 13A-Z and 14A-P.

FIGS. 5A-D are graphs illustrating that hybrid analysis indicates selection for co-evolution of tRNA pools and genes sequences to preserve the ramp.

Translation efficiency profiles with native and non-native tRNA pools for start codon line-up. A. The translation efficiency profile of S. cerevisiae. B. The translation efficiency profile of S. cerevisiae using Y. lipolytica tRNA pool. C. The translation efficiency profile of Y. lipolytica. D. The translation efficiency profile of Y. lipolytica using S. cerevisiae tRNA pool. The black bolded line represents the actual calculated tAI profile; the grey lines represent the mean+−3 standard deviations of the tAI profiles of randomized sets of gene.

See also FIGS. 12 and 15-21.

Figure 6A:
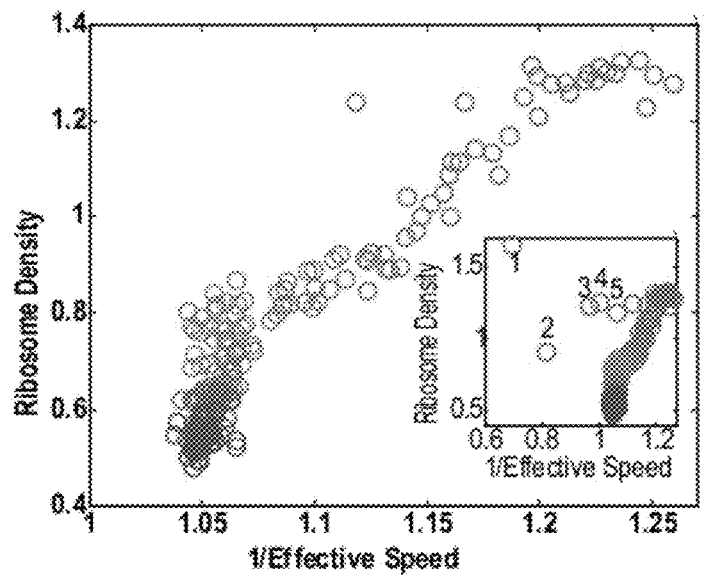
Figure 6B:
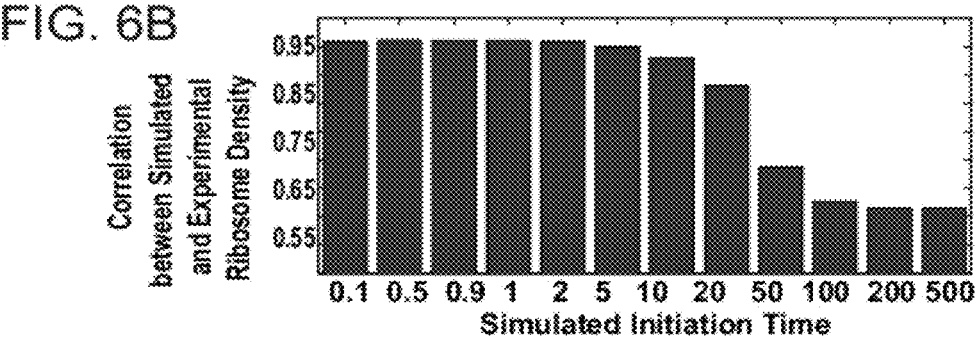
Figure 6C:
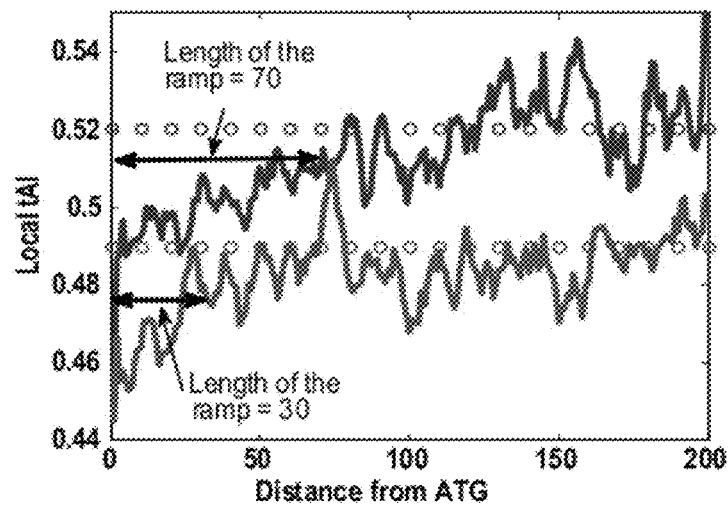

FIGS. 6A-C illustrate that experimentally measured ribosome density negatively correlates with computed translation efficiency.

A. Correlation between experimentally measured ribosomal density (Ingolia et al., 2009), and the reciprocal of the simulated speed profile when not considering the first five codons (which are outliers) and when considering all the codons (the sub-figure at the lower right corner). Dots are color coded according to codon location along genes, with green most dots representing codons that are close to the ATG, and codons that are farthest away are in red. The density and speed profiles were obtained by averaging the profiles at each position of the genes in the *S. cerevisiae* genome. The speed profile was obtained by simulating ribosomal scan of all the transcripts in this species. The Pearson correlation between density and 1/speed is 0.93 ($p<10^{-75}$). The correlation between density and the reciprocal of original "nominal" translation efficiency profile is lower, $r=0.5749$ ($p=10^{-28}$).

B. The correlation between the mean profile of ribosome density (Ingolia et al. (Ingolia et al., 2009)) and the mean profile of simulated ribosome density (Methods) at a resolution of single codons for different simulated ribosome binding initiation time (units of the translation time of the slowest codon; see Methods for definition).

C. The translation efficiency profile of genes with the top and the lowest ribosomal density distribution. As can be seen, the extent of ramping decreases at lowly dense genes.
The results remain significant also after controlling for the length of the genes (genes with higher ribosome density tend to be shorter). Specifically, the group of the 20% genes with the lowest ribosome density after removing the 50% longest genes (the final mean length is 1433; ramp length 30) have longer ramp than the group of the 20% genes with the highest ribosome density after removing the 50% shortest genes (the final mean length is 1447; ramp length 89). See also FIG. 22.

Figure 7A:
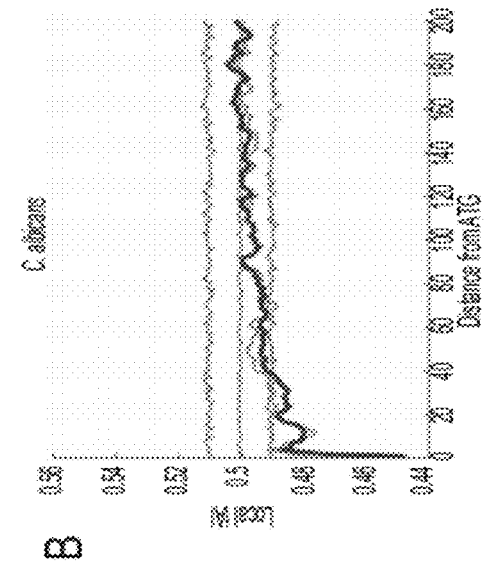
Figure 7B:
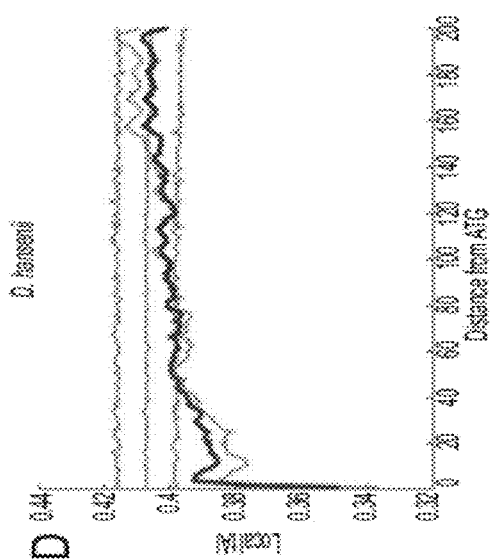
Figure 7C:
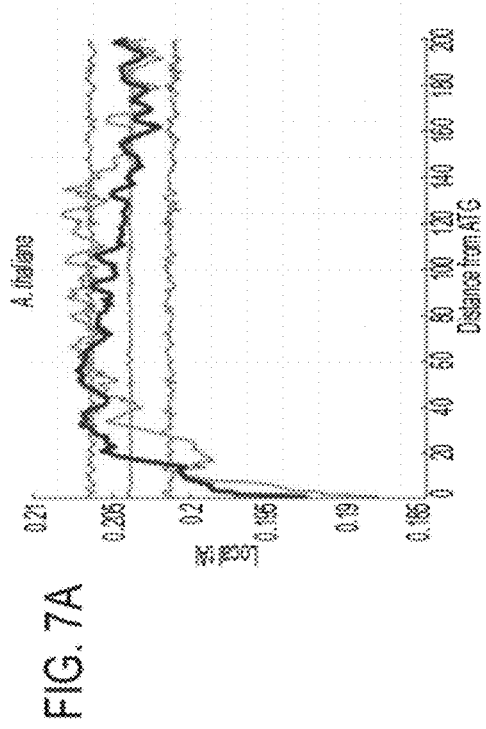
Figure 7D:
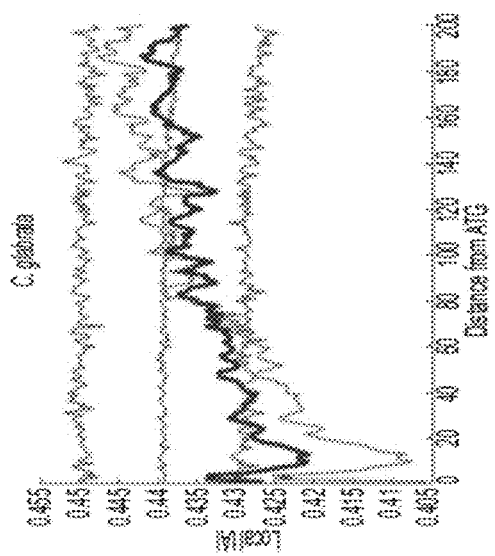
Figure 7E:
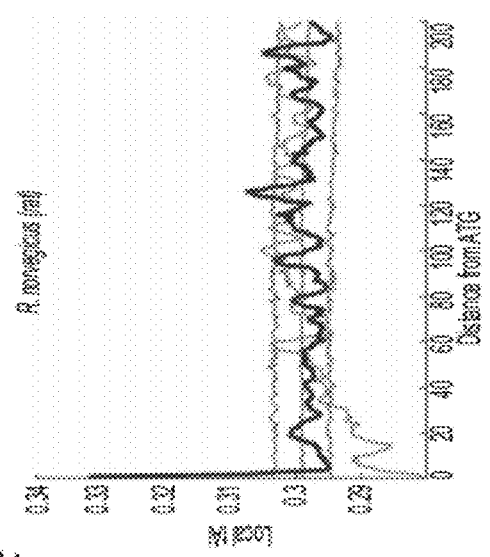
Figure 7F:
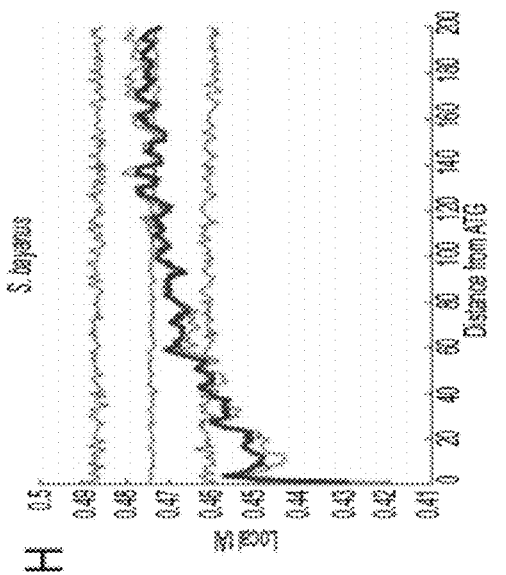
Figure 7G:
Figure 7G:
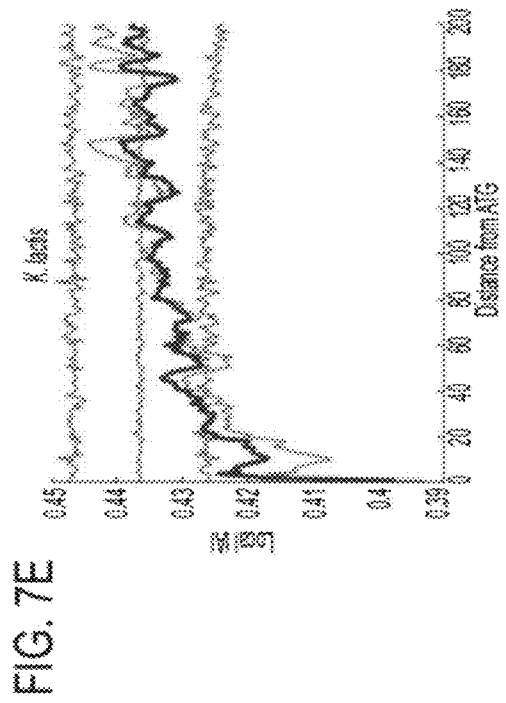
Figure 7H:
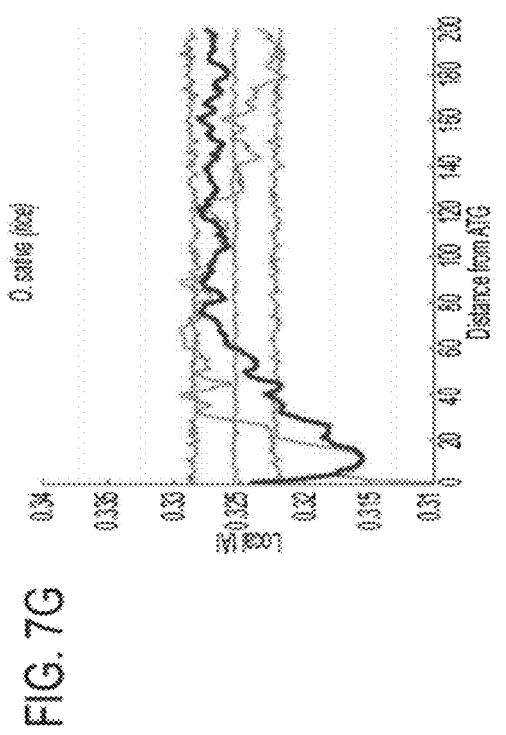
Figure 7J:
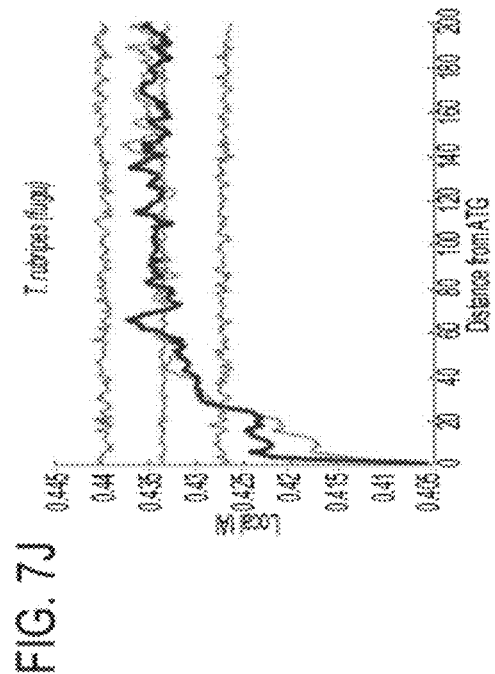
Figure 7L:
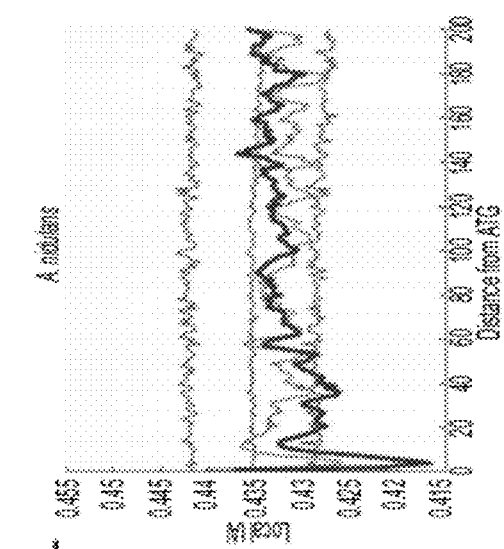
Figure 7I:
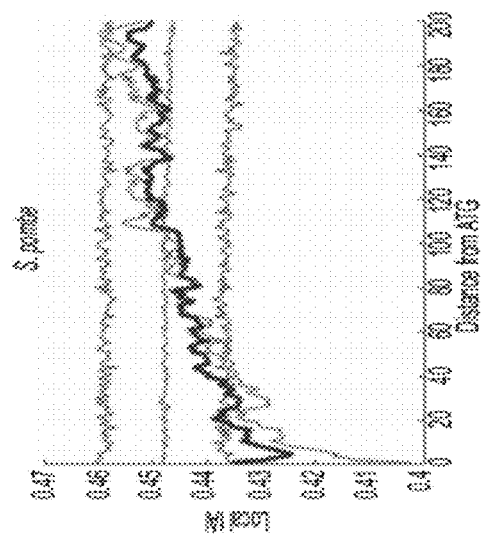
Figure 7K:
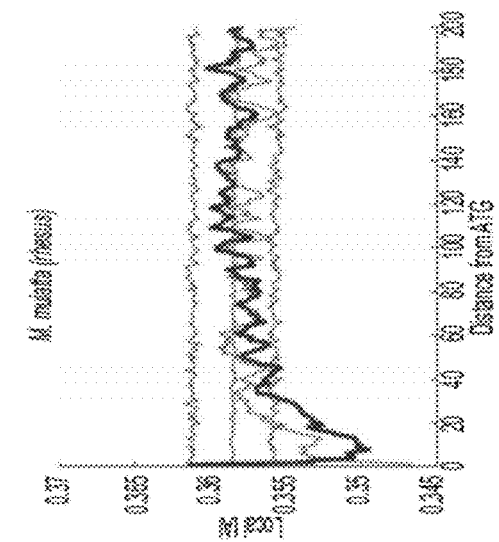
Figure 7R:
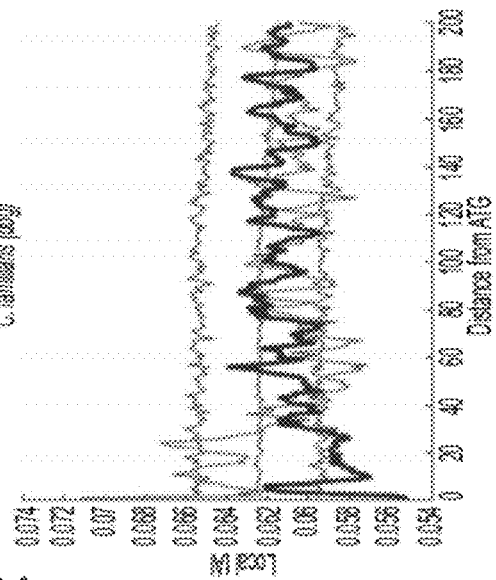
Figure 7Q:
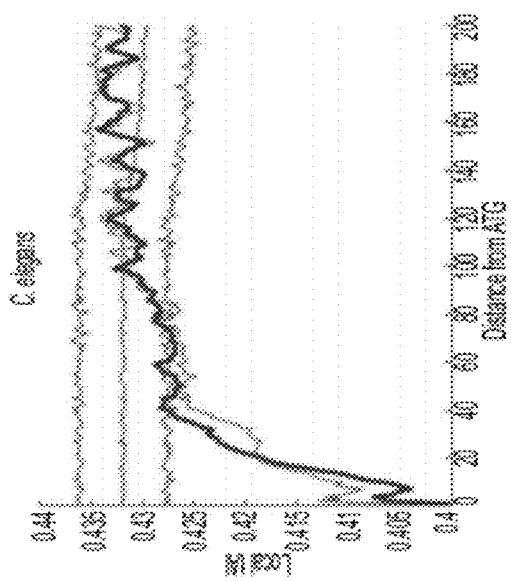
Figure 7S:
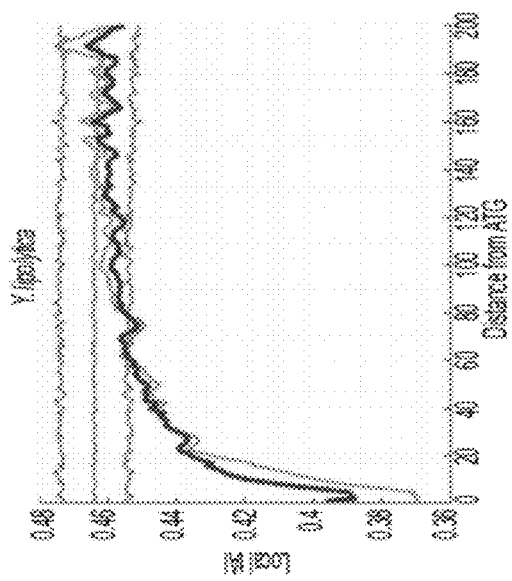
Figure 8B:
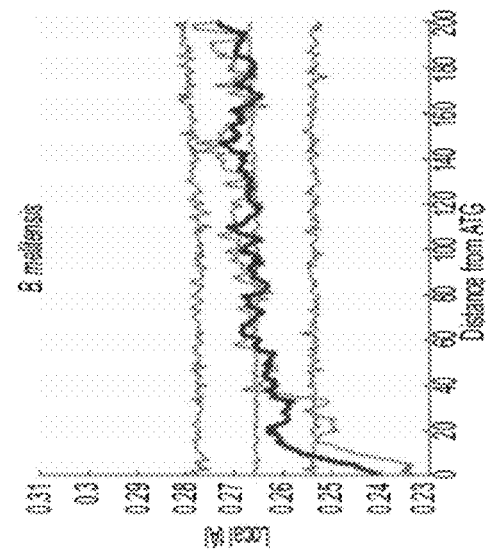
Figure 8D:
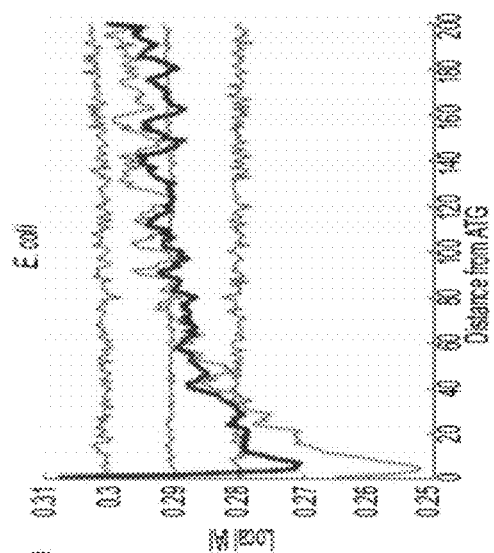
Figure 8A:
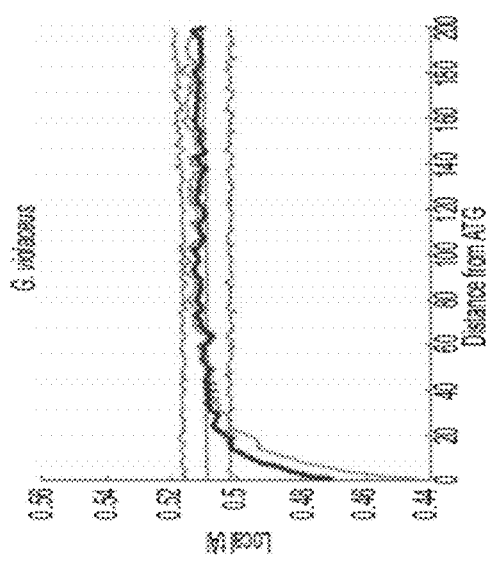
Figure 8C:
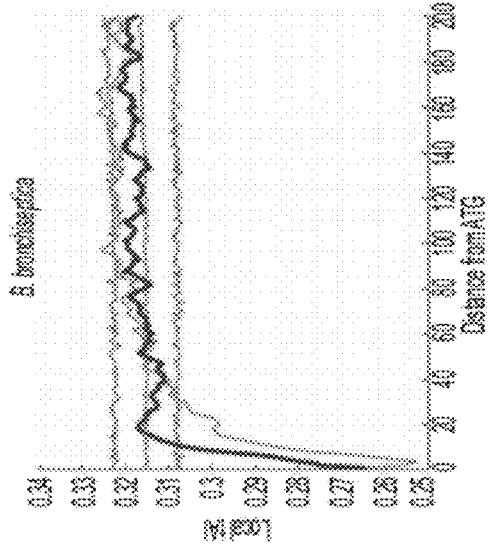
Figure 9B:
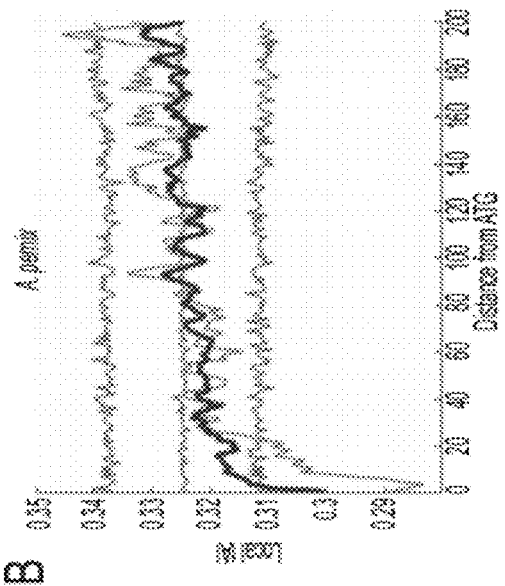
Figure 9D:
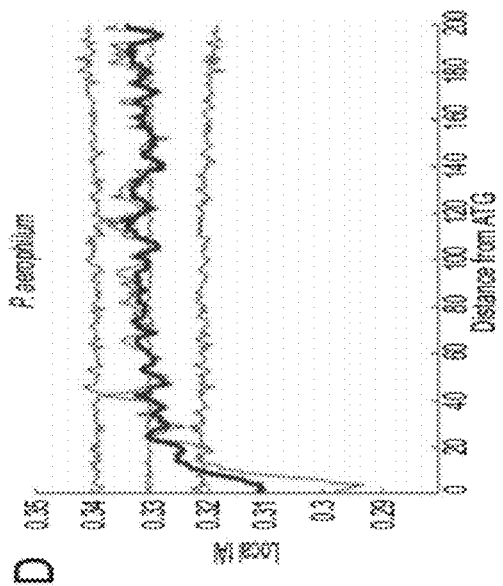
Figure 9A:
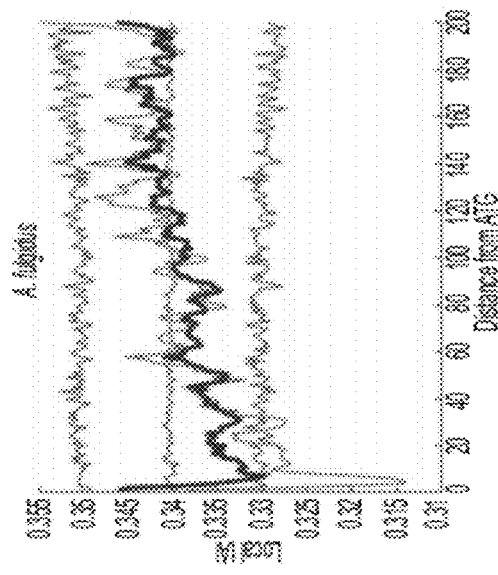
Figure 9C:
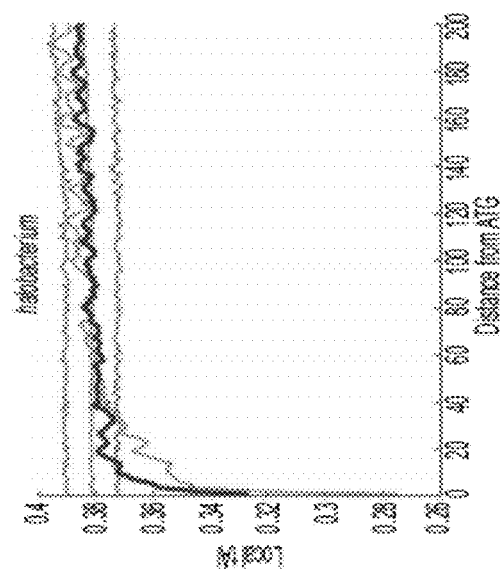

FIGS. 7A-S are graphs illustrating the translation efficiency profiles of various eukaryotic organisms. For each organism there is a figure which describes the alignment to the start codon. Each figure contains the smoothed averaged tAI profile (blue), the randomized profile+−3 standard deviations (green), and averaged AAtAI profile (red; after subtracting the mean of the AAtAI and adding the mean of the tAI).

FIGS. 8A-D are graphs illustrating the translation efficiency profiles of various bacterial organisms. For each organism there is a figure which describes the alignment to the start codon. Each figure contains the smoothed averaged tAI profile (blue), the randomized profile+−3 standard deviations (green), and averaged AAtAI profile (red; after subtracting the mean of the AAtAI and adding the mean of the tAI).

FIGS. 9A-D are graphs illustrating the translation efficiency profiles of various archaic organisms. For each organism there is a figure which describes the alignment to the start codon. Each figure contains the smoothed averaged tAI profile (blue), the randomized profile+−3 standard deviations (green), and averaged AAtAI profile (red; after subtracting the mean of the AAtAI and adding the mean of the tAI).

FIGS. 10A-D are graphs illustrating tRNA levels vs. copy number in different points of the Dioxic shift experiment.

Figure 10A:
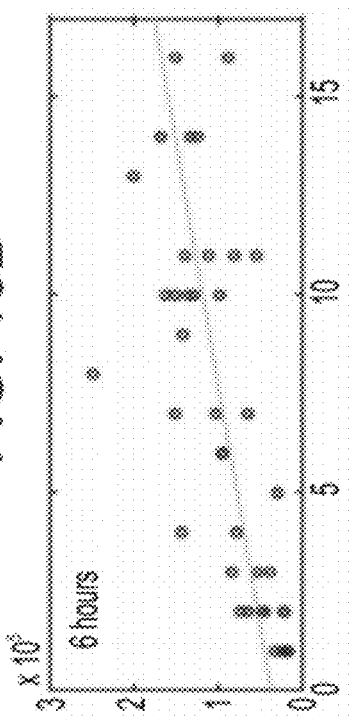
Figure 10B:
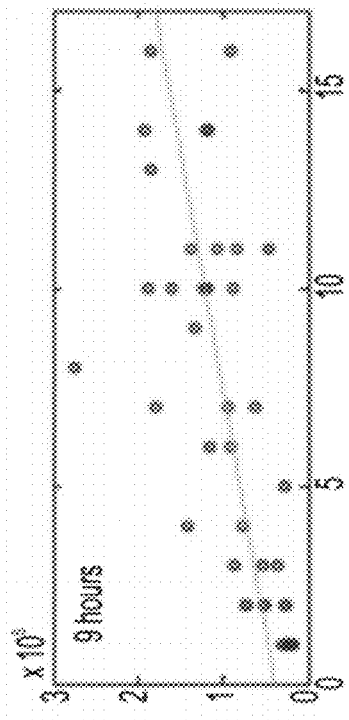
Figure 10C:
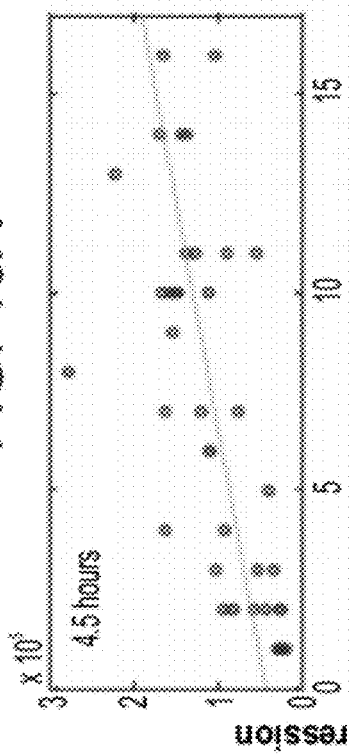
Figure 10D:
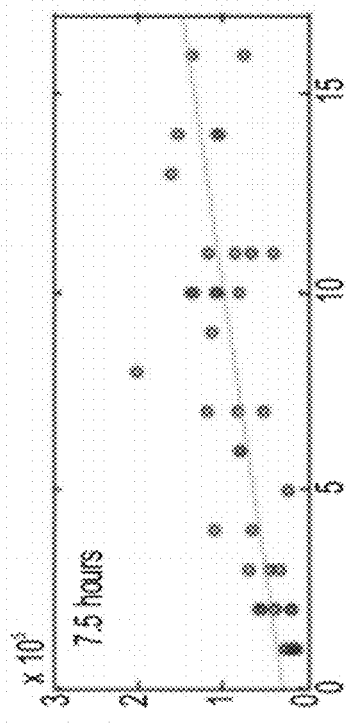
Figure 10E:
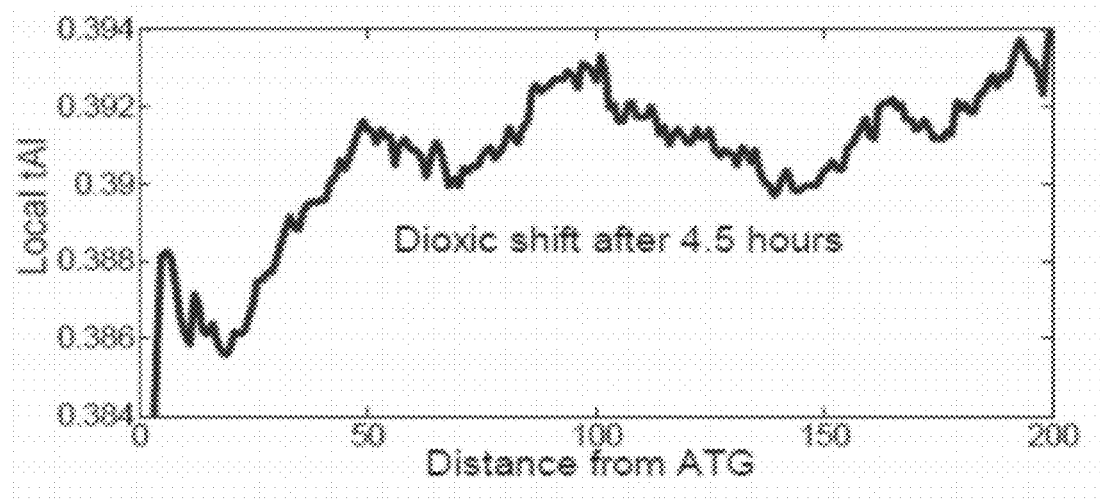
Figure 10F:
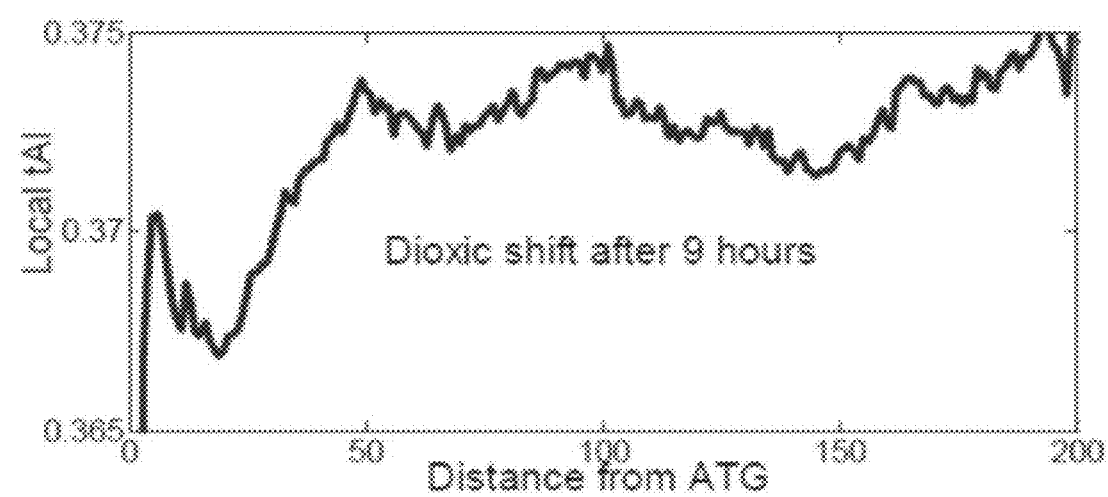

FIGS. 10E-F are graphs illustrating the translation efficiency profile (smoothed) based on tRNA expression levels in Dioxic shift after 4.5 hours (B.) and after 9 hours (C.); the other time points have similar profile. The length of the ramp in different points of the experiment are: point 0 h:23; point 4.5 h:28; point 6 h:30; point 7.5 h:30; point 9 h:30.

Figures 11A, 11B:
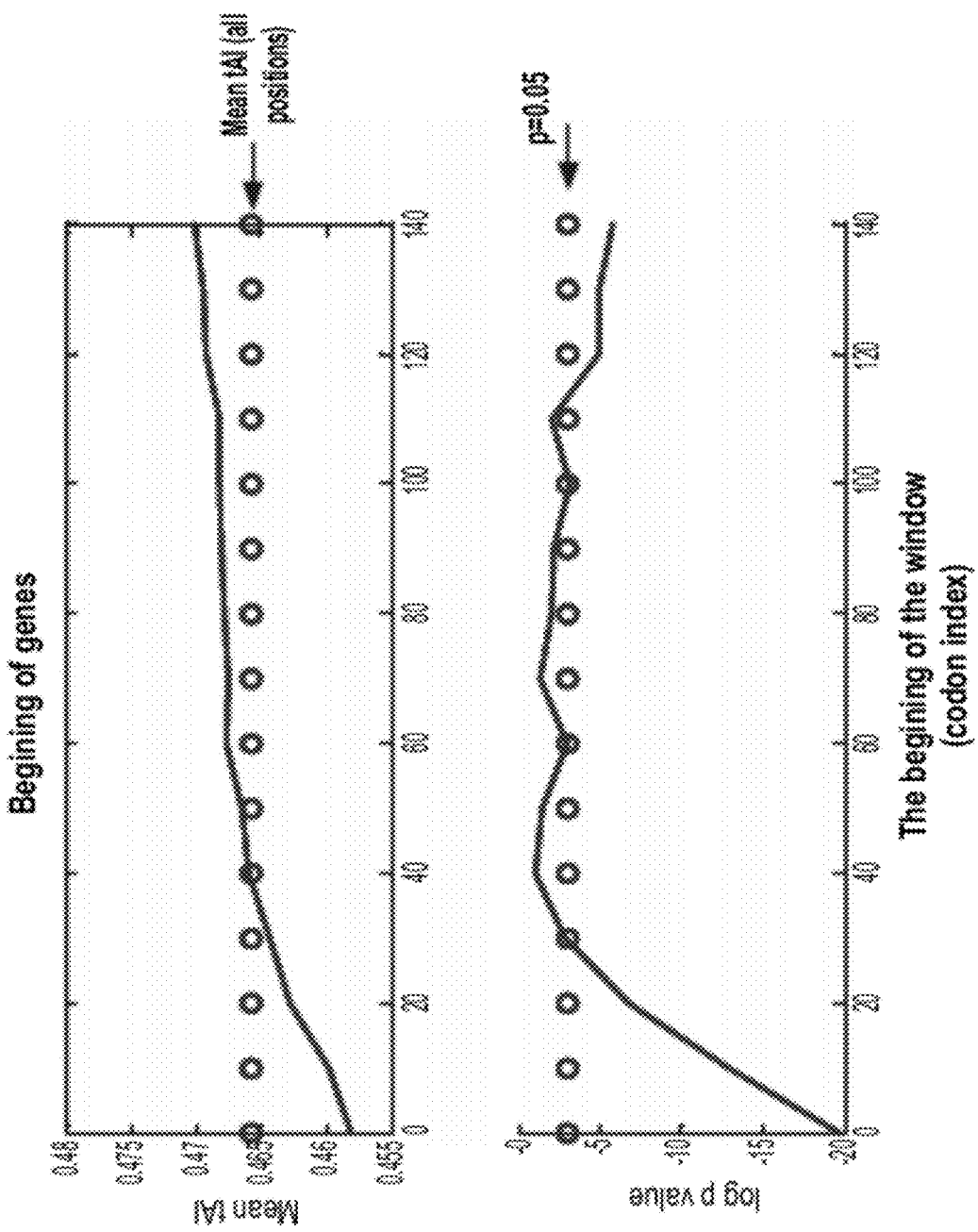
Figure 11C:
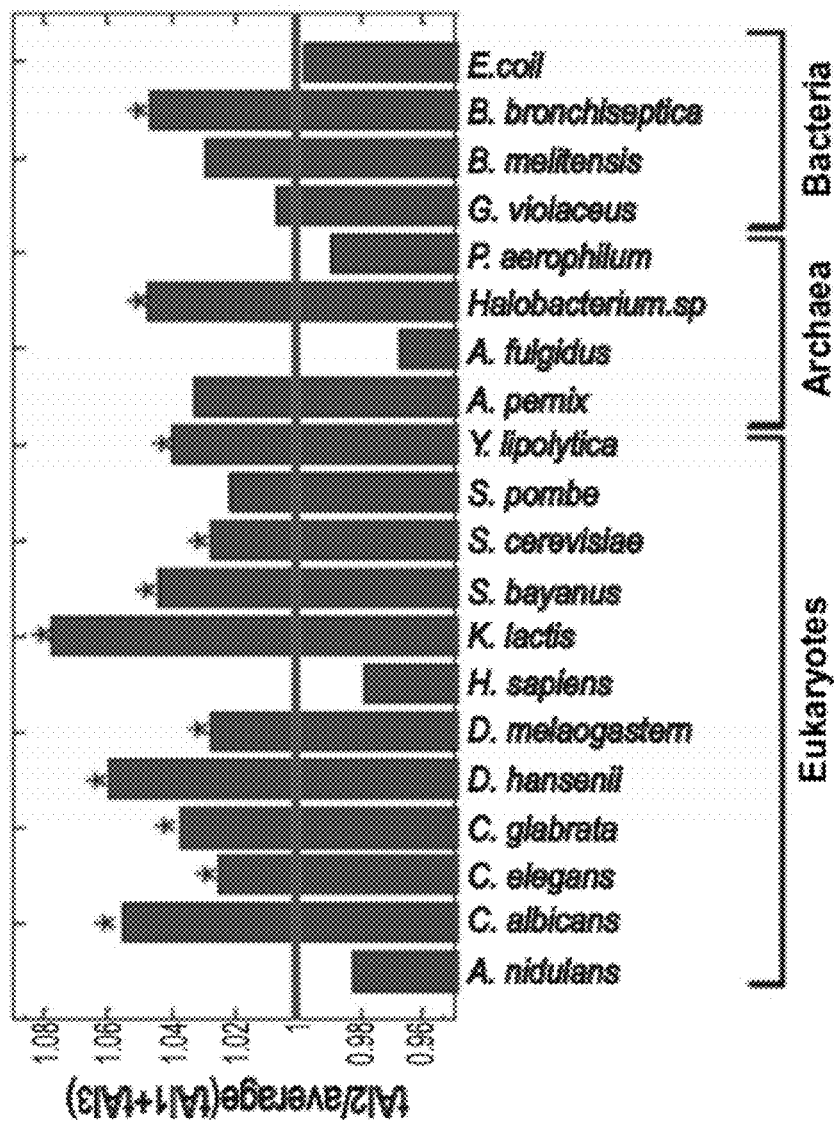

FIGS. 11A-C are graphs illustrating computing the length of the ramp for *S. Cerevisiae*. The length of the ramp for a local profile of tAI was computed by comparing the mean (KS-test) of sliding windows of length 20 to the mean of the profile of local tAI from codon 1 to codon 200. The region at the beginning corresponding to windows whose mean is significantly lower than the mean of the entire profile was defined as the length of the ramp. A. Mean tAI of sliding windows compared to the mean tAI of all positions (dotted). B. P-value for each sliding window compared to the a cut-off p-value=0.05 (dotted). C. The local tAI of the second codon from the ATG codon divided by the mean tAI of the first and the third codons for various organisms. Organisms where this ratio is significantly high are marked with an asterisk (empirical p-value<0.05/20; by comparison to the distribution of the ratios between the tAI of codon i and the mean tAI of codons i−1 and i+1 over all the codons along the translation efficiency profile; the p-value is the fraction of positions with lower/higher ratio). In most of the organisms (14 out of 20) this ratio is larger than one (the red line), in 11 organisms this ratio was significantly high; the ratio was not significantly low in any of the analyzed organisms.

Figure 12:
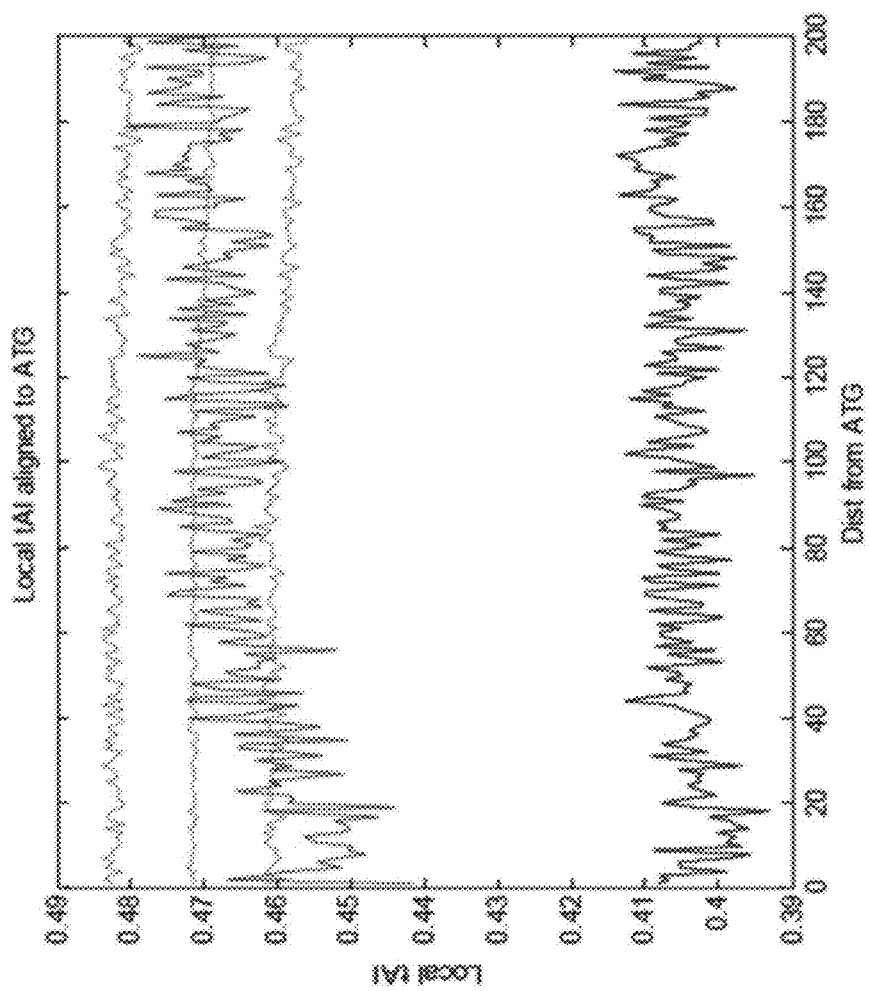

FIG. 12 is a graph illustrating control for gradients of GC content. The GC content cannot explain the profile of local tAI in *S. Cerevisae*. In order to randomize each sequence, but retain the local GC content at each codon, the codons were divided into 10 groups, according to the number of times G or C appear in them. For each sequence, every codon was replaced by a randomly chosen codon from the same group of the original codon. The local tAI profile and the averaged genome profile were then calculated as described in the Methods. The figure contains the local tAI profile (red), the randomized (permutated) profile +−3 standard deviations (black) and the averaged profile of the GC-content preserving randomized genome (blue). The profile clearly shows that keeping the GC content of a gene is not enough to generate the local tAI increasing profile.

Figure 13A:
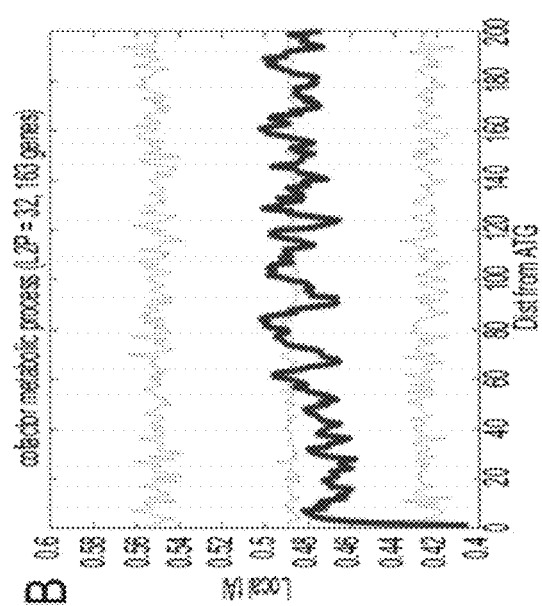
Figure 13B:
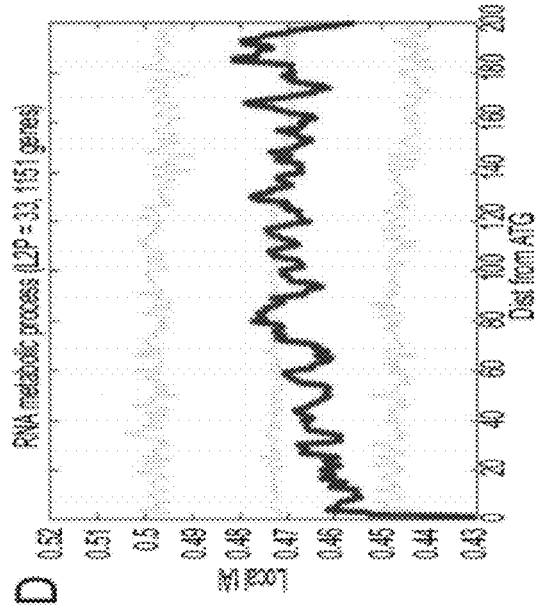
Figure 13C:
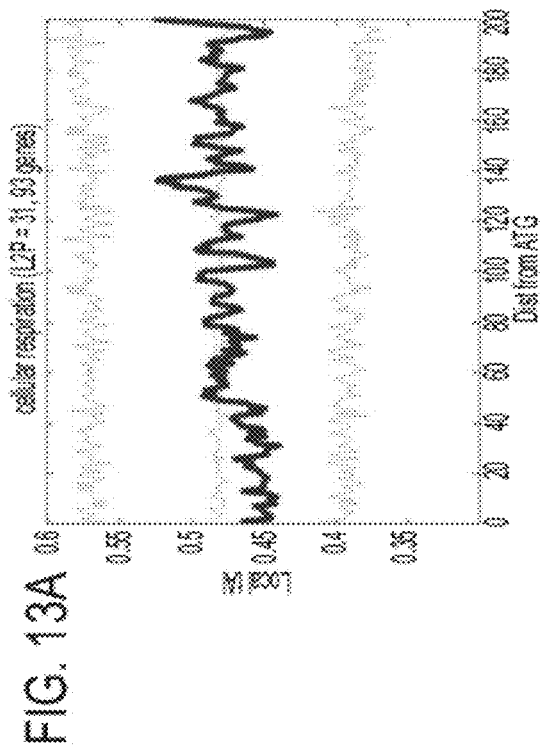
Figure 13D:
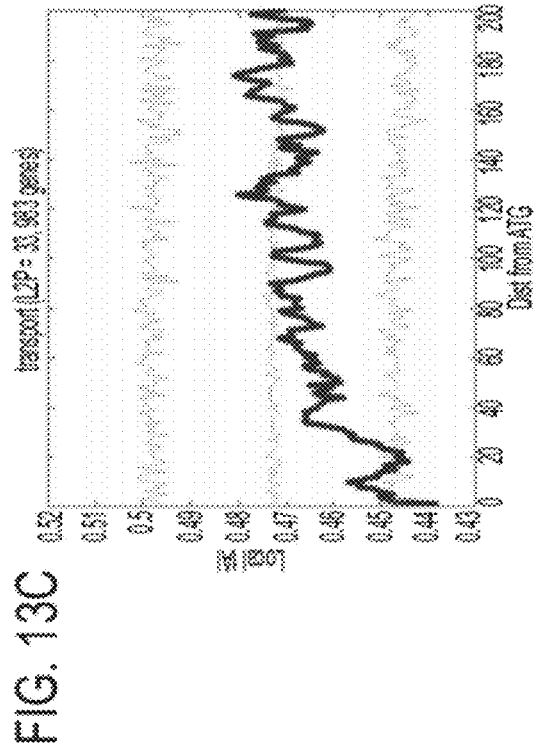
Figure 13E:
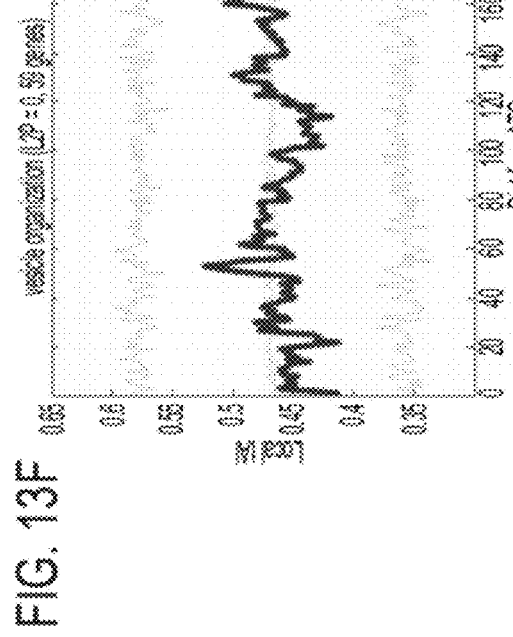
Figure 13F:
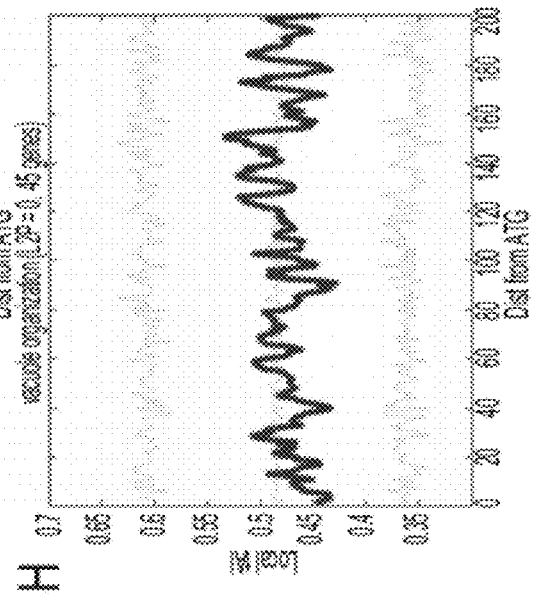
Figure 13G:
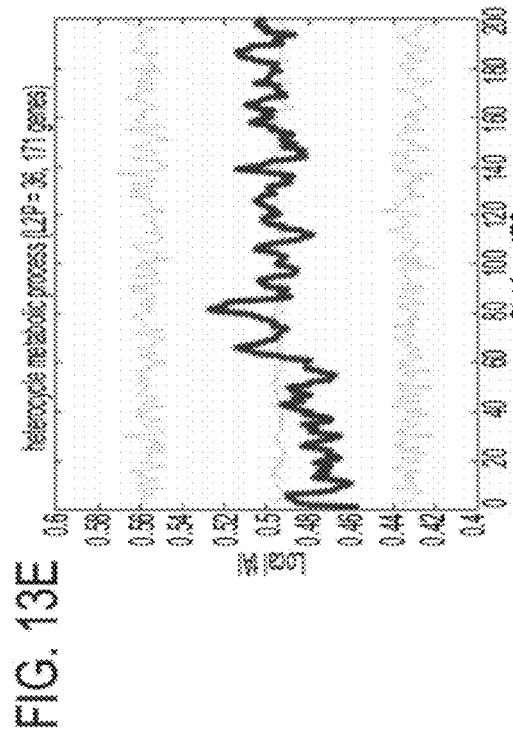
Figure 13H:
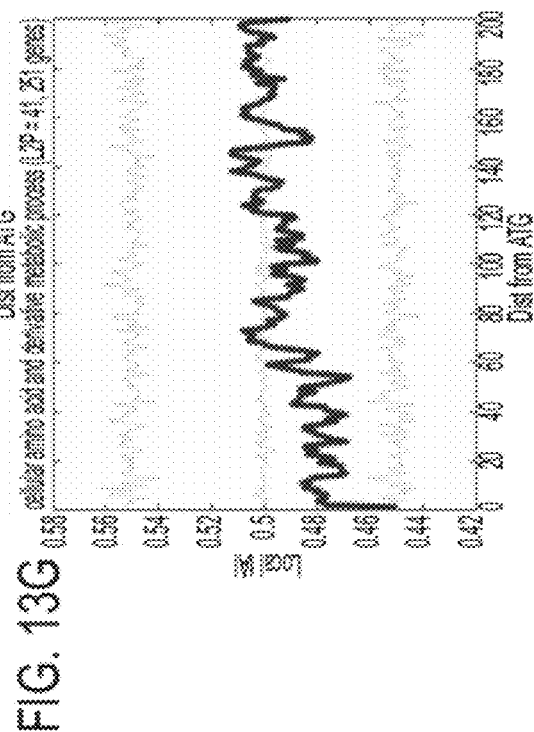
Figure 13I:
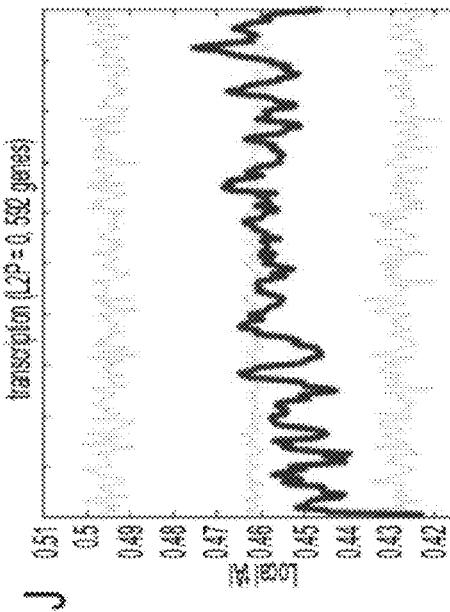
Figure 13J:
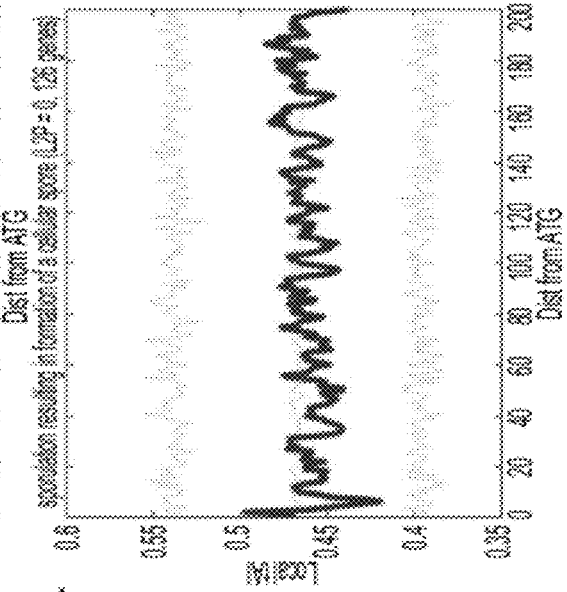
Figure 13K:
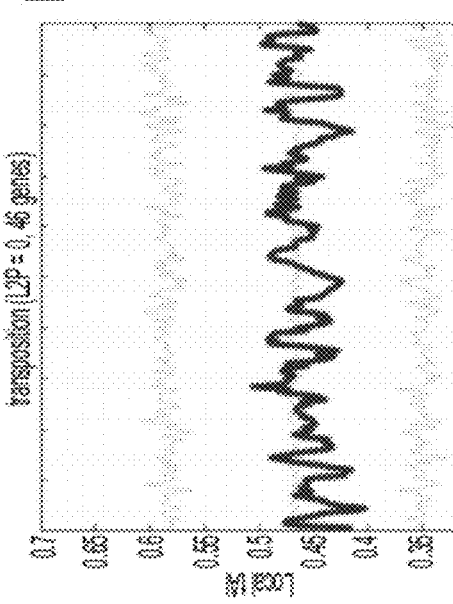
Figure 13L:
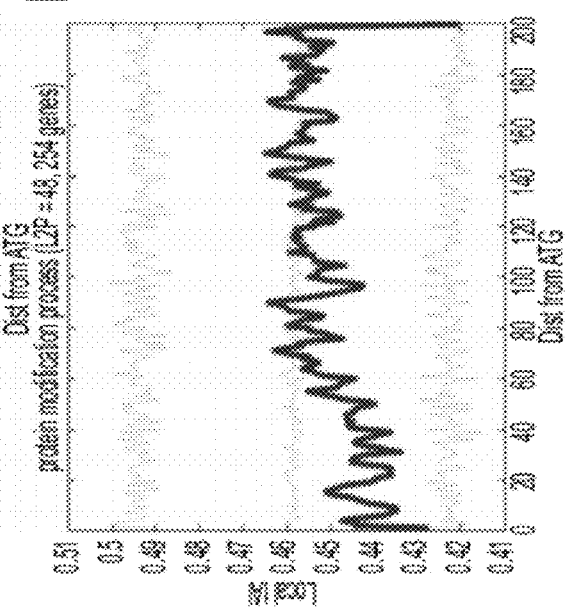
Figure 13M:
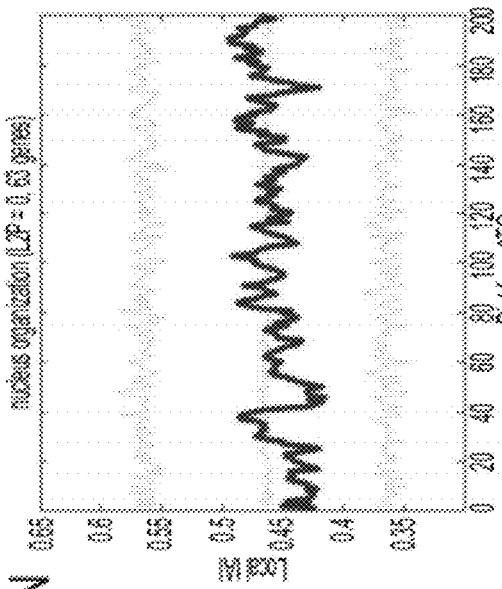
Figure 13N:
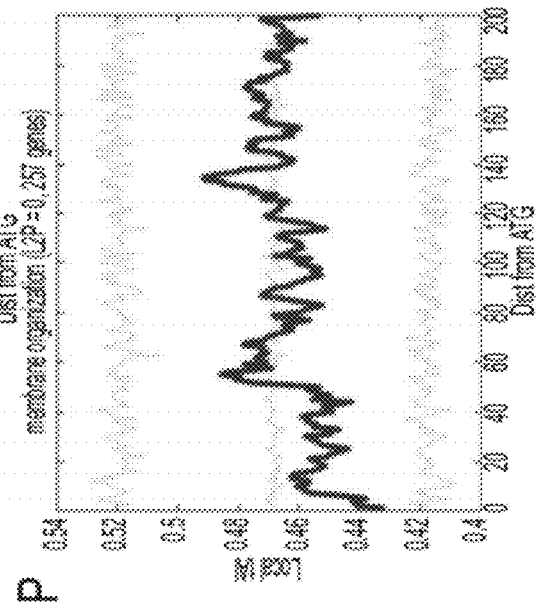
Figure 13O:
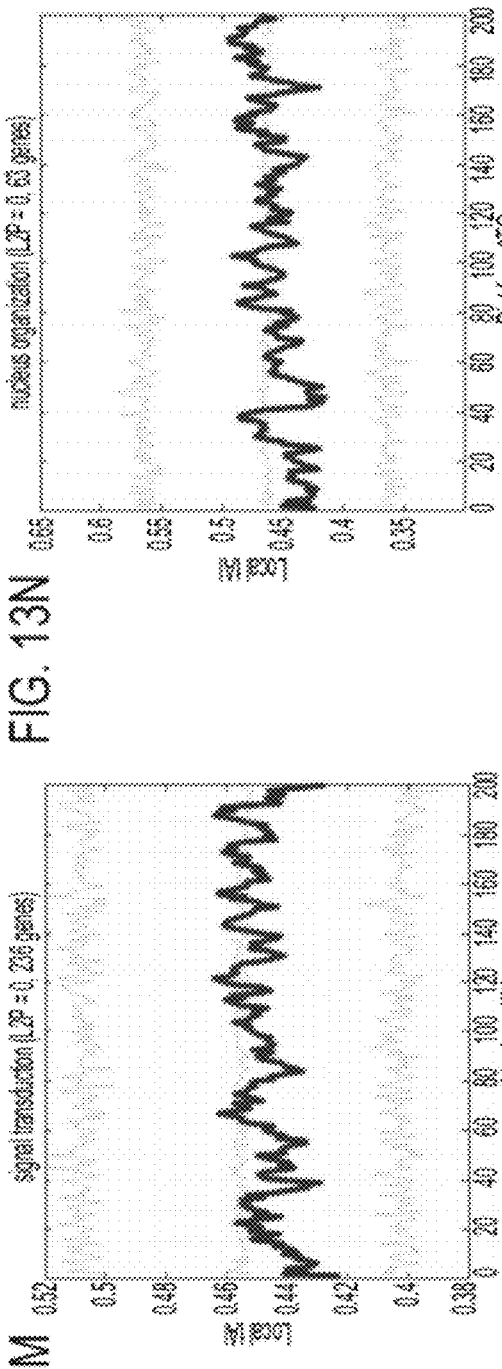
Figure 13P:
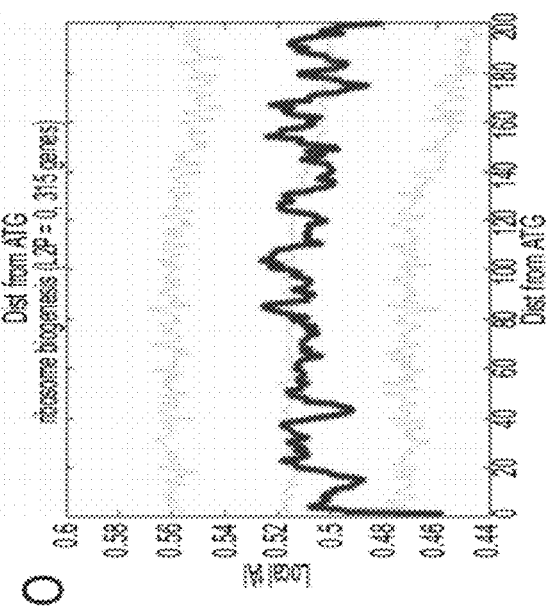
Figure 13Y:
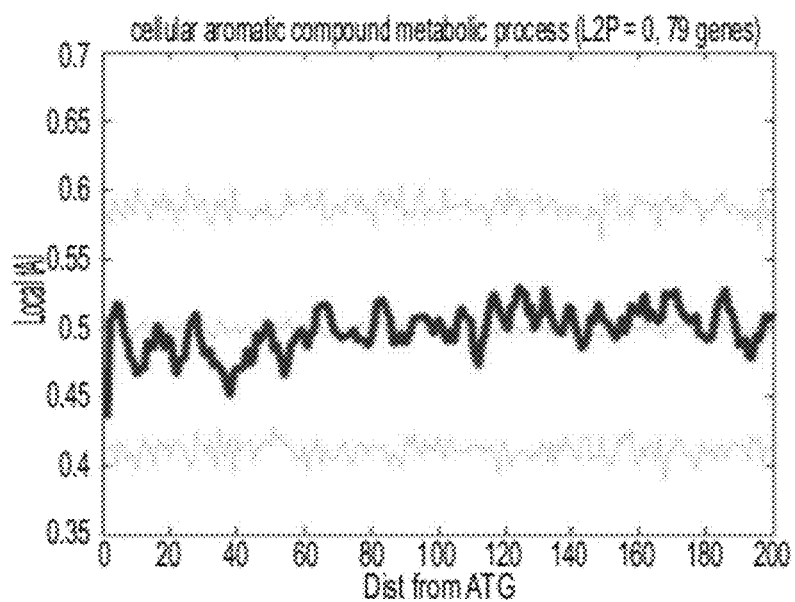
Figure 13Z:
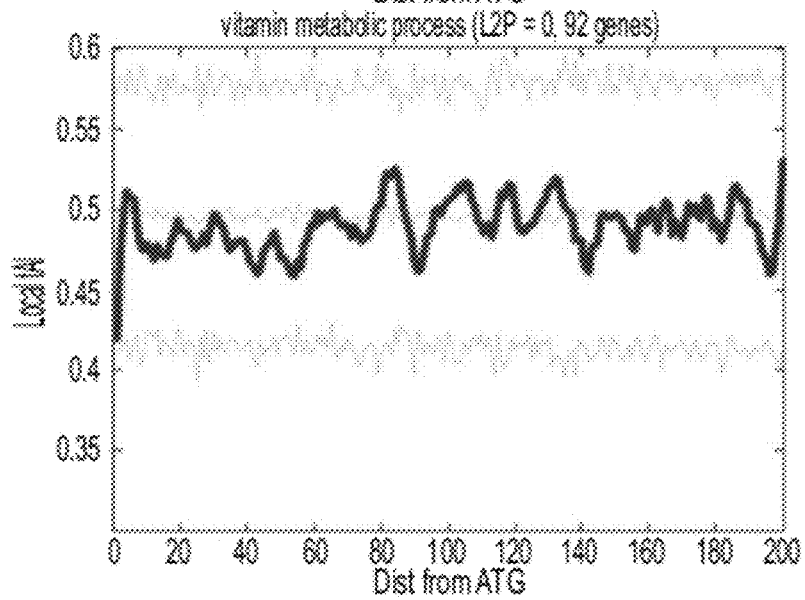

FIGS. 13A-Z are graphs illustrating the translation efficiency profiles of different GO categories. For each GO slim (42 categories) there is a figure which describes the alignment to the start codon. Each figure contains the smoothed averaged tAI profile (blue), the randomized profile +−3 standard deviations (black).

Figure 14A:
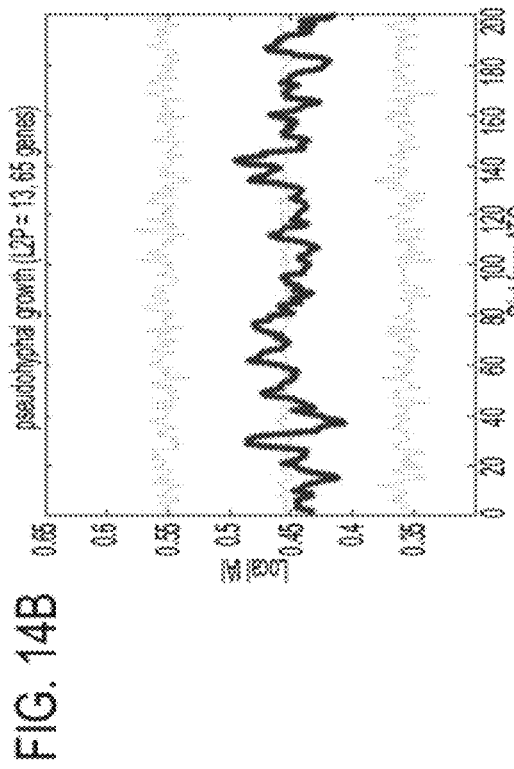
Figure 14B:
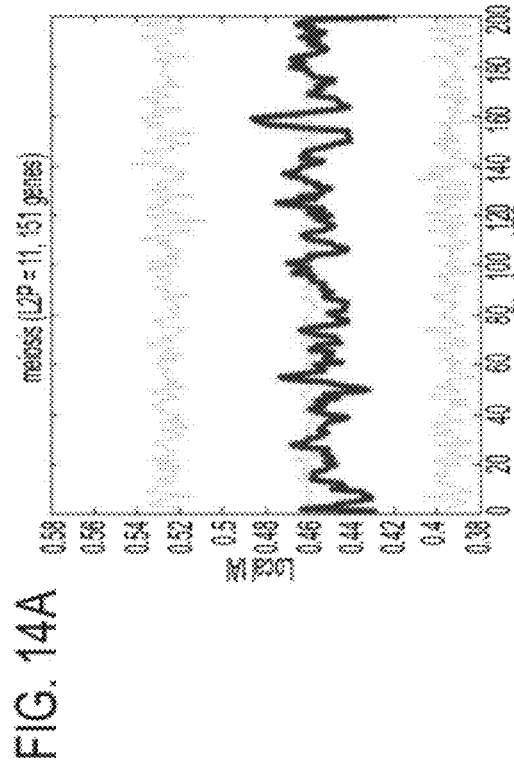
Figure 14C:
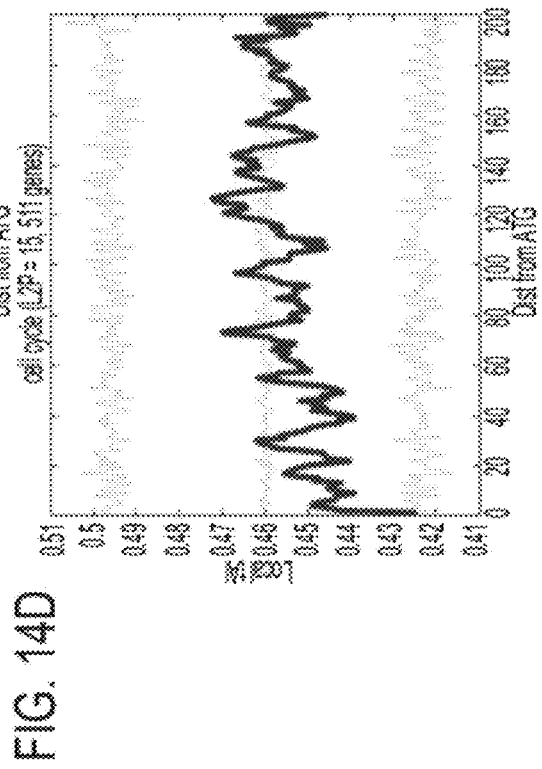
Figure 14D:
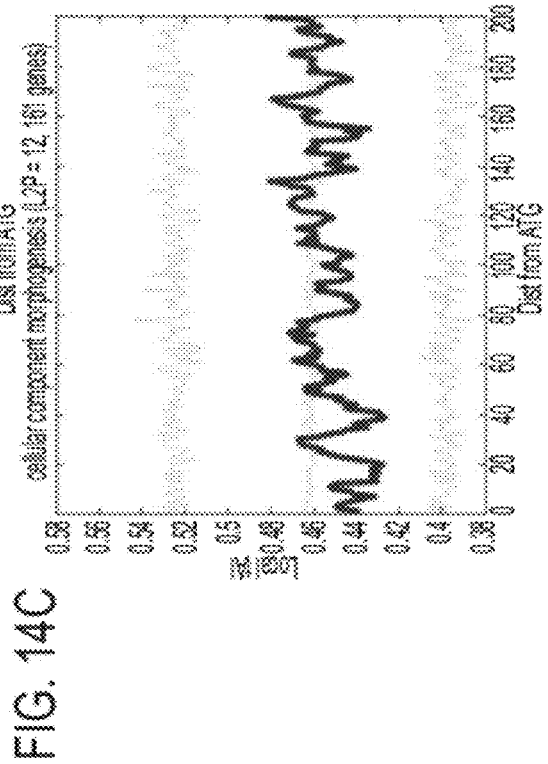
Figure 14E:
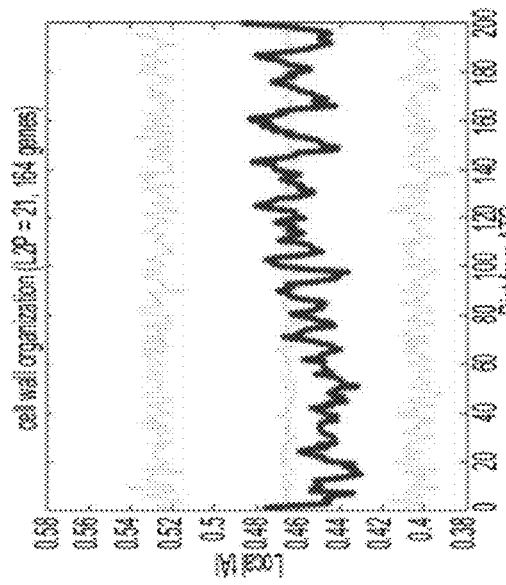
Figure 14G:
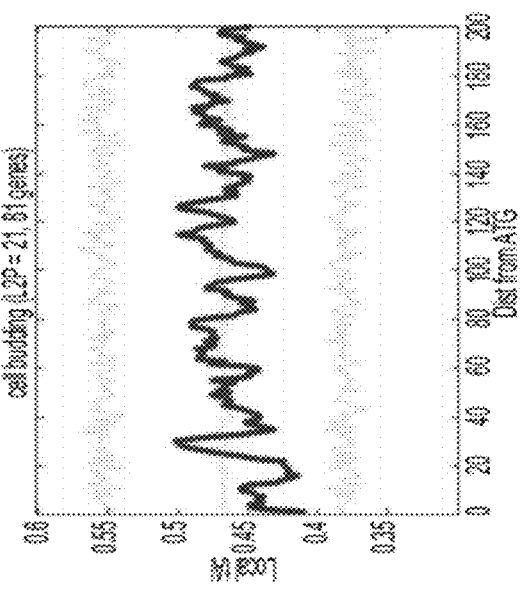
Figure 14F:
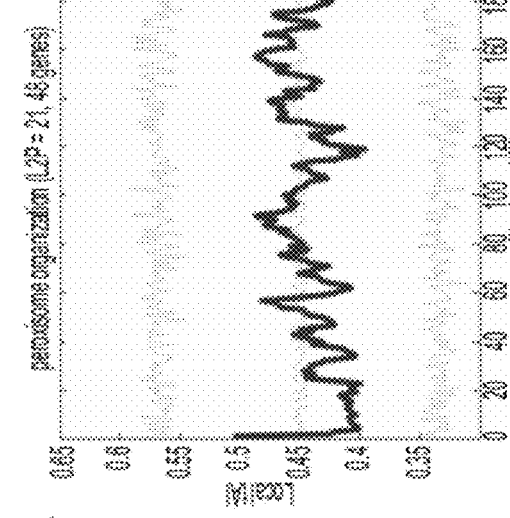
Figure 14H:
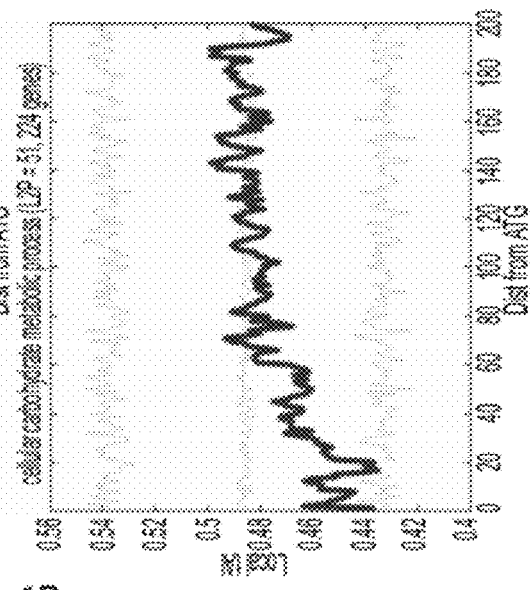
Figures 14M, 14N, 14O, 14P:
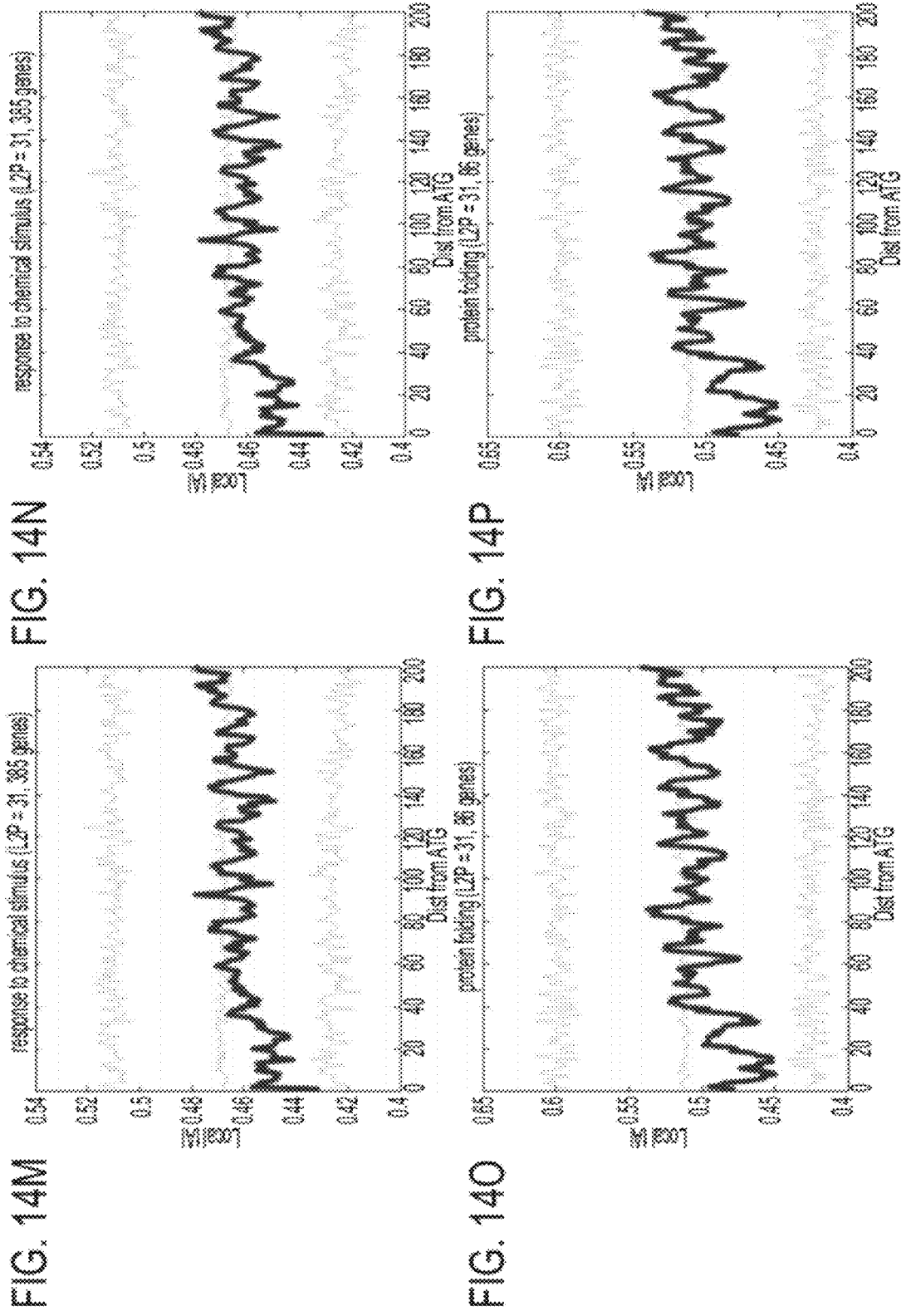

FIGS. 14A-P are graphs illustrating the translation efficiency profiles of different GO categories. For each GO slim (42 categories) there is a figure which describes the alignment to the start codon. Each figure contains the smoothed averaged tAI profile (blue), the randomized profile +−3 standard deviations (black).

Figure 15:
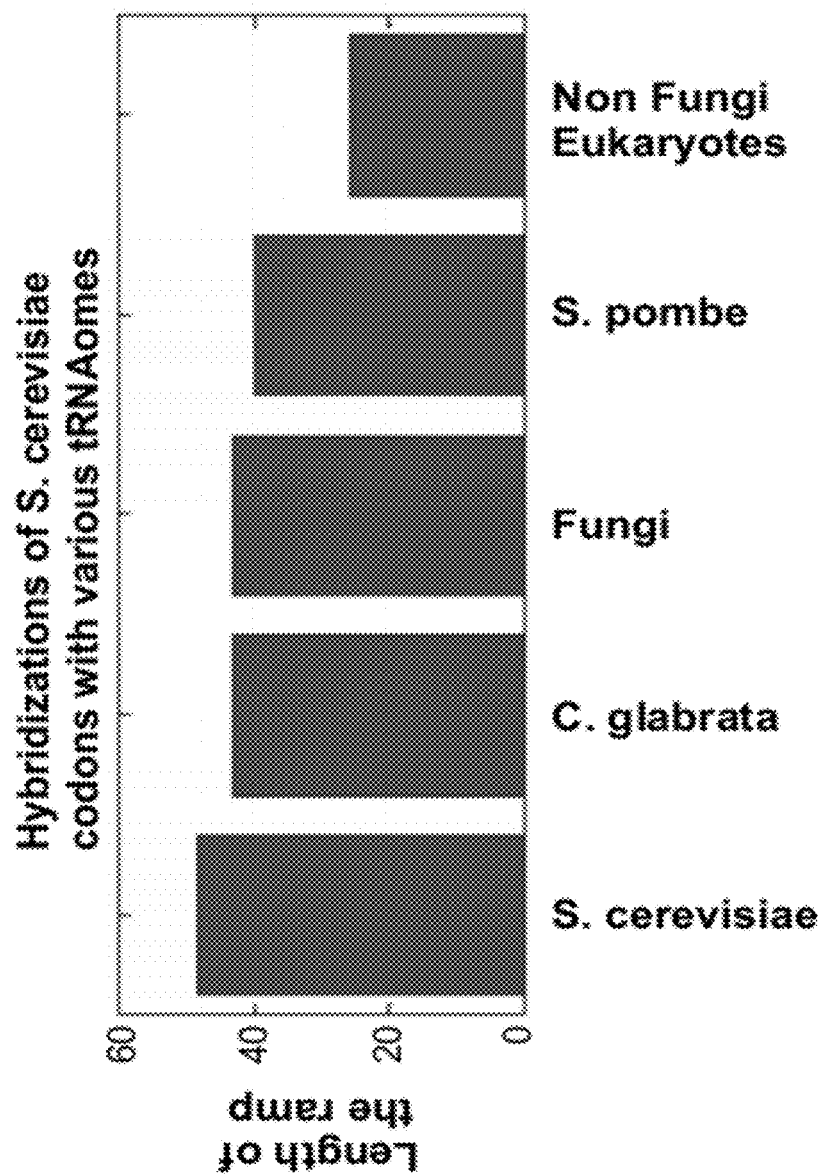

FIG. 15 is a bar graph illustrating that the length of the ramp decreases when translating *S. cerevisiae* ORFs with tRNAomes of organisms with increasing evolutionary distance.

Figure 16J:
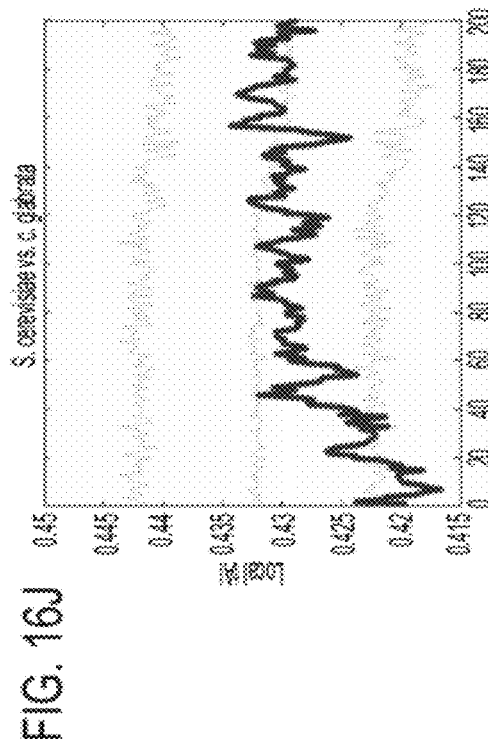
Figure 16L:
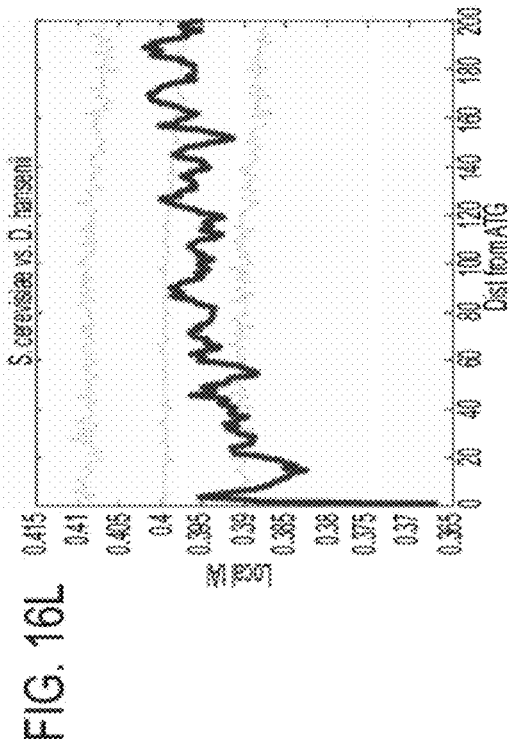
Figure 16I:
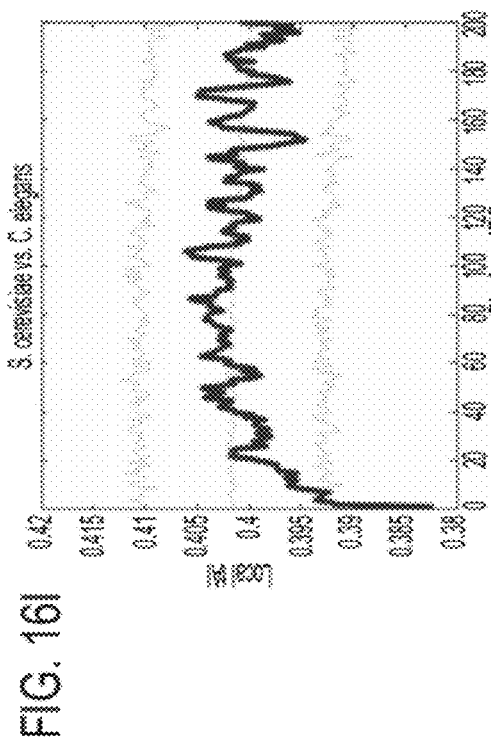
Figure 16K:
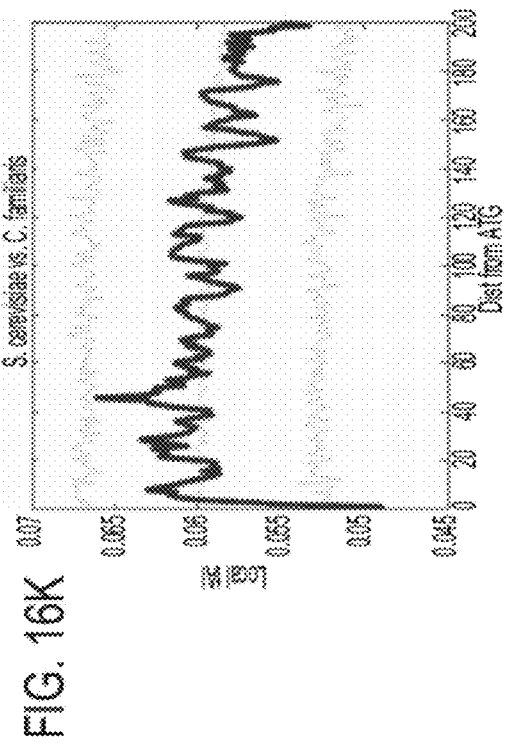
Figure 16M:
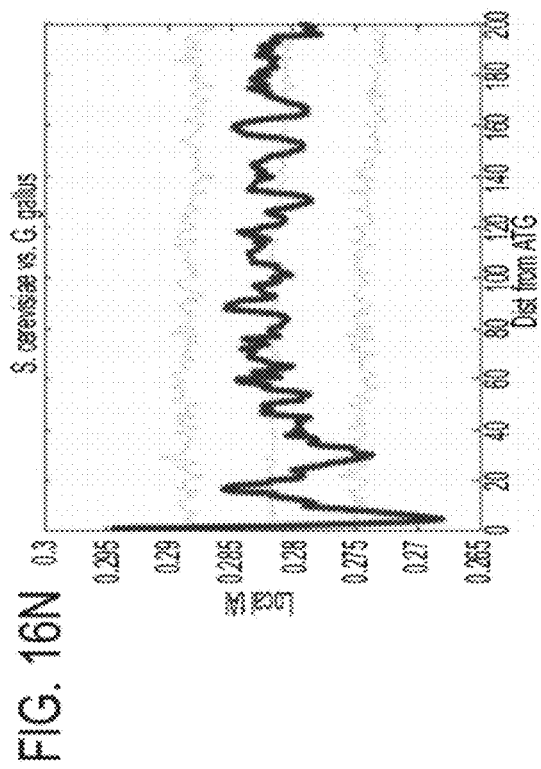
Figure 16O:
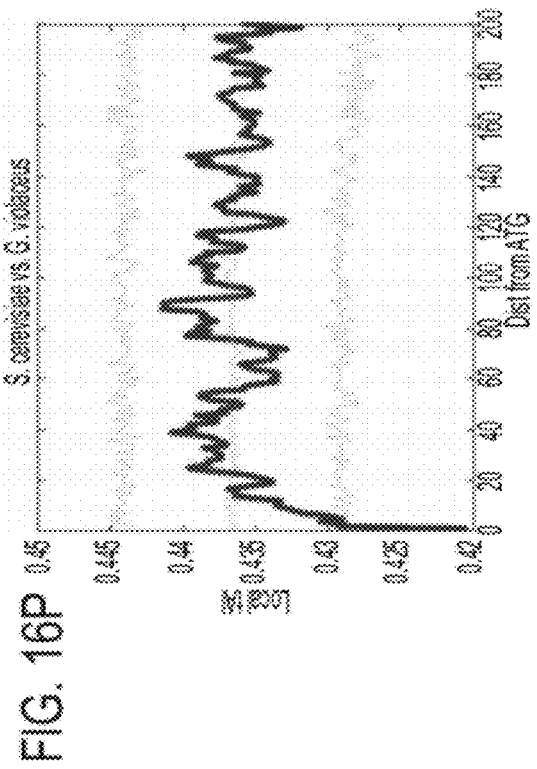
Figure 16N:
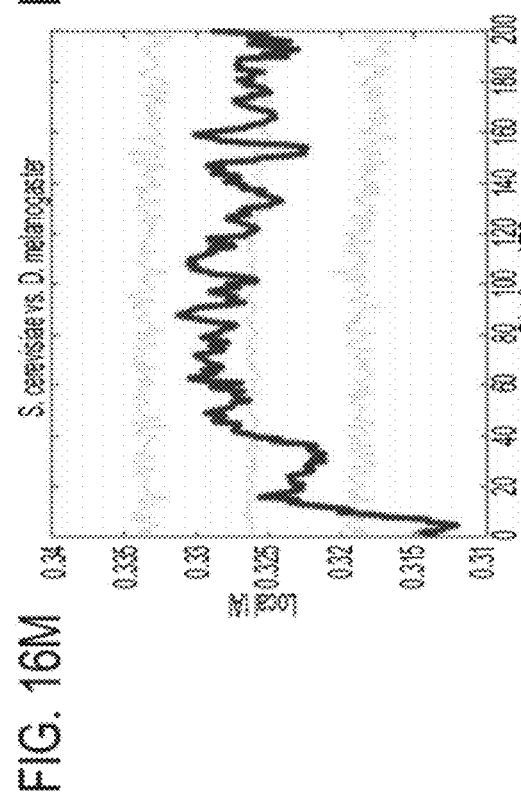
Figure 16P:
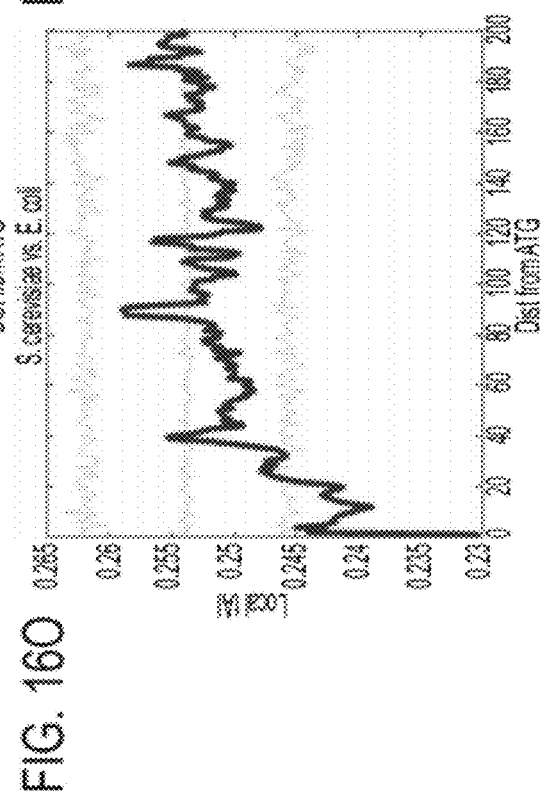
Figure 16Q:
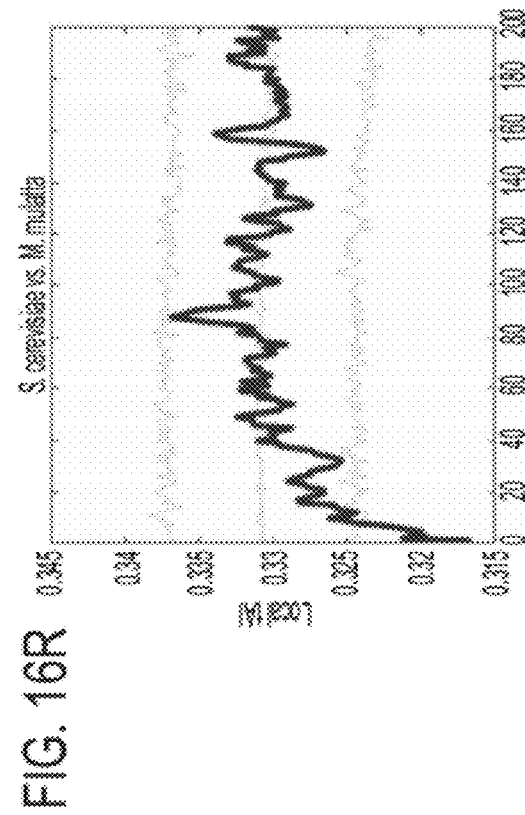
Figure 16R:
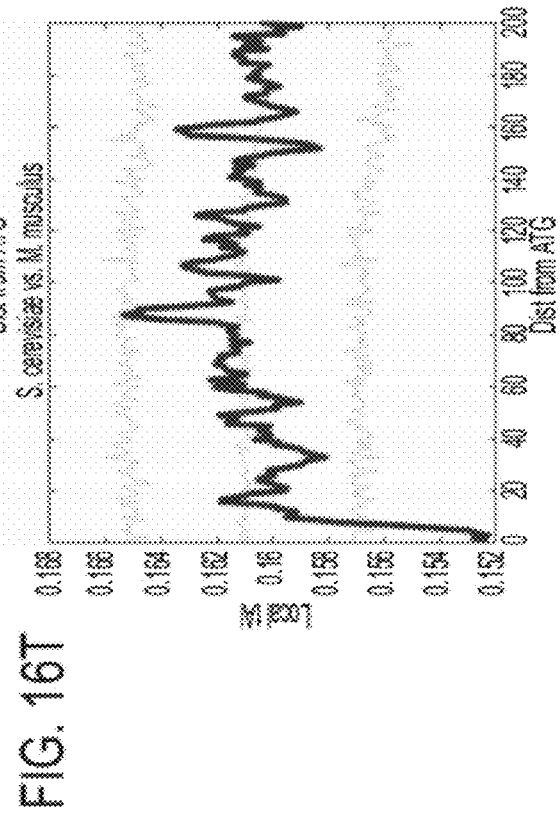
Figure 16S:
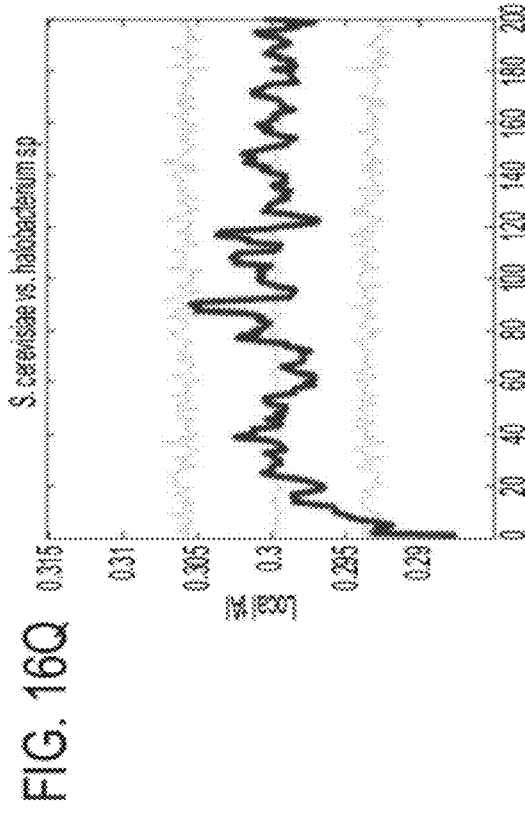
Figure 16T:
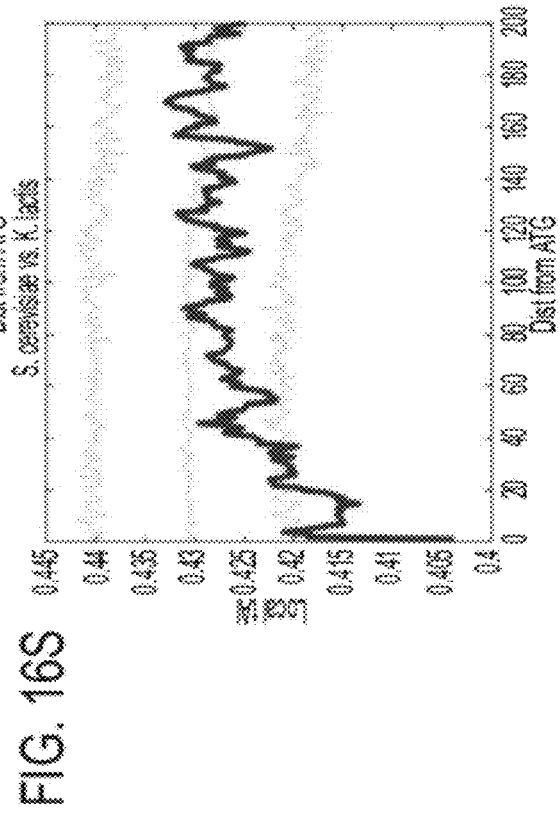

FIGS. 16A-X are graphs illustrating the translation efficiency of *S. cerevisiae* using the tRNA pool of other organisms.

Figure 17A:
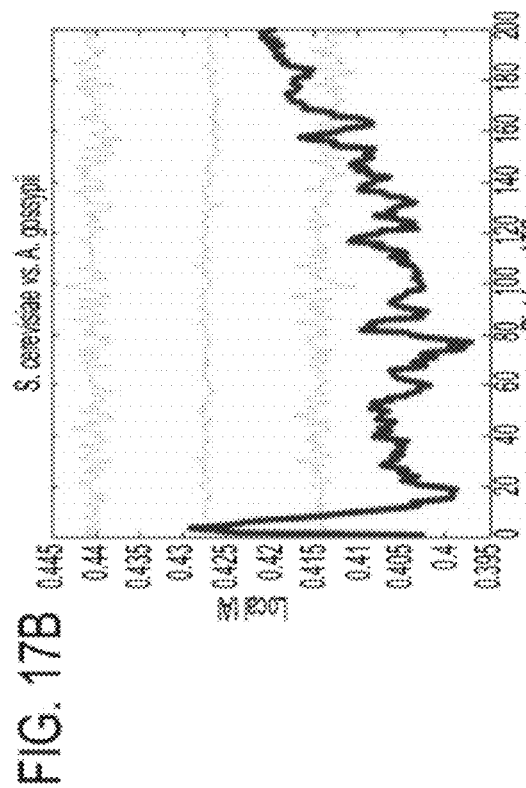
Figure 17B:
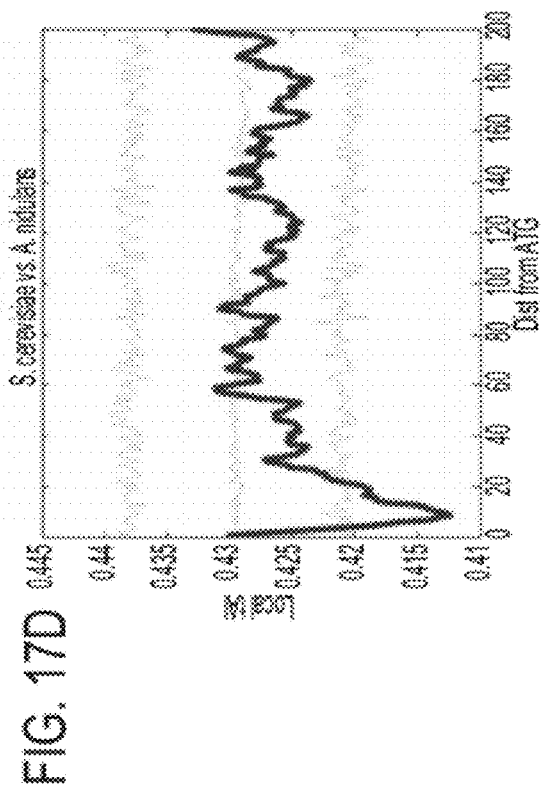
Figure 17C:
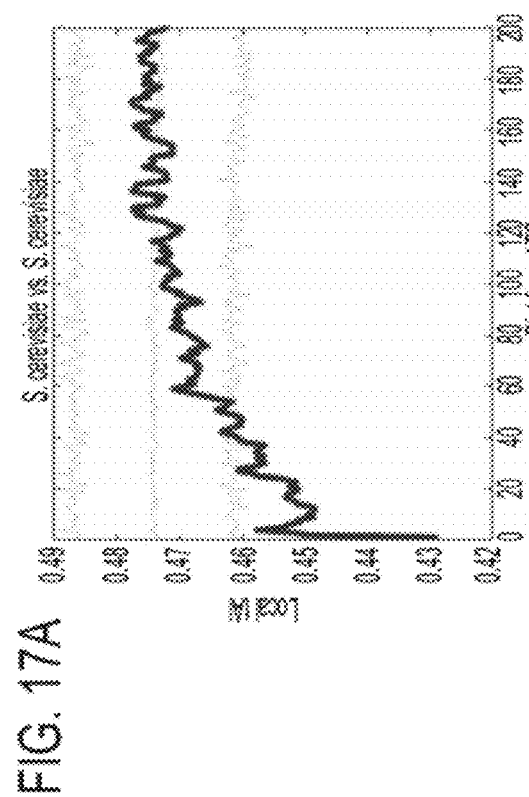
Figure 17D:
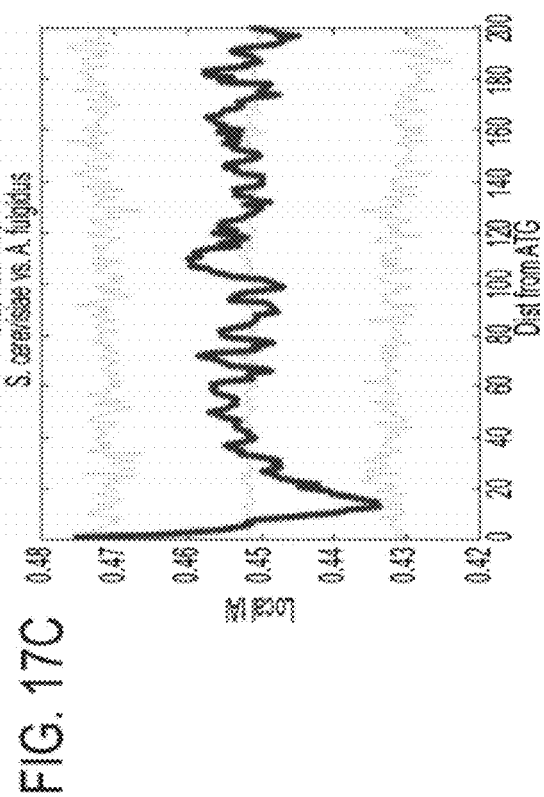
Figure 17E:
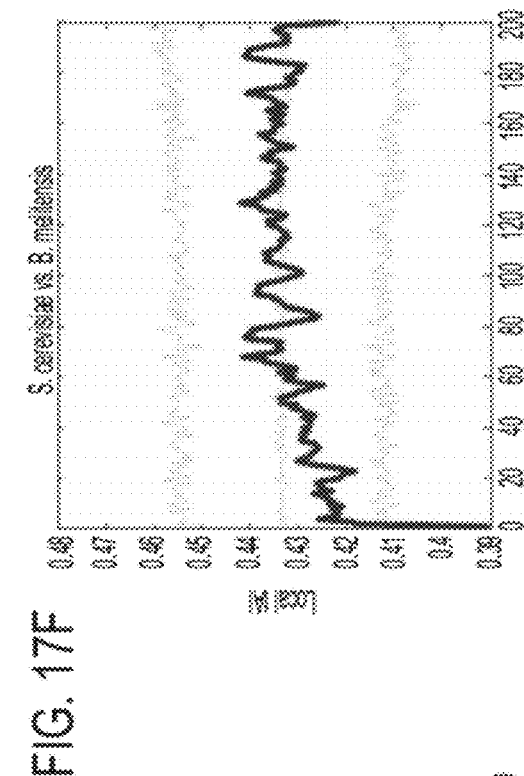
Figure 17F:
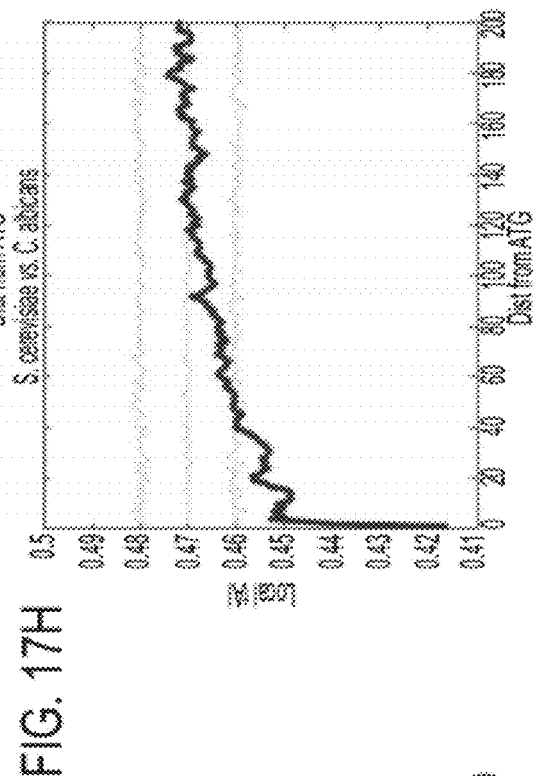
Figure 17G:
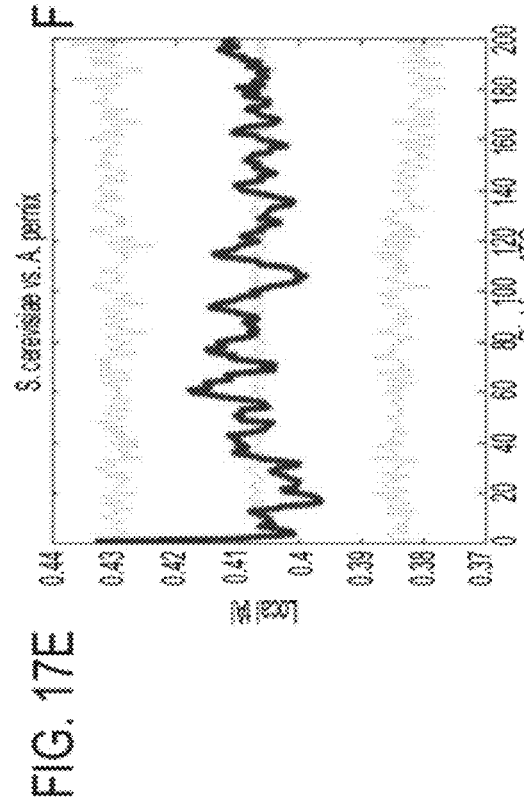
Figure 17H:
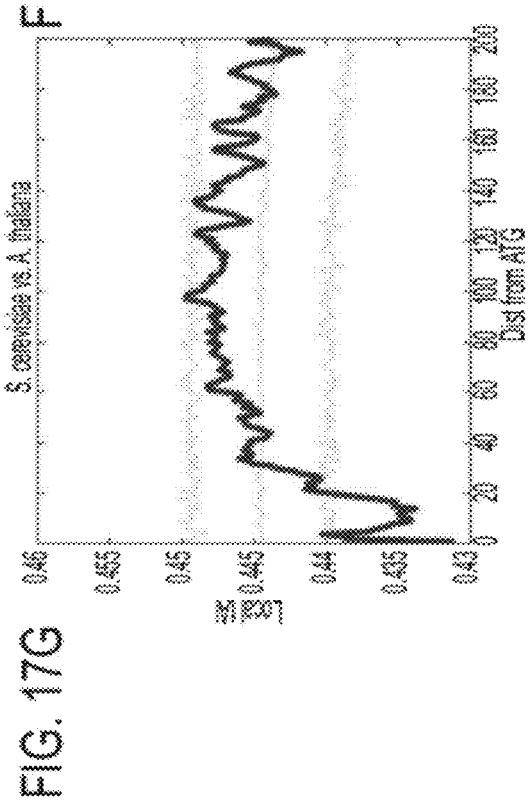
Figures 17I, 17J:
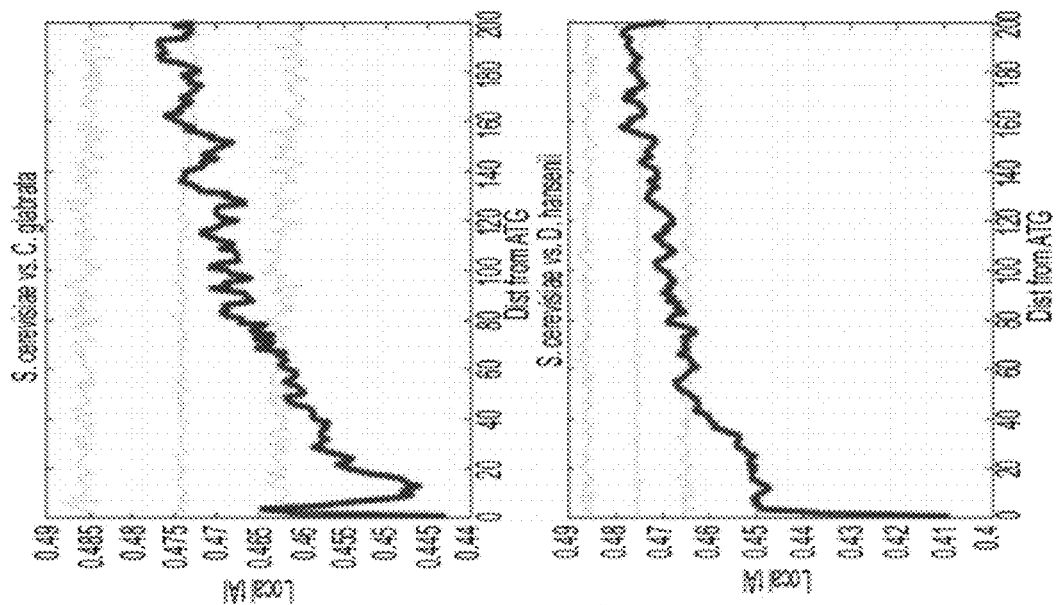
Figures 17K, 17L:
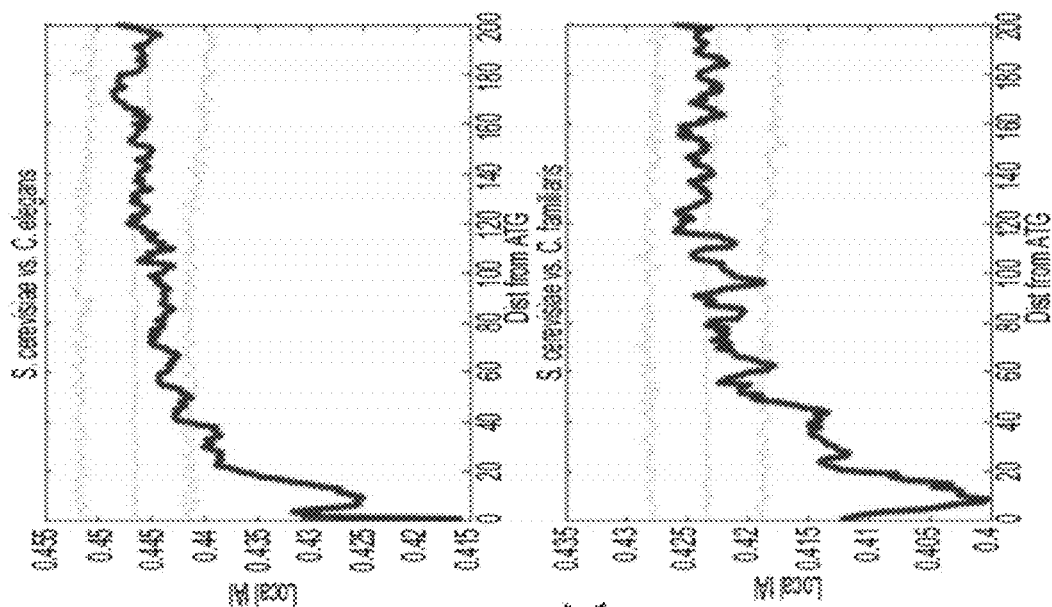
Figure 17R:
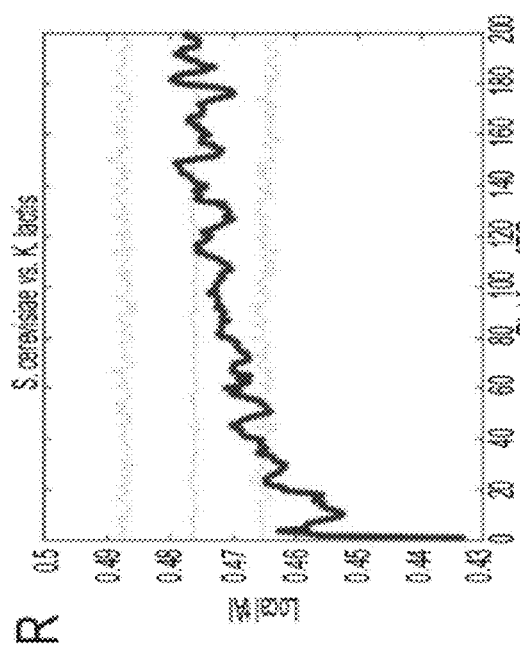
Figure 17T:
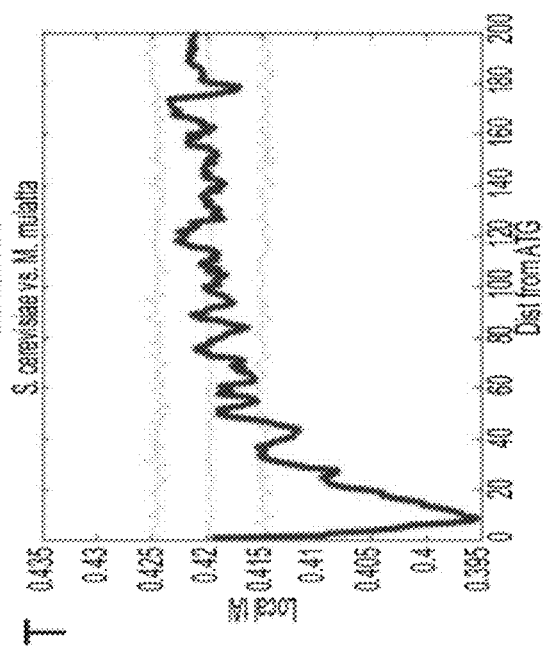
Figure 17Q:
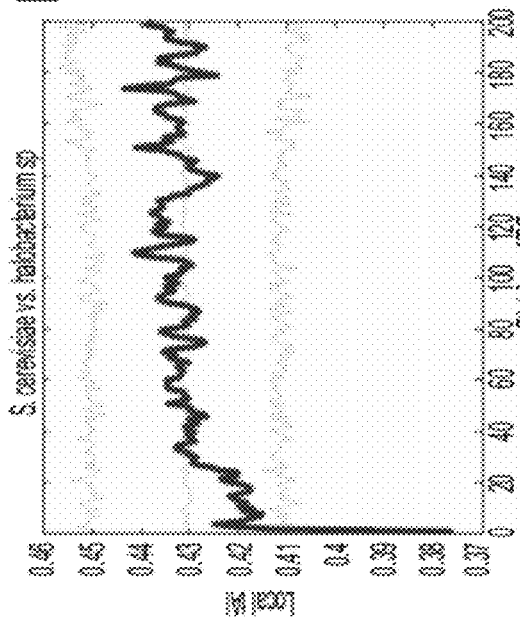
Figure 17S:
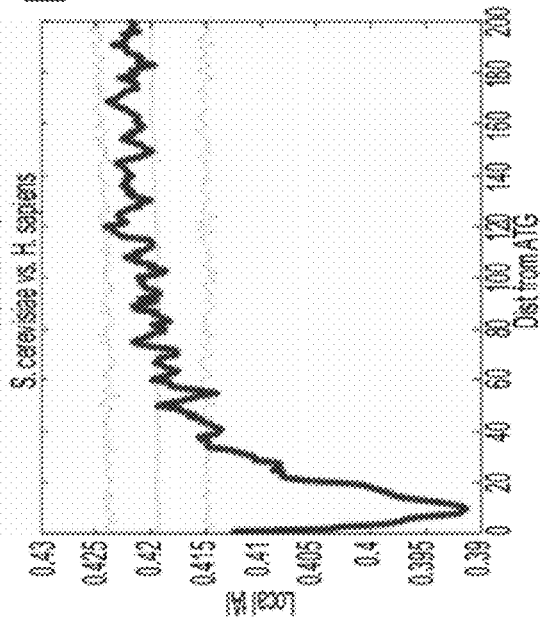
Figure 17U:
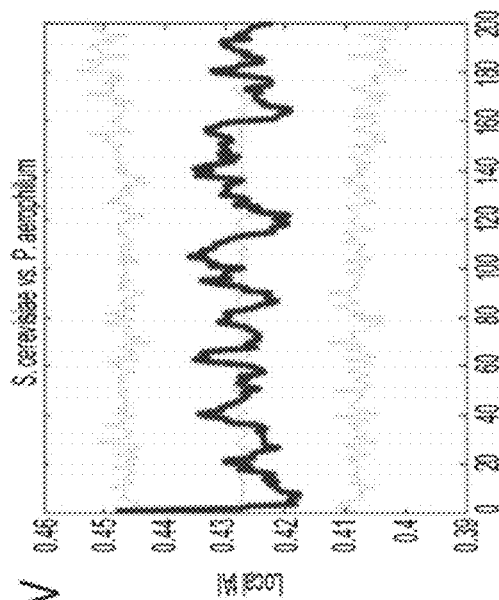
Figure 17V:
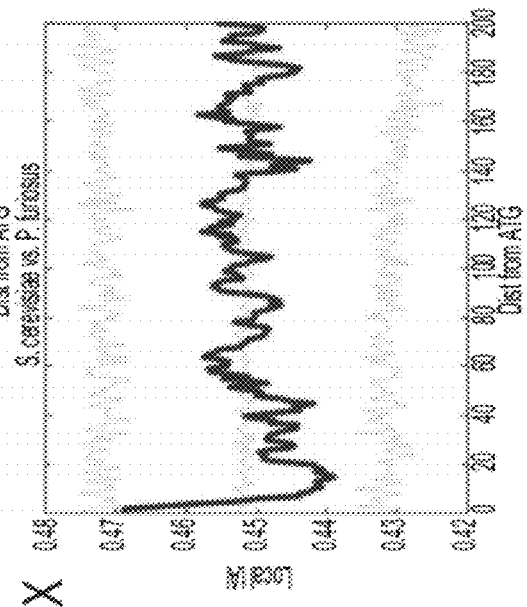
Figure 17W:
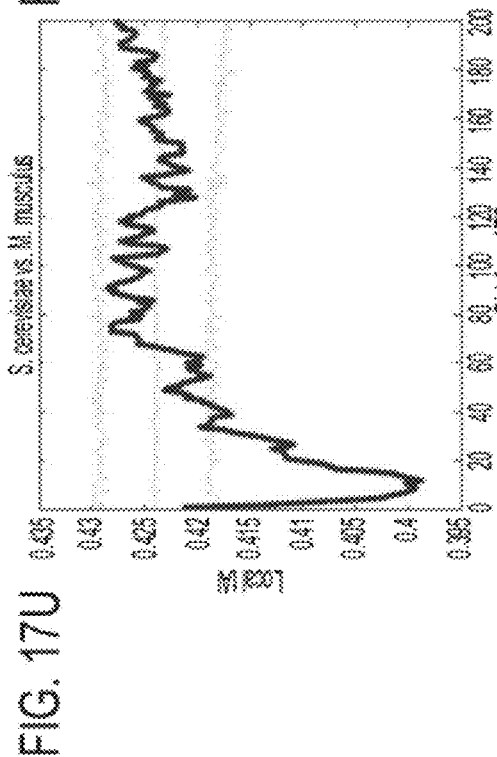
Figure 17X:
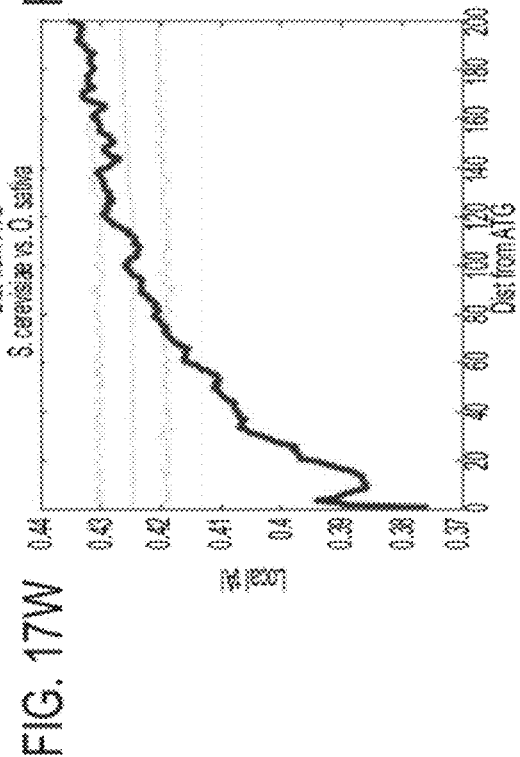

FIGS. 17A-Z are graphs illustrating the translation efficiency profile of various organisms when using the tRNA pool of *S. cerevisiae*.

Figure 18A:
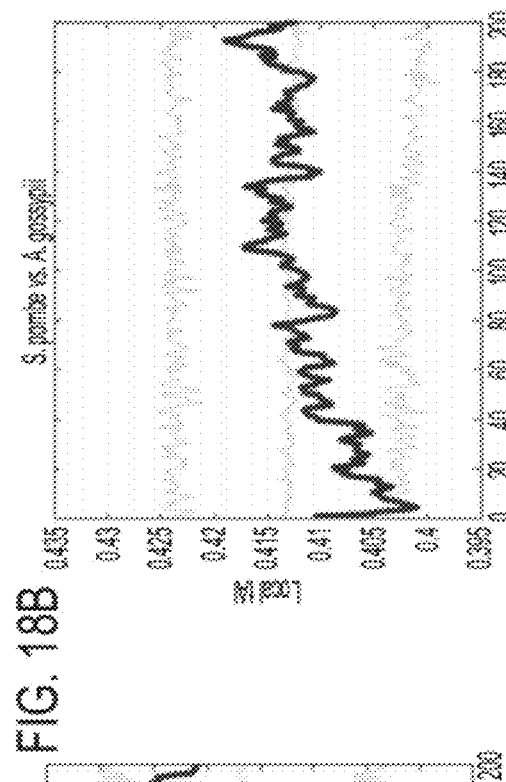
Figure 18B:
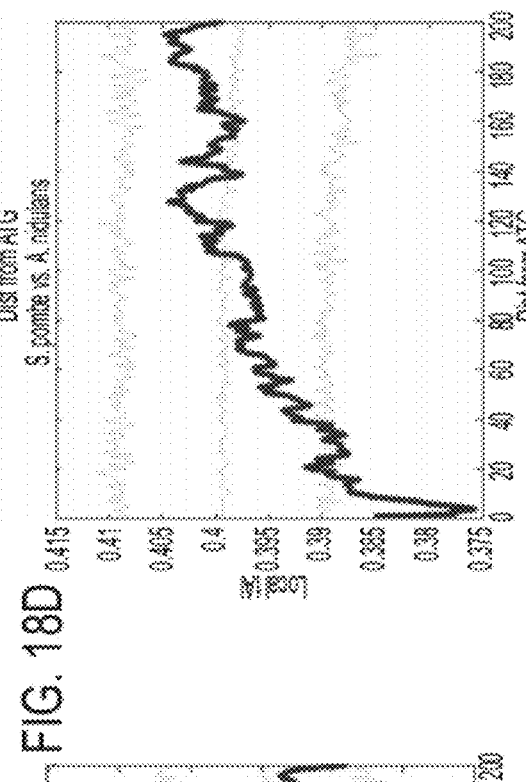
Figure 18C:
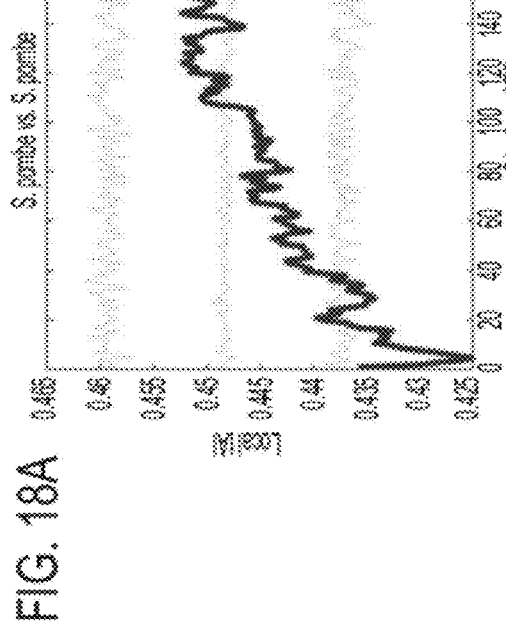
Figure 18D:
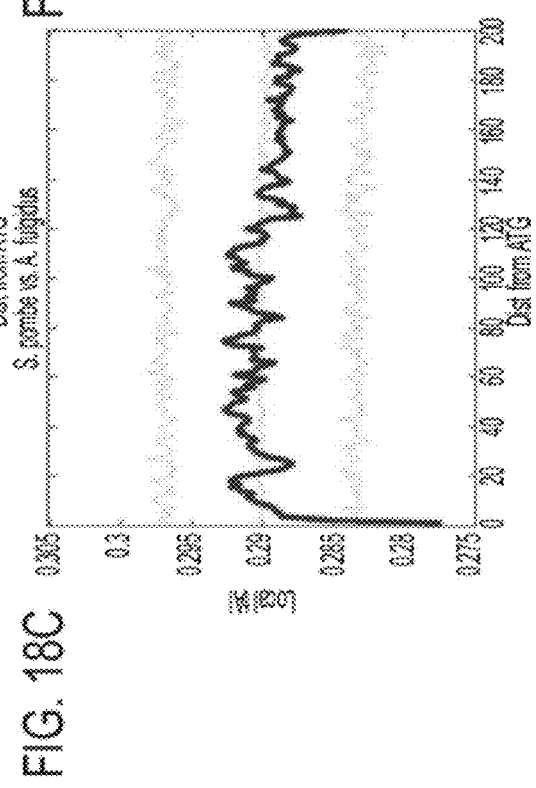
Figure 18F:
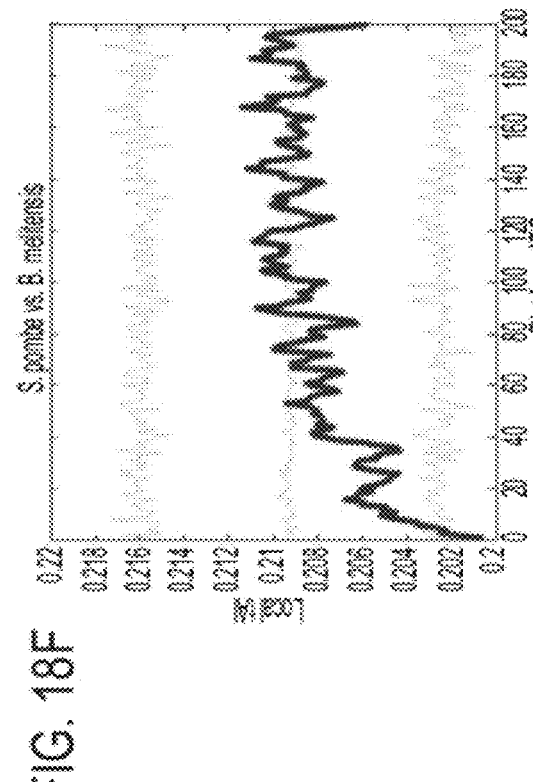
Figure 18H:
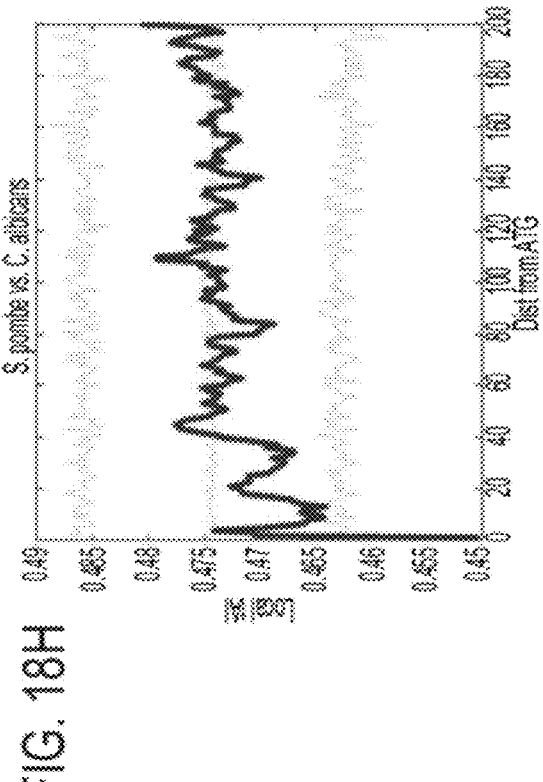
Figure 18E:
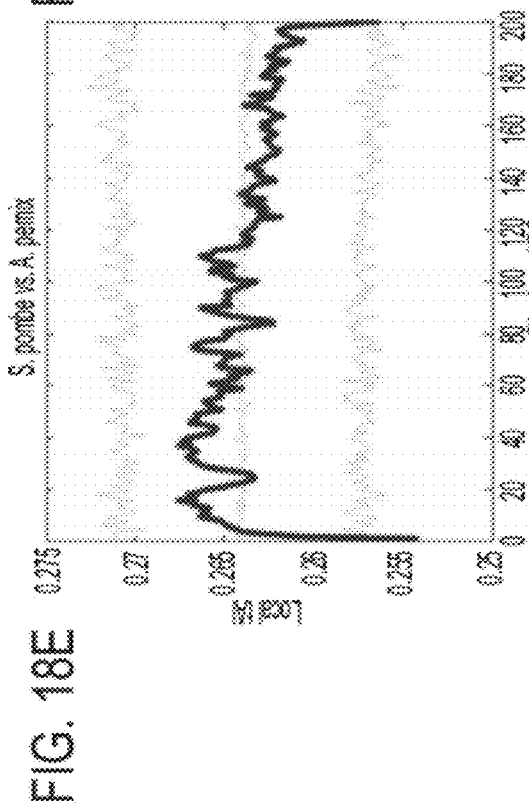
Figure 18G:
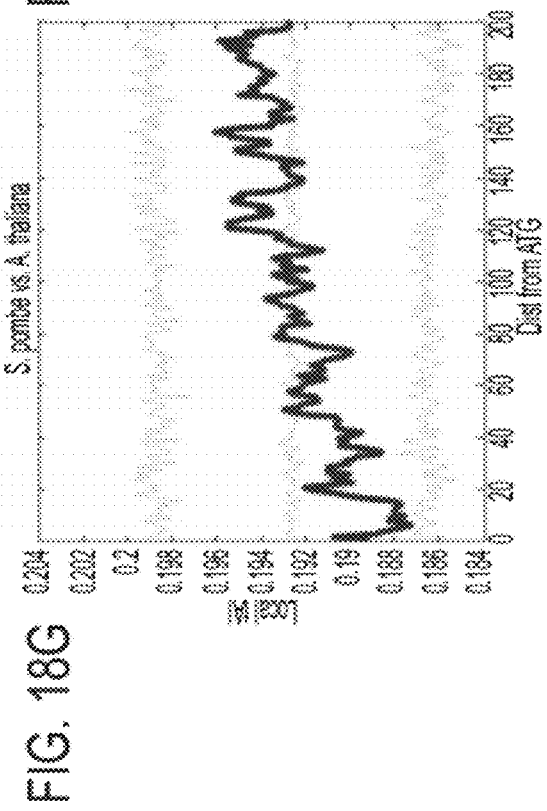
Figure 18M:
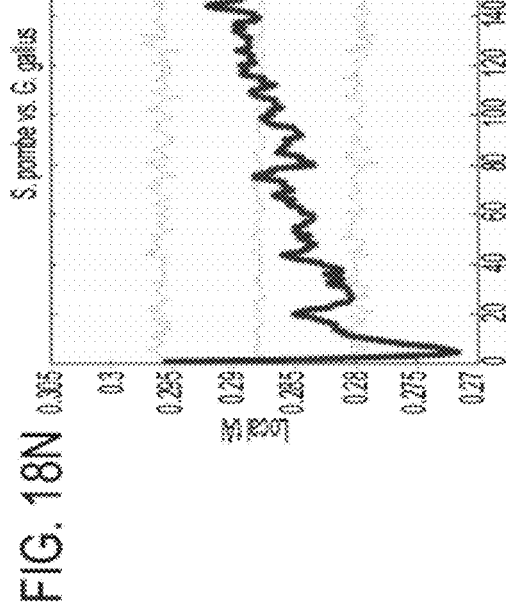
Figure 18N:
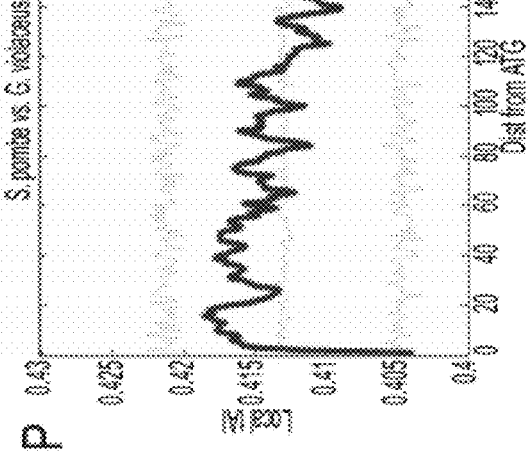
Figure 18O:
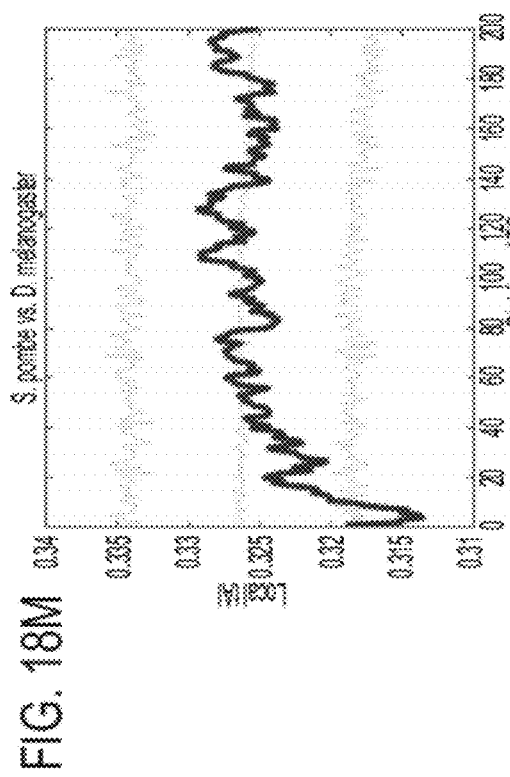
Figure 18P:
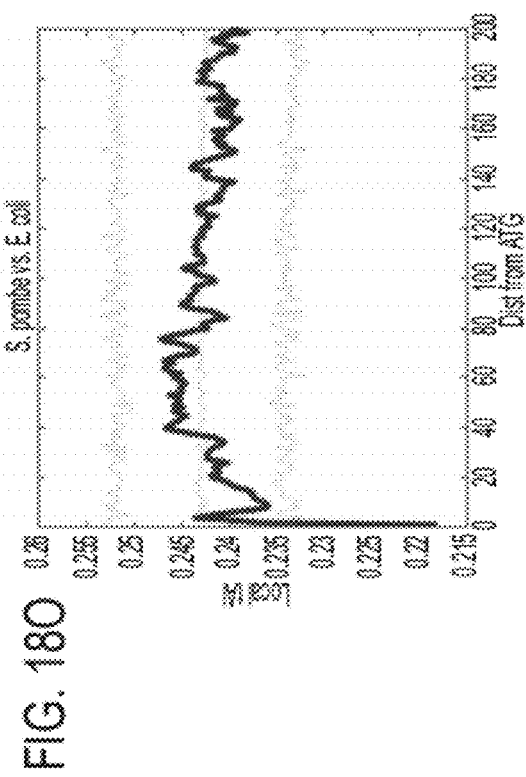
Figure 18Q:
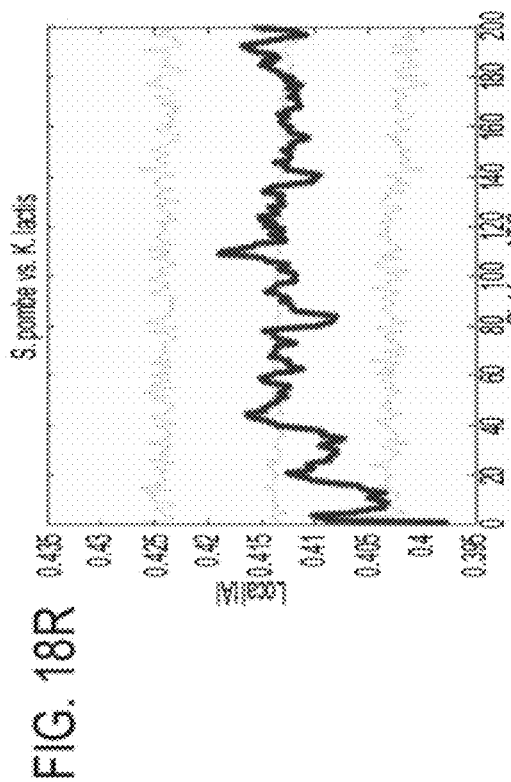
Figure 18S:
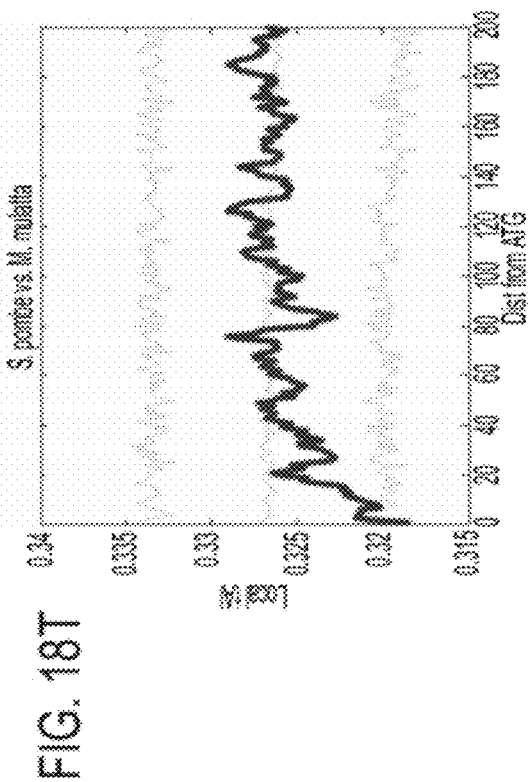
Figure 18R:
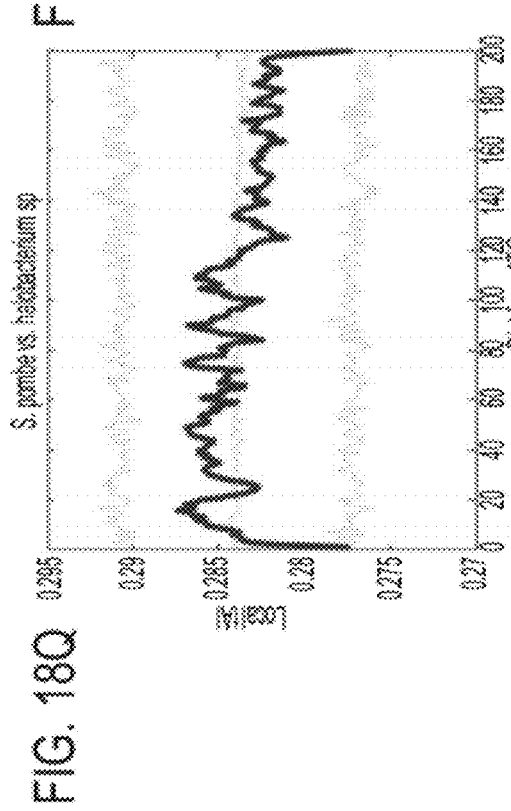
Figure 18T:
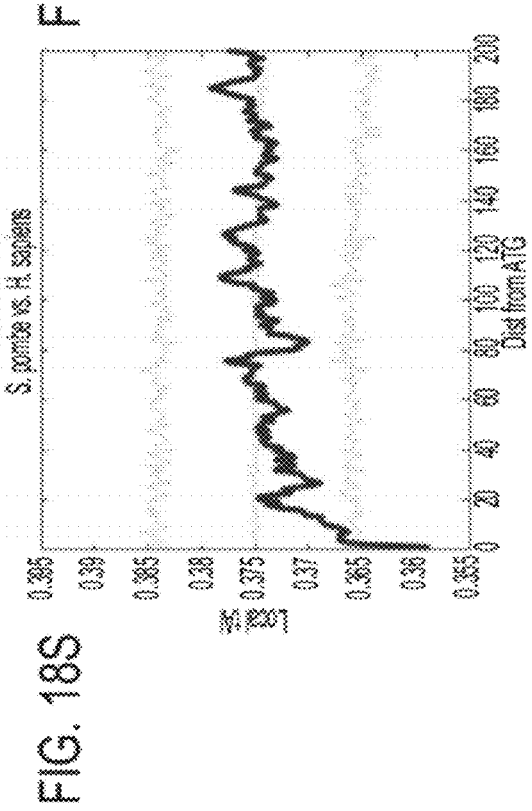
Figure 18U:
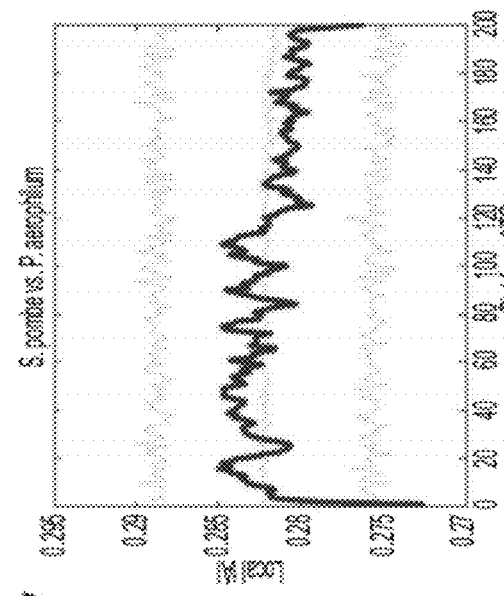
Figure 18V:
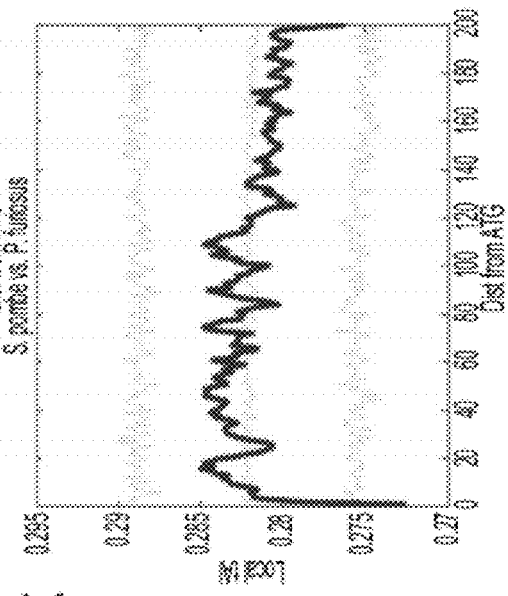
Figure 18W:
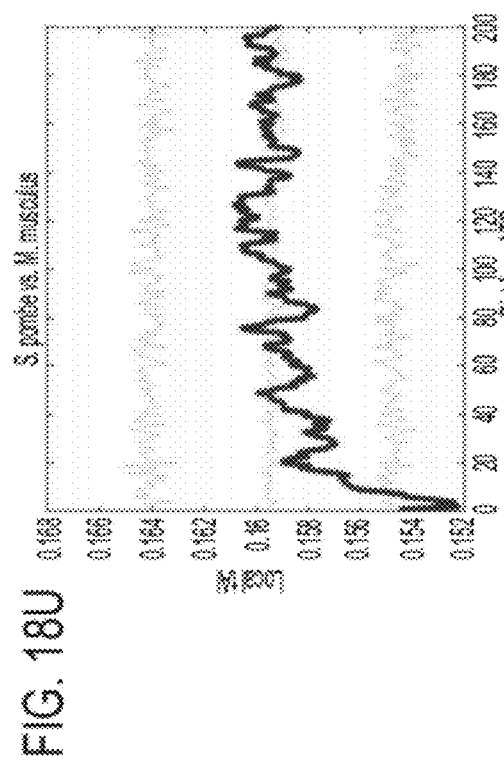
Figure 18X:
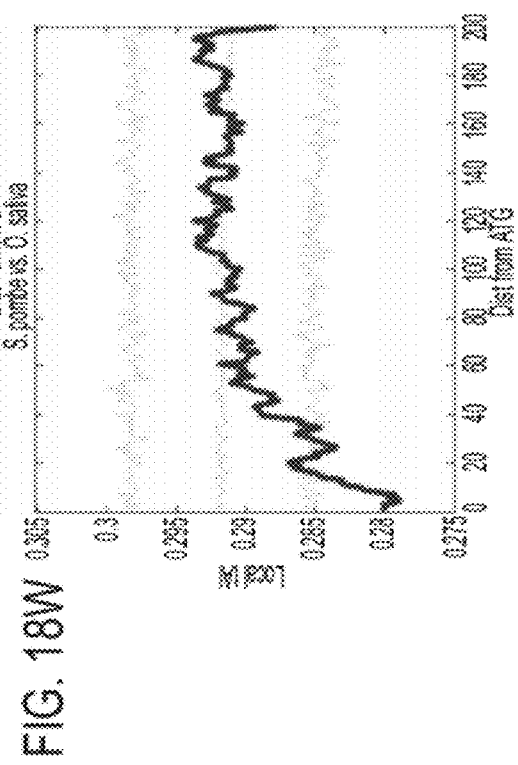
Figures 18Y, 18Z:
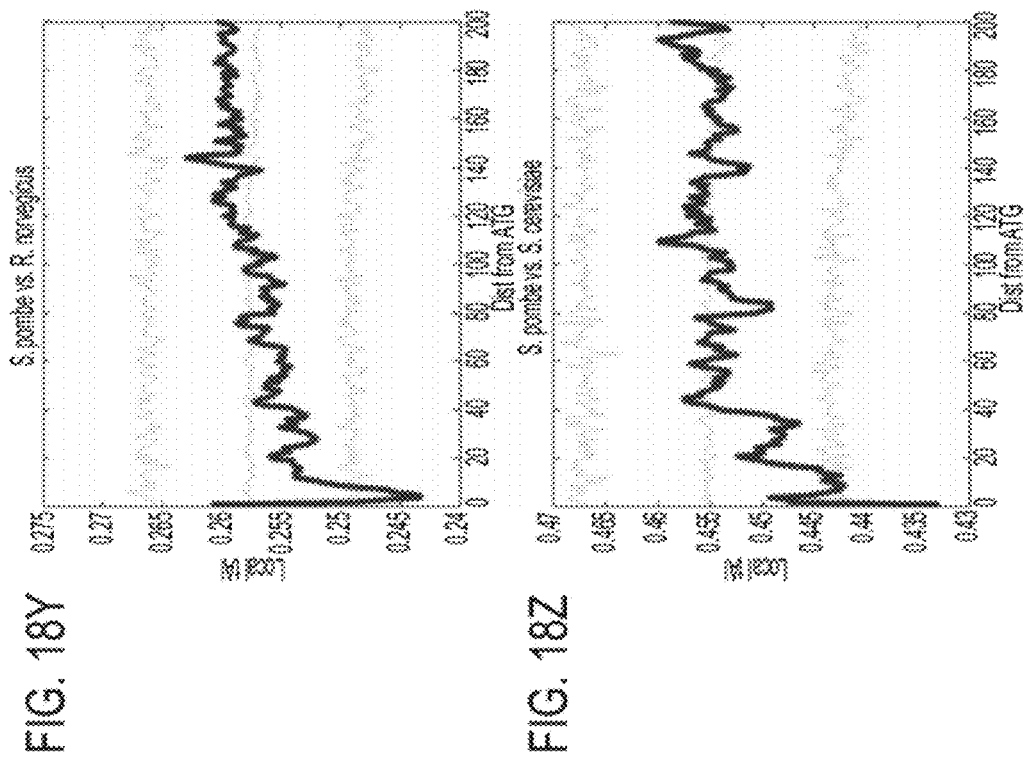

FIGS. 18A-Z are graphs illustrating the translation efficiency profile of *S. pombe* using the tRNA pool of other organisms.

Figure 19E:
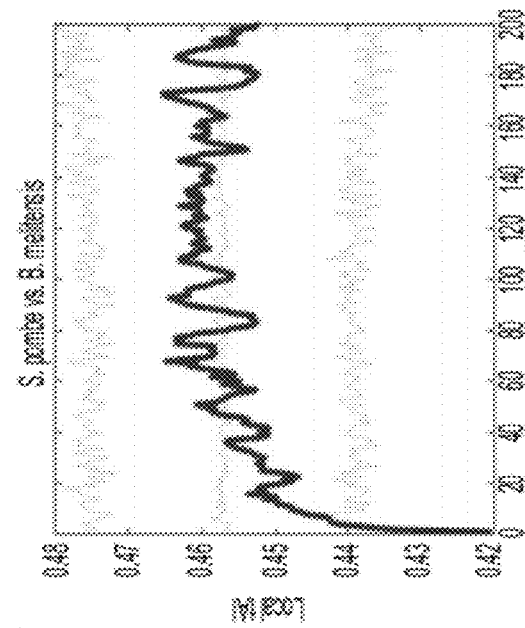
Figure 19F:
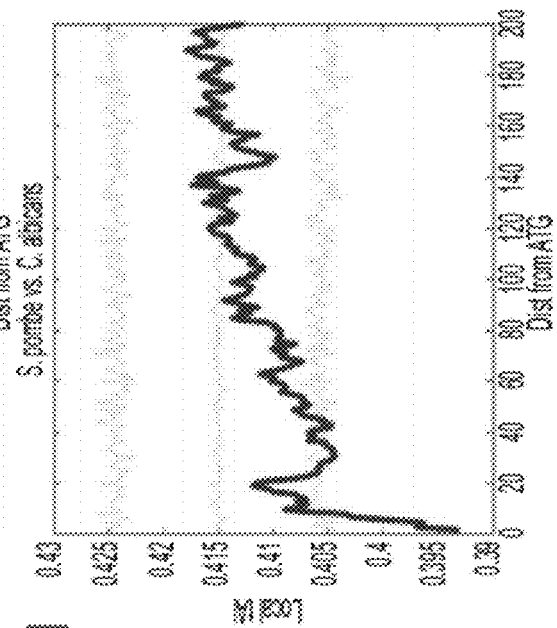
Figure 19G:
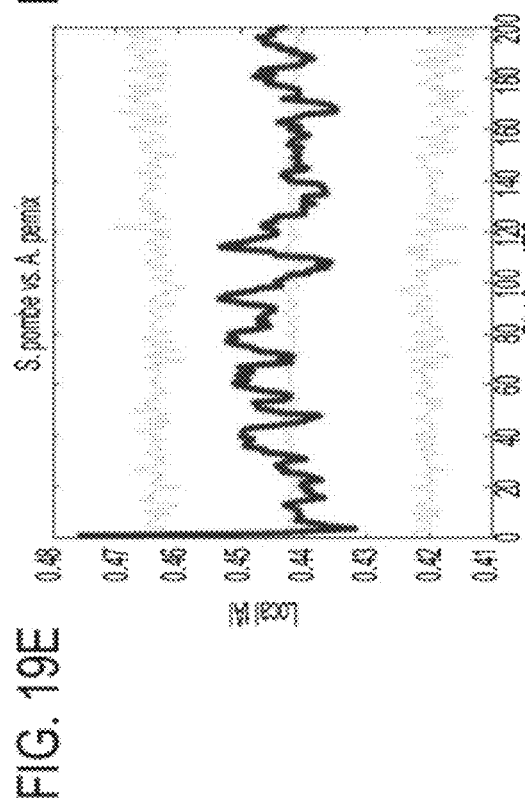
Figure 19H:
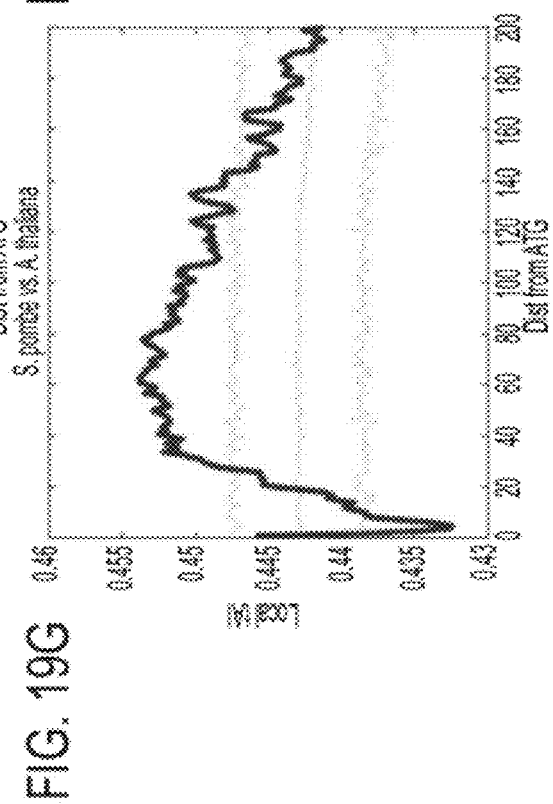
Figure 19N:
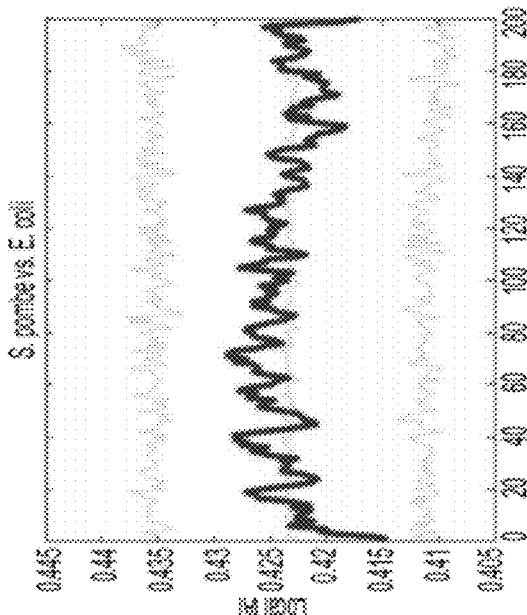
Figure 19P:
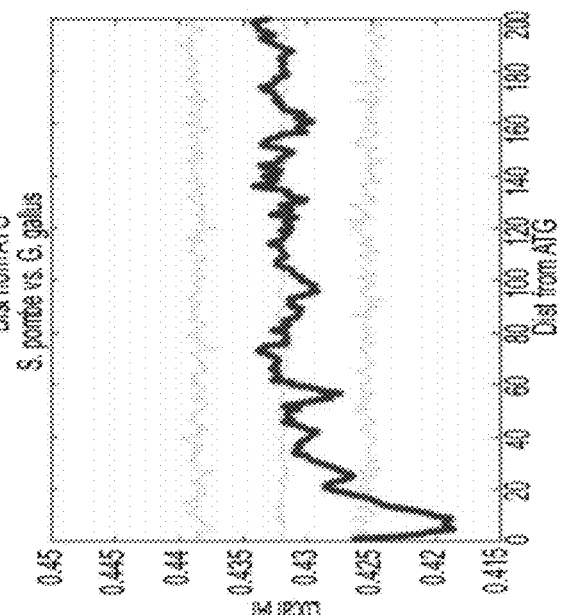
Figure 19M:
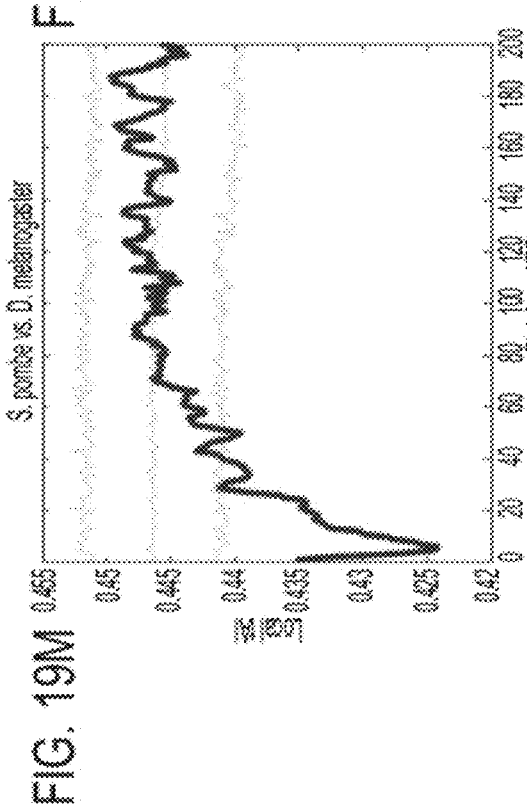
Figure 19O:
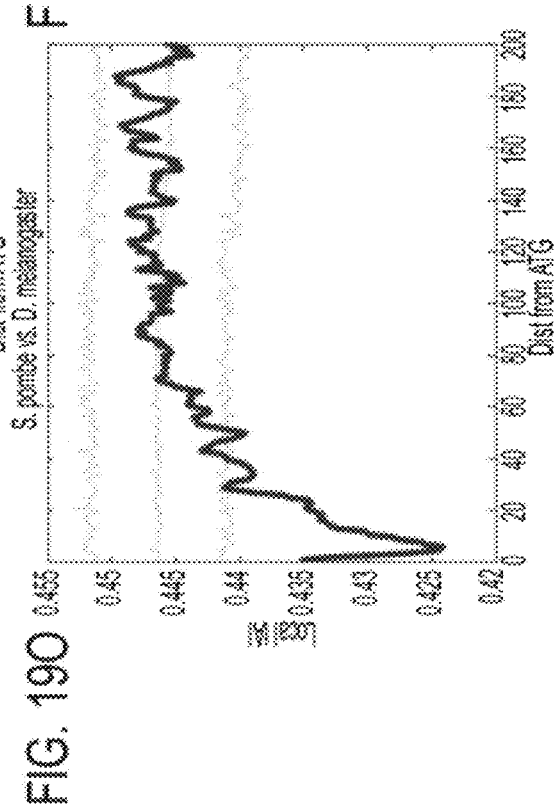
Figure 19U:
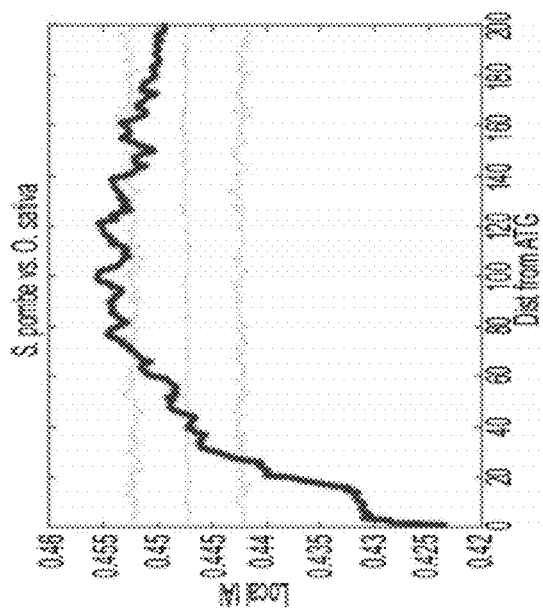
Figure 19V:
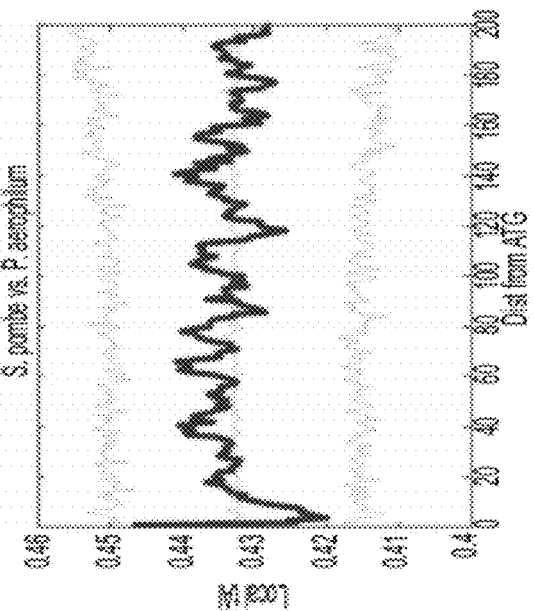
Figure 19W:
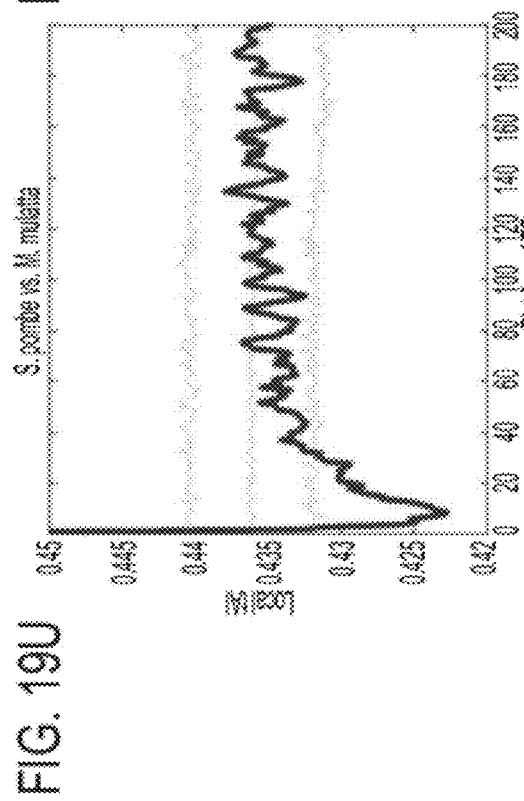
Figure 19X:
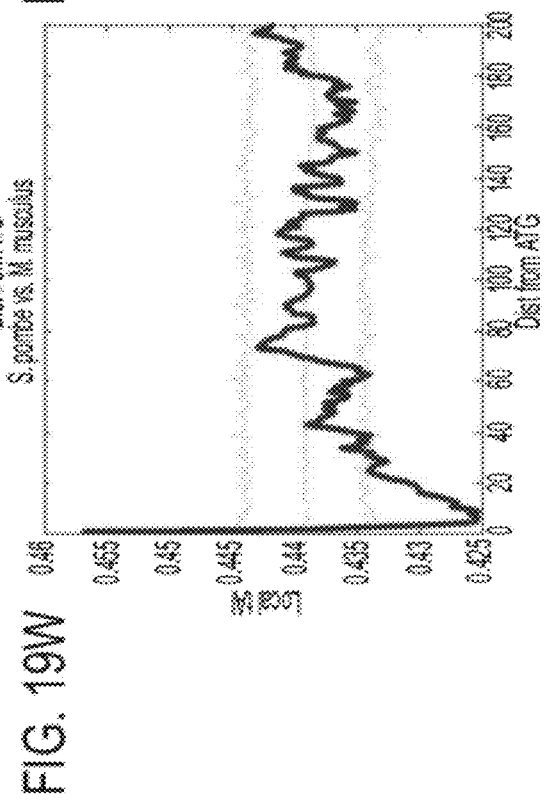
Figures 19Y, 19Z:
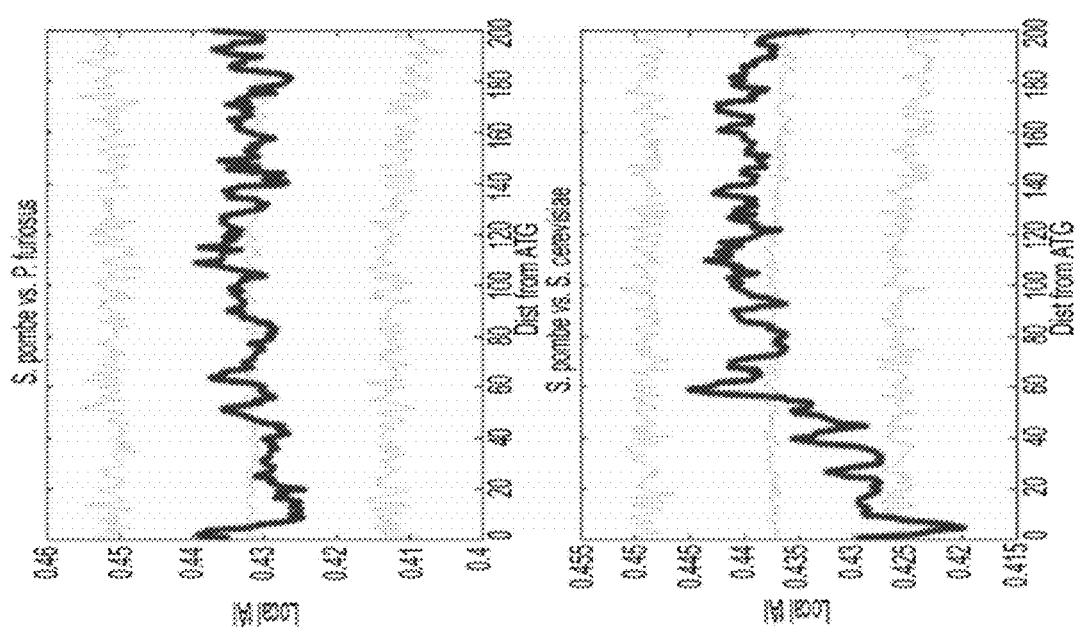

FIGS. 19A-Z are graphs illustrating the translation efficiency profile of various organisms when using the tRNA pool of *S. pombe*.

Figure 20A:
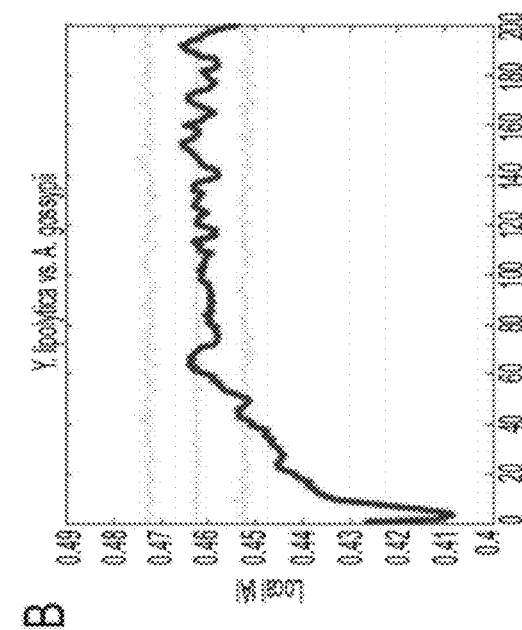
Figure 20B:
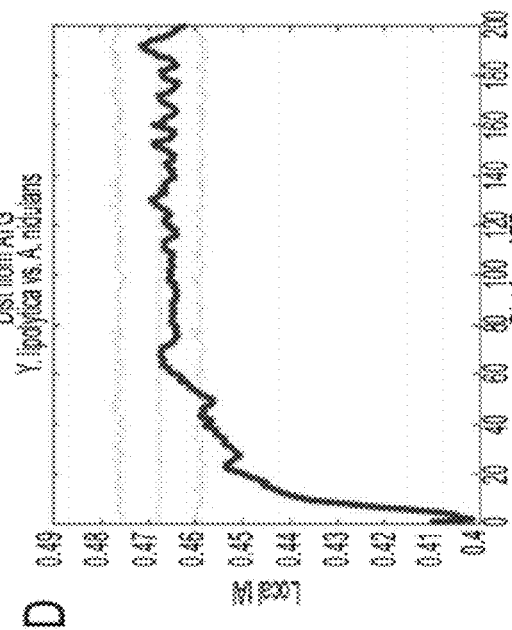
Figure 20C:
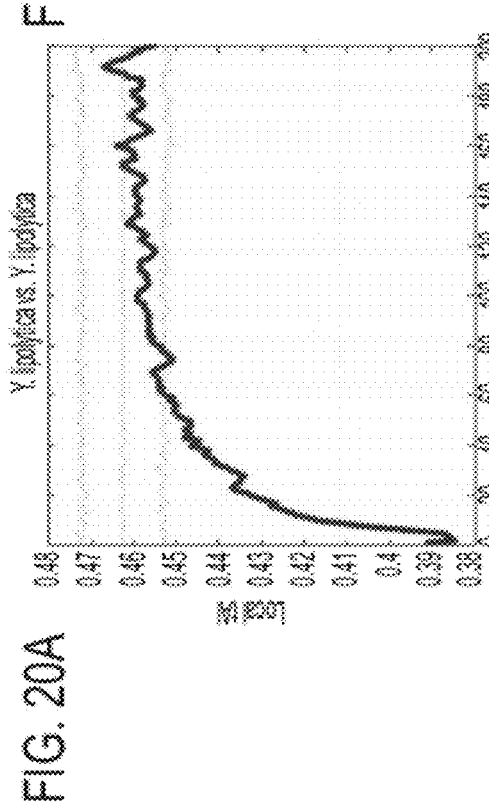
Figure 20D:
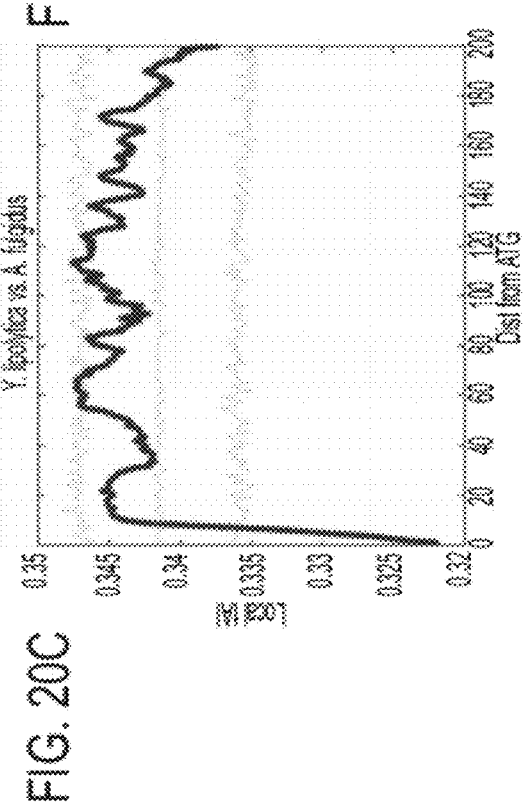
Figure 20E:
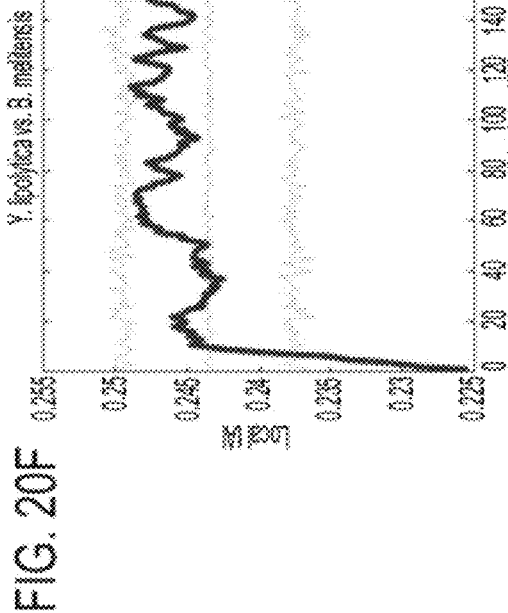
Figure 20F:
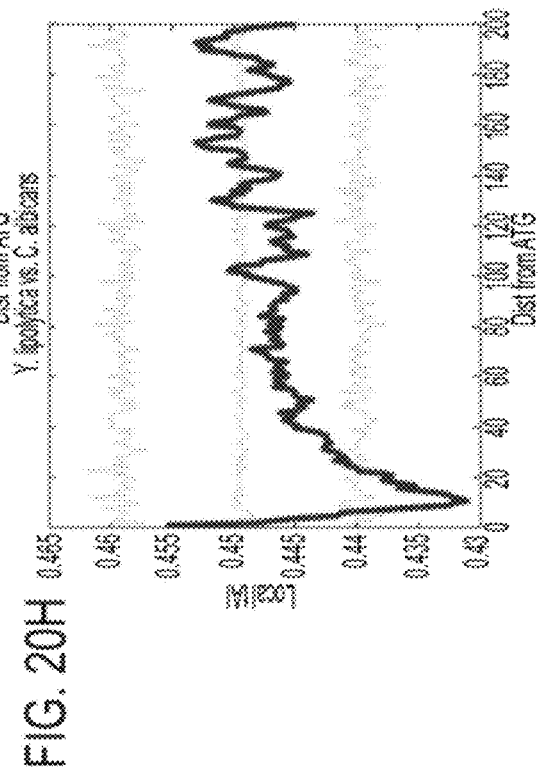
Figure 20G:
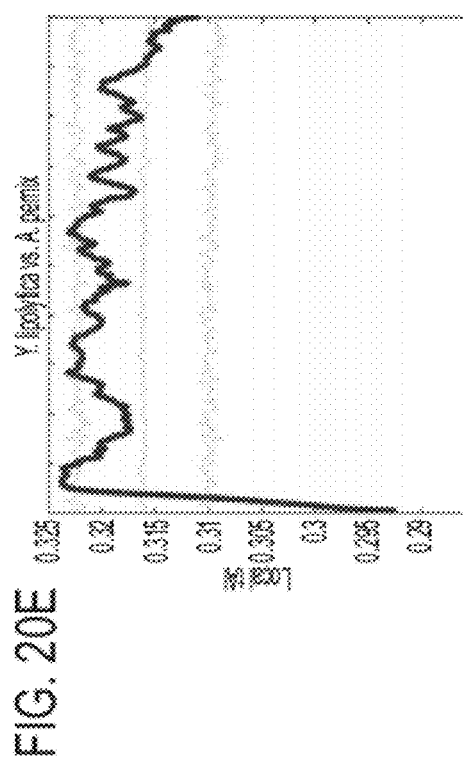
Figure 20H:
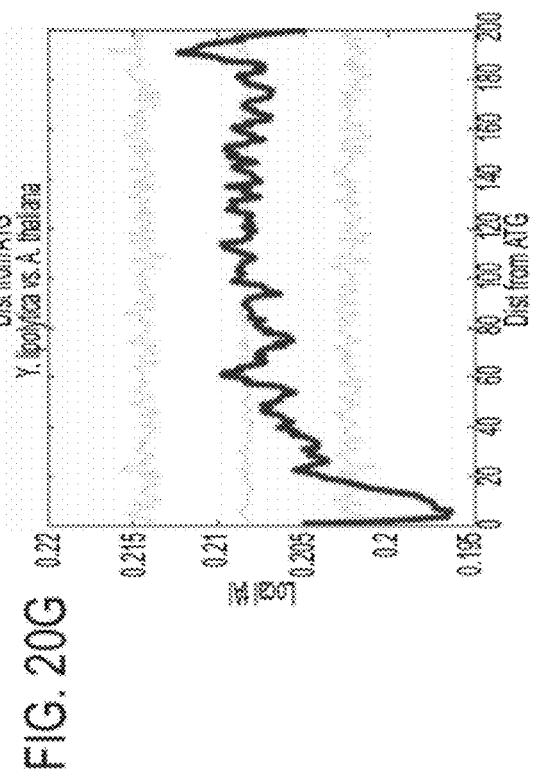
Figure 20I:
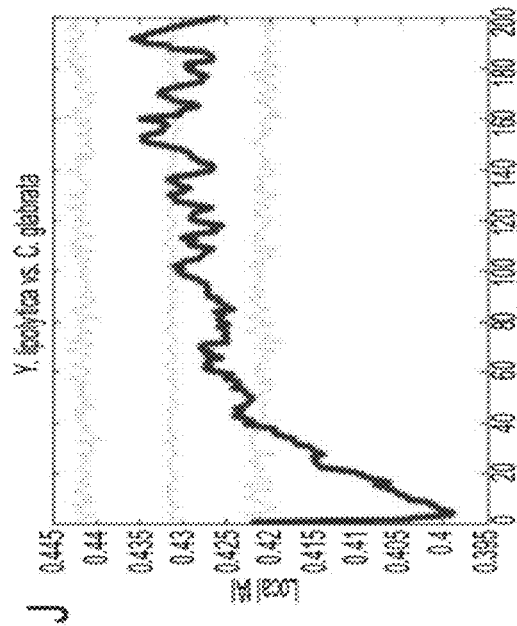
Figure 20K:
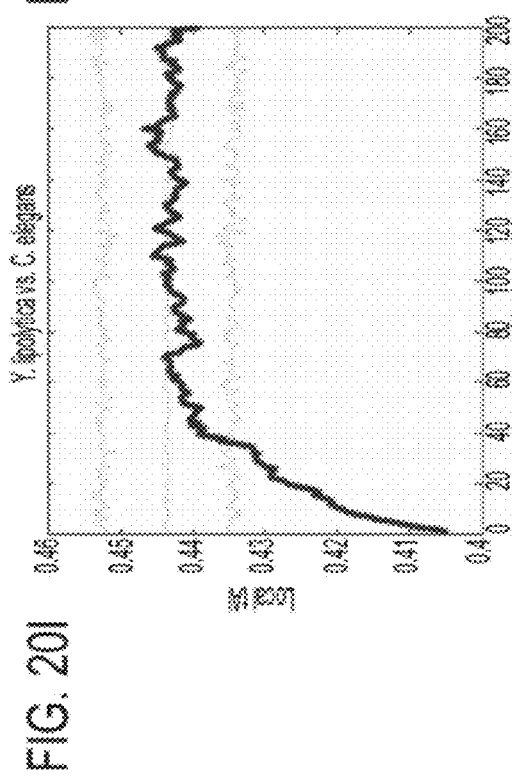
Figure 20J:
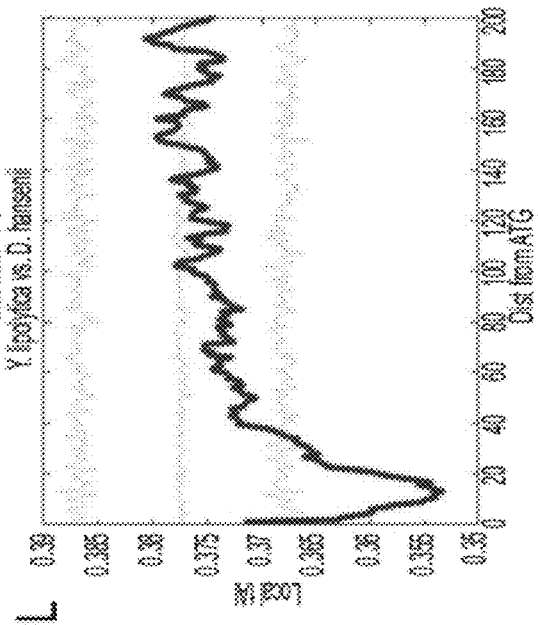
Figure 20L:
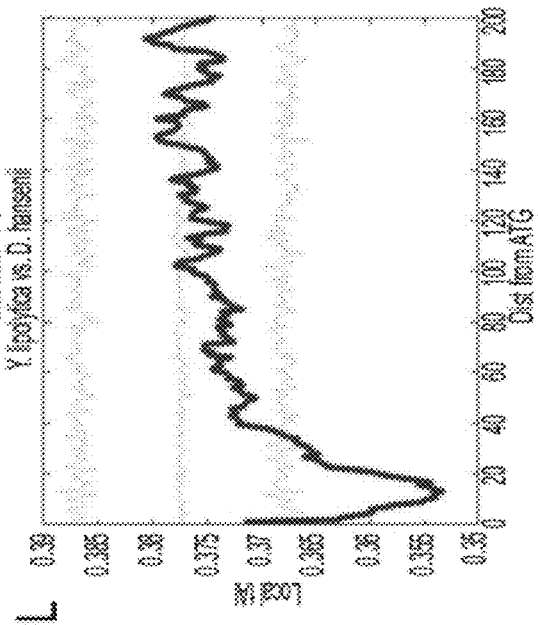
Figure 20Q:
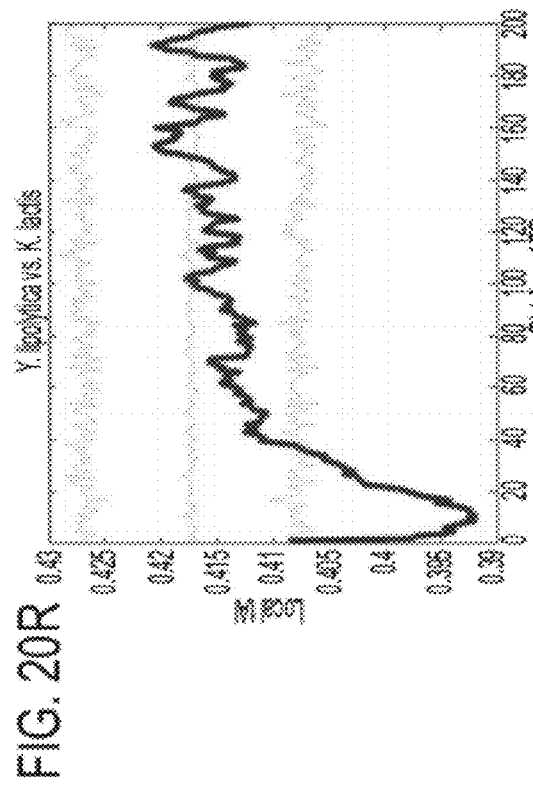
Figure 20R:
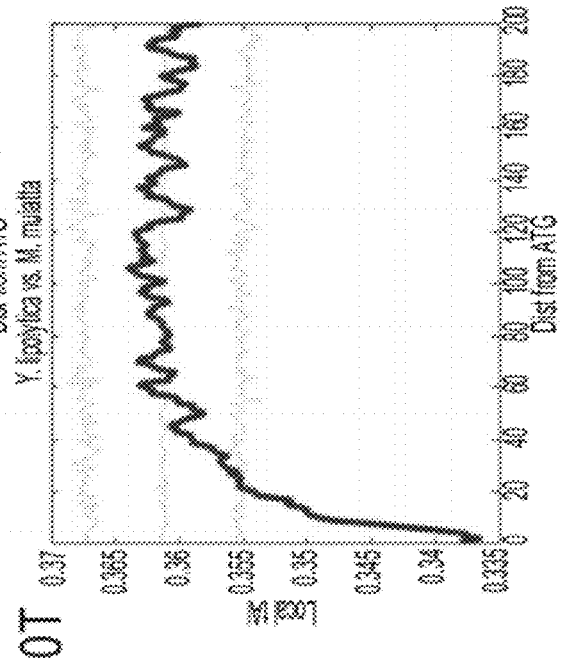
Figure 20S:
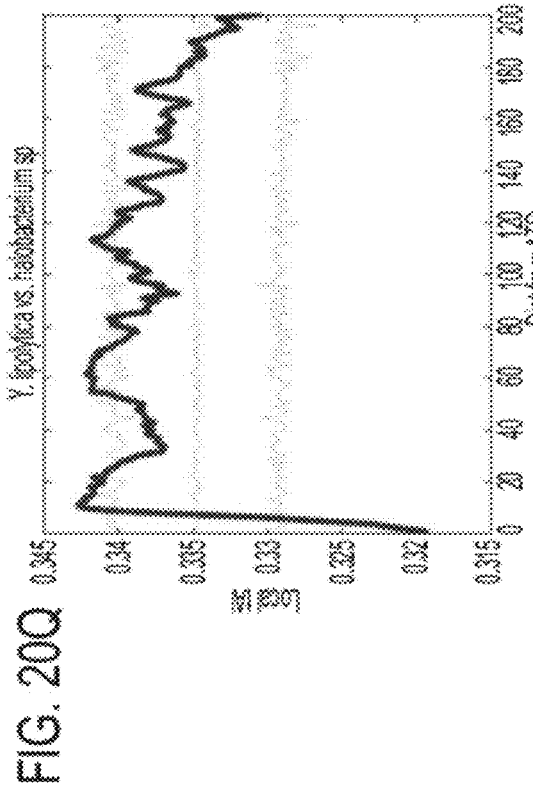
Figure 20T:
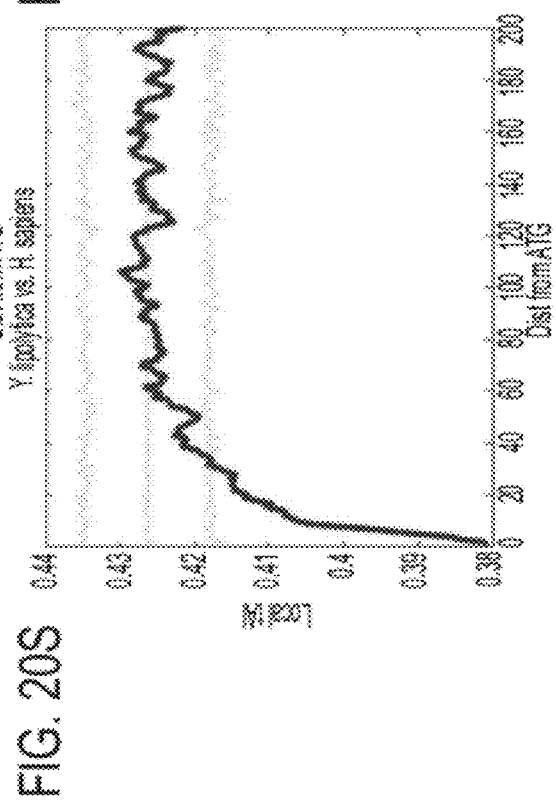
Figure 20V:
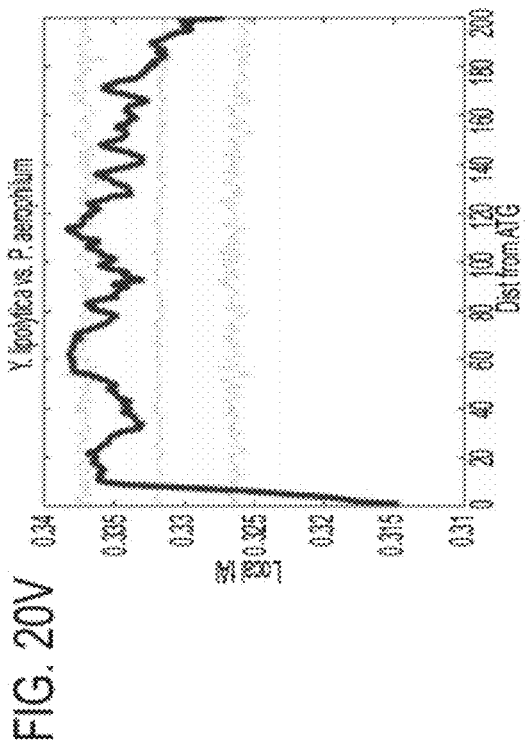
Figure 20X:
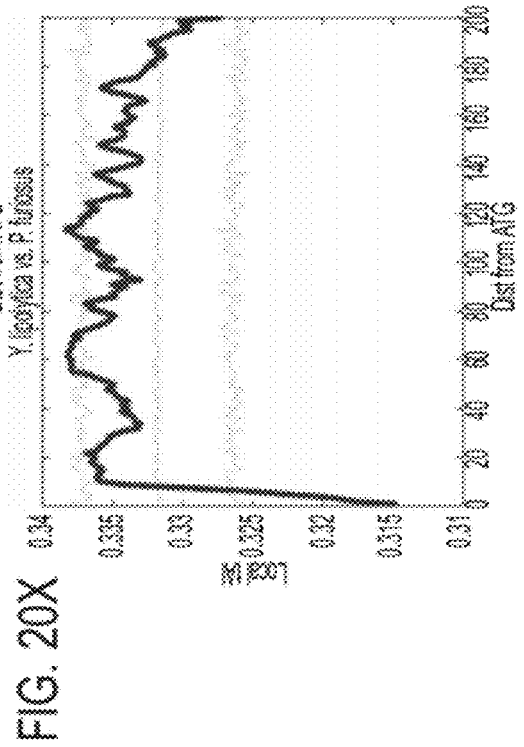
Figure 20U:
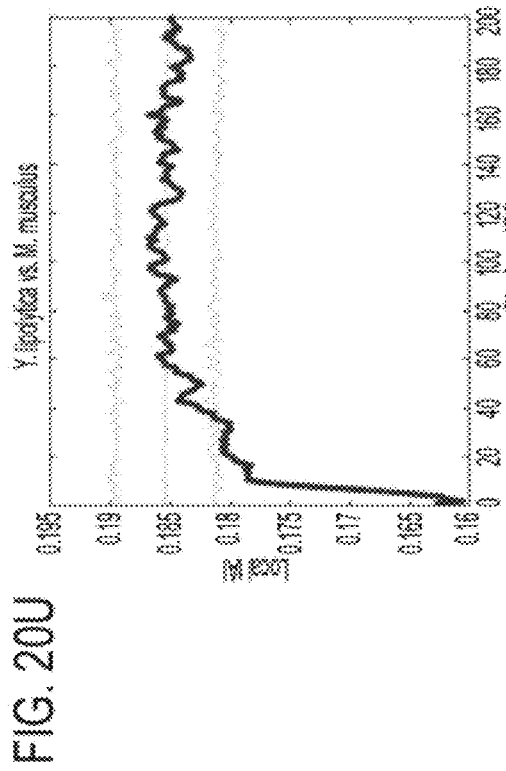
Figure 20W:
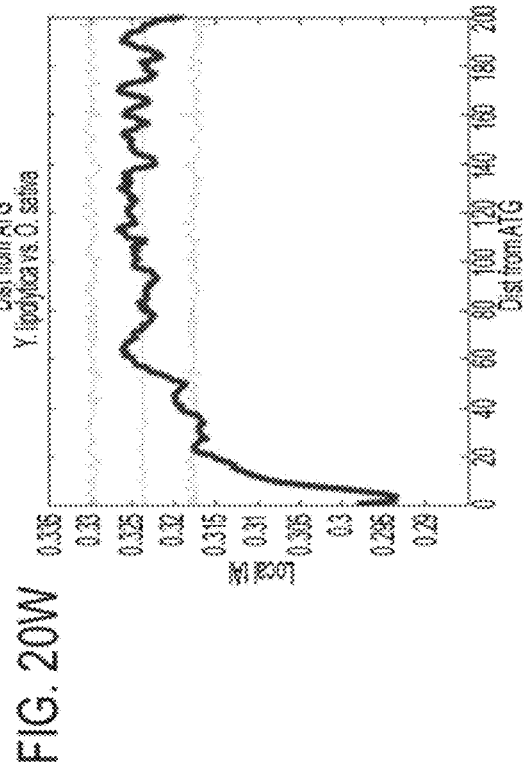
Figures 20Y, 20Z:
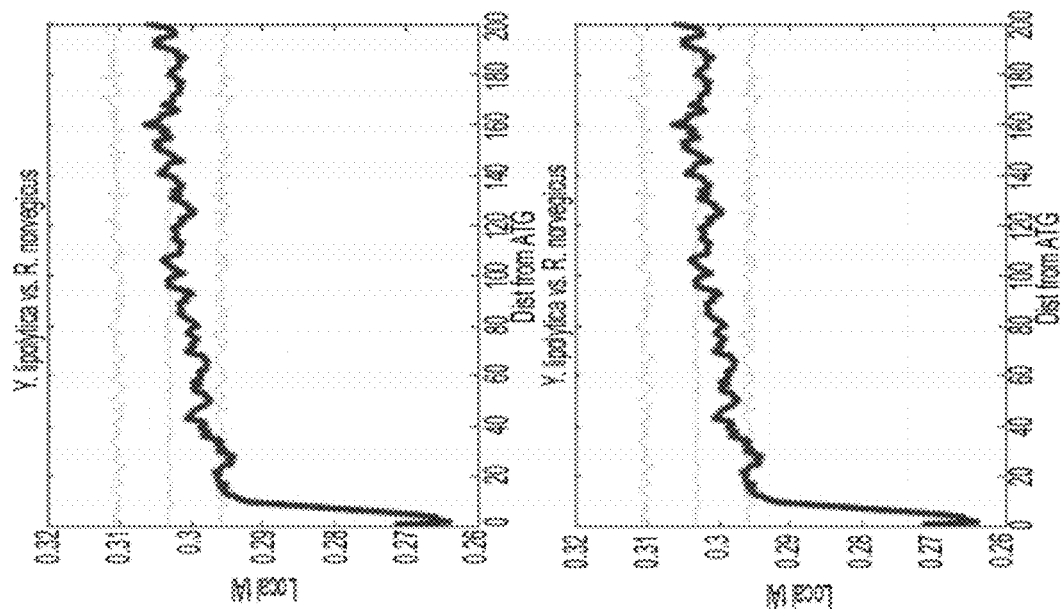

FIGS. 20A-Z are graphs illustrating the translation efficiency profile of *Y. lipolytica* using the tRNA pool of other organisms.

Figures 21A, 21B, 21C, 21D:
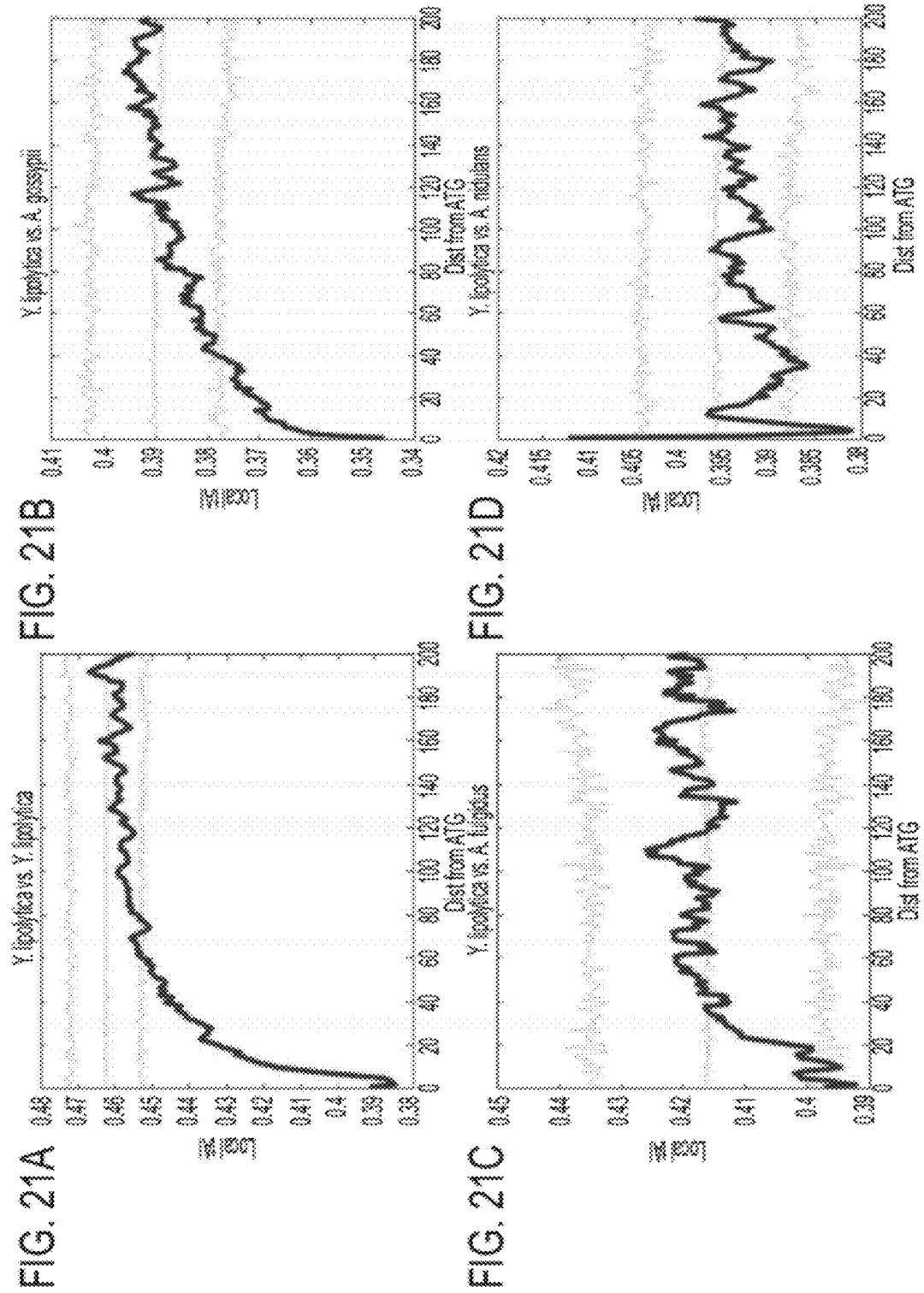
Figure 21I:
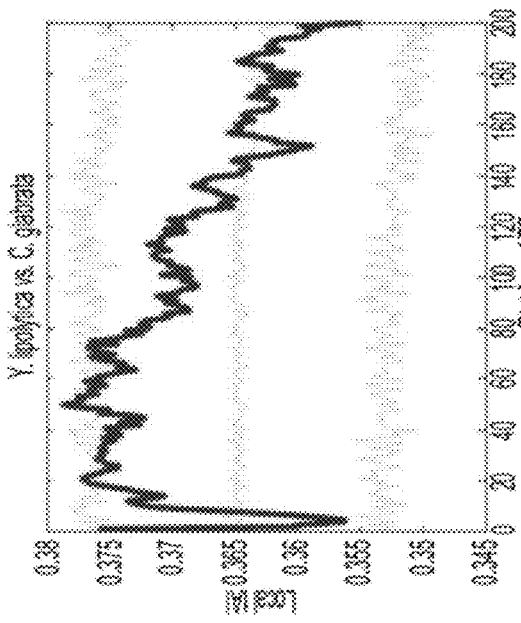
Figure 21J:
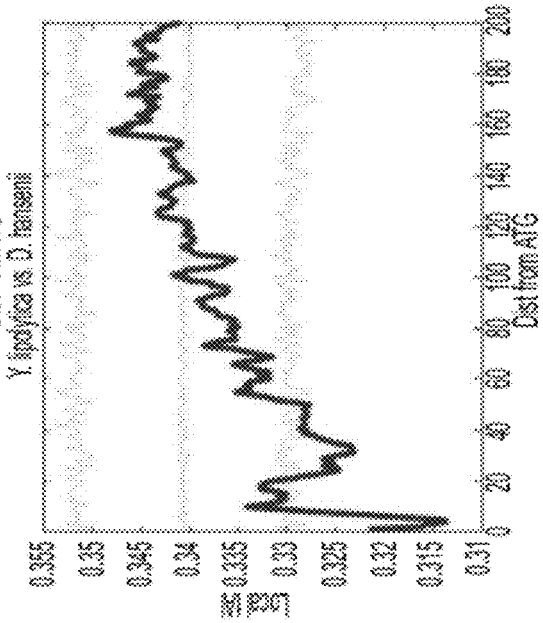
Figure 21K:
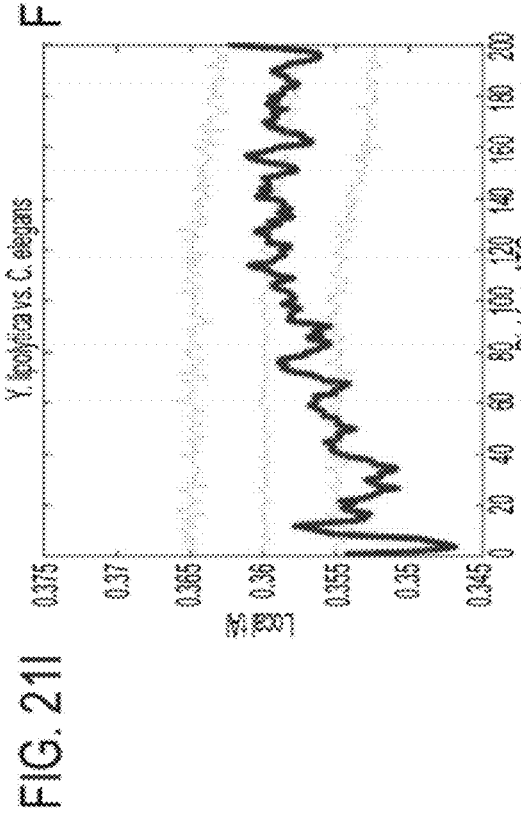
Figure 21L:
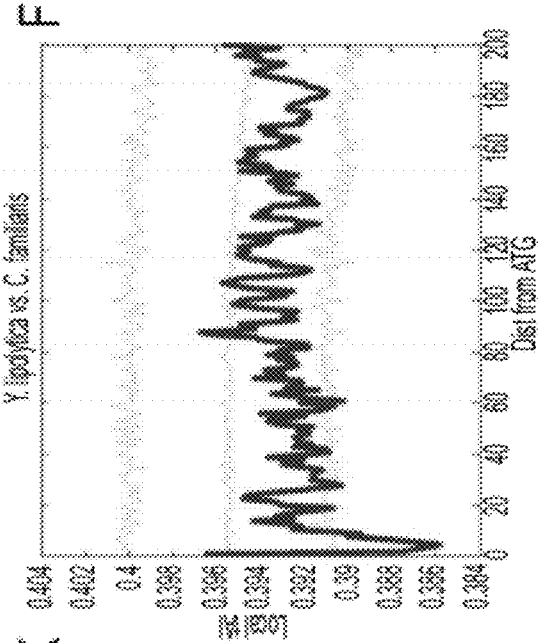
Figure 21M:
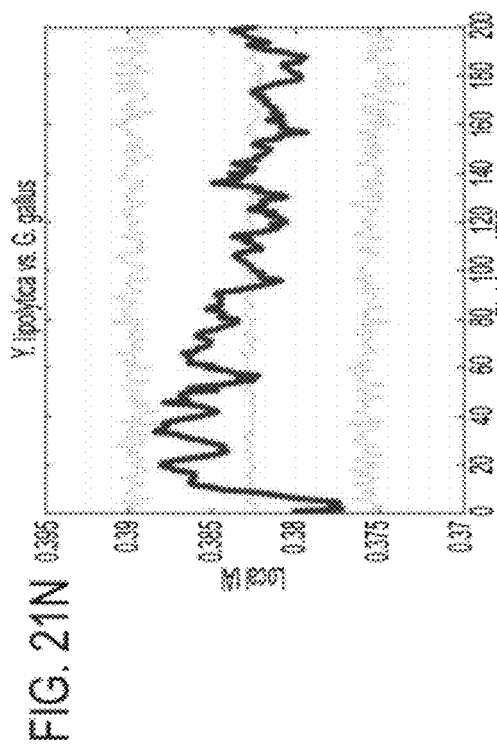
Figure 21N:
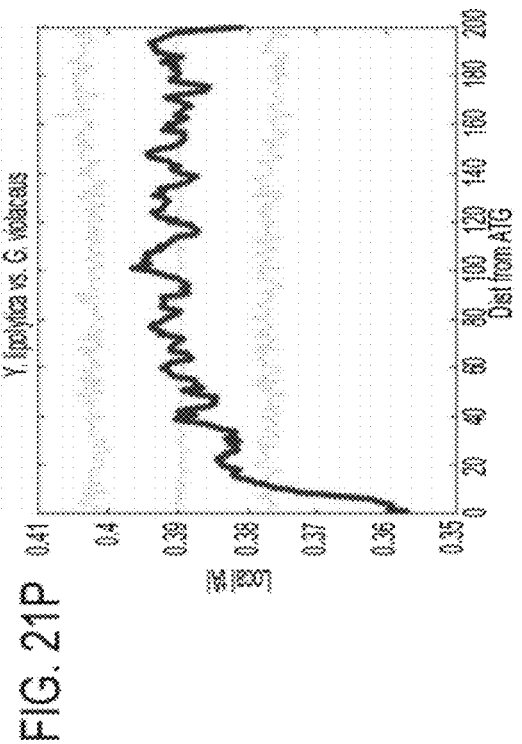
Figure 21O:
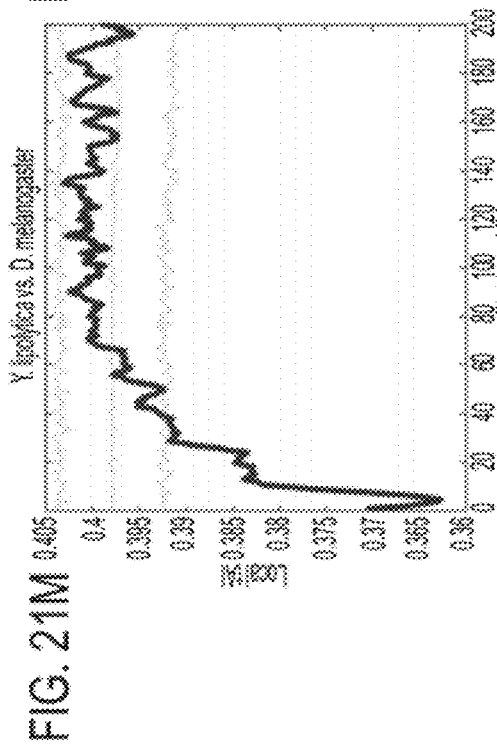
Figure 21P:
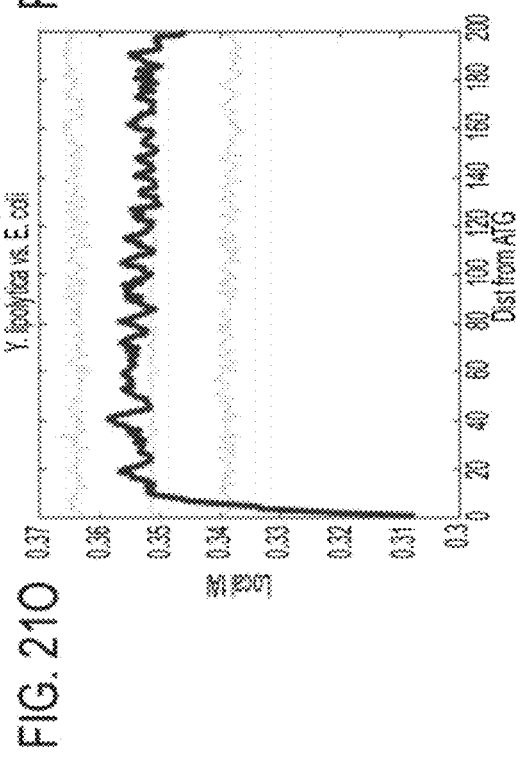
Figures 21Y, 21Z:
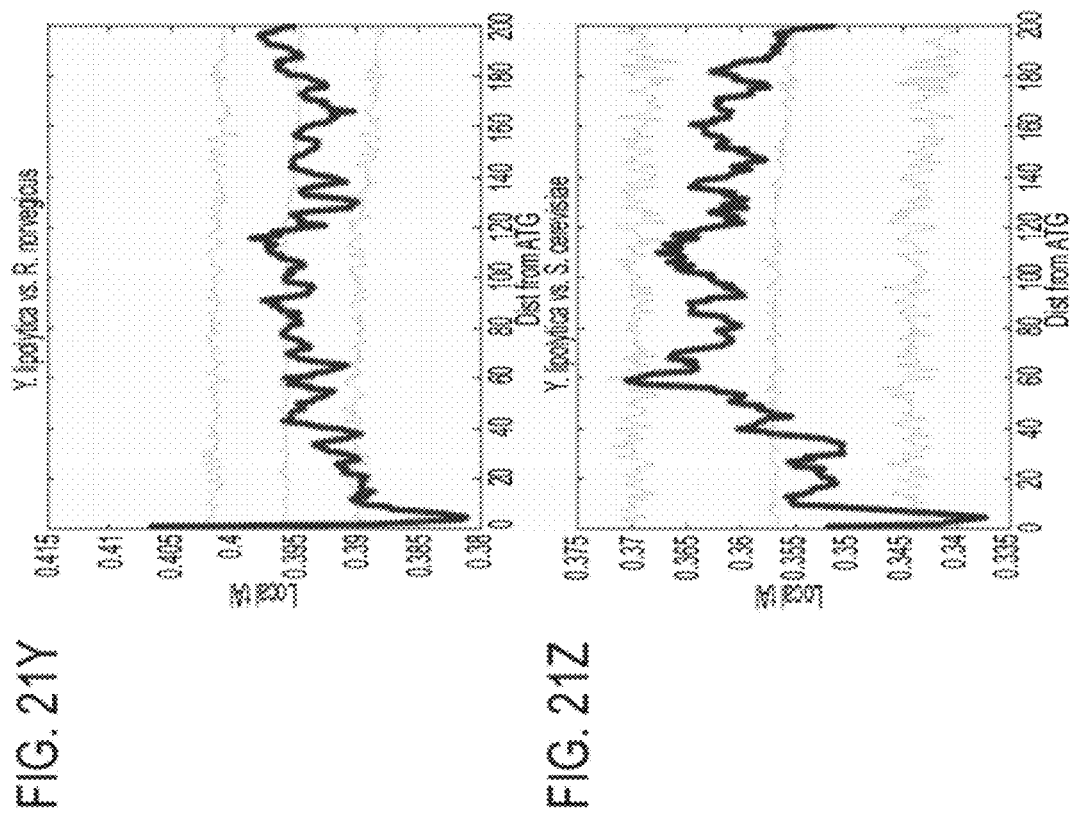

FIGS. 21A-Z are graphs illustrating the translation efficiency profile of various organisms when using the tRNA pool of *Y. lipolytica*.

Figure 22:
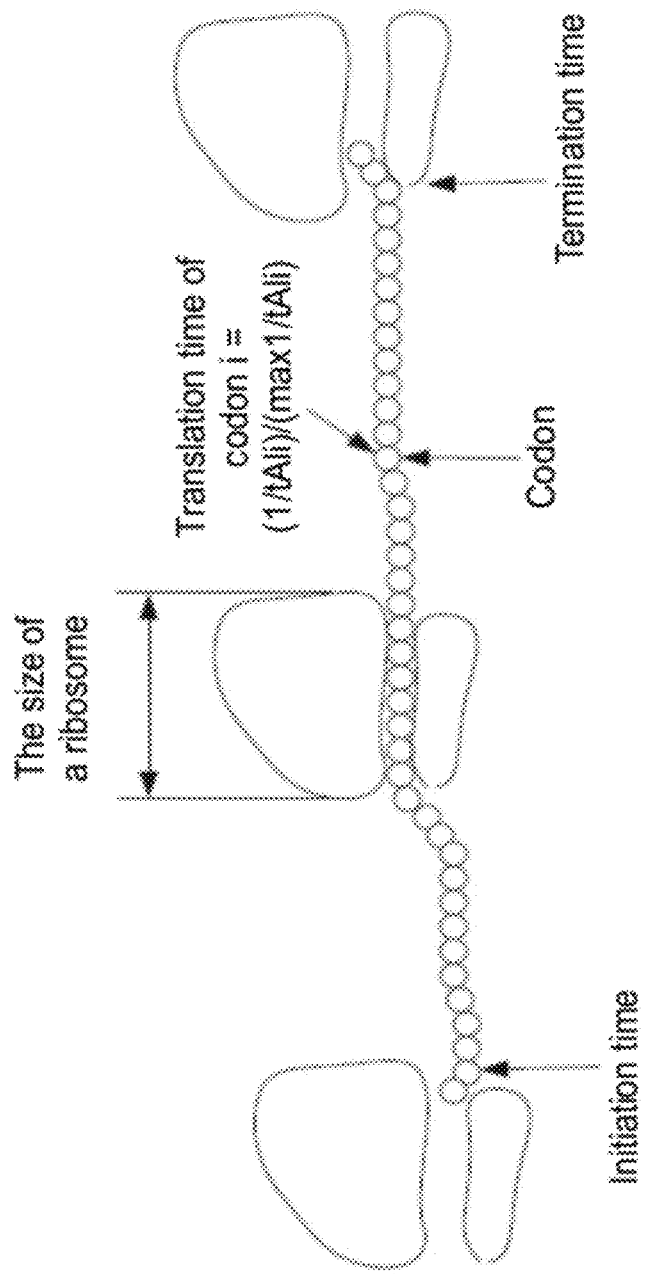
Figure 23A:
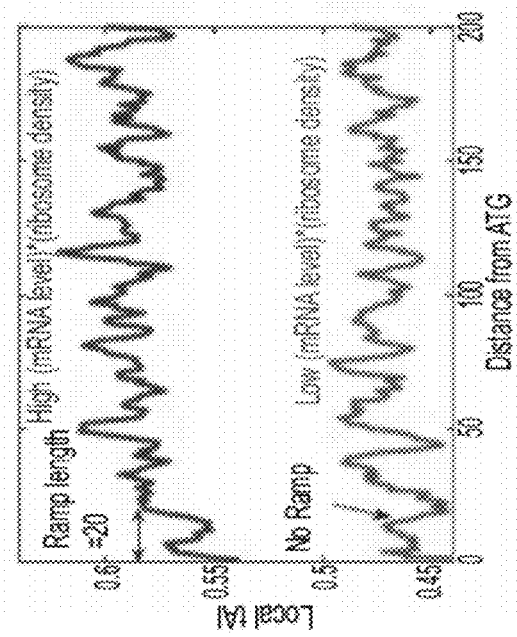
Figure 23B:
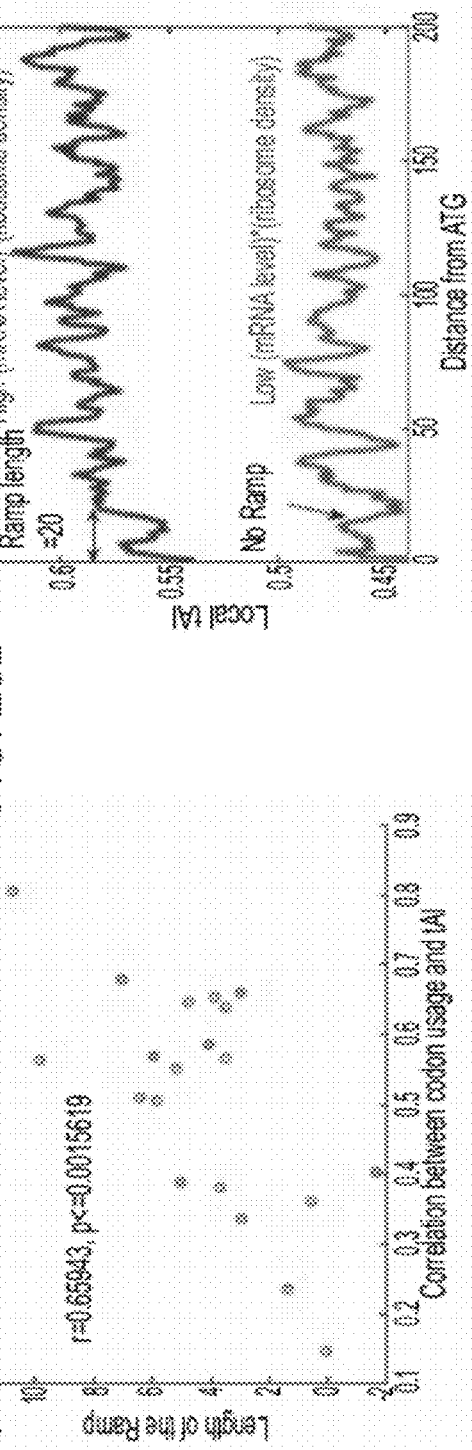
Figure 23D:
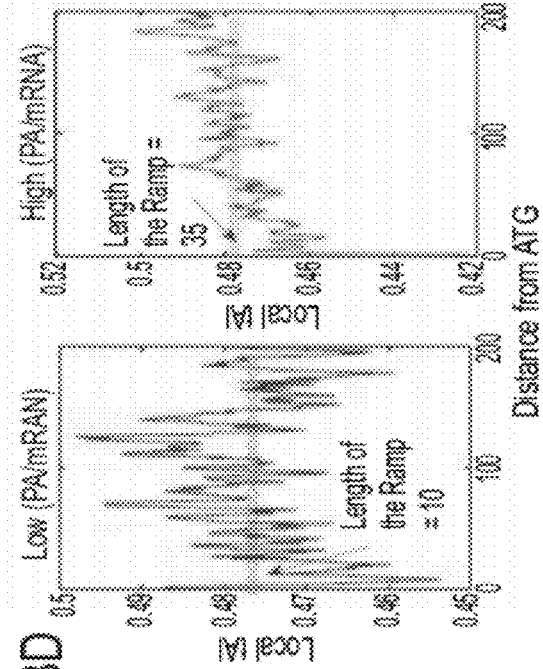
Figure 23C:
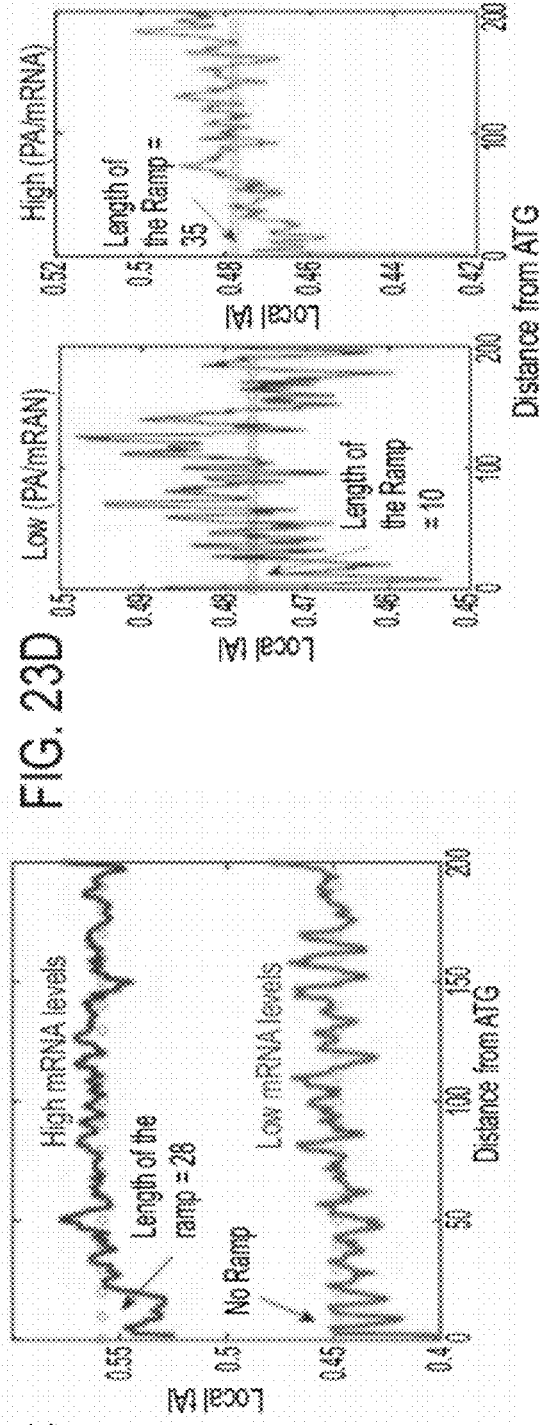

FIG. 22 is a model illustrating ribosome movement (from Zhang et al).

FIGS. 23A-D are graphs illustrating the relationship between the length of the ramp and codon usage, ribosome density, mRNA levels and (protein abundance)/mRNA.

Figure 24A:
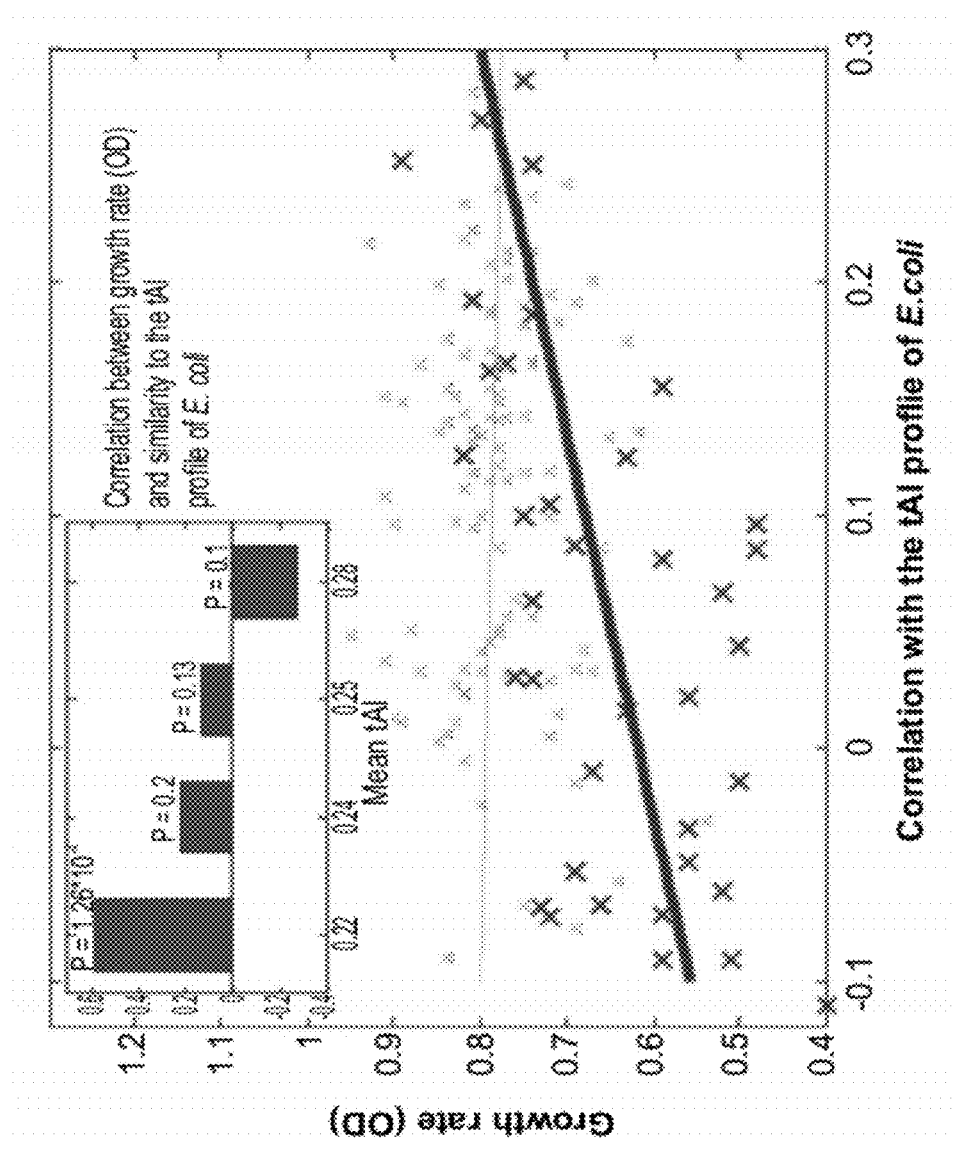
Figure 24B:
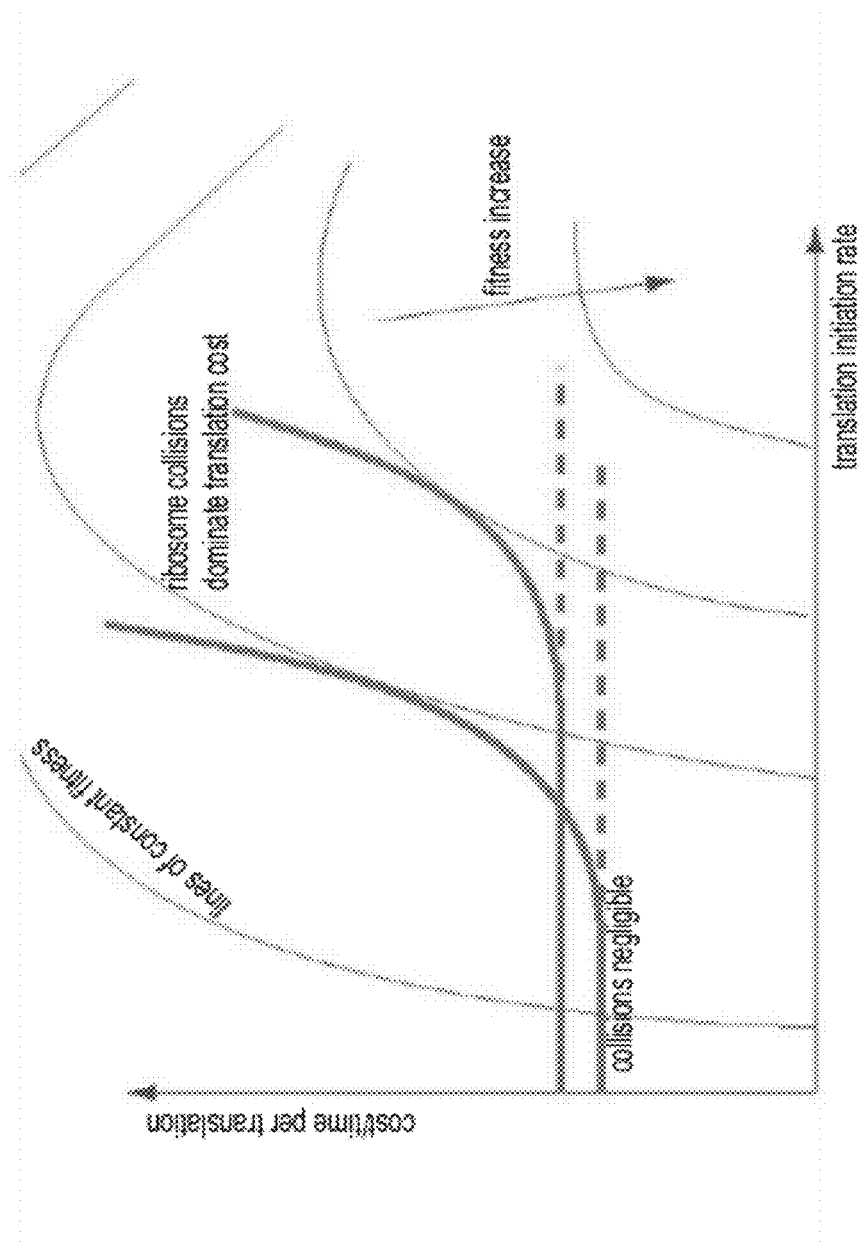

FIGS. 24A-B are graphs illustrating the effect of ramping on fitness, production, and expression cost.

A. Growth rate (measured by OD) of each GFP variant (Kudla et al., 2009). vs. similarity (measured by Spearman correlation) between the translation efficiency profile of the variant and the averaged profile of all endogenous genes in *E. coli*. Upper left corner: The above correlation computed separately for quadrants of the GFPP library binned according to their tAI values. Main figure: Dot plot of the growth rate vs. similarity to the genomic translation efficiency profile of *E. coli* for the different variants in the in the GFP library (correlation coefficient r=0.2; p=0.014); points that are related to the lowest tAI quadrant bin in the sub-figure are colored blue, other points are red.

B. A conceptual model depicting the value in selection for ramping in transcripts with high translation rates. The relationship between translation initiation rate and cost of translation per protein is compared for transcripts with (red) and without (blue) ramp designs. At low translation initiation rates, the ribosomes move independently of one another, thus the cost of translation per protein is independent of the initiation rate. The ramp design incurs a cost because it slows down the ribosomes. At high translation initiation rates, however, ribosome traffic jams increasingly dominate the cost of translation. In this regime, ramping reduces the cost of protein production at a given production level, and increases the production capacity at a given cost. The translation initiation rate and the degree of ramping are two knobs that evolution can tune to maximize fitness, which, in the case shown, favor the ramp. The iso-fitness lines reflect increase in fitness with protein production rate, and the decreases with the total cost of translation. See also FIG. 23 and FIGS. 25A-B.

FIG. 25A is a table which provides a comparison (measures 1-9 of Example 7) of an artificial profile of the non-decreasing translation efficiency to various random profiles (columns 1-6). Each p-value denotes the probability to get better or equal performances according to the corresponding measure in the corresponding random model; red denotes low and green denotes high. '*' denotes that the initial non-decreasing profile is one of the optimal solutions.

FIG. 25B is a table which provides a comparison (measures 1-9) of the *S. Cerevisae* genome efficiency to two randomized versions of the genome (columns 1-2); p-value were computed as before. The nine measures of quality are 1) Number of ribosome initiations before reaching steady state (RISS). 2) Time to reach steady state (TSS). 3) Initiation time at steady state (IT). 4) Translation time at steady state (TT). 5) Number of ribosomes per mRNA at steady state (RPM). 6) Number of codons translated per "second" (arbitrary time unit; CPS). 7) Number of ribosome collisions at steady state (RCSS). 8) Number of ribosome collisions till steady state (RCTSS). 9) Translation efficiency, number of codons translated per "second" per ribosome: 5)/4) (CPSPR).

Figure 26:
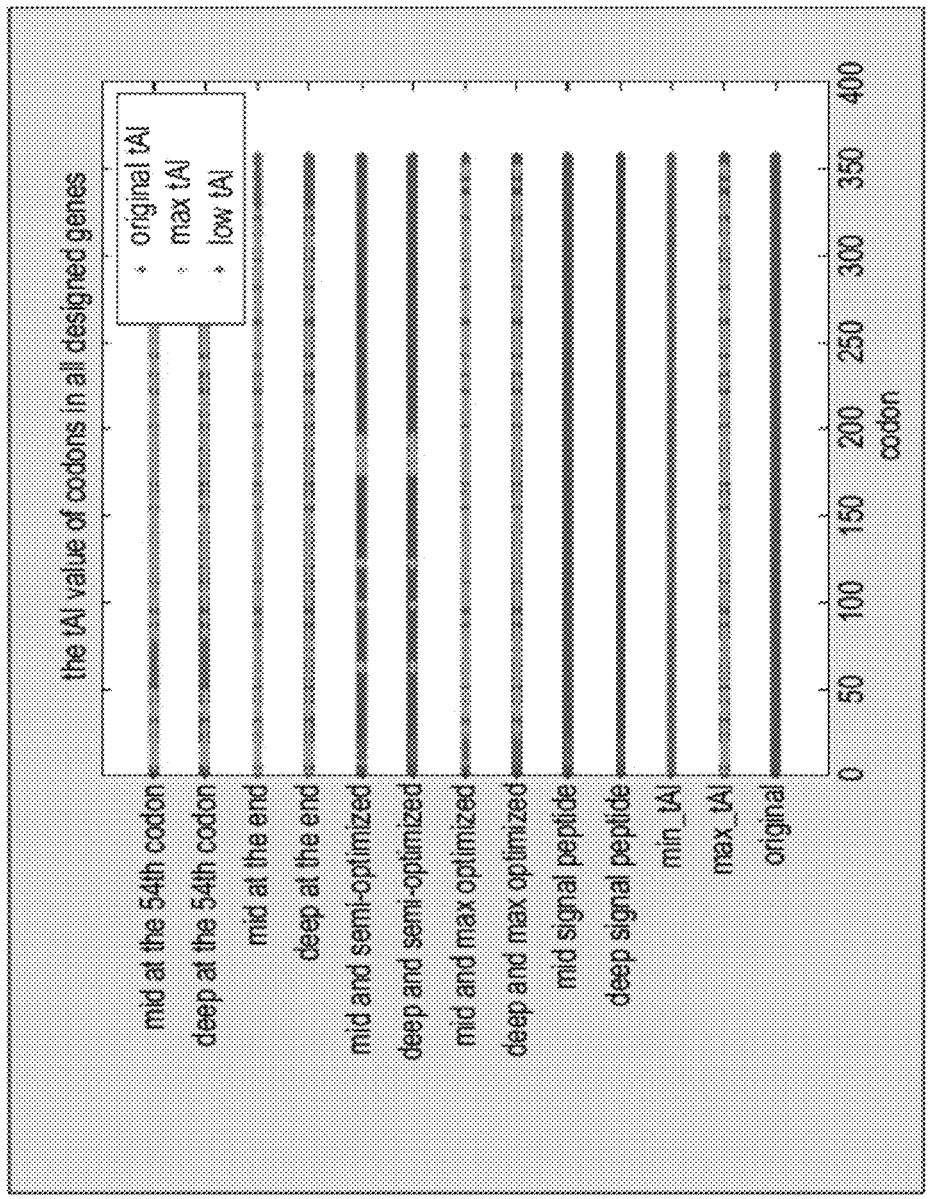

FIG. 26 is a graph illustrating the tAI values in exemplary polynucleotides generated according to embodiments of the present invention.

Figure 27:
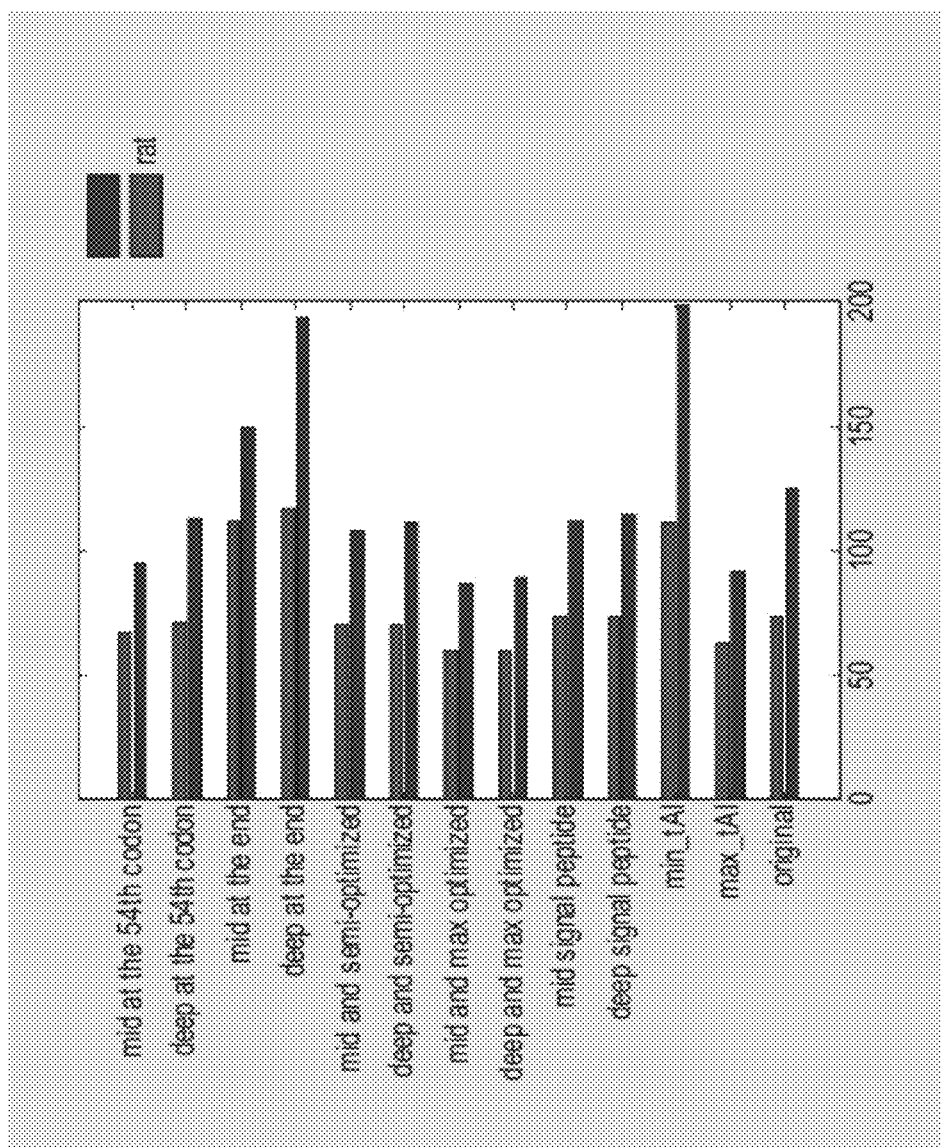

FIG. 27 is a graph illustrating anticipated translation time of the exemplary polynucleotides generated according to embodiments of the present invention in mice and rats.

Figure 28:
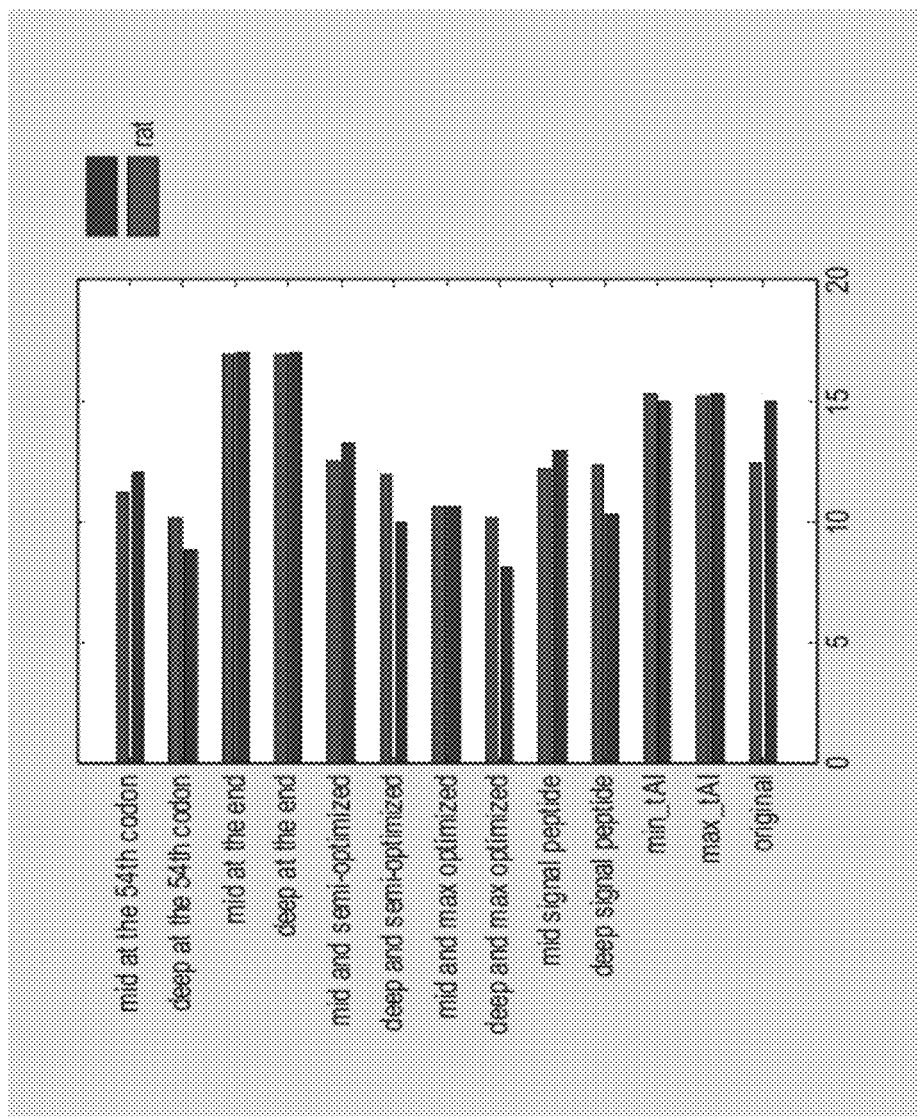

FIG. 28 is a graph illustrating anticipated number of ribosomes on the exemplary polynucleotides generated according to embodiments of the present invention in mice and rats.

Figure 29:
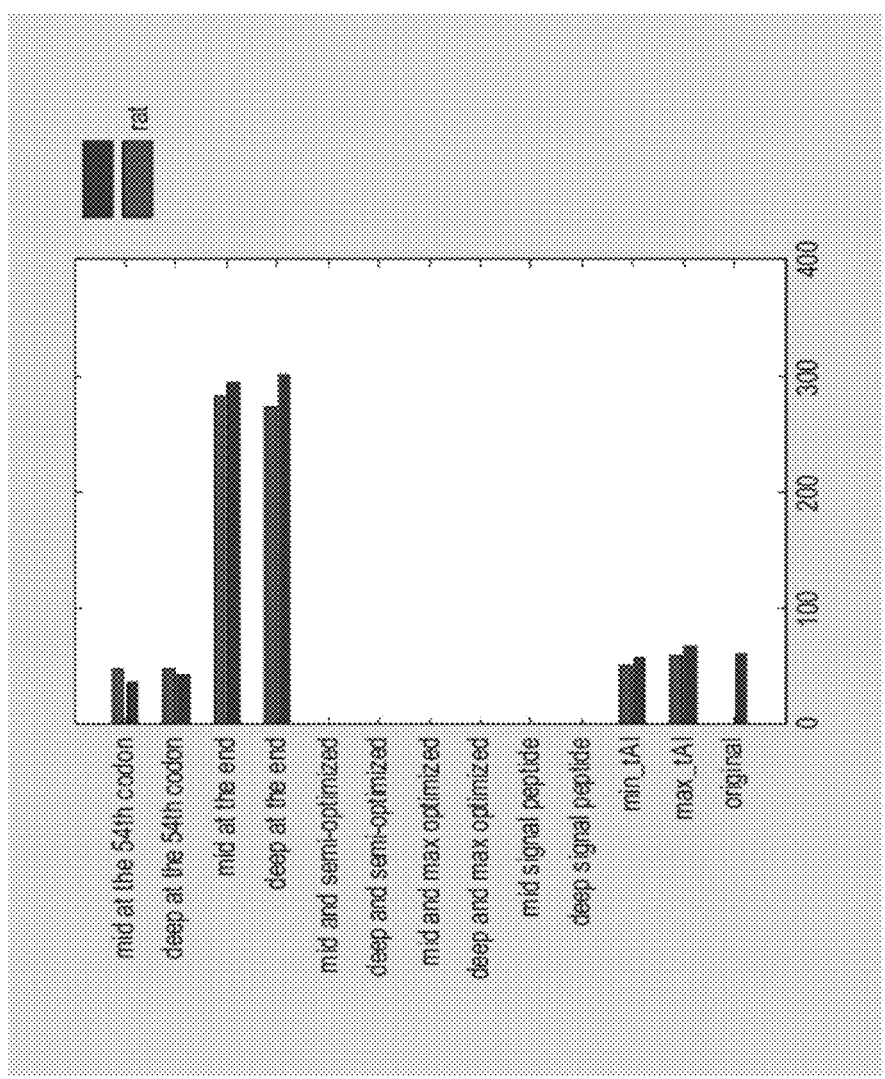

FIG. 29 is a graph illustrating anticipated number of collisions using the exemplary polynucleotides generated according to embodiments of the present invention in mice and rats.

Figure 30:
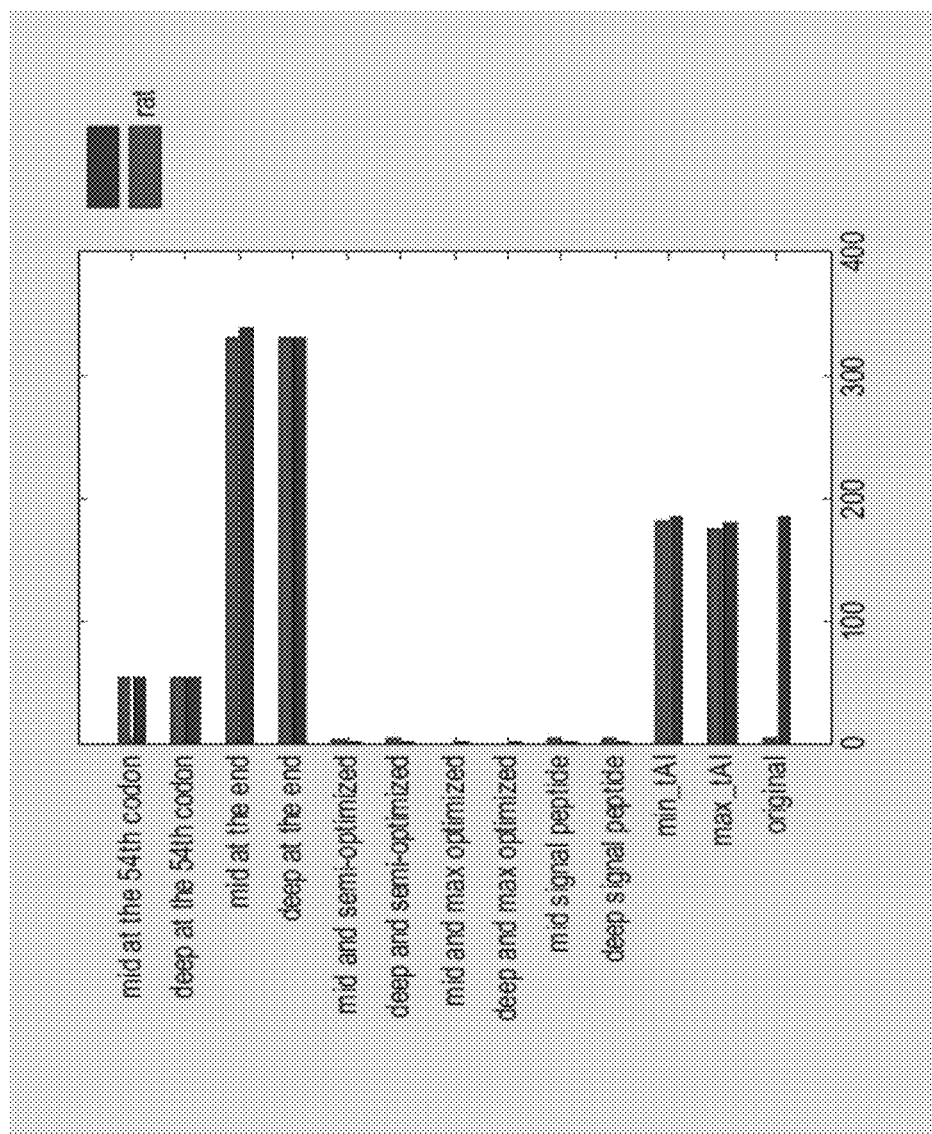

FIG. 30 is a graph illustrating maximum location using the exemplary polynucleotides generated according to embodiments of the present invention in mice and rats.

Figure 31:
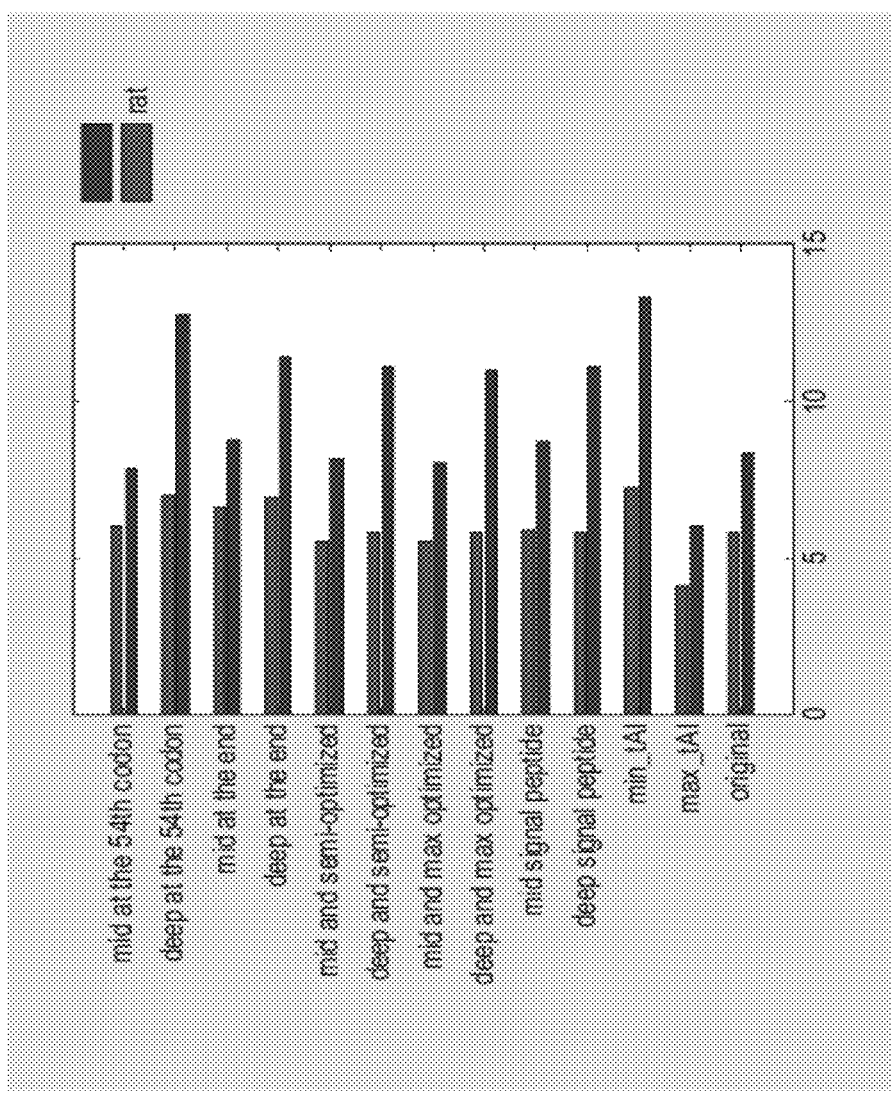

FIG. 31 is a graph illustrating maximum value using the exemplary polynucleotides generated according to embodiments of the present invention in mice and rats.

Figure 32:
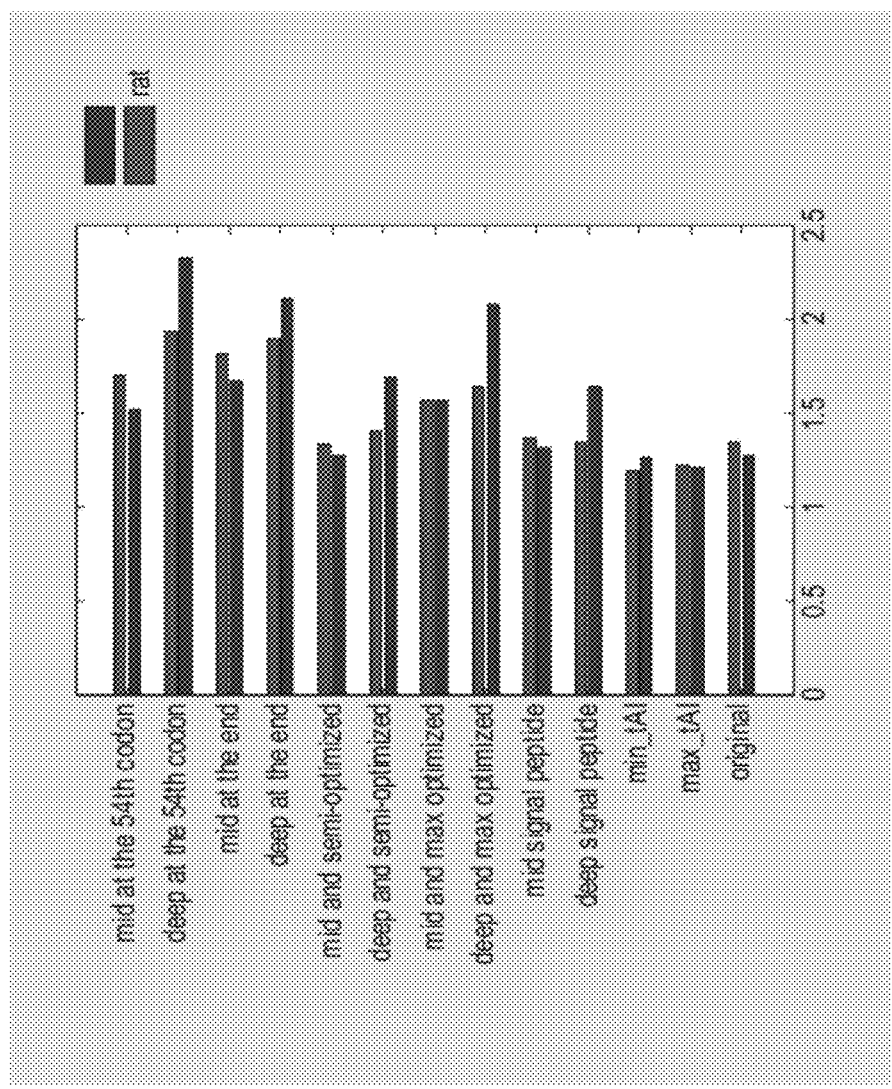

FIG. 32 is a graph illustrating relative strength using the exemplary polynucleotides generated according to embodiments of the present invention in mice and rats.

Figure 33:
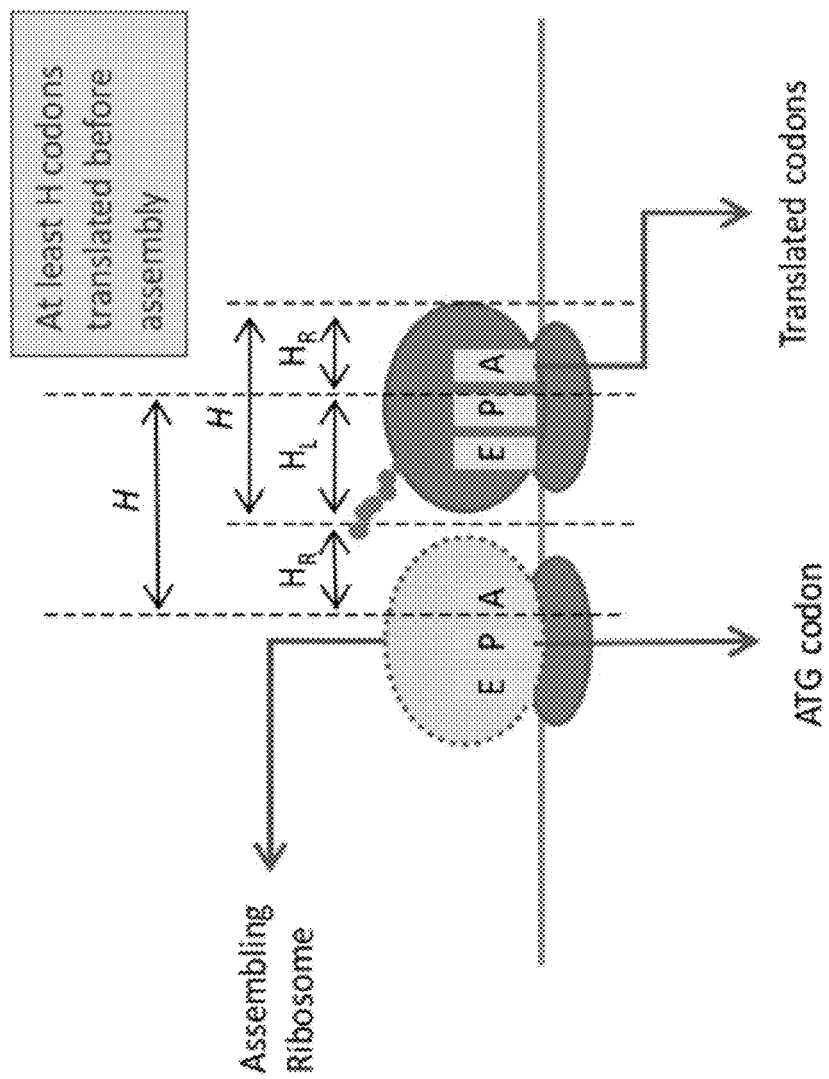

FIG. 33 illustrates two consecutive ribosomes, on the same mRNA, with the second one (left) currently being assembled on the ATG. The size of a ribosome in the figure is H codons. $H_L$ is the distance from the ribosome A-site to the left end of the ribosome, $H_R$ is the distance from the A-site to the right end of the ribosome. The illustration shows that the minimum distance between two ribosomes' A-sites is H which is also "one ribosome size". It can also be seen that in order for the second ribosome to start assembling on the ATG the first ribosome should have cleared the assembly area, e.g. translate H codons.

Figure 34B:
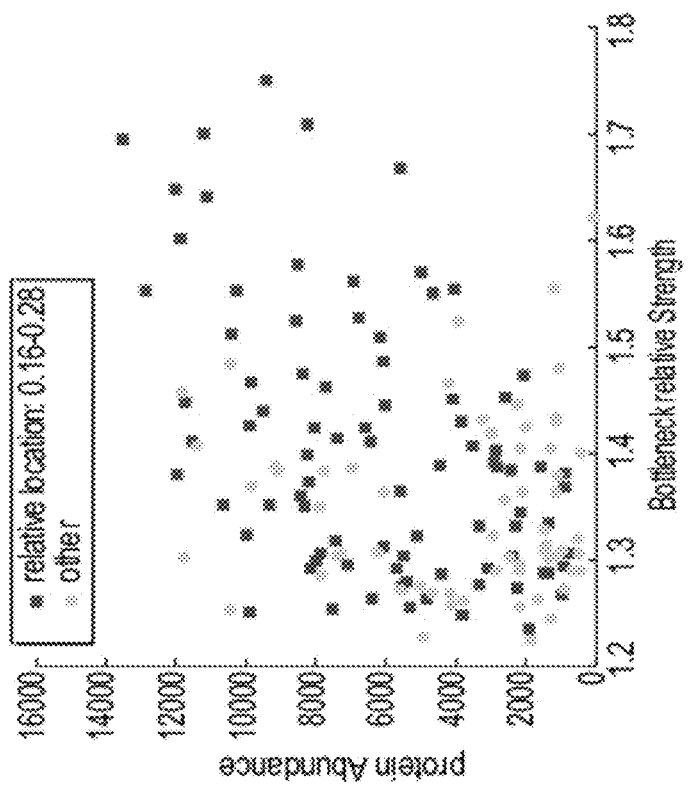
Figure 34A:
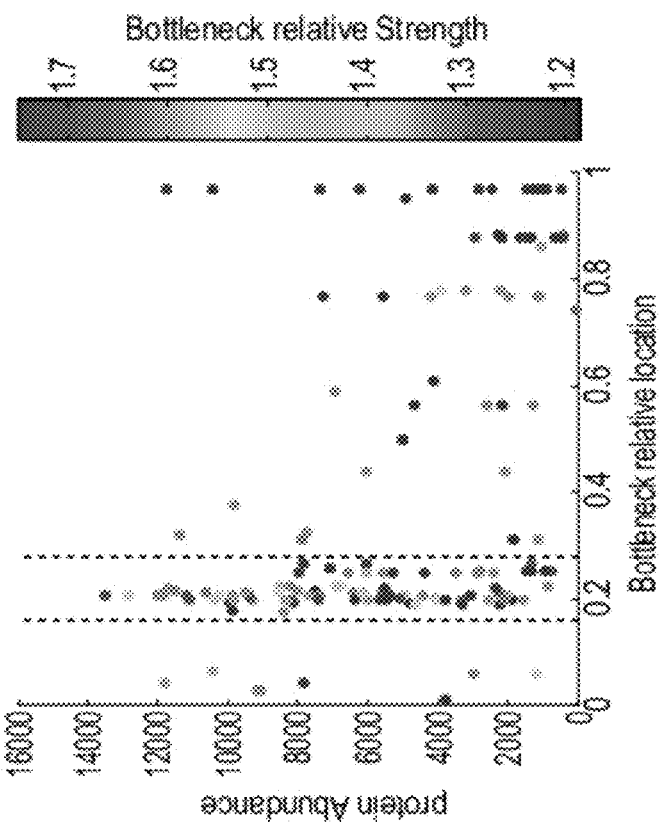

FIGS. 34A-B are plots illustrating protein abundance vs. bottleneck relative location and strength in the GFP library. FIG. 34A: Plotted are all the genes in the GFP library. The x-axis is the relative location of the bottleneck in every gene; the Y-axis is the per-cell protein abundances. The color of each dot is the relative strength of the bottleneck in every gene. 86 of the genes are located between the 2 black lines that correspond to relatively early bottlenecks i.e. relative location between 0.16 and 0.28. FIG. 34B: The correlation between the bottleneck relative strength and per-cell protein abundance for all the genes in the GFP library. The 86 genes which have a relative location between 0.16-0.28 appear in red squares, and the rest of the genes are grey circles.

Figure 35B:
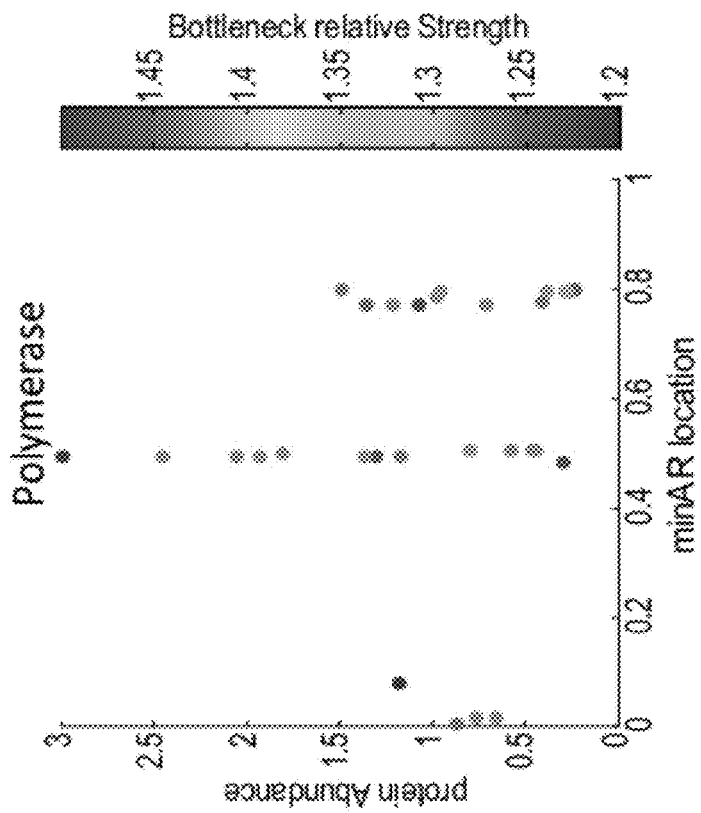
Figure 35A:
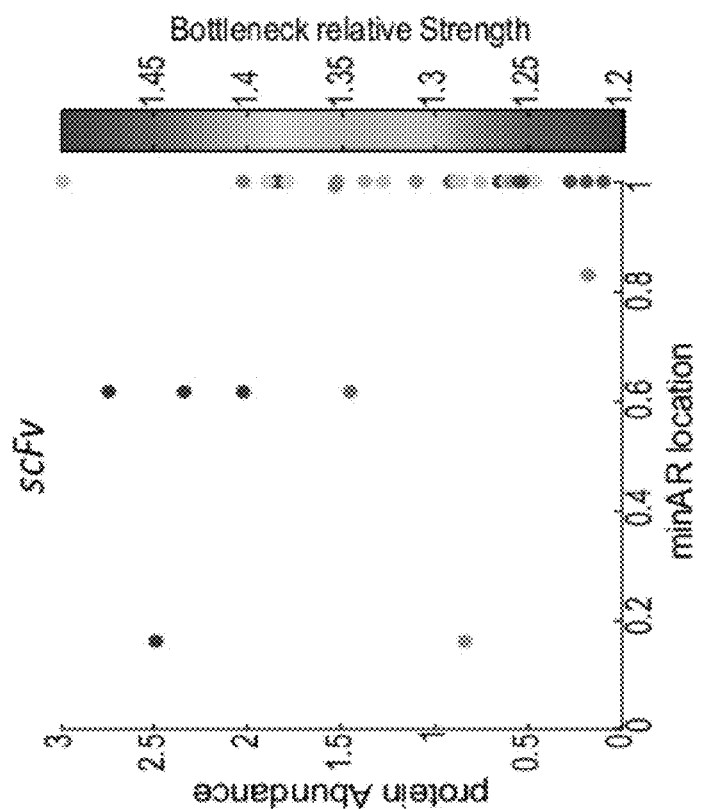

FIGS. 35A-B are plots illustrating protein abundance vs. bottleneck relative location of data from Welch et al. [PLoS One 2009, 4(9):e7002]'s libraries. FIG. 35A plots all the scFv genes and FIG. 35B plots all the Polymerase genes. In both figures the x-axis is the gene's relative location, the Y-axis is the per-cell protein abundance and the color is the gene's relative strength.

Figure 36B:
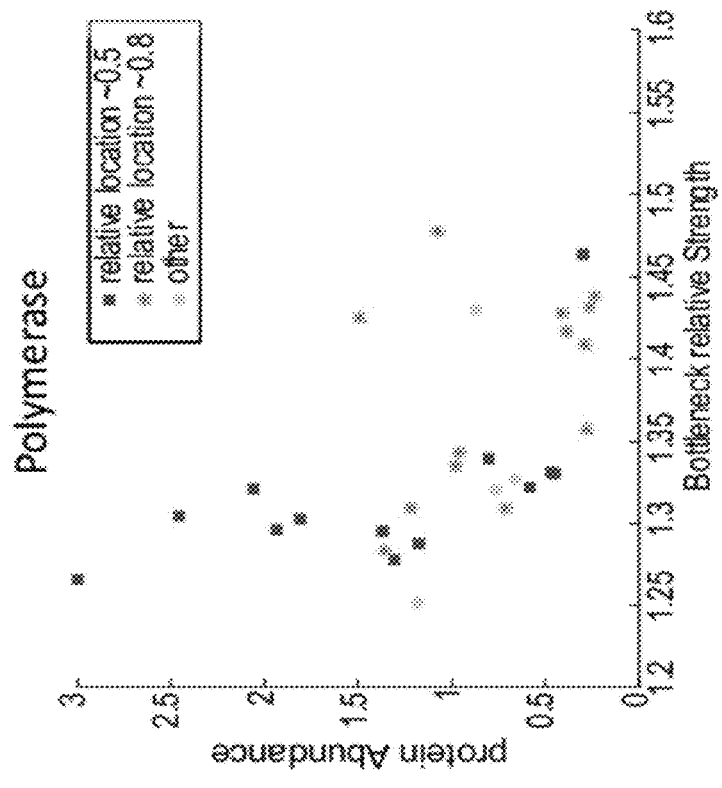
Figure 36A:
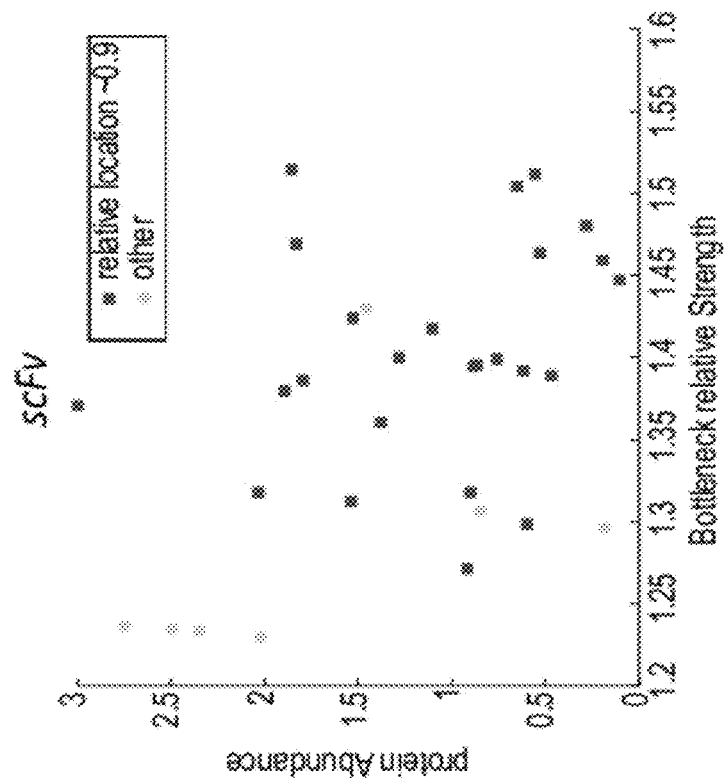

FIGS. 36A-B are plots illustrating protein abundance vs. bottleneck relative strength, data from the scFv and the Polymerase libraries. In FIG. 36A are plotted are all the scFv genes, and in FIG. 36B are all the Polymerase genes. In both figures the x-axis is the gene's relative strength, the Y-axis is the per-cell protein abundance and the color is the gene's relative strength. Genes with different relative locations are marked by different colors (see legend) to show the correlation between the relative strength and the protein abundance for genes with the same bottleneck location.

Figure 37:
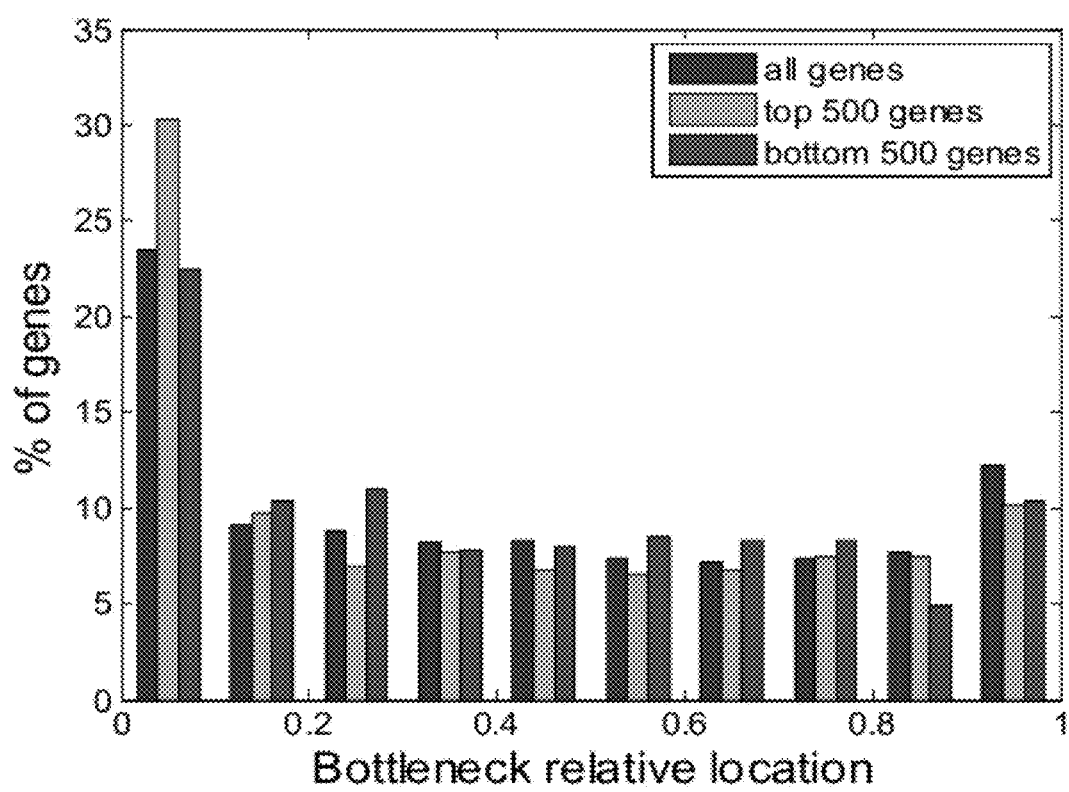

FIG. 37 is a bar graph illustrating the distribution of the bottleneck relative location of the *E. coli* genes. The Figure shows the distribution of the bottleneck relative location for three groups of *E. coli* genes: 1. All genes (blue) 2. Highly expressed genes (green) 3. Lowly expressed genes (red). For all groups only genes longer than 100 codons are shown (This cut-off maintains 90% of the *E. coli* genes). This resulted in 442 highly expressed genes (out of the top 500) and 473 lowly expressed genes (out of the bottom 500).

Figures 38A, 38B, 38C:
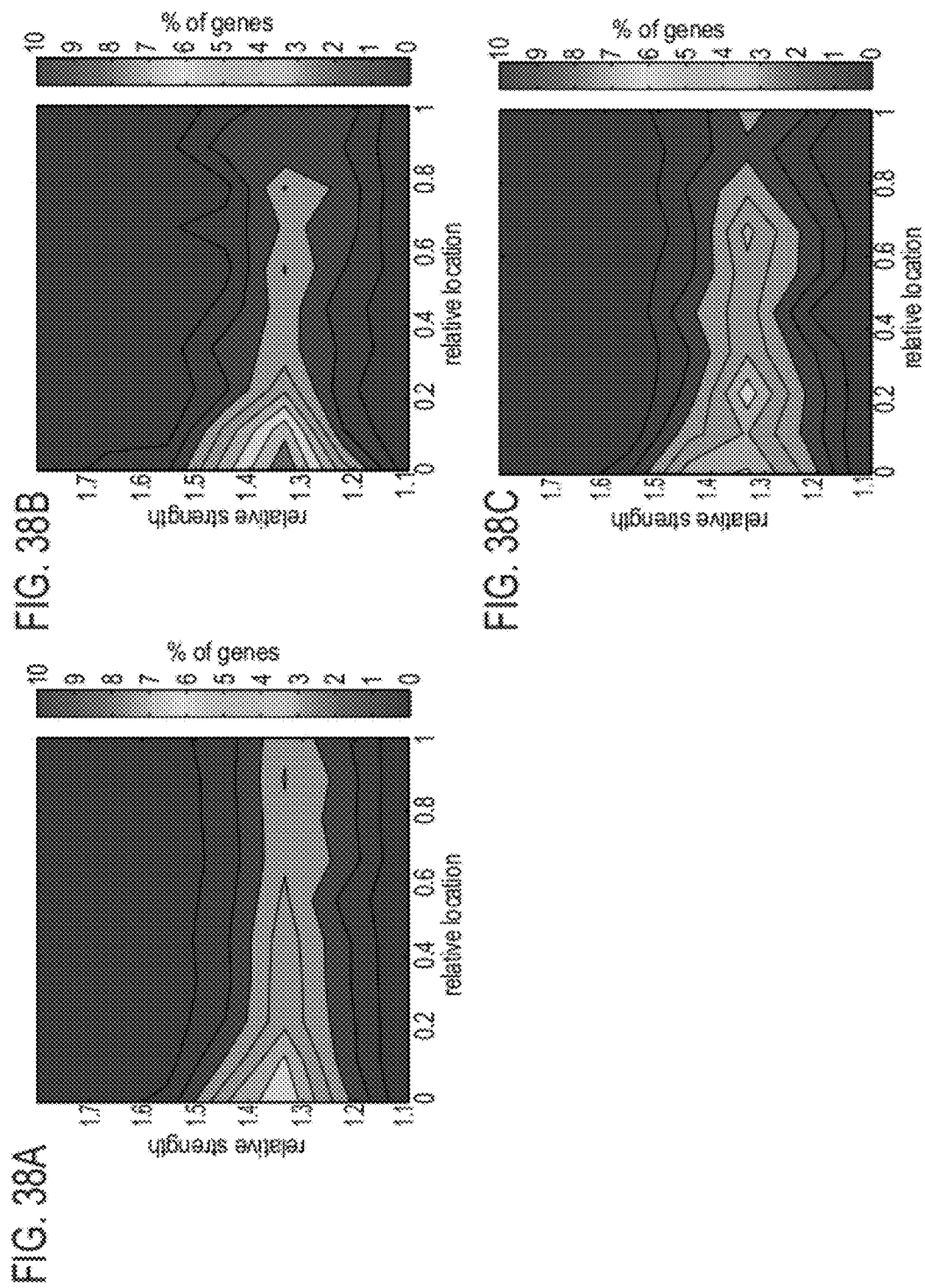

FIGS. 38A-C illustrate the distribution (2D histogram) of the bottleneck of the *E. coli* genes. X-axis is the relative location, Y-axis the relative strength and the color is the % of genes having a bottleneck matching the parameters. FIG. 38A: all *E. coli* genes longer than 100 (well above region size and still maintain 90% of the *E. coli* genes) codons were plotted. FIG. 38B: only the highest expressed genes were plotted. The 500 genes which have the highest transcript levels were chosen and from these the genes with 100 codons or longer were taken, making a total of 442 genes. FIG. 38C: only the lowest expressed genes were plotted. The 500 genes which have the lowest transcript levels were chosen and from these the genes with 100 or longer were taken, making a total of 473 genes.

Figure 39:
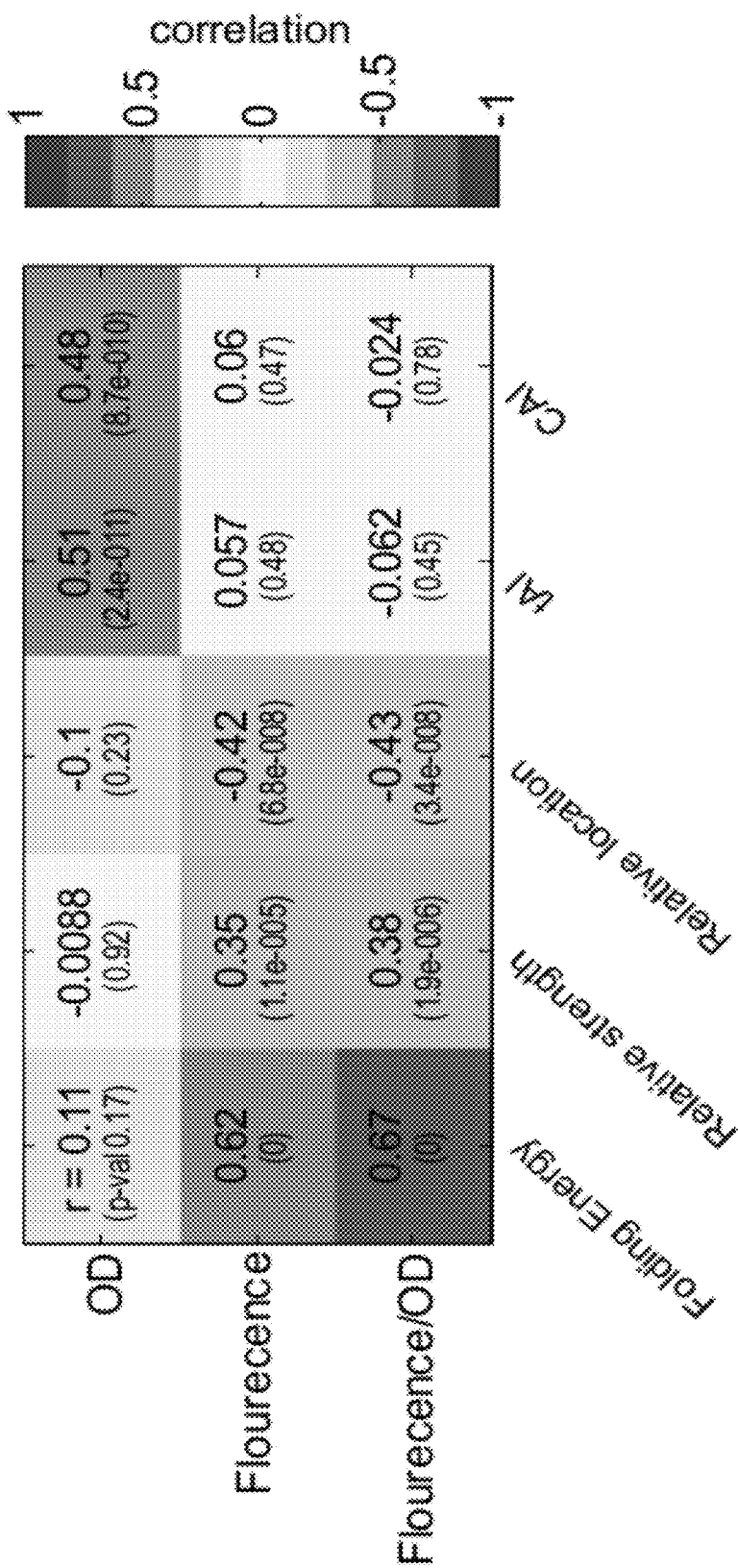

FIG. 39 is a graph illustrating the correlation between the GFP experimental measurement and transcript calculated parameters. In the x-axis there are different parameters that can be calculated from the transcript: folding energy of the initiation site calculated in Kudla et al. Science 2009, 324 (5924):255-258, the bottleneck parameters, the CAI and the tAI. In the y-axis are the OD measurement, the protein abundance and the per-cell protein abundance. The correlation value is indicated by both the color of the box and the number. The correlation p-value is written in the brackets.

Figure 40:
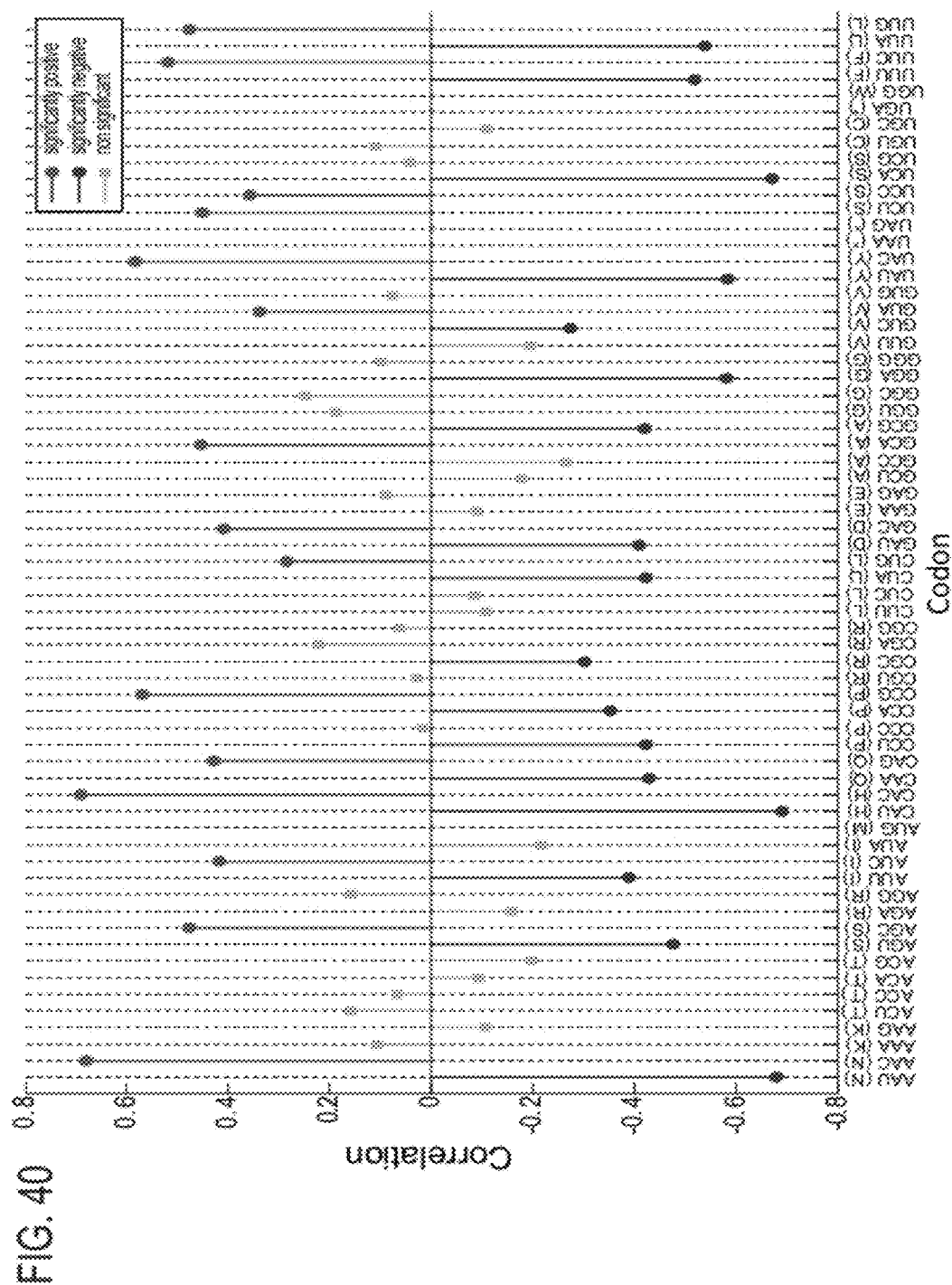

FIG. 40 is a plot illustrating the correlation between the codon usage in a transcript and the fitness. The bar indicates the Pearson correlation value between the codon frequency and the OD. In the x-axis are listed all the codons in the format: "codon (amino acid)". A correlation was determined to be significant if its p-value is below 0.05/61 (i.e. alpha=0.05 was corrected for the number of codons tested).

Red bars are codons for which there is a significantly positive correlation between their appearance and the OD. Blue bar are codons which have a significant negative correlation. For codons with no significant correlation grey squared bars are used. When no bar appears for a codon (for example AUG, UAA . . . ) it means that the usage of that specific codon was constant for all genes thus resulting with no correlation value. For usage of each amino acid in the GFP variant see Table 12 in the Examples section herein below.

Figures 41A, 41B:
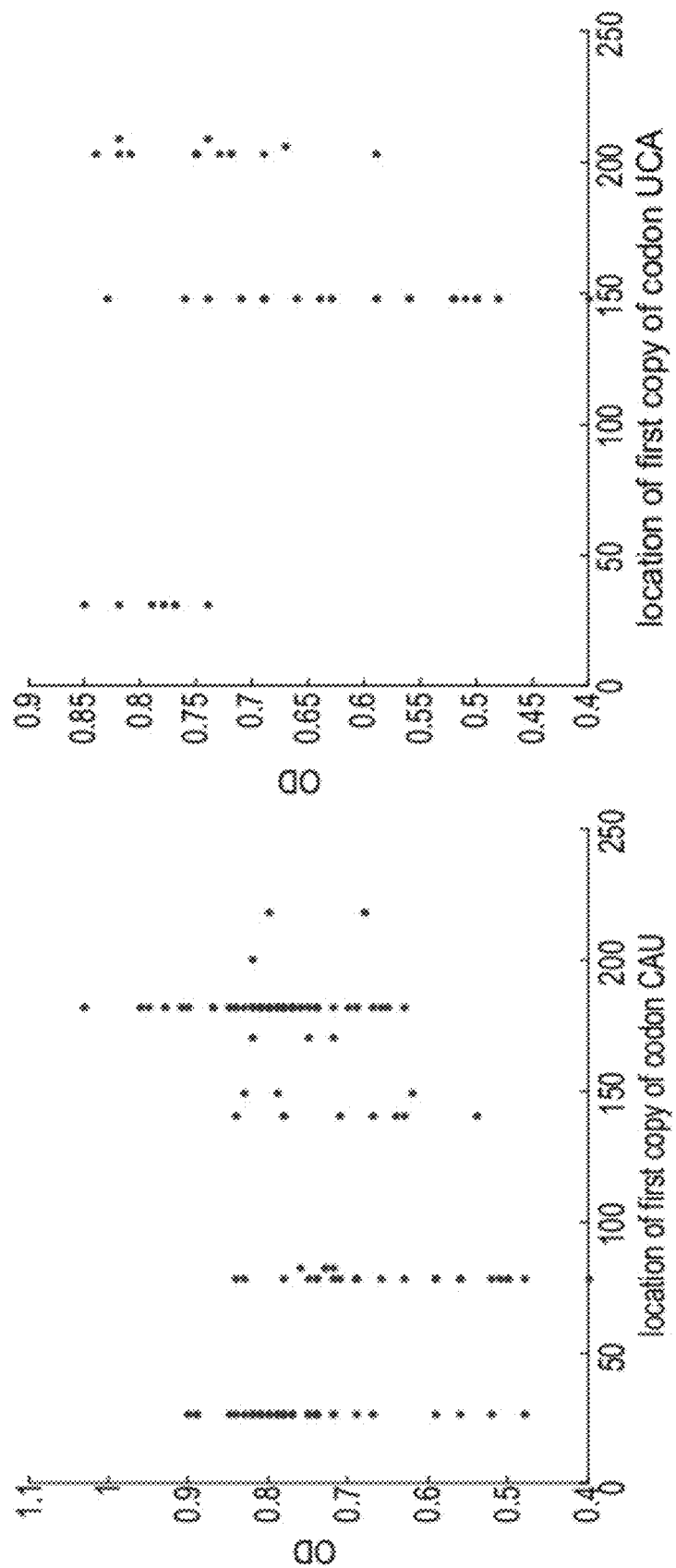

FIGS. 41A-B are plots illustrating the relationship of the location of first copy of a codon vs. the fitness. Each point represents a gene in the GFP library. FIG. 41A, plotted is the location of the first CAU codon for each GFP variant vs. the variants' OD. In FIG. 41B, the location of the first UCA codon in the GFP variants is plotted vs. the variants' OD.

DESCRIPTION OF SPECIFIC EMBODIMENTS OF THE INVENTION

The present invention, in some embodiments thereof, relates to recombinant protein production in heterologous systems.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

One of the most important factors for increasing efficiency of expression of recombinant proteins in heterologous systems is the adaptation of the codon usage of the transcript gene to the typical codon usage of the host. Thus, in the design process of a nucleic acid sequence to be inserted into a new host to express a certain protein in large amounts, codon usage optimization is usually one of the first steps. Up until presently, it was widely believed that if a gene which encodes a recombinant protein contains codons that are rarely used by the host, its expression level will not be maximal. Codon usage optimization basically involves altering the rare codons in the target gene so that they more closely reflect the codon usage of the host without modifying the amino acid sequence of the encoded protein.

So far, studies that gauged translation efficiency have mostly considered the average codon usage over entire genes. Such studies typically did not consider the order at which codons with low and high translation efficiency appear along the transcript. While it was shown before that the extent of codon bias changes along transcripts (8), it was not known whether gene sequences are arranged so as to determine specific levels of speed and accuracy of translation at various positions along transcripts.

The present inventors set out to ascertain whether the order of high efficiency and low efficiency codons along transcripts could govern the process of translation. It was hypothesized that such instructions could affect speed and processivity of translation and also the overall cost of protein production in cells.

Using complex mathematical analyses, the present inventors discovered a universally conserved translation efficiency profile that features low translation efficiency at the first ~30-50 codons of mRNAs. This feature is conserved in species that represent the three domains of life. The present inventors propose that the conserved translation efficiency profile may have been selected for in diverse species as it minimizes ribosome traffic jams and abortions, and as a consequence, the cost of protein expression.

Subsequently, the present inventors examined the effects of codon usage on translation efficiency by re-analysis of previously constructed synthetic expression libraries in *Escherichia coli*. It was shown that obeying the design observed in nature, namely localization of the bottleneck at the beginning of the ORF sequence, indeed promotes higher level of expression. This was especially true if the predicted dwell time of the ribosome at these bottleneck regions was sufficiently long. On the other hand the bottleneck characteristics did not affect the fitness of the host cell.

The present inventors propose exploitation of this naturally-occurring phenomena when performing codon optimization for heterologous gene expression. Specifically, a protein should be optimized in such a way that the translation efficiency at the first 30-50 codons is lower than the translation efficiency at the remaining codons.

Thus, according to one aspect of the present invention there is provided an isolated polynucleotide encoding a polypeptide of a species having a predetermined amino acid sequence, the polynucleotide having been modified so as to generate codons forming a suitable ramp sequence at the 5' end of the polynucleotide for increasing translation efficiency of the polynucleotide in cells of another species.

The phrase "an isolated polynucleotide" refers to a single or double stranded nucleic acid sequence which is isolated and provided in the form of an RNA sequence (i.e. comprising ribonucleotides), a complementary polynucleotide sequence (cDNA), a genomic polynucleotide sequence (i.e. comprising deoxyribonucleotides) and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The polynucleotides of this aspect of the present invention may encode polypeptides that are endogenous or exogenous to the host cell. The polypeptides may be intracellular polypeptides (e.g., a cytosolic protein), transmembrane polypeptides, or secreted polypeptides. Heterologous production of proteins is widely employed in research and industrial settings, for example, for production of therapeutics, vaccines, diagnostics, biofuels, and many other applications of interest. Exemplary therapeutic proteins that can be produced by employing the subject compositions and methods include but are not limited to certain native and recombinant human hormones (e.g., insulin, growth hormone, insulin-like growth factor 1, follicle-stimulating hormone, and chorionic gonadotropin), hematopoietic proteins (e.g., erythropoietin, C-CSF, GM-CSF, and IL-11), thrombotic and hematostatic proteins (e.g., tissue plasminogen activator and activated protein C), immunological proteins (e.g., interleukin), antibodies and other enzymes (e.g., deoxyribonuclease I). Exemplary vaccines that can be produced by the subject compositions and methods include but are not limited to vaccines against various influenza viruses (e.g., types A, B and C and the various serotypes for each type such as H5N2, H1N1, H3N2 for type A influenza viruses), HIV, hepatitis viruses (e.g., hepatitis A, B, C or D), Lyme disease, and human papillomavirus (HPV). Examples of heterologously produced protein diagnostics include but are not limited to secretin, thyroid stimulating hormone (TSH), HIV antigens, and hepatitis C antigens.

Proteins or peptides produced by the heterologous polypeptides can include, but are not limited to cytokines, chemokines, lymphokines, ligands, receptors, hormones, enzymes, antibodies and antibody fragments, and growth factors. Non-limiting examples of receptors include TNF type I receptor, IL-1 receptor type II, IL-1 receptor antagonist, IL-4 receptor and any chemically or genetically modified soluble receptors. Examples of enzymes include acetylycholinesterase, lactase, activated protein C, factor VII, collagenase (e.g., marketed by Advance Biofactures Corporation under the name Santyl); agalsidase-beta (e.g., marketed by Genzyme under the name Fabrazyme); dornase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-beta), interferon gamma (IFN-gamma), interferon gamma inducing factor I (IGIF), transforming growth factor beta (IGF-beta), RANTES (regulated upon activation, normal T-cell expressed and presumably secreted), macrophage inflammatory proteins (e.g., MIP-1-alpha and MIP-1-beta), Leishmnania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF alpha type II receptor, erythropoietin (EPO), insulin and soluble glycoproteins e.g., gp120 and gp160 glycoproteins. The gp120 glycoprotein is a human immunodeficiency virus (WIV) envelope protein, and the gp160 glycoprotein is a known precursor to the gp120 glycoprotein. Other examples include secretin, nesiritide (human B-type natriuretic peptide (hBNP)) and GYP-I.

Other heterologous products may include GPCRs, including, but not limited to Class A Rhodopsin like receptors such as Muscatinic (Muse.) acetylcholine Vertebrate type 1, Musc. acetylcholine Vertebrate type 2, Musc. acetylcholine Vertebrate type 3, Musc. acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykffin, C5a anaphylatoxin, Finet-leu-phe, APJ like, Interleukin-8 type A, Interleukin-8 type B, Interleukin-8 type others, C-C Chemokine type 1 through type 11 and other types, C-X-C Chemokine (types 2 through 6 and others), C—X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR10), Neuropeptide Y (type 1 through 7), Neuropeptide Y, Neuropeptide Y other, Neurotensin, Opioid (type D, K, M, X), Somatostatin (type 1 through 5), Tachykinin (Substance P(NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF, QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory 11 fam 1 through 13), Prostaglandin (prostaglandin E2 subtype EP 1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,11 GPR91, Purinoceptor P2RY5,8,9,10 GPR35,92,174, Purinoceptor P2RY12-14 GPR87 (JDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40, GP41, GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (TiR), Class D Fungal pheromone, Fungal pheromone A-Factor like (STE2, STE3), Fungal pheromone B like (BAR,BBR,RCB,PRA), Class E cAMP receptors, Ocular albinism proteins, Frizzled/Smoothened family, frizzled Group A (Fz 1&2&4&5&7-9), frizzled Group B (Fz 3 & 6), fizzled Group C (other), Vomeronasal receptors, Nematode chemoreceptors, Insect odorant receptors, and Class Z Archaeal/bacterial/fungal opsins.

Bioactive peptides may also be produced by the heterologous sequences of the present invention. Examples include: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleulin, denileukin diftitox, interferon alfa-n3 (injection), interferon alfa-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphnmate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10_(autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HW vaccine (oral), HPV vaccine, Tat Toxoid, YSPSL, CHS-13340, PTH(1-34) liposomal cream (Novasome), Ostabolin-C, PTH analog (topical, psoriasis), MBR1-93.02, MTB72F vaccine (tuberculosis), MVA-Ag85A vaccine (tuberculosis), FARA04, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, P1A, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S. pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH (1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In certain embodiments, the heterologously produced protein is an enzyme or biologically active fragments thereof. Suitable enzymes include but are not limited to: oxidoreductases, transferases, hydrolases, lyases, isomerases, and ligases. In certain embodiments, the heterologously produced protein is an enzyme of Enzyme Commission (EC) class 1, for example an enzyme from any of EC 1.1 through 1.21, or 1.97. The enzyme can also be an enzyme from EC class 2, 3, 4, 5, or 6. For example, the enzyme can be selected from any of EC 2.1 through 2.9, EC 3.1 to 3.13, EC 4.1 to 4.6, EC 4.99, EC 5.1 to 5.11, EC 5.99, or EC 6.1-6.6.

As used herein, the term "antibody" refers to a substantially intact antibody molecule.

As used herein, the phrase "antibody fragment" refers to a functional fragment of an antibody (such as Fab, F(ab')2, Fv or single domain molecules such as VH and VL) that is capable of binding to an epitope of an antigen.

According to one embodiment, the polypeptides are derived from a mammalian species for example human polypeptides.

According to one embodiment, the 5' end of the polynucleotides of the present invention are modified so as to increase translation efficiency of the polynucleotide in heterologous cells.

As used herein, the qualifier "heterologous" when relating to heterologous cells indicates that the species from which the cells are derived is not the same as the species of the polypeptide. For example, when the polypeptide has a human amino acid sequence, the cells in which it is expressed are non-human. Thus heterologous cells for the expression of human polypeptides include, but are not limited to bacterial cells (e.g. E. coli), fungal cells (e.g. S. cerevisiae cells), plant cells (e.g. tobacco), insect cells (lepidopteran cells) and other mammalian cells (Chinese Hamster Ovary cells).

The cells may be part of a cell culture, a whole organism, or a part of an organism.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantee, in particular monocotyledonous and dicotyledonous plants including a fodder or forage legume, ornamental plant, food crop, tree, or shrub. Algae and other non-Viridiplantae can also be used for the methods of the present invention.

Contemplated cells for the expression of human interferon beta 1a include for example Chinese Hamster Ovary (CHO) cells.

Contemplated cells for the expression of human interferon beta 1b include for example E. coli cells.

Contemplated cells for the expression of human interferon gamma include for example E. coli cells.

Contemplated cells for the expression of human growth hormone include for example E. coli cells.

Contemplated cells for the expression of human insulin include for example E. coli cells.

Contemplated cells for the expression of interleukin II include for example E. coli cells.

Contemplated cells for the expression of follicle stimulating hormone include for example CHO cells.

The translation efficiency of a polynucleotide is reflected by the amount of recombinant protein expressed therefrom, per cell over a fixed length of time, and/or by the viability of the producing cells. Thus, the translation efficiency may be increased if the modified polynucleotide serves to increase the amount of protein expressed from the cell and/or serves to increase viability of a cell.

The translation efficiency profile of a polynucleotide is defined, for each codon position, as the estimated availability of the tRNAs that participate in translating that codon. The profile is high at codons that correspond to abundant tRNAs and low at codons that correspond to rare tRNAs. According to one embodiment, the tRNA-adaptation index (tAI) is used to evaluate translation efficiency (see Examples section herein below) at each codon. The tAI measure of a polynucleotide may be defined as the (geometric) average of tRNA availability values over all the codons in the gene (see Examples section herein below). For each codon, the tAI considers the availability of the tRNA with the perfectly matched anti-codon along with weighted contributions from imperfect codon-anticodon pairs, reflecting wobble interactions.

In order to form a suitable ramp at the 5' end of a particular polynucleotide, the codon usage for the first 30-50 amino acids should be selected such that the average rate of translation is at least 1.3, 1.5, 1.7, 2, 2.25 or even 2.5 times slower at the ramp compared to the rest of the polynucleotide. Thus, the nucleic acid sequence of the ramp sequence is selected such that during expression, ribosome progression is retarded at the 5' end of the polynucleotide (e.g. mRNA) or 5' end of an mRNA transcribed from a DNA polynucleotide, as compared to the polynucleotide lacking the modification.

It will be appreciated that the nucleic acid sequence of the ramp is restricted such that the amino acid sequence of the encoded polypeptide is not altered. Accordingly, the exact position and length of the ramp will vary for each polynucleotide.

The modifications to the polynucleotides of the present invention are also limited in that they should minimize the effect on the folding free energy of the mRNA secondary structure. According to one embodiment the change in folding free energy is no more than 20%, no more than 10% and even no more than 5%. Methods of analyzing secondary structure of mRNAs include the M-fold (Ref PMID: 12824337) and the Vienna package algorithms (Ref: PMID: 1282434).

Selection of the nucleic acid sequence of the ramp sequence is determined partly based on the nucleic acid sequence of the remaining section of the polynucleotide. Thus for example if there are regions (e.g. 21 nucleotide regions) in the polynucleotide which are slow (i.e. have a low average tAI), then the nucleic acid sequence of the ramp is selected such that it is even slower, thus becoming the slowest region (i.e. has the lowest average tAI) in the entire polynucleotide sequence, in order to prevent ribosome jamming past the ramp point.

As mentioned, the ramp sequence typically does not retard expression by more than 2.5 fold and no less than 1.3 fold compared to the rest of the polynucleotide. Accordingly, the nucleic acid sequence of the ramp sequence does not have to be adjusted such that the codons have the minimum tAI (which may be stressful for the cell) but some mid value as long as the relative speed is within the set parameters.

The 5' end of the naturally-occurring or native polypeptide-encoding nucleotide sequence may already, in advance of any modification, contain a number of codons that correspond to a statistically, non-favored codon in a particular species—i.e. codons that correspond to low abundance tRNAs. Therefore, codon "deoptimization" of the 5' end of the native polypeptide encoding nucleotide sequence may comprise determining which codons, within the native polypeptide-encoding nucleotide sequence, correspond to a high abundance tRNA, and modifying these codons in accordance with the codon usage Tables 1-3 provided herein below to produce a codon "deoptimized" derivative.

The phrase "codon deoptimization" refers to the selection of appropriate DNA nucleotides for use within a structural gene or fragment thereof such that the generated codons correspond to low abundance tRNAs within a particular organism. It will be appreciated that the present invention that the codon deoptimization envisaged by the present invention serves to optimize efficiency of polypeptide expression.

The first 30-50 codons of the nucleotide sequence encoding the polypeptide may be comprised, 100 percent, of species non-preferred codon sequences, while encoding a polypeptide with the same amino acid sequence as that produced by the native polypeptide coding sequence. Alternatively, the first 30-50 codons of the modified nucleotide sequence encoding the polypeptide may only be partially comprised of species preferred codon sequences with remaining codons retaining nucleotide sequences derived from the native polypeptide coding sequence. The modified nucleotide sequence may be fully or partially "deoptimized" for species codon usage provided that the protein encoded by the modified nucleotide sequence is produced at a level higher than the protein encoded by the corresponding naturally occurring or native gene. For example, the first 30-50 codons of the modified polynucleotide sequence may comprise from about 60% to about 100% codons deoptimized for species expression. As another example, the first 30-50 codons of the modified polynucleotide sequence may comprise from 90% to 100% of codons "deoptimized" for species expression.

It will be appreciated that during codon "deoptimization" other modifications may be made to the polynucleotide sequence to enhance the efficiency of protein translation. Thus, for example one or more more-favored codons may be selected to delete existing ribosome attenuating sites or delete "restriction enzyme sites to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

Below are tables of all codons ranked according to their efficiency (base on the tAI values), higher rank=higher tAI value=more efficient→less preferred in the ramp for three cellular systems.

TABLE 1

Estimated CHO tRNAs (based on the mouse tRNA)

| rank | Amino-acid | Codon |
|------|------------|-------|
| 1 | 'C' | 'TGC' |
| 2 | 'C' | 'TGT' |
| 3 | 'K' | 'AAG' |
| 4 | 'M' | 'ATG' |
| 5 | 'A' | 'GCT' |
| 6 | 'D' | 'GAC' |
| 7 | 'E' | 'GAG' |
| 8 | 'G' | 'GGC' |
| 9 | 'N' | 'AAC' |
| 10 | 'A' | 'GCC' |
| 11 | 'A' | 'GCG' |
| 12 | 'V' | 'GTG' |

TABLE 1-continued

Estimated CHO tRNAs (based on the mouse tRNA)

| rank | Amino-acid | Codon |
|---|---|---|
| 13 | 'Q' | 'CAG' |
| 14 | 'I' | 'ATT' |
| 15 | 'A' | 'GCA' |
| 16 | 'K' | 'AAA' |
| 17 | 'L' | 'CTG' |
| 18 | 'Y' | 'TAC' |
| 19 | 'H' | 'CAC' |
| 20 | 'S' | 'TCT' |
| 21 | 'D' | 'GAT' |
| 22 | 'G' | 'GGT' |
| 23 | 'G' | 'GGG' |
| 24 | 'T' | 'ACT' |
| 25 | 'I' | 'ATC' |
| 26 | 'V' | 'GTT' |
| 27 | 'N' | 'AAT' |
| 28 | 'P' | 'CCA' |
| 29 | 'W' | 'TGG' |
| 30 | 'L' | 'CTT' |
| 31 | 'S' | 'AGC' |
| 32 | 'E' | 'GAA' |
| 33 | 'S' | 'TCC' |
| 34 | 'G' | 'GGA' |
| 35 | 'F' | 'TTC' |
| 36 | 'P' | 'CCT' |
| 37 | 'V' | 'GTC' |
| 38 | 'R' | 'AGG' |
| 39 | 'T' | 'ACC' |
| 40 | 'T' | 'ACG' |
| 41 | 'Q' | 'CAA' |
| 42 | 'R' | 'CGT' |
| 43 | 'Y' | 'TAT' |
| 44 | 'H' | 'CAT' |
| 45 | 'L' | 'CTC' |
| 46 | 'P' | 'CCG' |
| 47 | 'L' | 'TTG' |
| 48 | 'P' | 'CCC' |
| 49 | 'I' | 'ATA' |
| 50 | 'R' | 'CGA' |
| 51 | 'R' | 'AGA' |
| 52 | 'S' | 'AGT' |
| 53 | 'R' | 'CGG' |
| 54 | 'R' | 'CGC' |
| 55 | 'F' | 'TTT' |
| 56 | 'T' | 'ACA' |
| 57 | 'L' | 'TTA' |
| 58 | 'S' | 'TCG' |
| 59 | 'S' | 'TCA' |
| 60 | 'L' | 'CTA' |
| 61 | 'V' | 'GTA' |

TABLE 2

Estimated E. coli tRNAs

| rank | Amino-acid | Codon |
|---|---|---|
| 1 | 'M' | 'ATG' |
| 2 | 'K' | 'AAA' |
| 3 | 'V' | 'GTA' |
| 4 | 'L' | 'CTG' |
| 5 | 'R' | 'CGT' |
| 6 | 'N' | 'AAC' |
| 7 | 'E' | 'GAA' |
| 8 | 'G' | 'GGC' |
| 9 | 'Y' | 'TAC' |
| 10 | 'I' | 'ATC' |
| 11 | 'A' | 'GCA' |
| 12 | 'D' | 'GAC' |
| 13 | 'R' | 'CGC' |
| 14 | 'Q' | 'CAG' |
| 15 | 'T' | 'ACG' |
| 16 | 'F' | 'TTC' |
| 17 | 'S' | 'TCC' |

TABLE 2-continued

Estimated E. coli tRNAs

| rank | Amino-acid | Codon |
|---|---|---|
| 18 | 'Q' | 'CAA' |
| 19 | 'T' | 'ACC' |
| 20 | 'V' | 'GTC' |
| 21 | 'A' | 'GCC' |
| 22 | 'K' | 'AAG' |
| 23 | 'N' | 'AAT' |
| 24 | 'G' | 'GGT' |
| 25 | 'V' | 'GTG' |
| 26 | 'L' | 'TTG' |
| 27 | 'S' | 'TCG' |
| 28 | 'Y' | 'TAT' |
| 29 | 'P' | 'CCG' |
| 30 | 'I' | 'ATT' |
| 31 | 'R' | 'AGG' |
| 32 | 'D' | 'GAT' |
| 33 | 'G' | 'GGG' |
| 34 | 'E' | 'GAG' |
| 35 | 'L' | 'TTA' |
| 36 | 'S' | 'TCA' |
| 37 | 'C' | 'TGC' |
| 38 | 'W' | 'TGG' |
| 39 | 'L' | 'CTC' |
| 40 | 'L' | 'CTA' |
| 41 | 'P' | 'CCC' |
| 42 | 'P' | 'CCA' |
| 43 | 'H' | 'CAC' |
| 44 | 'R' | 'CGG' |
| 45 | 'T' | 'ACA' |
| 46 | 'S' | 'AGC' |
| 47 | 'R' | 'AGA' |
| 48 | 'G' | 'GGA' |
| 49 | 'A' | 'GCG' |
| 50 | 'F' | 'TTT' |
| 51 | 'S' | 'TCT' |
| 52 | 'T' | 'ACT' |
| 53 | 'V' | 'GTT' |
| 54 | 'A' | 'GCT' |
| 55 | 'R' | 'CGA' |
| 56 | 'C' | 'TGT' |
| 57 | 'L' | 'CTT' |
| 58 | 'P' | 'CCT' |
| 59 | 'H' | 'CAT' |
| 60 | 'S' | 'AGT' |
| 61 | 'I' | 'ATA' |

TABLE 3

Estimated Yeast (S. cerevisiae)

| rank | Amino-acid | Codon |
|---|---|---|
| 1 | 'K' | 'AAG' |
| 2 | 'D' | 'GAC' |
| 3 | 'G' | 'GGC' |
| 4 | 'V' | 'GTT' |
| 5 | 'E' | 'GAA' |
| 6 | 'I' | 'ATT' |
| 7 | 'L' | 'TTG' |
| 8 | 'S' | 'TCT' |
| 9 | 'T' | 'ACT' |
| 10 | 'R' | 'AGA' |
| 11 | 'A' | 'GCT' |
| 12 | 'M' | 'ATG' |
| 13 | 'P' | 'CCA' |
| 14 | 'V' | 'GTC' |
| 15 | 'F' | 'TTC' |
| 16 | 'N' | 'AAC' |
| 17 | 'I' | 'ATC' |
| 18 | 'Q' | 'CAA' |
| 19 | 'Y' | 'TAC' |
| 20 | 'S' | 'TCC' |
| 21 | 'T' | 'ACC' |
| 22 | 'A' | 'GCC' |

TABLE 3-continued

Estimated Yeast (*S. cerevisiae*)

| rank | Amino-acid | Codon |
|---|---|---|
| 23 | 'A' | 'GCA' |
| 24 | 'D' | 'GAT' |
| 25 | 'G' | 'GGT' |
| 26 | 'L' | 'TTA' |
| 27 | 'H' | 'CAC' |
| 28 | 'K' | 'AAA' |
| 29 | 'E' | 'GAG' |
| 30 | 'T' | 'ACA' |
| 31 | 'W' | 'TGG' |
| 32 | 'R' | 'CGT' |
| 33 | 'S' | 'TCA' |
| 34 | 'V' | 'GTA' |
| 35 | 'I' | 'ATA' |
| 36 | 'R' | 'AGG' |
| 37 | 'F' | 'TTT' |
| 38 | 'N' | 'AAT' |
| 39 | 'R' | 'CGC' |
| 40 | 'C' | 'TGC' |
| 41 | 'Q' | 'CAG' |
| 42 | 'Y' | 'TAT' |
| 43 | 'P' | 'CCG' |
| 44 | 'H' | 'CAT' |
| 45 | 'L' | 'CTA' |
| 46 | 'G' | 'GGA' |
| 47 | 'G' | 'GGG' |
| 48 | 'V' | 'GTG' |
| 49 | 'T' | 'ACG' |
| 50 | 'P' | 'CCT' |
| 51 | 'S' | 'AGC' |
| 52 | 'S' | 'TCG' |
| 53 | 'C' | 'TGT' |
| 54 | 'A' | 'GCG' |
| 55 | 'P' | 'CCC' |
| 56 | 'R' | 'CGA' |
| 57 | 'L' | 'CTC' |
| 58 | 'R' | 'CGG' |
| 59 | 'L' | 'CTG' |
| 60 | 'S' | 'AGT' |
| 61 | 'L' | 'CTT' |

Generation of similar tables for additional species is well within the capacity of one of skill in the art and is based on the tRNA repertoire of that species. Such information for fully sequenced species is available in public databases (www dotlowelabdotucscdotedu/GtRNAdb/). If a species is not fully sequenced tables of the closest available species may be used.

Below is an exemplary method for determining a ramp sequence for a given polynucleotide which encodes a polypeptide:

1. Average the gene with a moving average (e.g. 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides).
2. Look for the potential of the gene: the maximum tAI value of each codon and the minimum one.
    a. Identify a region at the beginning of the gene that has potentially very slow codons.
3. Change the codons in the chosen region so:
    a. The slowest region will be the current chosen region and not the genes original region
    b. The relative time of the region will be slower than the relative time of the gene ~1.6
    c. Other slow regions will be significantly faster than the ramp region.

According to one embodiment, the nucleic acid sequence of the ramp region is non-modified and the nucleic acid sequence of the remaining polynucleotide is modified for optimal codon usage compared to the polynucleotide sequence in the ramp. In that way the relative speed of the ribosome is slower at the ramp region of the polynucleotide compared with the non-ramp region of the polynucleotide.

According to another embodiment, the nucleic acid sequence of the ramp region is modified for codon "deoptimization" and the nucleic acid sequence of the non-ramp region is modified for codon optimization.

According to another embodiment, the nucleic acid sequence of the ramp region is modified for codon "deoptimization" and the nucleic acid sequence of the non-ramp region is not modified.

The phrase "codon optimization" refers to the selection of appropriate DNA nucleotides for use within a structural gene or fragment thereof that approaches codon usage within a particular organism. Therefore, an optimized gene or nucleic acid sequence refers to a gene in which the nucleotide sequence of a native or naturally occurring gene has been modified in order to utilize statistically-preferred or statistically-favored codons within an organism. The nucleotide sequence typically is examined at the DNA level and the coding region optimized for expression in a particular organism determined using any suitable procedure.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (www dotkazusa dotor dotjp/codon/). The Codon Usage Database contains codon usage tables for a number of different species, with each codon usage table having been statistically determined based on the data present in Genbank.

By using such tables to determine the most preferred or most favored codons for each amino acid in a particular species, a naturally-occurring nucleotide sequence encoding a protein of interest can be codon optimized for that particular species. This is affected by replacing codons that may have a low statistical incidence in the particular species genome with corresponding codons, in regard to an amino acid, that are statistically more favored.

It will be appreciated that other modifications are also envisaged by the present inventors down-stream from the ramp that attenuate the ribosome to ensure free flow from that point on.

According to one embodiment, the polynucleotide of the present invention encodes a polypeptide that comprises a signal peptide.

Preferably the codon usage in the signal peptide is deoptimized, as further described herein above.

As used herein, the phrase "signal peptide" refers to a peptide linked in frame to the amino terminus of a polypeptide and directs the encoded polypeptide into a cell's secretory pathway.

According to one embodiment, the polypeptide encodes a signal peptide having a native sequence as set forth in SEQ ID NO: 1.

An exemplary signal peptide sequence suitable for high expression of a polypeptide in Chinese Hampster Ovary cells is set forth in SEQ ID NOs: 2-7.

Exemplary sequences of human low density lipoprotein receptor (LDLR) polypeptide modified according to the teachings of the present invention are provided in NOs: 8-20.

According to another embodiment, the 3' terminus of the polynucleotide encodes a histidine tag. It will be appreciated that in order to avoid a ramp sequence at the 3' terminus of the gene, the codon used for histidine should not be a deoptimized codon sequence. Thus, for example, in the case of bacteria, the codon used for histidine tag should not be CAU, but rather CAC.

In order to express the polypeptides from the polynucleotides of the present invention in heterologous cell systems, the polynucleotides are ligated into nucleic acid expression vectors, such that the polynucleotide sequence is under the transcriptional control of a cis-regulatory sequence (e.g., promoter sequence).

As mentioned a variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Constitutive promoters suitable for use with this embodiment of the present invention include sequences which are functional (i.e., capable of directing transcription) under most environmental conditions and most types of cells such as the cytomegalovirus (CMV) and Rous sarcoma virus (RSV).

Inducible promoters suitable for use with this embodiment of the present invention include for example the tetracycline-inducible promoter (Srour, M. A., et al., 2003. Thromb. Haemost. 90: 398-405) or IPTG.

The expression vector according to this embodiment of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression vector in order to increase the translation efficiency of a polypeptide expressed from the expression vector of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Expression vectors containing regulatory elements from eukaryotic viruses such as retroviruses can also be used by the present invention. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the $^{35}$S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

It is expected that during the life of a patent maturing from this application many relevant recombinant proteins will be developed and the scope of the term polypeptide is intended to include all such polypeptides a priori.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Data Sources of Information: The tRNA copy numbers and the coding sequences of the nine yeasts were downloaded from the work of Man and Pilpel (5). The tRNA copy number of the other organisms were downloaded from the Genomic tRNA Database (lowelabdotucscdotedu/GtRNAdb/) (27). The coding sequences of the fly and the worm were downloaded from BioMart (28) on August 2008; the coding sequences of other eukaryotes were downloaded from NCBI on May 2009. The coding regions of all the archaea and bacteria were downloaded from NCBI (wwwdotncbidotnlm-dotnihdotgov/Ftp/) on August 2008. The mRNA levels and protein abundance was downloaded from the work of Ghaem-maghami (23).

Per nucleotide ribosome density of 1525 genes was obtained from the work of Ingolia et al. (1); when density was compared to speed (tAI) or simulated density the same set of genes was used as in (1).

Version of GFP protein with synthetic random codon bias and corresponding measurements of growth rate (OD) were obtained from the work of Kudla et al. (22). Information about the length of the eukaryotic/prokaryotic ribosome footprinted mRNA segment was downloaded from BioNumbers (www dotbionumbersdothmsdotharvarddotedu/). The lists of ribosomal proteins were downloaded from (29).

Computing tAI, AAtAI: This subsection will briefly describe the different measures for translation efficiency used in this work. Two measures for translation efficiency were used: tAI and AAtAI. As explained below, the latter was used as a control for a potential amino acid sequence bias.

The tAI: The tAI was computed in a similar way to the way it was computed in the work of dos Reis et al. (4). This measure gauges the availability of tRNAs for each codon along an mRNA. As codon-anti-codon coupling is not unique due to wobble interactions, several anti-codons can recognize the same codon, with different efficiency weights (see Reis et al. for all the relations between codon—anti-codons).

Let $n_i$ be the number of tRNA isoacceptors recognizing codon i. Let $tCGN_{ij}$ be the copy number of the jth tRNA that recognizes the ith codon, and let $S_{ij}$ be the selective constraint on the efficiency of the codon-anticodon coupling. The absolute adaptiveness, $W_i$, for each codon i may be defined as:

$$W_i = \sum_{j=1}^{n_i} (1 - S_{ij}) tCGN_{ij} \quad \text{(Eq. 1a)}$$

From $W_i$ $w_i$ may be obtained, which is the relative adaptiveness value of codon i by normalizing the $W_i$'s values (dividing them by the maximal of all 61$W_i$).

$$w_i = W_i/(\max W_i), \quad \text{(Eq. 1b)}$$

The final tAI of a gene, g, is the following geometric mean:

$$tAIg = \left( \prod_{k=1}^{lg} w_{i_{kg}} \right)^{1/lg} \quad \text{(Eq. 2)}$$

Where $i_{kg}$ is the codon defined by the k'th triplet on gene g; and lg is the length of the gene (excluding stop codons).

One change was made compared to the computations of Reis et al.; the $S_{ij}$-values were re-inferred by performing hill-climbing optimization of the Spearman correlation between protein abundance and translation efficiency in S. cerevisae. For this purpose protein abundance measurements of Ghaem-maghami et al. (23) were used. The $S_{ij}$-values can be organized in a vector (S-vector) as described in (4); each component in this vector is related to one wobble nucleoside-nucleoside paring: I:U, G:U, G:C, I:C, U:A, I:A, etc. The final S-vector obtained by our optimization was [0 0 0 0 0.561 0.28 0.9999 0.68 0.89].

The AAtAI:

The Amino Acid tAI (AAtAI) was computed similarly to the tAI. The only change is that each $w_i$ is obtained from $W_i$ by dividing it by the maximal $W_i$ of all codons coding the same Amino Acid that codon i codes for. Thus, the AAtAI reflects normalization by the maximal possible tAI of a given protein sequence.

Computing Local tAI, and AAtAI: In the case of the tAI, the local profile of a gene was defined as the vector of the tAI values assigned to the gene's codons (omitting the first ATG), i.e.:

$$\text{Local\_tAI}_{Gene_i} = (tAI_{c_2}, tAI_{c_3}, \ldots, tAI_{c_n})$$

where $c_i$ is the codon at position i in the gene ($c_n$ is the codon before the stop codon).

For a particular species, all the genes in the genome were lined up once according to their start codon, and once according to their stop codon, and averaged head and tail profiles were calculated as:

$$\overline{\text{Local\_tAI}_{start}} = (\overline{tAI_2}, \overline{tAI_3}, \overline{tAI_4}, \ldots)$$

$$\overline{\text{Local\_tAI}_{end}} = (\overline{tAI_n}, \overline{tAI_{n-1}}, \overline{tAI_{n-2}}, \ldots)$$

where:

$$\overline{tAI_i} = \sum_{Genes_i} tAI_{c_i} / |Genes_i|$$

and $Genes_i$ is the number of genes with at least i+1 codons. The local values for AAtAI were computed in a similar way—the present inventors considered AAtAI of codons instead of codons' tAI.

Profiles of AAtAI describe tAI after controlling for amino acid bias. Thus, these profiles were expected to be similar to the profiles of the tAI if indeed the observed tAI profile is related to translation efficiency and not amino-acid bias.

Randomized profiles of translation efficiency: To verify that the observed translation efficiency profile is not a result of the fact that the genes were registered by the start/stop codon, the following control was performed:

Each coding sequence was randomly shuffled, and the average genome profile was calculated. This process was repeated 100 times. The mean and standard deviation of the 100 sets of profile was then calculated for each position. The randomized profiles were compared to the original profile.

Simulation of Ribosomal Movement: To explore the movement of ribosomes along the mRNA sequences a simulation was used, based on the model of Zhang et al. (14) (see FIG. 22). By this model, a single codon translation time is determined per ribosome by the translation time of that codon (i.e. the tAI of the codon) and the potential presence of a ribosome in front of it: if there is no ribosome in front of the given ribosome its velocity is solely governed by the translation efficiency profile, yet to maintain a required minimal distance between the subsequent ribosomes, if there is a ribosome in front of the given one, it was delayed until the ribosome in front of it has proceeded on. Other parameters of the simulations are: The minimum distance between two consecutive ribosomes, the ribosome binding time, and the termination time—the time required for the ribosome to release the mRNA.

Measurement of the tRNA Pool in S. cerevisiae: logarithmic culture ($2.5 \times 10^6$ cells/ml) of S. cerevisae cells (Strain 4741: MATa; his3Δ1; leu2Δ0; met15Δ0; ura3Δ0) was grown on YPD medium (2% yeast extract, 1% peptone, 1% dextrose) at 30° C. until reaching stationary phase. During growth glucose concentration in the media was measured using UV test kit (Boehringer Mannheim catalog number 716251) and the diauxic shift was identify. At 1.5 hours intervals during growth, samples were taken and frozen in liquid nitrogen. RNA was extracted using MasterPure™ (EPICENTER Biotechnologies), and hybridize to tRNA microarray as described in (30-32). Briefly, the basic protocol consists of four steps starting from total RNA: (i) deacylation to remove remaining amino acids attached to the tRNA, (ii) selective Cy3/Cy5 labeling of tRNA, (iii) hybridization on commercially printed arrays, and (iv) data analysis.

Example 1

A Universally Conserved Translation Efficiency Profile

The translation efficiency profile of a gene is defined, for each codon position, as the estimated availability of the tRNAs that participate in translating that codon. The profile is high at codons that correspond to abundant tRNAs and low at codons that correspond to rare tRNAs. In particular, the tRNA-adaptation index (tAI) was used to evaluate translation efficiency ((4), and Methods, above) at each codon. The tAI measure of an entire gene, developed following the classical Codon Adaptation Index (3), is defined as the (geometric) average of tRNA availability values over all the codons in the gene (see Methods, above). For each codon, the tAI considers the availability of the tRNA with the perfectly matched anti-codon, along with weighted contributions from imperfect codon-anticodon pairs, reflecting wobble interactions. While the original tAI measure is defined as an averaged value over the entire gene (Methods, Equation 2, herein above), here each codon along the sequence was considered separately in what was defined as the "local tAI" of a codon (see Methods, Equation 1). Tables 4—herein below presents the genomic tRNA copy number of some of the analyzed organisms. The first column is the codon that is recognized by each tRNA. The second column is the corresponding anti-codon and columns 3-9 are the genomic copy number or each tRNA in 7 organisms.

TABLE 4

| Codon | anti-codon | tRNA copy number -- S. Cerevisiae | tRNA copy number -- Human | tRNA copy number -- E. coli K12 | tRNA copy number -- C. elegance | tRNA copy number -- M. musculus | tRNA copy number -- D. melanogaster | tRNA copy number -- Aeropyrum pernix |
|---|---|---|---|---|---|---|---|---|
| TTT | AAA | 0 | 0 | 0 | 0 | 0 | 0 | 0 |
| TTC | GAA | 10 | 12 | 2 | 14 | 7 | 8 | 1 |
| TTA | TAA | 7 | 7 | 1 | 4 | 4 | 4 | 1 |
| TTG | CAA | 10 | 7 | 1 | 7 | 4 | 4 | 1 |
| TCT | AGA | 11 | 11 | 0 | 15 | 9 | 8 | 0 |
| TCC | GGA | 0 | 0 | 2 | 0 | 1 | 0 | 1 |
| TCA | TGA | 3 | 5 | 1 | 9 | 3 | 2 | 1 |
| TCG | CGA | 1 | 4 | 1 | 6 | 3 | 4 | 1 |
| TAT | ATA | 0 | 1 | 0 | 0 | 0 | 0 | 0 |
| TAC | GTA | 8 | 14 | 3 | 19 | 10 | 9 | 1 |
| TAA | TTA | 0 | 2 | 0 | 0 | 1 | 0 | 0 |
| TAG | CTA | 0 | 1 | 0 | 0 | 0 | 0 | 0 |
| TGT | ACA | 0 | 0 | 0 | 0 | 0 | 0 | 0 |
| TGC | GCA | 4 | 30 | 1 | 13 | 57 | 7 | 1 |
| TGA | TCA | 0 | 3 | 1 | 1 | 2 | 1 | 0 |
| TGG | CCA | 6 | 9 | 1 | 12 | 8 | 8 | 1 |
| CTT | AAG | 0 | 12 | 0 | 19 | 8 | 5 | 0 |
| CTC | GAG | 1 | 0 | 1 | 0 | 0 | 0 | 1 |
| CTA | TAG | 3 | 3 | 1 | 3 | 3 | 2 | 1 |
| CTG | CAG | 0 | 10 | 4 | 6 | 10 | 8 | 1 |
| CCT | AGG | 2 | 10 | 0 | 6 | 7 | 7 | 0 |
| CCC | GGG | 0 | 0 | 1 | 0 | 0 | 0 | 1 |
| CCA | TGG | 10 | 7 | 1 | 32 | 8 | 5 | 1 |
| CCG | CGG | 0 | 4 | 1 | 4 | 3 | 5 | 1 |
| CAT | ATG | 0 | 0 | 0 | 1 | 1 | 0 | 0 |
| CAC | GTG | 7 | 11 | 1 | 19 | 10 | 5 | 1 |
| CAA | TTG | 9 | 11 | 2 | 20 | 6 | 4 | 1 |
| CAG | CTG | 1 | 21 | 2 | 7 | 10 | 8 | 1 |
| CGT | ACG | 6 | 7 | 4 | 19 | 6 | 10 | 0 |
| CGC | GCG | 0 | 0 | 0 | 1 | 0 | 0 | 1 |
| CGA | TCG | 0 | 6 | 0 | 10 | 5 | 10 | 1 |
| CGG | CCG | 1 | 5 | 1 | 2 | 3 | 0 | 3 |
| ATT | AAT | 13 | 14 | 0 | 21 | 11 | 9 | 0 |
| ATC | GAT | 0 | 8 | 3 | 0 | 1 | 0 | 1 |

TABLE 4-continued

| Codon | anti-codon | tRNA copy number -- S. Cerevisiae | tRNA copy number -- Human | tRNA copy number -- E. coli K12 | tRNA copy number -- C. elegance | tRNA copy number -- M. musculus | tRNA copy number -- D. melanogaster | tRNA copy number -- Aeropyrum pernix |
|---|---|---|---|---|---|---|---|---|
| ATA | TAT | 2 | 5 | 0 | 8 | 5 | 2 | 0 |
| ATG | CAT | 10 | 20 | 8 | 20 | 18 | 12 | 3 |
| ACT | AGT | 11 | 10 | 0 | 17 | 9 | 9 | 0 |
| ACC | GGT | 0 | 0 | 2 | 0 | 0 | 0 | 1 |
| ACA | TGT | 4 | 6 | 1 | 10 | 4 | 6 | 1 |
| ACG | CGT | 1 | 6 | 2 | 7 | 5 | 3 | 1 |
| AAT | ATT | 0 | 1 | 0 | 0 | 0 | 0 | 0 |
| AAC | GTT | 10 | 32 | 4 | 20 | 14 | 12 | 1 |
| AAA | TTT | 7 | 17 | 6 | 15 | 11 | 6 | 1 |
| AAG | CTT | 14 | 17 | 0 | 31 | 19 | 13 | 1 |
| AGT | ACT | 0 | 0 | 0 | 0 | 0 | 0 | 0 |
| AGC | GCT | 2 | 8 | 1 | 9 | 8 | 6 | 1 |
| AGA | TCT | 11 | 6 | 1 | 8 | 5 | 3 | 1 |
| AGG | CCT | 1 | 5 | 1 | 4 | 5 | 3 | 1 |
| GTT | AAC | 14 | 11 | 0 | 19 | 8 | 6 | 0 |
| GTC | GAC | 0 | 0 | 2 | 0 | 1 | 0 | 1 |
| GTA | TAC | 2 | 5 | 5 | 5 | 3 | 2 | 2 |
| GTG | CAC | 2 | 16 | 0 | 6 | 11 | 7 | 2 |
| GCT | AGC | 11 | 29 | 0 | 22 | 19 | 12 | 0 |
| GCC | GGC | 0 | 0 | 2 | 0 | 0 | 0 | 1 |
| GCA | TGC | 5 | 9 | 3 | 8 | 11 | 2 | 1 |
| GCG | CGC | 0 | 5 | 0 | 4 | 10 | 3 | 1 |
| GAT | ATC | 0 | 0 | 0 | 0 | 0 | 0 | 0 |
| GAC | GTC | 16 | 19 | 3 | 27 | 16 | 14 | 1 |
| GAA | TTC | 14 | 13 | 4 | 17 | 8 | 6 | 1 |
| GAG | CTC | 2 | 13 | 0 | 24 | 13 | 19 | 1 |
| GGT | ACC | 0 | 0 | 0 | 0 | 1 | 0 | 0 |
| GGC | GCC | 16 | 15 | 4 | 16 | 14 | 14 | 1 |
| GGA | TCC | 3 | 9 | 1 | 36 | 7 | 6 | 1 |
| GGG | CCC | 2 | 7 | 1 | 3 | 7 | 0 | 1 |
| Sum |  | 273 | 519 | 87 | 879 | 433 | 299 | 50 |

Table 5 provides the tAI of codons in some of the analyzed organisms. First column is the codon that is recognized by each tRNA; the second column is the corresponding anti-codon and columns 3-9 are the tAI of all the codons in 7 organisms.

TABLE 5

| Codon | anti-codon | S. Cerevisiae | Human | E. coli K12 | C. elegance | D. melanogaster | Aeropyrum pernix |
|---|---|---|---|---|---|---|---|
| TTT | AAA | 0.27032 | 0.161002 | 0.10975 | 0.170722 | 0.167878 | 0.132229 |
| TTC | GAA | 0.615764 | 0.366748 | 0.25 | 0.388889 | 0.382409 | 0.301205 |
| TTA | TAA | 0.431034 | 0.213936 | 0.125 | 0.111111 | 0.191205 | 0.301205 |
| TTG | CAA | 0.753695 | 0.282396 | 0.165 | 0.23 | 0.25239 | 0.39759 |
| TCT | AGA | 0.67734 | 0.336186 | 0.10975 | 0.416667 | 0.382409 | 0.132229 |
| TCC | GGA | 0.487685 | 0.242054 | 0.25 | 0.3 | 0.275335 | 0.301205 |
| TCA | TGA | 0.184797 | 0.152845 | 0.125 | 0.250042 | 0.095641 | 0.301205 |
| TCG | CGA | 0.12069 | 0.171149 | 0.165 | 0.246667 | 0.221797 | 0.39759 |
| TAT | ATA | 0.216256 | 0.218399 | 0.164625 | 0.231694 | 0.188862 | 0.132229 |
| TAC | GTA | 0.492611 | 0.449878 | 0.375 | 0.527778 | 0.43021 | 0.301205 |
| TAA | TTA | 0.250203 | 0.061128 | 0.163204 | 0.309469 | 0.260491 | 0.271835 |
| TAG | CTA | 0.250203 | 0.050122 | 0.163204 | 0.309469 | 0.260491 | 0.271835 |
| TGT | ACA | 0.108128 | 0.402506 | 0.054875 | 0.158528 | 0.146893 | 0.132229 |
| TGC | GCA | 0.246305 | 0.91687 | 0.125 | 0.361111 | 0.334608 | 0.301205 |
| TGA | TCA | 0.250203 | 0.091687 | 0.125 | 0.027778 | 0.047801 | 0.271835 |
| TGG | CCA | 0.369458 | 0.304401 | 0.165 | 0.342222 | 0.397706 | 0.301205 |
| CTT | AAG | 0.027032 | 0.366748 | 0.054875 | 0.527778 | 0.239006 | 0.132229 |
| CTC | GAG | 0.061576 | 0.264059 | 0.125 | 0.38 | 0.172084 | 0.301205 |
| CTA | TAG | 0.184729 | 0.091724 | 0.125 | 0.083386 | 0.095626 | 0.301205 |
| CTG | CAG | 0.059113 | 0.334963 | 0.54 | 0.193333 | 0.413002 | 0.39759 |
| CCT | AGG | 0.123153 | 0.305623 | 0.054875 | 0.166667 | 0.334608 | 0.132229 |
| CCC | GGG | 0.08867 | 0.220049 | 0.125 | 0.12 | 0.240918 | 0.301205 |
| CCA | TGG | 0.615776 | 0.213967 | 0.125 | 0.888906 | 0.239039 | 0.301205 |
| CCG | CGG | 0.197044 | 0.190709 | 0.165 | 0.395556 | 0.315488 | 0.39759 |
| CAT | ATG | 0.189224 | 0.147586 | 0.054875 | 0.259472 | 0.104924 | 0.132229 |
| CAC | GTG | 0.431034 | 0.336186 | 0.125 | 0.547778 | 0.239006 | 0.301205 |
| CAA | TTG | 0.554187 | 0.336186 | 0.25 | 0.555558 | 0.191205 | 0.301205 |

TABLE 5-continued

| Codon | anti-codon | S. Cerevisiae | Human | E. coli K12 | C. elegance | D. melanogaster | Aeropyrum pernix |
|---|---|---|---|---|---|---|---|
| CAG | CTG | 0.238916 | 0.749389 | 0.33 | 0.372222 | 0.443595 | 0.39759 |
| CGT | ACG | 0.369458 | 0.213936 | 0.5 | 0.539972 | 0.478011 | 0.132229 |
| CGC | GCG | 0.26601 | 0.154034 | 0.36 | 0.407778 | 0.344168 | 0.301205 |
| CGA | TCG | 0.000037 | 0.183395 | 0.00005 | 0.277831 | 0.478059 | 0.301205 |
| CGG | CCG | 0.061576 | 0.211491 | 0.125 | 0.144444 | 0.152964 | 1 |
| ATT | AAT | 0.800493 | 0.535208 | 0.164625 | 0.583333 | 0.43021 | 0.132229 |
| ATC | GAT | 0.576355 | 0.552567 | 0.375 | 0.42 | 0.309751 | 0.301205 |
| ATA | TAT | 0.123233 | 0.152855 | 0.163204 | 0.222281 | 0.095645 | 0.271835 |
| ATG | CAT | 0.615764 | 0.611247 | 1 | 0.555556 | 0.573614 | 0.903614 |
| ACT | AGT | 0.67734 | 0.305623 | 0.10975 | 0.472222 | 0.43021 | 0.132229 |
| ACC | GGT | 0.487685 | 0.220049 | 0.25 | 0.34 | 0.309751 | 0.301205 |
| ACA | TGT | 0.246373 | 0.183405 | 0.125 | 0.277825 | 0.28685 | 0.301205 |
| ACG | CGT | 0.140394 | 0.242054 | 0.29 | 0.283333 | 0.235182 | 0.39759 |
| AAT | ATT | 0.27032 | 0.459902 | 0.2195 | 0.243889 | 0.251816 | 0.132229 |
| AAC | GTT | 0.615764 | 1 | 0.5 | 0.555556 | 0.573614 | 0.301205 |
| AAA | TTT | 0.431034 | 0.519563 | 0.75 | 0.416667 | 0.286807 | 0.301205 |
| AAG | CTT | 1 | 0.685819 | 0.24 | 0.994444 | 0.713193 | 0.39759 |
| AGT | ACT | 0.054064 | 0.107335 | 0.054875 | 0.10975 | 0.125908 | 0.132229 |
| AGC | GCT | 0.123153 | 0.244499 | 0.125 | 0.25 | 0.286807 | 0.301205 |
| AGA | TCT | 0.67734 | 0.183374 | 0.125 | 0.222222 | 0.143403 | 0.301205 |
| AGG | CCT | 0.278325 | 0.211491 | 0.165 | 0.182222 | 0.189293 | 0.39759 |
| GTT | AAC | 0.862069 | 0.336186 | 0.10975 | 0.527778 | 0.286807 | 0.132229 |
| GTC | GAC | 0.62069 | 0.242054 | 0.25 | 0.38 | 0.206501 | 0.301205 |
| GTA | TAC | 0.123239 | 0.152845 | 0.625 | 0.138942 | 0.095631 | 0.60241 |
| GTG | CAC | 0.162562 | 0.537897 | 0.2 | 0.211111 | 0.365201 | 0.795181 |
| GCT | AGC | 0.67734 | 0.886308 | 0.10975 | 0.611111 | 0.573614 | 0.132229 |
| GCC | GGC | 0.487685 | 0.638142 | 0.25 | 0.44 | 0.413002 | 0.301205 |
| GCA | TGC | 0.30795 | 0.27515 | 0.375 | 0.222283 | 0.09566 | 0.301205 |
| GCG | CGC | 0.098522 | 0.240831 | 0.12 | 0.182222 | 0.173996 | 0.39759 |
| GAT | ATC | 0.432512 | 0.254921 | 0.164625 | 0.32925 | 0.293786 | 0.132229 |
| GAC | GTC | 0.985222 | 0.580685 | 0.375 | 0.75 | 0.669216 | 0.301205 |
| GAA | TTC | 0.862069 | 0.397311 | 0.5 | 0.472222 | 0.286807 | 0.301205 |
| GAG | CTC | 0.399015 | 0.52445 | 0.16 | 0.817778 | 1 | 0.39759 |
| GGT | ACC | 0.432512 | 0.201253 | 0.2195 | 0.195111 | 0.293786 | 0.132229 |
| GGC | GCC | 0.985222 | 0.458435 | 0.5 | 0.444444 | 0.669216 | 0.301205 |
| GGA | TCC | 0.184729 | 0.275061 | 0.125 | 1 | 0.286807 | 0.301205 |
| GGG | CCC | 0.182266 | 0.301956 | 0.165 | 0.403333 | 0.091778 | 0.39759 |
| Sum |  |  | 19.95131878 | 20000 | 35.999712 | 20.92006443 | 7.562637545 |

Table 6 provides measurements of tRNA abundance based on micro-array dedicated to in S. cerevisiae. First column is the genomic tRNA copy number of all the codons in S. cerevisiae. Second column is the tAI of all the codons in S. cerevisiae. Third column is the codons. Fourth column is the amino acid that corresponds to each codon. Fifthe column is the anti codons. Sixth column is the probe name for each codon. Seventh column is the Cy5 value at time 0. Eighth column is the Cy3 value at time 0. Ninth column is the relative expression levels of each probe after 4.5 hours. . Tenth column is the relative expression levels of each probe after 6 hours. Eleventh column is the relative expression levels of each probe after 7.5 hours. Twelfth column is the relative expression levels of each probe after 9 hours.

TABLE 6

| Copy-no | tAI (new S vector - do not change the first 4) | Codon | Amino Acid | anti-codon | Prob | Cy5 values | Cy3 values | 4.5/0, avg | 6/0, avg | 7.5/0, avg | 9 h/0 h, avg |
|---|---|---|---|---|---|---|---|---|---|---|---|
| 2 | 0.123239 | GTA | Val | TAC | Val-8 (2) | 15701 | 18144 | 3.61 | 3.13 | 2.44 | 3.25 |
| 2 | 0.162562 | GTG | Val | CAC | Val-7 (2) | 22094 | 22557 | 4.22 | 3.34 | 2.58 | 3.29 |
| 14 | 0.862069 | GTT | Val | AAC | Val-6 (14) | 42907 | 45649 | 3.34 | 3.08 | 2.47 | 2.79 |
| 8 | 0.492611 | TAC | Tyr | GTA | Tyr-3 (8*) | 47627 | 43761 | 5.79 | 5.20 | 4.20 | 5.78 |
| 6 | 0.369458 | TGG | Trp | CCA | Trp-3 (6*) | 28472 | 31764 | 3.85 | 3.28 | 2.78 | 3.20 |
| 4 | 0.246373 | ACA | Thr | TGT | Thr-8 (4) | 22636 | 24962 | 4.09 | 3.40 | 2.82 | 3.37 |
| 1 | 0.140394 | ACG | Thr | CGT | Thr-7 (1) | 8071 | 8790 | 3.68 | 3.10 | 2.38 | 3.02 |
| 11 | 0.67734 | ACT | Thr | AGT | Thr-6 (11) | 26190 | 30679 | 2.10 | 2.10 | 1.52 | 1.74 |

TABLE 6-continued

| Copy-no | tAI (new S vector - do not change the first 4) | Codon | Amino Acid | anti-codon | Prob | Cy5 values | Cy3 values | 4.5/0, avg | 6/0, avg | 7.5/0, avg | 9 h/0 h, avg |
|---|---|---|---|---|---|---|---|---|---|---|---|
| 1 | 0.12069 | TCG | Ser | CGA | Ser-9(1) = Ser-11 | 20893 | 28482 | 1.29 | 1.57 | 1.28 | 1.40 |
| 11 | 0.67734 | TCT | Ser | AGA | Ser-8 (11) | 42365 | 49284 | 2.98 | 2.63 | 1.99 | 2.52 |
| 3 | 0.184797 | TCA | Ser | TGA | Ser-11(3) = Ser-9 | 25123 | 33682 | 1.35 | 1.52 | 1.32 | 1.44 |
| 2 | 0.123153 | AGC | Ser | GCT | Ser-10 (2*) | 26070 | 35264 | 1.61 | 1.69 | 1.47 | 1.92 |
| 10 | 0.615776 | CCA | Pro | TGG | Pro-6 (10*) | 56197 | 55894 | 2.77 | 2.67 | 2.45 | 3.35 |
| 2 | 0.123153 | CCT | Pro | AGG | Pro-5 (2) | 7394 | 9862 | 3.41 | 2.87 | 2.39 | 3.55 |
| 10 | 0.615764 | TTC | Phe | GAA | Phe-3 (10*) | 39613 | 41674 | 3.70 | 3.26 | 2.67 | 2.97 |
| 0 | NaN | TGA | Stop | TCA | NaN | NaN | NaN | NaN | NaN | NaN | NaN |
| 0 | NaN | TAG | Stop | CTA | NaN | NaN | NaN | NaN | NaN | NaN | NaN |
| 0 | NaN | TAA | Stop | TTA | NaN Met-5 (5), Met-6i (5) consider only | NaN | NaN | NaN | NaN | NaN | NaN |
| 10 | 0.615764 | ATG | Met | CAT | Met-5 | 32745 | 34375 | 3.40 | 2.99 | 2.45 | 2.67 |
| 7 | 0.431034 | AAA | Lys | TTT | Lys-4 (7*) | 37312 | 45074 | 4.35 | 4.02 | 3.18 | 4.81 |
| 14 | 1 | AAG | Lys | CTT | Lys-3 (14) | 35076 | 47960 | 3.89 | 3.55 | 2.94 | 3.31 |
| 3 | 0.184729 | CTA | Leu | TAG | Leu-14 (3*) | 31179 | 32495 | 3.27 | 2.67 | 2.21 | 2.74 |
| 7 | 0.431034 | TTA | Leu | TAA | Leu-13 (7) | 23734 | 25827 | 3.18 | 2.69 | 2.17 | 2.61 |
| 1 | 0.061576 | CTC | Leu | GAG | Leu-12 (1) | 6194 | 7418 | 3.20 | 2.75 | 2.06 | 2.65 |
| 10 | 0.753695 | TTG | Leu | CAA | Leu-11 (10*) | 48013 | 48592 | 3.15 | 2.84 | 2.26 | 2.54 |
| 2 | 0.123233 | ATA | Ile | TAT | Ile-6 (2*) | 19123 | 20433 | 4.31 | 3.38 | 2.73 | 3.73 |
| 13 | 0.800493 | ATT | Ile | AAT | Ile-5 (13) | 53246 | 52643 | 4.16 | 3.75 | 3.01 | 3.47 |
| 7 | 0.431034 | CAC | His | GTG | His-3 (7) | 40780 | 40922 | 2.92 | 2.49 | 2.00 | 2.29 |
| 3 | 0.184729 | GGA | Gly | TCC | Gly-8 (3) | 29982 | 31110 | 1.79 | 1.76 | 1.46 | 1.75 |
| 16 | 0.985222 | GGC | Gly | GCC | Gly-7 (16) | 33639 | 36647 | 3.10 | 2.59 | 2.24 | 2.71 |
| 2 | 0.182266 | GGG | Gly | CCC | Gly-6 (2) | 9821 | 11583 | 2.74 | 2.35 | 2.00 | 2.61 |
| 14 | 0.862069 | GAA | Glu | TTC | Glu-3 (16) | 60512 | 60773 | 2.80 | 2.76 | 2.53 | 3.18 |
| 9 | 0.554187 | CAA | Gln | TTG | Gln-4 (10) | 42204 | 47713 | 3.64 | 3.35 | 2.66 | 3.16 |
| 4 | 0.246305 | TGC | Cys | GCA | Cys-3 (4) | 40898 | 43555 | 3.96 | 3.48 | 2.67 | 3.46 |
| 16 | 0.985222 | GAC | Asp | GTC | Asp-3 (15) | 52982 | 52557 | 3.12 | 2.83 | 2.55 | 3.50 |
| 10 | 0.615764 | AAC | Asn | GTT | Asn-3 (10) | 52475 | 58373 | 3.16 | 3.07 | 2.56 | 3.05 |
| 6 | 0.369458 | CGT | Arg | ACG | Arg-9 (6) | 25143 | 34497 | 4.34 | 3.79 | 3.13 | 4.56 |
| 11 | 0.67734 | AGA | Arg | TCT | Arg-12 (11) | 48753 | 50111 | 2.81 | 2.85 | 2.40 | 2.81 |
| 1 | 0.278325 | AGG | Arg | CCT | Arg-11 (1) | 5020 | 7891 | 4.08 | 3.64 | 3.01 | 4.04 |
| 1 | 0.061576 | CGG | Arg | CCG | Arg-10 (1) | 6557 | 8773 | 3.91 | 3.23 | 2.47 | 3.70 |
| 11 | 0.67734 | GCT | Ala | AGC | Ala-6 (11) | 32063 | 33449 | 2.78 | 2.51 | 2.08 | 2.59 |
| 5 | 0.30795 | GCA | Ala | TGC | Ala-5 (5) | 11549 | 14538 | 3.42 | 2.54 | 1.98 | 2.38 |
| 0 | 0.27032 | TTT | Phe | AAA | 0 | 0 | 0 | 0.00 | 0.00 | 0.00 | 0.00 |

TABLE 6-continued

| Copy-no | tAI (new S vector - do not change the first 4) | Codon | Amino Acid | anti-codon | Prob | Cy5 values | Cy3 values | 4.5/0, avg | 6/0, avg | 7.5/0, avg | 9 h/0 h, avg |
|---|---|---|---|---|---|---|---|---|---|---|---|
| 0 | 0.108128 | TGT | Cys | ACA | 0 | 0 | 0 | 0.00 | 0.00 | 0.00 | 0.00 |
| 0 | 0.487685 | TCC | Ser | GGA | 0 | 0 | 0 | 0.00 | 0.00 | 0.00 | 0.00 |
| 0 | 0.216256 | TAT | Tyr | ATA | 0 | 0 | 0 | 0.00 | 0.00 | 0.00 | 0.00 |
| 0 | 0.62069 | GTC | Val | GAC | 0 | 0 | 0 | 0.00 | 0.00 | 0.00 | 0.00 |
| 0 | 0.432512 | GGT | Gly | ACC | 0 | 0 | 0 | 0.00 | 0.00 | 0.00 | 0.00 |
| 0 | 0.098522 | GCG | Ala | CGC | 0 | 0 | 0 | 0.00 | 0.00 | 0.00 | 0.00 |
| 0 | 0.487685 | GCC | Ala | GGC | 0 | 0 | 0 | 0.00 | 0.00 | 0.00 | 0.00 |
| 0 | 0.432512 | GAT | Asp | ATC | 0 | 0 | 0 | 0.00 | 0.00 | 0.00 | 0.00 |
| 0 | 0.027032 | CTT | Leu | AAG | 0 | 0 | 0 | 0.00 | 0.00 | 0.00 | 0.00 |
| 0 | 0.059113 | CTG | Leu | CAG | 0 | 0 | 0 | 0.00 | 0.00 | 0.00 | 0.00 |
| 0 | 0.26601 | CGC | Arg | GCG | 0 | 0 | 0 | 0.00 | 0.00 | 0.00 | 0.00 |
| 0 | 0.0124 | CGA | Arg | TCG | 0 | 0 | 0 | 0.00 | 0.00 | 0.00 | 0.00 |
| 0 | 0.197044 | CCG | Pro | CGG | 0 | 0 | 0 | 0.00 | 0.00 | 0.00 | 0.00 |
| 0 | 0.08867 | CCC | Pro | GGG | 0 | 0 | 0 | 0.00 | 0.00 | 0.00 | 0.00 |
| 0 | 0.189224 | CAT | His | ATG | 0 | 0 | 0 | 0.00 | 0.00 | 0.00 | 0.00 |
| 0 | 0.576355 | ATC | Ile | GAT | 0 | 0 | 0 | 0.00 | 0.00 | 0.00 | 0.00 |
| 0 | 0.054064 | AGT | Ser | ACT | 0 | 0 | 0 | 0.00 | 0.00 | 0.00 | 0.00 |
| 0 | 0.487685 | ACC | Thr | GGT | 0 | 0 | 0 | 0.00 | 0.00 | 0.00 | 0.00 |
| 0 | 0.27032 | AAT | Asn | ATT | 0 | 0 | 0 | 0.00 | 0.00 | 0.00 | 0.00 |
| 2 | 0.399015 | GAG | Glu | CTC | | | | | | | |
| 1 | 0.238916 | CAG | Gln | CTG | | | | | | | |

Table 7 presents the correlation between tRNA copy number and tRNA abundance in human tissues (Dittmar et al 2006). Each column includes the correlation and the corresponding p-value in a different tissue.

TABLE 7

| Brain | Liver | Vulva | Testis | Ovary | Thymus | Lymph Node | Spleen | HeLa/HEK 293 |
|---|---|---|---|---|---|---|---|---|
| 0.8294 | 0.7322 | 0.6956 | 0.7130 | 0.7000 | 0.6056 | 0.6419 | 0.7732 | 0.7855 |
| (1.0634e−012) | (7.3537e−009) | (8.0567e−008) | (2.7018e−008) | (6.1638e−008) | (8.2319e−006) | (1.5250e−006) | (3.0198e−010) | (1.0185e−010) |

Typically the tAI uses the copy number of tRNA genes in the genome as a proxy for their abundance in the cytoplasm. Although this is a common assumption (see Example 5, Tables 4-7, herein above and (5, 10, 11)), the present inventors set to examine it in *S. cerevisiae* using a micro-array dedicated to the tRNAs in this species (17-19).

Specifically, the correlation between tRNA abundance and their gene copy number was examined in yeast cells growing on a rich medium. tRNA abundance measurements were based on the Cy3 and Cy5 fluorescence values of each tRNA on the array using a unique labeling method that relies only on the single-stranded 3'NCCA in every tRNA (demonstration of the feasibility of the method was done by quantitative comparison to 2D PAGE analysis of tRNAs (12-14)). It was found that indeed tRNA gene copy numbers are relatively highly correlated with their expression levels at rich medium conditions (r=0.76 over 39 tRNA species, see FIG. 1 and FIGS. 10A-F). It was also found that this correlation remains relatively high even when yeast undergoes a major metabolic shift, termed 'diauxic shift' (12), from fermenting to respiratory conditions (correlation between 0.65 and 0.71)—see Tables 4-7 herein above.

The array analysis indicates that the tRNA gene copy number provides a reasonable proxy, and it was therefore used, in *S. cerevisiae*, and in the rest of the species too, in all subsequent tAI calculations. The present inventors started by inspecting the averaged translation efficiency profiles of all the genes in a given genome. In order to observe an averaged translation efficiency profile for all the genes in a particular genome, all genes were lined up according to their start codon and an average local tAI value at each position was calculated (see Methods, herein above). In parallel, all the genes in each genome were lined up relative to the stop codon and the average was computed across all genes in the last position, the penultimate etc. Altogether genomes of 27 organisms were analyzed with representatives from all three domains of life (FIGS. 7A-S, 8A-D and 9A-D).

As seen in FIG. 2, FIGS. 10A-F, 11A-C and 12, in almost all species examined, the averaged translation efficiency profile reveals several remarkably conserved features: Translation appears to start with relatively low efficiency codons for about the first ~30-50 positions, referred to herein as the low efficiency ramp' or the 'ramp' for short. The ramp region is then followed by a plateau with ~5-10% higher translation efficiency on a genome average. A clear outlier in the ramp is the second codon position, which follows the initiating methionine, that shows high efficiency compared to its neighboring codons in the majority of the species (FIGS. 11A-C). This design might support a fast release and recycling of the initiating methionine tRNA. In most of the examined eukaryotic species, predominantly in fungi, the profile shows an increase in efficiency towards the last ~50 codons of the genes, which are higher in Fungi by up to 5% than the value at the plateau in the middle section of genes (FIG. 2F). Properly randomized sequences (and also some particular gene sets, see below) do not give rise to such signals (FIGS. 2, 10A-F, 11A-C and 12).

While the averaged profile over all genes in the genome is relatively smooth, the profile of single genes is often noisy. Still it was important to inspect single genes, identify those that contribute the most to the observed averaged signal, and to examine the possibility that other weaker signals may have been missed at the genome-average level. Accordingly, the "bottleneck" region was defined and identified in each individual gene—a sequence window of length 15 codons (that correspond to the length of the ribosome footprint region on mRNAs (13)), with the highest averaged values of 1/(local tAI) (i.e. 15 codons with the longest dwell time in a gene). FIG. 3 shows the distribution of locations of the bottleneck regions along all genes in two remotely-related yeast species, *S. cerevisiae* and *S. pombe*. Both distributions show a consistent picture—a clear tendency to have the bottleneck relatively early along the genes. Other than this region there are no other regions in that show any pronounced preference to contain bottlenecks. This picture shows that the ramp is a superposition of the translation efficiency profile of a relatively high number of genes (e.g. the bottleneck of 1330 genes is within the first 54 codons).

The analyses presented so far addressed individual genes on one hand and averages of entire genomes on the other. An intermediate level is that of sets of genes that share a biological function. The present inventors considered genes that share the same GO slim categories (22). FIGS. 4A-B, FIGS. 13A-Z and FIGS. 14A-P show the averaged profiles of genes from representative categories. It was found that the genes from many of the GO slim categories show the ramp design. For example, genes that share the GO categories 'cellular carbohydrate metabolic process' and 'transport' demonstrate a very clear ramp. Not less important, other gene sets, e.g. those that share the GO categories 'transcription' and 'nucleus organization' do not have a ramp (see more example in FIG. 4B and FIGS. 13A-Z and 14A-P). Interestingly, the presence of the ramp is seen even among categories with very different absolute translation efficiency levels. For example, FIG. 4C shows the local translation efficiency profile of cytosolic and mitochondrial ribosomal proteins in *S. cerevisiae*. Interestingly, although selection acted to enhance overall efficiency of the cytosolic ribosomal proteins, the initial region shows lower efficiency relative to the rest of the genes.

Beyond inspection of single genes, gene sets, and genome average, the highest level of averaging is from multiple genomes; in particular the present inventors averaged all the eukaryotic profiles and all the prokaryotic ones. Notably, the length of the ramp (see FIGS. 11A-C for a description of how the length of the ramp was computed) in eukaryotes and prokaryotes is around 1-3 ribosomes (depending on the definition of the actual number of nucleotides that are covered by a single ribosome (1, 13-18). The ratio between the length of the ramp in eukaryotes and prokaryotes (mean ramp length in prokaryotes 24 codons; mean ramp length in eukaryotes is 34.5 codons; the ratio between these lengths is 1.43) may correspond to a difference in the size of the footprinted region of the eukaryotic and prokaryotic ribosomes on transcripts.

The present inventors next wanted to examine if the ramp is maintained during an environmental change. For that the present inventors returned to the diauxic shift experiment in which was found some changes in the relative representation of the various tRNAs in the tRNA pool (FIGS. 10A-F and 11A-C). The ramp for all genes was computed and measured tRNA levels were used at each time point, instead of the static gene copy numbers. It was found that the ramp is largely maintained genome-wide (FIGS. 10A-F and 11A-C).

Example 2

The Universal Translation Efficiency Profile is Under Selection

The translation efficiency profile is highly conserved in evolution, but this fact by itself is not a guarantee that the profile is under direct selection. An alternative might be that the profile is conserved as a by-product of selection acting on other features. The present inventors have examined and excluded several specific alternatives.

Initially, the possibility that the observed profile is conserved merely because the tRNA pool and codon biases are sufficiently conserved was examined. According to this null hypothesis the inter-species differences in the tRNA pool and the coding sequences are small enough to maintain the translation efficiency even if the profile was not under direct selection. The translation efficiency profile of all the genes from one species was computed using the tRNA pool of another. This procedure was repeated for various pairs of species. This is a simple computational resemblance of true species hybridization experiments that are used to tell apart the contribution of cis and trans acting factors, so far mainly done in transcription research (18-20). In one such hybrid analysis, the *S. cerevisiae* genes were translated using the E lipolytica tRNA pool, and in a reciprocal analysis the coding sequences of *Y. lipolytica* were translated using the tRNA pool from *S. cerevisiae*. These two species were selected since their tRNA pools and their codon bias have diverged quite significantly (5), yet both species display the conserved translation efficiency profile. FIG. 5 shows that in these hybrids the ramp region is much shorter and shallower. More generally, the ramp region becomes shorter and shallower when hybridizing *S. cerevisiae* with tRNA pools of organisms with increasing evolutionary distances, and also when examining additional pairs of species (FIGS. 15-21A-Z). These results indicate that the tRNA pools and the codon preferences have sufficiently diverged between species so as to eliminate the translation efficiency profile if it were not directly selected for. Thus, it may be concluded that a co-evolution of the tRNA pool and the coding sequences took place in each species so as to conserve the translation efficiency profile. This suggestion is in-line with the general indications of the emergence of codon bias from co-evolution (19).

The second null hypothesis relates to the possibility that the observed translation efficiency profile results from selection acting at the amino-acid sequence level. In contrast to this possibility, it was found that in the region of the initial ramp the actual codon chosen among all possible codons of the given amino acid is often the one with low efficiency (see the red plots corresponding to the AAtAI profile in FIGS. 7-9; see Methods for explanations about the AAtAI profile). Beyond the ramp region, codon choice does not show this bias. This result excludes the possibility that the observed profile is a by-product of constraints at the protein sequence level.

Likewise, another potential alternative reason for the observed profile was excluded, that it is a by-product of a putative position-dependent variation in the GC content along genes (FIG. 22).

It is thus concluded that the translation efficiency profiles are not only universally conserved but are also probably under direct selection, presumably due to direct effect on fitness.

Example 3

Codon-tRNA Adaptation May Determine Translation Speed and Ribosome Density Along Transcripts A central question thus is what actual physical or biochemical quantity is encoded by the translation efficiency profile. One interesting possibility is that the values of the local tAI determine the local speed of movement of the translating ribosome through each codon along mRNAs. According to this hypothesis the ribosomes are moving on average more slowly at the ramp region. The hypothesis that the observed profile determines the speed of the ribosome at each position generates a clear prediction about the density of ribosomes at any given position. Assuming that ribosome distributions on mRNAs are at steady-state (e.g. assuming little, or no pre-mature abortions of ribosomes), the flux of ribosomes through a codon position x, is given by:

$$j(x)=v(x)*f(x),$$

where $v(x)$ is the speed of translation at the position x, and $f(x)$ is the density of ribosomes at that position. In other words, if the translation efficiency profile is a speed profile we expect it to be inversely correlated with a ribosome density profile along genes. In particular our profile predicts a high density of ribosomes at the first 30-50 codon positions.

The averaged ribosome density on transcripts (number of ribosomes divided by the length of the transcript) had been previously measured for most of the genes in the S. cerevisiae genome (9). Recently, ribosome densities at a single base resolution were measured genome-wide for thousands of transcripts in the S. cerevisiae genome (1). The measured distribution features high density of ribosome at the 5' most 50 codons and a plateau from that point on (1, 4). Thus, the low efficiency ramp that was computationally observed coincides well with the experimentally observed region of high ribosomal density. In general, comparing the experimentally measured ribosomal density with the reciprocal of the translation efficiency profile reveals relatively high similarity (Pearson correlation $r=0.5749$; $p=10^{-28}$).

It was further realized that imperfections in the correlation between density and the reciprocal of the translation efficiency profile might reflect a discrepancy between the translation efficiency profile and the actual speed of ribosomes, e.g. due to ribosome traffic jams. Accordingly, the local tAI-based speed profile will be termed the "nominal speed profile". At low translation initiation rate, the ribosome may indeed move according to this speed profile. Yet at higher initiation rate, ribosomes may start to jam and hence might move with a different local speed, which is termed the "effective speed profile". To estimate the effective speed profile and its deviation from the nominal speed profile at each position ribosome movement was simulated on transcripts ((14), FIG. 22 and Methods). The basic rule that governs the movement in the simulation is that a ribosome proceeds through a given codon position according to the nominal translation speed profile, unless it collides with the ribosome in front of it, in which case it halts until that ribosome proceeds forward. The simulation for each gene was run separately and the effective speed profiles and the simulated profiles of ribosome densities were inferred. Strikingly, when the single-gene effective speed profiles were averaged (with same averaging as done for the density profiles (1)), it was found that the reciprocal of the obtained effective speed profile highly correlates ($r=0.93$; $p<10^{-75}$; FIG. 6A) with the experimental density profile. Similarly, when the profiles of ribosome densities were averaged, it was found that the computed density profiles highly resembles the experimental one (up to $r=0.96$; FIG. 6B). The main free parameter of the simulation is the translation initiation rate—the inverse of the time required for a ribosome to attach to, and assemble on, an mRNA (see FIG. 22 and Methods). The present inventors thus experimented with a whole range of feasible initiation rates. As can be seen, the high correlation between the experimental and computed densities is maintained throughout a broad range of initiation rates (FIG. 6B). Only at very low initiation rates (i.e. high initiation times), where traffic jams are not formed, the simulated density resembles to a lesser extent the experimental one (FIG. 6B).

Together these results constitute an indication that codon-tRNA adaptation may serve as a code that determines ribosomal translation speed. These results also suggest that translation speed, and hence ribosome density, may be encoded in gene sequences and the tRNA pool. The agreement between the computational and the experimental profiles also indirectly lend support to the assumptions of the codon—tRNA adaptation model, e.g. that tRNA gene copy numbers are a good predictor of the tRNA abundance (4). A corollary of this conclusion is that the computed profile is a simple means to predict the shape of the ribosomal density function in other species, and that the density function seen in yeast is likely conserved. This result also suggests how potential changes in the relative amounts of particular tRNAs (11, 32) might modify the profile of ribosome density in a given species or a given condition. For instance, if the concentration of a rare tRNA, whose matched codons mainly concentrate close to 5' ends of genes, is elevated at a given condition the result might be a more flat density function.

Finally, under conditions of amino acid starvation too, the first 40-50 codons show high ribosomal density (1); this increased ribosomal density seems more pronounced than the one that is observed in YEPD. Based on the correlation demonstrated between ribosome density and reciprocal of speed, it may be suggested that the speed of the ribosome is slower at the beginning of genes also in this condition; namely, in S. cerevisiae, the ramp is maintained (and is probably more pronounced) also in starvation condition (though, the tRNA pool may change in starvation; see, for example, (20)).

Additional factors are likely involved in setting the speed and density of the ribosome. In particular the folding energy of the mRNA secondary structure appears to be highly relevant too (21, 22) and it remains to be investigated how tRNA availability and mRNA structure interact in determining the final density profile.

Example 4

The Potential Fitness Advantages of the Translation Efficiency Profile

The conclusion from the density and speed analysis is that the ramp limits the speed of ribosomes at the first dozens of codons on transcripts, and generates as a consequence a high density area. The generation of a short high density section at the 5' region of mRNAs may give raise to a jam-free region at the rest of the transcript since ribosomes that passed the bottleneck are less likely to jam. Under this assumption, ramping would be needed mainly for genes with high overall ribosome density since these genes are more prone to jamming. In addition, it is conceivable that a jam in a gene with high mRNA copy number is likely to be more detrimental than a comparable jam that occurs in a low mRNA copy number gene. The present inventors thus returned to the ribosomal density (1) and mRNA copy number data (23), and characterized each gene by its mRNA copy number, its ribosome density, or by multiplying its mRNA copy number by its ribosome density, and looked separately on genes at the top and bottom 10% of the distribution of these features. It was found that genes with highest ribosomal density, mRNA level or the product of ribosome density and mRNA levels display a stronger ramp than genes with the lowest level of these features (FIG. 6C). It was verified that this signal is not a result of difference in protein length between the two gene sets (FIG. 6C). It is noted that the length of the slow ramp is a meaningful parameter since across the various species it is significantly correlated with the extent of selection for translation efficiency (FIGS. 23A-D). In addition, similar analysis demonstrated that the signal of the ramp is stronger in genes with higher protein-to-mRNA abundance ratio (FIGS. 23A-D). In that respect it is noted that the ramp design is "universal" as it is observed in all analyzed species, yet it is expected that only a strategic portion of the genes in each genome will feature this design—primarily genes that need to operate at high production level, and not in other genes.

A recent study (22) now provides an opportunity to measure in a more direct way the effect of obeying the translation efficiency profile on the organism's fitness. In that study, 154 versions of the gene encoding the Green fluorescent protein (GFP) were synthesized such that the 3rd codons positions were randomized. Each version was driven by a strong promoter, expressed in *E. coli*, and cells' fitness was measured for each strain (22). That study presented an experimental evidence that average codon bias might minimize the burden of protein expression on the cell (22). Although this GFP library was not designed for the purpose of testing the effects of the ramp, it was still found that some GFP versions have a profile that somewhat resembles the ramp, whereas others do not show this feature. Reassuringly, a modest, yet significant correlation between the extent to which a GFP variant obeys the translation efficiency profile and the fitness of the strain that expresses it (r=0.2; p-value=0.014; FIG. 24A) was found. Further, the genes in the library were partitioned according to their average tAI value and 25% of the variants with the lowest tAI values were focused on—these genes could generate the highest burden on fitness due to potential over-all low translation efficiency (22). Among those genes there exists a higher correlation (r=0.6, n=37, p-value=$1.26*10^{-4}$) between the extent of agreement with the translation efficiency profile and the fitness (FIG. 24A). Thus, especially among genes with lower translation efficiency (and hence higher ribosome density) obeying the translation efficiency profile is crucial for minimizing fitness reduction. This observation thus suggests that the ramp in translation efficiency profile observed in endogenous genes may have been selected for minimizing the cost of protein expression due to translation.

The data of Kudla et al. can be used for understanding the relation between ramp, fitness and the component of the initiation rate (relative to the elongation rate) that is determined by the properties of the 5'UTRs: All the GFP variants have identical 5'UTR and thus identical (absolute) initiation rate; however, as the coding sequences were randomized, the elongation rate (measured by the tAI) is different for different GFP variants. Thus, the different GFP variants have different relative initiation to-elongation rates; the relative initiation rate is higher when the tAI is lower. FIG. 24 A(inset), thus, demonstrate that the ramp is more important when the relative initiation rate is higher.

Discussion

The Potential Role of the Ramp in the Context of Initiation Control: Translation initiation is a prime point of control since it governs the binding and assembly of the ribosome and the initiation machinery on the transcript. These processes mainly take place at the 5' UTR of genes. The ramp described herein may represent an important next stage of translational control which modulates the parameters set by the previous initiation stage. The ramp may thus couple between initiation and elongation, and add unique regulatory features, stemming from the fact that it is "written" on a translated sequence:

Robustness and Economy—Reduction of Expression Cost by Filtering Out randomness: One knob that an mRNA has in controlling translation is the ribosome binding rate at the 5' UTR. This knob controls both the average spacing between ribosomes (and hence the protein production rate at steady-state), and also the fluctuations around this spacing. As the knob is turned to increase the protein production rate, these fluctuations become increasingly more likely to generate events of too closely spaced ribosomes that can jam and, potentially, also abort translation. Thus, fluctuations become increasingly more costly. The ramp, however, may provide a second and independent knob that can tune down the variance, set by initiation rate, in the spacing between ribosomes. The ramp consists of dozens of codons, each determining a separate random event of tRNA binding, and thus serves as a very effective noise filter—the probability that through the passage of a given ribosome, all the codons in the ramp will allow fast movement of the ribosome, and potentially collision with the ribosome ahead of it, is practically zero. Of course such ramp design is not needed for proteins with very low binding rate—these are unlikely to jam anyway, and indeed the extent of ramping decreases at lowly dense genes in the yeast genome (FIG. 6C).

Potential for Gene-Specific and Condition-Specific Control: The ramp may encode an interesting sensing capability—the low efficiency codons at the beginning of transcripts may allow high sensitivity to the abundance level of amino acid-loaded tRNAs in the cell. As such it may provide a simple mechanism for early, thus low-cost, abortion in case of paucity of raw material. In more general terms, compared to control through the UTR, the ramp has a potential to control differentially individual genes under different conditions. Indeed it may be seen that different functional gene sets, may represent different designs of the ramp. It also may be predicted that the shape of the ramp may change for particular genes across conditions, e.g. if the concentration of some of the tRNAs is modulated relative to others. The ramp may thus encode for gene-specific and condition-specific dynamic control of early translation elongation.

A Range of Potential Physiological Roles of the Ramp: The ramp in protein translation has the potential of reducing traffic jamming of ribosomes. Reduction in jamming is, in turn, desired for several reasons. First it reduces the total amount of time that ribosomes are sequestered on a given transcript, thus diverted from translating others. Second, jammed ribosomes, which halt at slow codons (24) are more likely to spontaneously fall-off since they spend more time on the transcript. Ribosomal abortions may also occur due to collisions between jammed ribosomes, thus ramps may be advantageous in preventing spontaneous and collision-dependent abortions. On top of that, the ramp may limit most abortions which do occur, to the beginning of the transcripts. This may be desired since in these regions fall-off is least wasteful. Thus low speed at the beginning may reflect reduced purifying pressure against early abortion, or a pressure to concentrate abortions at early stages if they reduce late, costly ones. In that respect the elevation in translation speed towards the end of transcripts (seen mainly among the fungi) may reflect a deliberate selective pressure to avoid late abortions.

It may be assumed that at a given level of protein expression the cost of production increases with the total time ribosomes spend on mRNAs. While the initial ramp may increase that time (and hence the cost) at the initial section of transcripts, it may result in overall shorter time of sequestering translating ribosomes. Thus if ramping decreases the probability of jamming it may reduce the cost of gene expression at a given production level, and increases the production capacity at a given cost (FIG. 24B). Note however, that when initiation rate is low, jamming is less likely and hence ramping may only come with a slowing-down cost with no gain (FIG. 24B), explaining why low ribosome density genes have a shorter ramp (FIG. 6C).

A profile of translation speed may also correspond to a position-specific profile of translation errors—longer dwell times, at slow codons, may result not only in abortion but also in higher translation error probabilities (7, 25). According to this notion it may be predicted that beginnings of proteins may accumulate more translation mutations compared to other regions in proteins. The speed profile may also constitute an essential code for proper protein folding (38, 39).

It is interesting that many of these considerations may apply to other bio-polymerization process, and to molecular motor movements. For example, it would be interesting if transcription too, and the motor proteins such as kinesin implement a similar design to alleviate some of the "process costs" or the effects of stochasticity (40, 41).

REFERENCES

1. Ingolia N T, Ghaemmaghami S, Newman J R, & Weissman J S (2009) Genome-wide analysis in vivo of translation with nucleotide resolution using ribosome profiling *Science* 324, 218-223.
2. Gray N K & Hentze M W (1994) Regulation of protein synthesis by mRNA structure *Molecular Biology Reports* 19, 195-200.
3. Sharp P M & Li W H (1987) The codon Adaptation Index—a measure of directional synonymous codon usage bias, and its potential applications *Nucleic Acids Res* 15, 1281-1295.
4. dos Reis M, Savva R, & Wernisch L (2004) Solving the riddle of codon usage preferences: a test for translational selection *Nucleic Acids Res* 32, 5036-5044.
5. Man O & Pilpel Y (2007) Differential translation efficiency of orthologous genes is involved in phenotypic divergence of yeast species *Nat Genet.* 39, 415-421.
6. Akashi H (2003) Translational Selection and Yeast Proteome Evolution *Genetics* 164, 1291-1303.
7. Drummond D A & Wilke C O (2008) Mistranslation-Induced Protein Misfolding as a Dominant Constraint on Coding-Sequence Evolution 134, 341-352.
8. Qin H, Wu W B, Comeron J M, Kreitman M, & Li W H (2004) Intragenic spatial patterns of codon usage bias in prokaryotic and eukaryotic genomes *Genetics* 168, 2245-2260.
9. Arava Y, Wang Y, Storey J D, Liu C L, Brown P O, et al. (2003) Genome-wide analysis of mRNA translation profiles in Saccharomyces cerevisiae *Proc Natl Acad Sci USA* 100, 3889-3894.
10. Tuller T, Kupiec M, & Ruppin E (2007) Determinants of protein abundance and translation efficiency in S. cerevisiae *PLoS Comput Biol* 3, e248.
11. Percudani R, Pavesi A, & Ottonello S (1997) Transfer RNA gene redundancy and translational selection in Saccharomyces cerevisiae *J Mol Biol* 268, 322-330.
12. DeRisi J L, Iyer V R, & Brown P O (1997) Exploring the metabolic and genetic control of gene expression on a genomic scale *Science* 278, 680-686.
13. Milo R, Jorgensen P, Moran U, Weber G, & Springer M (2009) BioNumbers—the database of key numbers in molecular and cell biology *Nucleic Acids Res* 23, 23.
14. Zhang S, Goldman E, & Zubay G (1994) Clustering of low usage codons and ribosome movement *J Theor Biol* 170, 339-354.
15. Menetret J F, Neuhof A, Morgan D G, Plath K, Radermacher M, et al. (2000) The structure of ribosome-channel complexes engaged in protein translocation *Mol Cell* 6, 1219-1232.
16. Zhu J, Penczek P A, Schroder R, & Frank J (1997) Three-dimensional reconstruction with contrast transfer function correction from energy-filtered cryoelectron micrographs: procedure and application to the 70S *Escherichia coli* ribosome *J Struct Biol* 118, 197-219.
17. Kaczanowska M & Ryden-Aulin M (2007) Ribosome biogenesis and the translation process in *Escherichia coli Microbiol Mol Biol Rev* 71, 477-494.
18. Alberts B, Johnson A, Lewis J, Raff M, Roberts K, et al. (2002) *Molecular Biology of the Cell* (New York).
19. Vetsigian K & Goldenfeld N (2009) Genome rhetoric and the emergence of compositional bias *Proc Natl Acad Sci USA* 106, 215-220.
20. Dittmar K A, Sorensen M A, Elf J, Ehrenberg M, & Pan T (2005) Selective charging of tRNA isoacceptors induced by amino-acid starvation *EMBO Rep* 6, 151-157.
21. Tuller T, Waldman Y, Kupiec M, & Ruppin E (2010) Translation Efficiency Is Determined By Both Codon Bias and Folding Energy *Proc. Natl. Acad. Sci. U.S.A., in press.*
22. Kudla G, Murray A W, Tollervey D, & Plotkin J B (2009) Coding-sequence determinants of gene expression in *Escherichia coli Science* 324, 255-258.
23. Ghaemmaghami S, Huh W K, Bower K, Howson R W, Belle A, et al. (2003) Global analysis of protein expression in yeast *Nature* 425, 737-741.
24. Li X, Hirano R, Tagami H, & Aiba H (2006) Protein tagging at rare codons is caused by tmRNA action at the 3' end of nonstop mRNA generated in response to ribosome stalling *Rna* 12, 248-255.
25. Kurland C G (1992) Translational accuracy and the fitness of bacteria *Annu Rev Genet.* 26, 29-50.
26. Graslund S, Nordlund P, Weigelt J, Hallberg B M, Bray J, et al. (2008) Protein production and purification *Nat Methods* 5, 135-146.
27. Lowe T M & Eddy S R (1997) tRNAscan-SE: a program for improved detection of transfer RNA genes in genomic sequence *Nucleic Acids Res* 25, 955-964.
28. Durinck S, Moreau Y, Kasprzyk A, Davis S, De Moor B, et al. (2005) BioMart and Bioconductor: a powerful link between biological databases and microarray data analysis *Bioinformatics* 21, 3439-3440.
29. Hirschman J E, Balakrishnan R, Christie K R, Costanzo M C, Dwight S S, et al. (2006) Genome Snapshot: a new resource at the *Saccharomyces* Genome Database (SGD) presenting an overview of the *Saccharomyces cerevisiae* genome. *Nucleic Acids Res* 34, D442-445.
30. Dittmar K A, Goodenbour J M, & Pan T (2006) Tissue-specific differences in human transfer RNA expression *PLoS Genet.* 2, e221.
31. Zaborske J M, Narasimhan J, Jiang L, Wek S A, Dittmar K A, et al. (2009) Genome-wide analysis of tRNA charging and activation of the eIF2 kinase Gcn2p *J Biol Chem* 284, 25254-25267.
32. Pavon-Eternod M, Wei M, Pan T, & Kleiman L (2009) Profiling non-lysyl tRNAs in HIV-1 *Rna* 9, 9.

33. Dittmar K A, Mobley E M, Radek A J, & Pan T (2004) Exploring the regulation of tRNA distribution on the genomic scale *J Mol Biol* 337, 31-47.

Example 5

Justification for Using tAI

The tAI is based on the genomic tRNA copy number (tGCN) as a surrogate measure for the cellular abundances of tRNAs; it is justified by several observations. First we provide here a direct experimental support for the correlation between tRNA gene copy number and expression levels in yeast. Second, in the past, in many organisms, it has been observed that the in vivo concentration of a tRNA bearing a certain anticodon is highly proportional to the number of gene copies coding for this tRNA type. Specifically, in *S. cerevisiae* a correlation of r=0.91 (1) was reported. In *B. subtilis*, a correlation of 0.86 between tRNA copy number and tRNA abundance was reported (2). Similarly, previous papers reported about significant correlation between genomic tRNA copy number and tRNA abundance in *E. coli* (3, 4). A related interesting result is the analysis of (5) who measured the translation rate of two glutamate codons: GAA and GAG. They found them to have a threefold difference in translation rate (21.6 and 6.4 codons per second, respectively). Remarkably, the WI of these codons, which is based on the tRNA pool and affinity of codon-anti-codon coupling and is the basis for the tAI calculation, captures the ratio of translation rate between the two codons. Calculating $w_i$ values for *E. coli* we found that the ratio between the $w_i$ of GAA and GAG is 3.125 (0.5/0.16) as compared to the 3.34 reported in the experiments (21.4/6.4). This result suggests that there is a direct relation between the adaptation of a codon to the tRNA pool, based on the genomic tRNA copy number, and the time it takes to translate it. Finally, the correlation between tRNA copy number and tRNA abundance in human tissues (brain, liver, vulva, testis, ovary, thymus, lymph node, spleen; (6)) is between 0.605 (Thymus) and 0.83 (Brain) (see Tables 4-7).

Third, a recent study showed that in *S. cerevisiae* the promoters of many of the Trna genes have a low predicted affinity to the nucleosome, suggesting a constitutive expression with little transcriptional regulation capacity (7). Thus, for fully sequenced genomes, the relative concentrations of the various tRNAs in the cell, and therefore the optimality of the various codons in terms of translation, can be approximated using the respective tRNA gene copy numbers in the genome. Additionally, the tAI has been shown to be highly correlated (r=0.63 for *S. cerevisiae*) to protein expression levels (8, 9). It was found that even among genes with similar transcript levels, higher tAI often corresponds to higher protein abundance (8).

This definition stems from an early observation of a trend of increasing codon usage bias with increasing gene expression levels in a sample of *E. coli* genes (10), and that tRNA concentrations are rate limiting in the elongation of nascent peptides (11). The translation efficiency, as defined above, has also been shown to be correlated with translation rate and accuracy (12), phenotypic divergence of yeast species (8), evolutionary rate (13), and to also play part in protein functionality (14).

Example 6

Inference of tRNA Expression Levels in Human Tissues

Dittmar et al. [24 PLoS Genetics 2006] have characterized the expression levels of tRNA across various human tissues relative to the brain. In order to get an estimate of the absolute tRNA pool in each tissue we employed an optimization procedure.

Briefly, instead of assuming that the tRNA levels in the brain are determined by the tRNA copy numbers, the inventors allowed their levels to vary and, while maintaining the tRNA expression ratios reported in the work of Dittmar et al. as constraints, they maximized the overall correlation between tAI and expression levels across the tissues with both expression data and relative tRNA values.

Formaly, let i T denote the inferred vector of tRNA levels in tissue i (i=1 denotes the brain); let ( )i tAI T denote the corresponding vector of gene tAI when using Tas proxy of tRNA levels; let i GE demote the vector gene expression in tissue i; Let R(˙,˙) denote spearman correlation.

The following optimization problem was solved:
Optimize ([R tAI T), tAI (T), . . . ],[GE(T), GE(T), . . . ])
Such that:
1) For every i each entry in i T is larger than 0 if the copy number of the corresponding entry is larger than 0; otherwise the entry remains 0.
2) The ratios between the expression levels of tRNAs in each tissue (i=1, 2, . . . ) relative to the brain (i 1=) are identical to the results reported in (PLoS Genetics 2006).

To solve this problem the optimization approach of Nelder-Mead (16) was employed.

Example 7

Implementing the Model of Zhang et al. on Artificial Genes and on the Genome of *S. cerevisae* to Show the Optimality of the Nondecreasing Profile At the first stage, artificial genes were generated with three types of codons (based on the tAI of codons in *S. cerevisae*): Fast (tAI=1), slow (tAI=0.0271; a weighted average of the three slowest codons in *S. Cerevisae*), and medium (tAI=0.43; a weighted average of all the codons in *S. Cerevisae* considering codon bias). All the results were compared to an artificial gene with an 'optimal' profile of translation efficiency where the first 50 codons are slow, the last 50 codons were fast, and the others codons are medium (a total of 500 codons). For comparison 6 randomized versions of the 'optimal' profile were generated: 1) Random permutation of the codons of the initial 'optimal' profile. 2) Random permutation of codons 51-500 of the 'optimal' profile (codons 1-50 remain slow). 3) Random permutation of codons 1-450 of the 'optimal' profile (codons 451-500 remain fast). 4) Random cyclic shift of the codons of the 'optimal' profile. 5) Random cyclic shift of the codons of the 'optimal' profile while not touching the first 50 codons. 6) Random cyclic shift of the codons of the 'optimal' profile while not touching the last 50 codons.

Nine measures of quality were generated: 1) Number of ribosome initiations before reaching steady state (RISS). 2) Time to reach steady state (TSS). 3) Initiation time at steady state (IT). 4) Translation time at steady state (TT). 5) Number of ribosomes per mRNA at steady state (RPM). 6) Number of codons translated per "second" (arbitrary time unit; CPS). 7) Number of ribosome collisions at steady state (RCSS). 8) Number of ribosome collisions till steady state (RCTSS). 9) Translation efficiency, number of codons translated per "second" per ribosome: measure 5) divided by measure 4) (CPSPR).

As can be seen, the 'optimal' profile is not worse than all the random models by all criterions (see FIGS. 25A-B). Red denotes significantly low; green denotes significantly high. The simulations demonstrate that the slow translation at the beginning is significantly important for efficient translation and decreased number of ribosome collisions. On the other hand, the fast translation at the end does not seem to play an important role when measuring these readouts under the Zhang model.

In the second stage, the model of Zhang was implemented on all the *S. Cerevisae* genes. The local translation speed at each codon and at each gene was derived from the tAI of the codon (see Methods). Higher tAI corresponded to higher speed. The inventors compared the profiles of all the genes to two randomized versions of the input: 1) Random permutations of the codons of all the genes, and 2) Random shift of the codons of all the genes. To this end, the nine measures of quality mentioned above were used.

The simulation shows a similar trend as in the previous subsection. The original genome outperforms the two randomized genomes according to all the measures of quality (see FIGS. 25A-B).

Example 8

More Details about the Simulation of Ribosomal Movement

In case where the input to the simulation was a vector of tAI values, the inventors used the reciprocal of such values at each codon position as a proxy for the waiting time of the ribosome at the position. The translation time values were normalized to set the maximum translation time to 1.

The simulation has three main parameters: 1. The minimum distance between two consecutive ribosomes (H). 2. The ribosome binding time (the initiation time)—technically, it was defined as the time required for a ribosome to start translating the mRNA, measured from the moment the ribosome in front has cleared the initiation site (first H codons). 3. The termination time—the time required for the ribosome to release the mRNA.

The minimum distance between ribosomes was set to be 15 codons (see BioNumbers for the size of the ribosome). An initiation time of 0.9 was used and the termination time was set to 0.1. The value of the slowest codon (longest translation time) was also the same as in (15) (time=1). The reported results were not sensitive to changes of +−100% these parameters.

The steady-state parameters are defined by the translation parameters of a ribosome during the steady-state. The system reaches steady state when the following conditions are met: 1. At least one ribosome finished translating the mRNA.
2. The number of ribosomes translating the mRNA is constant (i.e. the initiation rate is equal to the release rate).

At steady state all the translation parameters are constant and one can define the following parameters: a) Total translation time: the time it takes a single ribosome to translate the mRNA. b) Number of ribosomes on the transcript: the number of initiations in the period of a single translation time. c) Average translation rate: length of the message (number of codons) divided by the translation time [i.e. number of codons translated per time unit]. d) Number of ribosomal collisions till steady state and at steady state. This is the number of events (per unit time) in which a ribosome cannot continue due to a ribosome in front of it till steady state and at steady state.

REFERENCES FOR EXAMPLES 5-7 ONLY

1. Percudani R, Pavesi A, & Ottonello S (1997) Transfer RNA gene redundancy and translational selection in *Saccharomyces cerevisiae* *J Mol Biol* 268, 322-330.
2. Kanaya S, Yamada Y, Kudo Y, & Ikemura T (1999) Studies of codon usage and tRNA genes of 18 unicellular organisms and quantification of *Bacillus subtilis* tRNAs: gene expression level and species-specific diversity of codon usage based on multivariate analysis *Gene* 238, 143-155.
3. Ikemura T (1981) Correlation between the abundance of *Escherichia coli* transfer RNAs and the occurrence of the respective codons in its protein genes: a proposal for a synonymous codon choice that is optimal for the *E. coli* translational system *J Mol Biol* 151, 389-409.
4. Dong H, Nilsson L, & Kurland C G (1996) Co-variation of tRNA abundance and codon usage in *Escherichia coli* at different growth rates *J Mol Biol* 260, 649-663.
5. Sorensen MA & Pedersen S (1991) Absolute in vivo translation rates of individual codons in *Escherichia coli*. The two glutamic acid codons GAA and GAG are translated with a threefold difference in rate *J Mol Biol* 222, 265-280.
6. Dittmar K A, Goodenbour J M, & Pan T (2006) Tissue-Specific Differences in Human Transfer RNA Expression *PLoS Genet.* 2, e221.
7. Segal E, Fondufe-Mittendorf Y, Chen L, Thastrom A, Field Y, et al. (2006) A genomic code for nucleosome positioning *Nature*.
8. Man O & Pilpel Y (2007) Differential translation efficiency of orthologous genes is involved in phenotypic divergence of yeast species *Nat Genet.* 39, 415-421.
9. Tuller T, Kupiec M, & Ruppin E (2007) Determinants of protein abundance and translation efficiency in *S. cerevisiae* *PLoS Comput Biol* 3, e248.
10. Sharp P M & Li W H (1986) An evolutionary perspective on synonymous codon usage in unicellular organisms *J Mol Evol* 24, 28-38.
11. Varenne S, Buc J, Lloubes R, & Lazdunski C (1984) Translation is a nonuniform process: Effect of tRNA availability on the rate of elongation of nascent polypeptide chains *Journal of Molecular Biology* 180, 549-576.
12. Akashi H (2003) Translational Selection and Yeast Proteome Evolution *Genetics* 164, 1291-1303.
13. Wall D P, Hirsh A E, Fraser H B, Kumm J, Giaever G, et al. (2005) Functional genomic analysis of the rates of protein evolution *Proc Natl Acad Sci USA* 102, 5483-5488.
14. Kimchi-Sarfaty C, Oh J M, Kim I-W, Sauna Z E, Calcagno A M, et al. (2007) A "Silent" Polymorphism in the MDR1 Gene Changes Substrate Specificity *Science* 315, 525-528.
15. Zhang S, Goldman E, & Zubay G (1994) Clustering of low usage codons and ribosome movement *J Theor Biol* 170, 339-354.
16. Lagarias J C, Reeds J A, Wright M H, & Wright P E (1998) Convergence Properties of the Nelder-Mead Simplex Method in Low Dimensions *SIAM J. Optim.* 9, 112-147.

Example 9

Optimization of LDLR Receptor Sequence

The human LDLR receptor coding sequence was modified according to the teachings of the present invention so as to increase the efficiency of expression in CHO cells. Since currently the public database does not contain the CHO cells tRNA repertoire, the present inventors used instead the tRNA pool of a close, fully-sequenced species, the mouse.

The following sequences DNA sequences are contemplated:
Original: SEQ ID NO: 8
Max_tAI: SEQ ID NO: 9

Min_tAI: SEQ ID NO: 10
Deep signal peptide: SEQ ID NO: 11
Mid signal peptide: SEQ ID NO: 12
Deep and max optimized: SEQ ID NO: 13
Mid and max optimized: SEQ ID NO: 14
Deep and semi-optimized: SEQ ID NO: 15
Mid and semi-optimized: SEQ ID NO: 16
Deep at the end: SEQ ID NO: 17
Mid at the end: SEQ ID NO: 18
Deep at the 54$^{th}$ codon: SEQ ID NO: 19
Mid at the 54$^{th}$ codon: SEQ ID NO: 20

FIG. 26 is a graph illustrating the tAI values in exemplary polynucleotides generated according to embodiments of the present invention. Table 8, herein below summarized various aspects of the exemplified polynucleotides.

TABLE 8

| name | # initiation to S.S. | trans. time at S.S. | # ribosomes | codon rate | # collisions | max Loc. | max value | minAR loc. | minAR strength |
|---|---|---|---|---|---|---|---|---|---|
| original | 54 | 125.0460 | 14.9469 | 2.8655 | 62 | 186 | 8.3660 | 0.5196 | 1.2763 |
| max_tAI | 20 | 92.2400 | 15.3288 | 3.8858 | 68 | 180 | 6.0174 | 0.5028 | 1.2187 |
| min_tAI | 41 | 198.9945 | 14.9688 | 1.8000 | 58 | 186 | 13.2939 | 0.5196 | 1.2658 |
| deep signal peptide | 12 | 114.8543 | 10.3541 | 3.1200 | 1 | 2 | 11.0926 | 0.0056 | 1.6483 |
| mid signal peptide | 14 | 112.4770 | 12.9056 | 3.1860 | 1 | 2 | 8.7153 | 0.0056 | 1.3225 |
| deep and max optimized | 10 | 89.7562 | 8.1059 | 3.9935 | 0 | 2 | 10.9778 | 0.0056 | 2.0876 |
| mid and max optimized | 12 | 86.8173 | 10.6733 | 4.1288 | 0 | 2 | 8.0389 | 0.0056 | 1.5805 |
| deep and semi-optimized | 12 | 111.3305 | 10.0364 | 3.2188 | 1 | 2 | 11.0926 | 0.0056 | 1.7006 |
| mid and semi-optimized | 15 | 108.3916 | 12.9235 | 3.3062 | 1 | 2 | 8.1537 | 0.0056 | 1.2839 |
| deep at the end | 19 | 194.0334 | 17.0020 | 1.8461 | 302 | 331 | 11.4124 | 0.9246 | 2.1185 |
| mid at the end | 21 | 149.9905 | 17.0571 | 2.3886 | 295 | 338 | 8.7934 | 0.9441 | 1.6824 |
| deep at the 54th codon | 10 | 112.9687 | 8.8679 | 3.1721 | 44 | 54 | 12.7391 | 0.1508 | 2.3365 |
| mid at the 54th codon | 14 | 94.7586 | 12.0440 | 3.7824 | 37 | 54 | 7.8677 | 0.1508 | 1.5262 |

FIGS. 27-32 illustrate the parameters presented in Table 8 graphically.

Example 10

Translation Efficiency of Synthetic Genes

Materials and Methods

The bottleneck is a region on the gene where the harmonic mean of the codons' tAI values is minimal. For all codons except codon CGA, the tAI values were calculated using dos Reis et al. s-values [2]; for codon CGA the value 0.1333 was used. This codon is translated with tRNA$_{ACG}$, however the s-value for this interaction is very high, resulting in a very low tAI value. This tAI is smaller by at least an order of magnitude from the smallest codon, causing all other codons to have a relatively high tAI disabling this analysis. Since CGA is actually translated by tRNA$_{ACG}$ the present inventors changed the s-value of this interaction to a more reasonable value, resulting in the above mentioned tAI value. Given the tRNA repertoire of *E. coli* this change affects only the tAI value of codon CGA.

The codon tAI values are assumed to be proportional to the speed of its translation [5]; higher tAI value, correspond to high tRNA abundance and affinity, thus faster translation. A harmonic mean of speeds is simply an arithmetic mean of the corresponding times. Hence looking for the region with the minimum harmonic mean of speed is equivalent to looking for the region which takes the longest time to translate.

For each region the harmonic mean of speed is:

$$\frac{n}{\sum_{c \in Region} \frac{1}{tAI_c}};$$

where n is the region size, and c is the set of all the codons in the region (n codons).

To find the bottleneck, a sliding window of length n over the gene was used. The harmonic mean was calculated for each window and the window with the minimum value was identified. It should be noted that since the present inventors are averaging the translation time in a window, an incorrect window size might in some cases result in an incorrect identification of the bottleneck. For example, if the estimated window size is too big it might mask a cluster of a few slowly translated codons, of a more relevant size, that are surrounded by relative fast codons. However in most cases the slow region is significant enough and its identification is not too sensitive to the window size. Indeed, as mentioned in the result section, the present results did not change qualitatively for window sizes in the range 14<n<30.

The bottleneck Window Size (n)

Under a maximal density scenario (fast initiation rate), the distance between two consecutive ribosomes will be minimal. In this case, when two ribosomes are translating the same mRNA simultaneously, the minimum possible distance between the two translated codon (one by each of the ribosome) is one ribosome size (H codons), FIG. 33. At any given moment during the translation process, two adjacent ribosomes would have translated exactly the same codons apart from the last H codons—the first of the two ribosomes has already translated them, and second is just about to start them. If the time it took the first ribosome to finish translating the nth codon $T(n,1)$ is larger than the time it takes the second ribosome to translate the n–Hth codon $T(n–H,2)$ the second ribosome will "bump" into the first one. That is, if $T(n,1) > T(n–H,2)$ a traffic jam will be created. $T(n,1)=B+\Sigma_{i=1}^{n}t(i)$, B is ribosome assembly time on the ATG and $t(i)$ is the time it takes to translate the ith codon. The second ribosome gains access to the ATG only when enough codons (minimum H) were cleared after being translated by the first ribosomes. As a result a traffic jam will be created if $Tw(k,H) > Tw(1,H)+B$ where $Tw(k,H)$ is the time to translate H consecutive codons starting from codon k ($Tw(k,H)=\Sigma_{i=k}^{k+H-1}t(i)$). Therefore the region of H codons with maximum translation time $$\left( \underset{k=1:mRNA\ length-H}{\operatorname{argmax}} (Tw(k, H)) \right)$$

determines whether and where a traffic jam will be created. Choosing n in the present bottleneck equation to be equal to H it is easy to see that the bottleneck is related to this maximum.

As can be seen from this analysis, the minimal distance between two ribosomes should determine the window size. The footprint of the ribosome, which is the actual protection of the ribosome from RNA degradation was determined quite accurately to be 10 codons [21]. Due to the structure of the ribosomes it is assumed that there should be some space between two consecutive 30S subunits. As a result, although only 10 codons are protected, the minimal distance between the two ribosomes should be larger. Therefore, the present inventors chose to adopt the average ribosome-to-ribosome distance measured by Brandt F et al. [22]. They measured the mean distance between the center of mass of two ribosomes on actual bacterial polysomes to be 21.6 nm [22] which is about 21 codons (0.34 nm per base). In this example, n was set to be equal to H, e.g. n is set to 21 codons.

The Bottleneck Parameters

A bottleneck is characterized by two parameters: its "location" and its "strength":

The "location" of the bottleneck is defined as the location in the gene of the bottleneck's first codon (k codons from the ATG).

The "strength" of the bottleneck is defined as the arithmetic average of $1/tAI$ values for the codons in the region, e.g.

$$\frac{1}{n} \sum_{c \in Region} \frac{1}{tAI_c}$$

(the inverse of the harmonic mean).

The relative strength of the bottleneck is defined as the strength of the bottleneck divided by the average $1/tAI$ for the entire gene, e.g.

$$\frac{\frac{1}{n} \sum_{c \in bottleneck} \frac{1}{tAI_c}}{\frac{1}{l} \sum_{c=1}^{l} \frac{1}{tAI_c}};$$

where l is the number of codon in the gene (excluding the stop codon).

The relative location of the bottleneck is defined as the location of the bottleneck divided by number of possible windows; e.g.

$$\frac{k}{l-n+1};$$

where k is the location of the bottleneck, and l is the length of the gene and n is the window size.

Per-Cell Protein Abundance

To get an estimate for protein expression per cell from GFP library data [13] the present inventors normalized the measured protein abundance, which is the protein abundance by optical density (OD) which serves here as a proxy for the population size, the OD.

The protein abundance levels for the data from Welch et al. were measured while keeping the OD constant. Therefore this protein abundance may be used as an already normalized protein level per cell.

E. coli Highly and Lowly Expressed Genes

The E. coli mRNA levels were taken from Lu et al. [23]. The highly expressed genes are the top 500 genes, and the lowest expressed genes are the bottom 500 genes (genes with no mRNA recorded were ignored). However, for both groups genes which are longer than 100 codons were used.

Finding the Main Anti-Correlated Codons

The present inventors used partial correlation to find the codons which contribute the most to the decrease in the cell's fitness. The highest contributors were filtered according to the following steps:

1. Find codons which have a negative correlation to the OD (29 codons). The present inventors were looking for codons which caused a decrease in the fitness hence, only anti-correlated codons.
2. For all codons left, the present inventors calculated the partial correlation matrix $M(i,j)$=partial correlation (codon i, OD|codon j).
3. Find the minimum absolute value of the partial correlation, for each codon.

Rank the codons in a descending order accordingly. This provides the codons with a correlation that cannot be explained by correlation to other codons (see Table 9, herein below for the list of all codons with p-value<0.1).

TABLE 9

| Codon | Minimum negative partial correlation (p-value) | Controlling codon in the partial correlation |
|---|---|---|
| UCA | −0.29 (0.0004) | CAU |
| CAU | −0.24 (0.003) | AAU |
| AGU | −0.17 (0.04) | UCA |
| AAU | −0.156 (0.06) | CAU |
| GGA | −0.156 (0.06) | CAU |
| GUC | −0.15 (0.07) | UCA |

The codon at the top of the list is UCA which is anti-correlation to the OD and its correlation cannot be explained by other codons. The second contributing codon is CAU which has the highest partial correlation (−0.36 p-value 8.5e-6) when controlling for the UCA codon. This codon is also the second codon in the ranked list. All other codons have a partial-correlation smaller than 0.2 with a p-value>=0.04 when controlling with one of the two codons (either UCA or CAU).

Calculating the Codon Usage in the Genome

The genome for *E. coli* B21 strain (which was used by Kudla et al.) was downloaded from NCBI; [Refseq: NC_012947 (Jan. 11, 2010)]. For each codon the present inventors counted its appearance in all the ORFs and normalized by the total number of codons.

Calculating the Codon Usage in the Transcriptome mRNA levels were taken from Lu et al. [23]. If a gene did not have a measurement it was assumed to have a zero mRNA level. The measurements were done with the *E. coli* strain K12 MG1655; thus the sequence used for the calculation was different from the genome codon usage. The sequence was downloaded from NCBI, [Refseq: NC_000913 (Apr. 1, 2010)]. The contribution of each gene was calculated by multiplying the mRNA levels measurements for the gene by the codon usage of the same gene. The contributions of all genes were summed for each codon and then divided by the total sum of all codons.

The Bottleneck Window Size (n)—Detailed Calculation

The bottleneck is the region that will have the most slowing down effect on the ribosome. This region will only have a bottleneck effect if it slows the ribosomes enough to affect consecutive ribosome. As explained in the following the size of this region has to be about the minimum ribosome-to-ribosome distance (denoted below as H).

The following definitions were made:
1. Traffic jam will be caused if the time it takes the first ribosome to finish translation of the nth codon is longer than the time it takes the second ribosome to finish translation of codon n−H. In this case the second ribosome will not be able to proceed to the (n−H+1)-th codon since it will collide with the first ribosome and hence will be delayed.
2. A ribosome can start assembling on the ATG when the first H codons (the minimum distance required between 2 ribosomes) are cleared from the preceding ribosome. Let B be the time it takes the ribosome to bind and assemble on the ATG.
3. If t(i) is the time it takes to translate codon i, and T(n,j) is the time it takes the $j^{th}$ ribosome to finish translation of the $n^{th}$ codon, where n is the codon at the leading edge of the ribosome.

then:
a. The time it takes the first ribosome to reach the $n^{th}$ codon:

$$T(n, 1) = B + \sum_{i=1}^{n} t(i)$$

b. The time it takes the second ribosome to reach the (n−H)-th codon:

$$T(n-H, 2) = \text{(time until the assembly site is cleared)} + B + \sum_{i=1}^{n-H} t(i) \xrightarrow{yields}$$

$$T(n-H, 2) = B + \sum_{i=1}^{H} t(i) + B + \sum_{i=1}^{n-H} t(i)$$

4. For a traffic jam to be created, the time for the first ribosome to finish translation of the $n^{th}$ codon should be longer than the time it takes the second ribosome to finish translation of the n−H codon:

$$T(n, 1) > T(n-H, 2) \xrightarrow{yields}$$

$$B + \sum_{i=1}^{n} t(i) > B + \sum_{i=1}^{H} t(i) + B + \sum_{i=1}^{n-H} t(i) \xrightarrow{yields} \sum_{i=n-H+1}^{n} t(i) > B + \sum_{i=1}^{H} t(i)$$

5. We define Tw(k, H) is the time to translate H consecutive codons starting from codon k (Tw(k,H)=$\sum_{i=k}^{k+H-1} t(i)$). Therefore, a traffic jam will be created if:

$$Tw(k,H) > B + Tw(1,H)$$

$$Tw(k,H) - Tw(1,H) > B$$

6. For any traffic jam to be created along the gene:

$$\underset{k=1:mRNA\ length-H}{argmax} (Tw(k, H)) - Tw(1, H) > B$$

Inspecting the slowest region (of H codons) for the specific gene (bottleneck strength), if the time to translate that region minus the time it takes to translate the first H codons is longer than the time to finish "assembling" the ribosome (B) than traffic jam will be created.

As can be seen from the equation the region size which determine whether two consecutive ribosomes will collide has the size of the minimum distance between 2 ribosomes.

Results

Looking for the effects of codon usage on the translation efficiency and whether the order of the codons is important the present inventors set out to re-analyze data from the three synthetic libraries [13, 14]. The original tAI value [2] is defined for an entire gene based on all its codons as:

$$tAI_g = \left( \prod_{k=1}^{\ell_g} w_{i_k} \right)^{1/\ell_g},$$

$l_g$ is the length of the gene in codons and $w_{i_k}$ is the relative adaptiveness value of the codon defined by kth triplet in the gene.

Here, the $w_i$ value of a single codon is referred to as the codon's tAI. This measure is an approximation of the codon's translation speed, since a codon is assigned with a high tAI if the various tRNAs that translate it are at high abundance and have high affinity towards it. Beside the tAI there are other alternative approximations for the codon's translation speed [8, 15, 16]. Note that all current models have approximation at their basis, necessarily introducing inaccuracies in analyses that are based on them.

To investigate the effect of regions with less than optimal codons, for each gene, the "bottleneck" was defined as a region of a fixed number of codons, n, where the (harmonic) mean of the codons' tAI value is minimal (the value of n is related to the distance between two consecutive ribosomes on the mRNA, see Methods). Assuming the codon's tAI value is an approximation for the translation speed then 1/tAI can be regarded as the codon's translation time and the bottleneck is the region with the longest average translation time.

The bottleneck of each gene is characterized by two parameters: the location of the bottleneck, i.e. number of codons from the ATG in which it occurs, and the "strength" of the bottleneck—the average time to translate all the codons within it. To allow comparisons between the different genes and libraries below the present inventors refer to the relative, rather than absolute, form of these variables—the relative location of the bottleneck is its location divided by the length of the gene, and the relative strength is the strength divided by the average strength (i.e. time it takes to translate the bottleneck regions divided by the total time of translation of the mRNA, or 1/tAI of the entire gene).

The present inventors first analyzed 154 synthetic GFP genes in a library constructed by Kudla et al. [13]. All the synthetic GFP variants had the same amino-acid sequence but different codon sequences. For these genes the bottleneck parameters were calculated using a window of length n=21 codons. Note that there is uncertainty regarding the exact value of this parameter (see Methods), however experimentation with other window sizes in the range 14<n<30 did not affect results qualitatively (not shown). FIG. 34A shows the relative location of the bottleneck of all GFP genes vs. the protein abundance of each translated gene (see Methods). The relative location is anti-correlated to the protein abundance (Pearson: −0.43 p-value $3.4·10^{-8}$; Spearman −0.46 p-value $2.8·10^{-9}$), indicating that genes that have the bottleneck closer to the ATG (designated here as "proximal bottleneck") tend to have a higher protein abundance levels compared to genes whose bottleneck are located towards the 3' end of the gene (designated "distal bottleneck").

As for the relative strength of the bottleneck, when examining the entire library of 154 genes, a modest yet significant correlation with the protein abundance (Pearson: 0.38 p-value $1.9·10^{-6}$; Spearman: 0.31 p-value $1.2·10^4$) was found, i.e. genes with long dwell times of the ribosome in the bottleneck regions tended to have higher expression levels. However, as seen in FIG. 34B, this correlation is mainly contributed by genes which have a proximal bottleneck. Focusing on 86 of the genes with a proximal bottleneck (located between relative positions 0.16 to 0.28) a significant positive correlation emerged between the relative strength and the protein abundance (Pearson: 0.47 p-value $3.9·10^{-6}$; Spearman 0.44 p-value $2.1·10^{-5}$).

Summarizing the analysis of the GFP library, the distribution of the codons along the transcript appears to affect the final GFP levels in the cell. A region of less efficient codons at the beginning of a transcript, e.g. a proximal bottleneck, seems to enables higher protein levels. For genes with a proximal bottleneck it is also beneficial to have a relative long dwell time of the ribosome, i.e. a strong enough bottleneck.

In another recent paper by Welch et al. [14] two different proteins were synthesized: the DNA polymerase of *Bacillus* phage and an antibody fragment (scFv). For each protein there are approximately 40 different sequences in which the amino-acid was kept the same while changing the codon sequence. For both proteins, the location of the bottleneck is quite far from the ATG in most synthetic variants (relative distance of ~0.5 and higher, FIGS. 35A-B), excluding the possibility to examine the effect of proximal bottleneck on the expression of these two proteins. Nonetheless the present inventors could still compute the correlation between the bottleneck's parameters to the protein abundance. Although less significant than in the case of the GFP library, both libraries showed an anti-correlation between the protein abundance levels and the relative location of the bottleneck, the Spearman correlation is −0.34 with p-value of 0.06, and −0.40, with p-value of 0.03 (Pearson: −0.34 p-value 0.06 and −0.16 p-value 0.40) for the scFv and the Polymerase respectively. In similarity to the GFP library such negative correlation indicates that proximal bottlenecks are often associated with higher expression levels. As was done for the GFP library, the present inventors looked at the correlation between the protein abundance and the bottleneck relative strength (FIGS. 36A-B) for specific locations, chosen based on FIG. 35 (for correlations see Table 10, herein below, which illustrates the correlations between the bottleneck relative strength to the protein abundance for the scFv and Polymerase libraries).

TABLE 10

| Protein | Relative location | Number of genes | Correlation with the bottleneck relative strength Pearson; Spearman | p-value Pearson; Spearman |
|---|---|---|---|---|
| scFv | 0.9-1 | 25 | −0.23; −0.32 | 0.27; 0.11 |
| scFv | 0-1 (All) | 42 | −0.43; −0.41 | 0.01; 0.02 |
| Polymerase | 0.48-0.52 | 13 | −0.60; −0.67 | 0.03; 0.015 |
| Polymerase | 0.76-0.82 | 13 | −0.38; −0.43 | 0.2; 0.14 |
| Polymerase | 0-1 (All) | 39 | −0.55; −0.67 | 0.0018; 7.1e−5 |

Interestingly, while in the case of the GFP library, a proximal bottleneck became more effective with increased relative strength, in the cases of scFv and the Polymerase, which featured distal bottleneck, the strength actually showed the opposite correlation, that is genes with long dwell times in the bottleneck regions showed lower protein abundance (Spearman: −0.43 p-value 0.02 and −0.67 p-value $7.1·10^{-5}$ for all genes of scFv and the Polymerase respectively). It is our understanding that a proximal bottleneck can have beneficial effects on protein production [5]. The bottleneck can delay the translating ribosome causing a ribosome backlog (when in polysome) but they can also reduce the density of the ribosome downstream. Proximal bottleneck minimizes the number of jammed ribosomes; thus reducing the ribosome sequestering and collisions, two potential causes for a decrease in protein production. Assuming the bottleneck reduces the density of ribosomes downstream, a slower bottleneck (that is a bottleneck with increased relative strength) will reduce even more downstream ribosome collisions, improving protein production, as seen with the GFP library. On the other hand a distal bottleneck which is at the end of the ORF causes a long backlog, with no beneficial effects on expression levels. Since bottleneck at the end of the ORF seems to mainly have negative effects on the protein translation rate, reducing its relative strength is beneficial, as seen in the case of the scFv and the Polymerase proteins.

To further verify the present assumption that the bottleneck may have beneficial effect on protein abundance when they are located at the beginning of the gene, the present inventors looked at the distribution of locations of the bottleneck in natural *E. coli* genes [Refseq: NC_012947], see FIG. 37 and FIGS. 38A-C). Indeed for most genes with a high bottleneck's relative strength (higher than 1.3) the bottleneck region is located in the first quadrant of the transcript (relative location smaller than 0.25). 41% of genes with a high relative strength are located in the first quadrant (hyper-geometric significant enrichment p-value $6.2·10^{-9}$) and only 22% are located in the fourth quadrant which is a significant depletion (hyper-geometric p-value $1·10^4$). Examining separately highly expressed genes (see Methods), FIG. 38B, a depletion of strong bottleneck from the fourth quadrant (18% of the genes hyper-geometric p-value 0.02) and enrichment in the first quadrant (49%, p-value 0.005) is also observed. In contrast a separate examination of lowly expressed genes (FIG. 38C) reveals no significant depletion or enrichment (depletion from the fourth quadrant 18% p-value 0.39, enrichment in the first quadrant 41% p-value 0.15).

Kudla et al. showed the folding energy of the mRNA near the initiation site influences translation rate [13]. It was suggested that a weak secondary structure enables the ribosome to bind faster to the mRNA, thus enabling a faster translation rate. These observations raised the possibility that the correlation presently observed between bottleneck location and protein abundance in the GFP library are due to the confounding effects of mRNA secondary structure stability. The present inventors thus carried out correlation analysis to verify that the correlations found still hold even when examining gene sets with similar mRNA folding energy. The present inventors calculated the partial correlation between the bottleneck's parameters and the per-cell protein abundance while controlling for the folding energy. Both the relative location correlation (Pearson −0.24 p-value 0.004; Spearman −0.27 p-value 9.5·10$^4$) and the relative strength at location 0.16-0.28 (FIGS. 34A-B) correlation (Pearson 0.3 p-value 0.006; Spearman 0.24, p-value 0.024) remained significant even after controlling for the folding energy, indicating that bottleneck's parameters correlations are significant on their own. Therefore although in the GFP library the folding energy significantly affects the protein abundance, the bottleneck location and strength also contribute to the changes in the protein levels.

The Cost of Production

For efficient translation the present inventors were interested not only in protein levels of the gene but also in the cost of its expression. Looking for the cost of production, the present inventors turned to look how introducing a new gene to the host cell influenced the cell fitness. The influence on fitness is in general a combination of the benefit of producing the protein with the burden it puts on the system. However, assuming that the genes from the heterologous libraries discussed here do not contribute to the fitness of the host cell, the fitness decline due to expression only reflect the pure cost of the production.

Kudla et al. showed that the measured optical density (OD), assumed to be proportional to the fitness of the host cell, is highly correlated with the CAI. Further analysis showed that the tAI is also correlated with OD (Pearson: 0.51 p-value 2.4·10$^{-11}$). These two similar measures describe the entire transcript and not a particular region within it. In contrast, the present inventors found that the bottleneck parameters which significantly correlate with protein abundance are not correlated with cell's fitness. Thus the factors that correlate with fitness and those correlating with protein abundance appear distinct in this library (FIG. 39). It seems that while specific regions of the transcript affect the protein abundance, the fitness is affected by the codon usage of the entire transcript.

Trying to understand the source for the correlation between the fitness and tAI or CAI, the present inventors turned to examine the effect of individual codon on the cell's fitness. The correlation between the usage frequency of each specific codon in the GFP sequence (number of copies of the codon in the sequence) and the fitness of the cell that was expressing that GFP variant was analyzed (FIG. 40). Interestingly, the extent of usage of some codons is negatively correlated with the fitness, it is positively correlated for others and the rest are not correlated with the fitness. The cases of negative correlation may indicate a burden on fitness due to using particular codons. In contrast, since fitness can only decrease due to GFP expression, cases of positive correlation between codon usage in a gene and its host fitness likely reflect artificially the negative correlation of synonym codons; that is the preference for not using its alternative codons rather than a preference for expressing the codon itself.

Thus, focusing on the codons that correlate negatively with fitness, three codons were detected whose usages correlate most significantly: CAU (Pearson correlation −0.69, p-value <10$^{-324}$), AAU (Pearson correlation −0.68, p-value<10$^{-324}$); and UCA (Pearson correlation −0.67, p-value 10$^{-324}$), FIG. 40, and Table 11 herein below.

TABLE 11

| Amino acid | Codon | # tRNA Copies | tAI | correlation | p-value | Codon usage in genome % | Codon usage in transcriptome % |
|---|---|---|---|---|---|---|---|
| N | AAU | 0 | 0.39 | −0.68 | <E−324 | 1.73 | 1.21 |
| N | AAC | 4 | 0.67 | 0.68 | <E−324 | 2.16 | 2.69 |
| K | AAA | 6 | 1.00 | 0.11 | 1.96E−01 | 3.37 | 4.25 |
| K | AAG | 0 | 0.32 | −0.11 | 1.96E−01 | 1.02 | 1.29 |
| T | ACU | 0 | 0.20 | 0.16 | 5.71E−02 | 0.89 | 1.30 |
| T | ACC | 2 | 0.33 | 0.07 | 4.09E−01 | 2.33 | 2.60 |
| T | ACA | 1 | 0.17 | −0.09 | 2.57E−01 | 0.68 | 0.48 |
| T | ACG | 1 | 0.22 | −0.20 | 1.64E−02 | 1.45 | 1.02 |
| S | AGU | 0 | 0.10 | −0.48 | 8.13E−10 | 0.86 | 0.54 |
| S | AGC | 1 | 0.17 | 0.48 | 8.13E−10 | 1.61 | 1.34 |
| R | AGA | 1 | 0.17 | −0.16 | 5.48E−02 | 0.18 | 0.10 |
| R | AGG | 1 | 0.22 | 0.16 | 5.48E−02 | 0.11 | 0.05 |
| I | AUU | 0 | 0.30 | −0.39 | 9.18E−07 | 3.05 | 2.57 |
| I | AUC | 3 | 0.50 | 0.42 | 1.21E−07 | 2.52 | 3.26 |
| I | AUA | 0 | 0.055 | −0.22 | 8.02E−03 | 0.41 | 0.19 |
| M | AUG | 7 (3.5, 3.5)* | 0.58 | NaN | NaN | 2.81 | 2.73 |
| H | CAU | 0 | 0.10 | −0.69 | <E−324 | 1.28 | 0.95 |
| H | CAC | 1 | 0.17 | 0.69 | <E−324 | 0.98 | 1.13 |
| Q | CAA | 2 | 0.33 | −0.43 | 5.75E−08 | 1.53 | 1.15 |
| Q | CAG | 2 | 0.44 | 0.43 | 5.75E−08 | 2.89 | 2.93 |
| P | CCU | 0 | 0.10 | −0.42 | 8.35E−08 | 0.69 | 0.57 |
| P | CCC | 1 | 0.17 | 0.02 | 8.45E−01 | 0.55 | 0.29 |
| P | CCA | 1 | 0.17 | −0.35 | 1.08E−05 | 0.83 | 0.73 |
| P | CCG | 1 | 0.22 | 0.57 | 4.65E−14 | 2.35 | 2.54 |
| R | CGU | 4 | 0.67 | 0.03 | 7.23E−01 | 2.11 | 2.88 |
| R | CGC | 0 | 0.48 | −0.30 | 1.92E−04 | 2.22 | 2.09 |
| R | CGA | 0 | 0.13 | 0.22 | 6.21E−03 | 0.35 | 0.17 |
| R | CGG | 1 | 0.17 | 0.06 | 4.53E−01 | 0.53 | 0.25 |

TABLE 11-continued

| Amino acid | Codon | # tRNA Copies | tAI | correlation | p-value | Codon usage in genome % | Codon usage in transcriptome % |
|---|---|---|---|---|---|---|---|
| L | CUU | 0 | 0.10 | −0.11 | 1.95E−01 | 1.10 | 0.79 |
| L | CUC | 1 | 0.17 | −0.08 | 3.08E−01 | 1.11 | 0.82 |
| L | CUA | 1 | 0.17 | −0.42 | 7.56E−08 | 0.39 | 0.20 |
| L | CUG | 4 | 0.72 | 0.29 | 4.45E−04 | 5.33 | 5.80 |
| D | GAU | 0 | 0.30 | −0.41 | 2.48E−07 | 3.20 | 2.97 |
| D | GAC | 3 | 0.50 | 0.41 | 2.48E−07 | 1.91 | 2.54 |
| E | GAA | 4 | 0.67 | −0.09 | 2.79E−01 | 3.97 | 4.80 |
| E | GAG | 0 | 0.21 | 0.09 | 2.79E−01 | 1.77 | 1.80 |
| A | GCU | 0 | 0.20 | −0.18 | 3.00E−02 | 1.54 | 2.31 |
| A | GCC | 2 | 0.33 | −0.27 | 1.13E−03 | 2.57 | 2.09 |
| A | GCA | 3 | 0.50 | 0.46 | 6.25E−09 | 2.02 | 2.23 |
| A | GCG | 0 | 0.16 | −0.42 | 9.49E−08 | 3.41 | 3.17 |
| G | GGU | 0 | 0.39 | 0.19 | 2.16E−02 | 2.48 | 3.39 |
| G | GGC | 4 | 0.67 | 0.25 | 2.44E−03 | 2.99 | 3.30 |
| G | GGA | 1 | 0.17 | −0.58 | 8.66E−15 | 0.78 | 0.47 |
| G | GGG | 1 | 0.22 | 0.10 | 2.39E−01 | 1.10 | 0.71 |
| V | GUU | 0 | 0.20 | −0.20 | 1.72E−02 | 1.83 | 2.66 |
| V | GUC | 2 | 0.33 | −0.27 | 7.94E−04 | 1.52 | 1.29 |
| V | GUA | 5 | 0.83 | 0.34 | 2.50E−05 | 1.10 | 1.39 |
| V | GUG | 0 | 0.27 | 0.08 | 3.52E−01 | 2.64 | 2.36 |
| Y | UAU | 0 | 0.30 | −0.58 | 7.11E−15 | 1.60 | 1.24 |
| Y | UAC | 3 | 0.50 | 0.58 | 7.11E−15 | 1.21 | 1.46 |
| * | UAA | 0 | 0.00 | NaN | NaN | 0.21 | 0.27 |
| * | UAG | 0 | 0.00 | NaN | NaN | 0.02 | 0.01 |
| S | UCU | 0 | 0.20 | 0.45 | 8.07E−09 | 0.84 | 1.19 |
| S | UCC | 2 | 0.33 | 0.36 | 7.79E−06 | 0.86 | 1.05 |
| S | UCA | 1 | 0.17 | −0.67 | <E−324 | 0.70 | 0.45 |
| S | UCG | 1 | 0.22 | 0.04 | 6.08E−01 | 0.90 | 0.60 |
| C | UGU | 0 | 0.10 | 0.11 | 1.84E−01 | 0.51 | 0.38 |
| C | UGC | 1 | 0.17 | −0.11 | 1.84E−01 | 0.65 | 0.52 |
| * | UGA | 0 | 0.00 | NaN | NaN | 0.09 | 0.06 |
| W | UGG | 1 | 0.17 | NaN | NaN | 1.53 | 1.11 |
| F | UUU | 0 | 0.20 | −0.52 | 1.22E−11 | 2.22 | 1.54 |
| F | UUC | 2 | 0.33 | 0.52 | 1.22E−11 | 1.65 | 2.05 |
| L | UUA | 1 | 0.17 | −0.54 | 1.70E−12 | 1.38 | 0.79 |
| L | UUG | 1 | 0.22 | 0.48 | 9.38E−10 | 1.36 | 0.91 |

For each codon the tables contains it amino acid, number of copies of complementary tRNA in the genome, its tAI value, the Pearson correlation with the OD measurements, the codon usage in the genome and the in the transcriptome. Except for the transcriptome all values are based on E. coli strain B, the transcriptome was calculated for E. coli K12 (see methods). When NaN (Not a Number) is listed it means that a correlation cannot be calculated due to a constant value of codons for all GFP variants
*Met is partly initiation tRNA and partly tRNA decoding regular Met codons. It was assumed that about half of the Met tRNAs are used for initiation.

Table 12 herein below lists that amino-acid usage in the GFP sequence. For each amino acid the table lists the number of times it is used in the GFP protein.

TABLE 12

| Amino acid | Copy number in GFP |
|---|---|
| A | 8 |
| R | 6 |
| N | 13 |
| D | 18 |
| C | 2 |
| Q | 8 |
| E | 16 |
| G | 22 |
| H | 9 |
| I | 12 |
| L | 21 |
| K | 20 |
| M | 6 |
| F | 12 |
| P | 10 |
| S | 10 |
| T | 16 |
| W | 1 |
| Y | 11 |
| V | 18 |

Further examination reveals inter-dependencies between the usage of some of these codons, in particular, the frequencies of CAU and AAU are highly correlated r=0.92, p-value $10^{-64}$ themselves (reasons for internal correlation may have to do with GFP construction methods, see Kudla et al.). Using partial-correlation analysis between the usages of each codon the present inventors identified codon UCA and codon CAU as the main codons contributing to the decrease in the fitness (see Methods).

The number of occurrences of the UCA codon, encoding for Serine, in a single gene varies between zero to three appearances. This codon is the rarest out of the six Serine codons in the E. coli genome [Refseq: NC_012947], though it is not extremely rare (12.2% of all Serine codons, and 0.7% of all 61 codons in the open reading frames of the genome, see Table 11, herein above). However, in the transcriptome (i.e. the genome, weighted by the mRNA expression level from each gene, see Methods) the UCA is one of the rarest codons (8.7% of all Serine codons and 0.45% of all 61 codons). The UCA codon is exclusively translated by the tRNA$_{UGA}$ [17]. The genome of E. coli has only one copy of this tRNA gene and, reassuringly, it was shown that a shortage of this tRNA decreases the cell's fitness [18]. The negative correlation between the copy number of the UCA codon and the fitness can thus imply that the increase usage of the UCA codon causes a shortage of the corresponding tRNA, causing a decrease in fitness. Regarding codons CAU and AAU, they are negatively correlated with fitness (and with one another) yet no apparent reason for this negative correlation was found.

Shortage of tRNAs explains some of the correlations between the usage of certain codons with the fitness; however, it is not clear through which mechanism a shortage of tRNAs affects the fitness. The extensive usage of codons that correspond to rare tRNAs can affect the fitness in at least one of two alternative means—it may consume the tRNAs and sequester them from participating in translation of other transcripts, or it may affect fitness due to the consumption of the ribosome that are delayed for longer time in the search for rare tRNAs. A simple means to distinguish between these two alternative options is to examine whether not only the number, but the location of such rare codons affect fitness. In particular, it may be expected that if the fitness-reducing effect of the rare codons is the jamming of ribosomes, then their utilization will be particularly harmful when located distally, closer to the 3' end. In contrast if the fitness-reducing effect is predominantly due to the consumption of rare tRNAs then it is not expected to show such location dependence. In reality the present inventors observed no correlation with the location (FIG. 41) suggesting that it is the consumption of the rare tRNA, in this case, that compromises fitness.

Conclusion

As shown a proximal and strong bottleneck is correlated with an increase in protein abundance. A proximal bottleneck can reduce the number of jammed ribosomes on the transcripts. Therefore, it can reduce both the number of occupied ribosomes and the number of delayed ribosomes. Delaying ribosomes on the mRNA might increase their abortion rate; thus causing early termination of the translation [19], reducing the protein levels. For ribosomes to jam, a fast initiation rate is required. This is usually the case in highly expressed genes, in cases of heterologous gene expression and in synthetic libraries such as discussed here where high protein levels are desired. Due to amino acid sequence constrains for some genes a naïve approach, using only optimal codons, might result in an unintentional distal bottleneck.

While the bottleneck parameters are correlated with the protein abundance they are not correlated with the fitness. This suggests that while the occupation of more ribosomes sequesters them from the cell's pool, for most genes in the GFP library it does not cause a shortage of ribosome; enabling the cell to continue translating other transcripts. The decrease in the fitness is correlated to the increased usage of codons UCA and CAU, suggesting a shortage of the complementary tRNAs.

The present results thus show that, along with mRNA stability, codon choice does affect translation efficiency, yet that naïve averaged measures such as CAI and tAI, do not capture this regulatory capacity. The results also show that while codon choices do affect both the translation efficiency and the cell's fitness, different aspects of the codon selection affect differently the production capacity and the costs. One direct conclusion from the present results relates to the popular usage of "His-tags"—chains of Histidine residues at C termini of genes in heterologous expression systems [20]. When using C-terminus His-tags in bacterial expression systems it would be thus advantageous to encode Histidine with CAC rather than with CAU for two reasons: firstly since CAU appears to correlate negatively with fitness, and secondly in order to avoid a bottleneck towards the end of the gene.

When trying to understand the cell system one realizes its processes are regulated on many different levels. As showed in this paper, synthetic gene libraries enabled the present inventors to control for a significant portion of the gene's variability and focus on the effects of regions with less than optimal codons (the bottleneck). The results further demonstrate how correlative conclusions made from observations of natural gene sequences can be complemented by synthetic genes, allowing decoding the sequence features which govern the efficiency of translation and it costs.

References For Example 10

1. Sharp P M, Li W H: The codon Adaptation Index—a measure of directional synonymous codon usage bias, and its potential applications. *Nucleic Acids Res* 1987, 15(3): 1281-1295.
2. dos Reis M, Savva R, Wernisch L: Solving the riddle of codon usage preferences: a test for translational selection. *Nucleic Acids Res* 2004, 32(17):5036-5044.
3. Man O, Pilpel Y: Differential translation efficiency of orthologous genes is involved in phenotypic divergence of yeast species. *Nat Genet.* 2007, 39(3):415-421.
4. Sharp P M, Li W H: An evolutionary perspective on synonymous codon usage in unicellular organisms *J Mol Evol* 1986, 24(1-2):28-38.
5. Tuller T, Carmi A, Vestsigian K, Navon S, Dorfan Y, Zaborske J, Pan T, Dahan O, Furman I, Pilpel Y: An evolutionarily conserved mechanism for controlling the efficiency of protein translation. *Cell* 2010, 141(2):344-354.
6. Clarke T Ft, Clark P L: Increased incidence of rare codon clusters at 5' and 3' gene termini:implications for function. *BMC Genomics* 2010 11:118.
7. Bulmer M: Codon usage and intragenic position. *J Theor Biol* 1988, 133(1):67-71.
8. Mitarai N, Sneppen K, Pedersen S: Ribosome collisions and translation efficiency: optimization by codon usage and mRNA destabilization. *J Mol Biol* 2008, 382(1):236-245.
9. Romano M C, Thiel M, Stansfield I, Grebogi C: Queueing phase transition: theory of translation. *Physical Review Letters* 2009, 102(19):198104-198300.
10. Greulich: Phase diagram and edge effects in the ASEP with bottlenecks. *Physica A: Statistical and Theoretical Physics* 2008, 387(8-9):1972.
11. Dong: Towards a model for protein production rates. *Journal of Statistical Physics* 2007, 128(1-2):21.
12. Shaw: Local inhomogeneity in asymmetric simple exclusion processes with extended objects. *Journal of Physics A: Mathematical and General (Formerly: Journal of Physics A: Mathematical, Nuclear and General) (Now: Journal of Physics A: Mathematical and Theoretical)* 2004, 37(6): 2105.
13. Kudla G, Murray A W, Tollervey D, Plotkin J B: Coding-sequence determinants of gene expression in *Escherichia coli. Science* 2009, 324(5924):255-258.
14. Welch M, Govindarajan S, Ness J E, Villalobos A, Gurney A, Minshull J, Gustafsson C: Design parameters to control synthetic gene expression in *Escherichia coli. PLoS One* 2009, 4(9):e7002.
15. Higgs P G, Ran W: Coevolution of codon usage and tRNA genes leads to alternative stable states of biased codon usage. *Mol Biol Evol* 2008, 25(11):2279-2291.
16. Ran W, Higgs P G: The influence of anticodon-codon interactions and modified bases on codon usage bias in bacteria. *Mol Biol Evol* 2010, 27(9):2129-2140.

17. Ishikura H, Yamada Y, Nishimura S: Structure of serine tRNA from *Escherichia coli*. I. Purification of serine tRNA's with different codon responses. *Biochim Biophys Acta* 1971, 228(2):471-481.
18. Yamada Y, Matsugi J, Ishikura H: tRNA1Ser(G34) with the anticodon GGA can recognize not only UCC and UCU codons but also UCA and UCG codons. *Biochim Biophys Acta* 2003, 1626(1-3):75-82.
19. Li X, Hirano R, Tagami H, Aiba H: Protein tagging at rare codons is caused by tmRNA action at the 3' end of nonstop mRNA generated in response to ribosome stalling. *Rna* 2006, 12(2):248-255.
20. Hengen P: Purification of His-Tag fusion proteins from *Escherichia coli. Trends Biochem Sci* 1995, 20(7):285-286.
21. Ingolia N T, Ghaemmaghami S, Newman J R, Weissman J S: Genome-wide analysis in vivo of translation with nucleotide resolution using ribosome profiling. *Science* 2009, 324(5924):218-223.
22. Brandt F, Etchells S A, Ortiz J O, Elcock A H, Hartl F U, Baumeister W: The native 3D organization of bacterial polysomes. *Cell* 2009, 136(2):261-271.
23. Lu P, Vogel C, Wang R, Yao X, Marcotte E M: Absolute protein expression profiling estimates the relative contributions of transcriptional and translational regulation. *Nat Biotechnol* 2007, 25(1):117-124.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated polynucleotide encoding a human polypeptide having a predetermined amino acid sequence, wherein the codon usage at the 5' end of the polynucleotide is modified such that the average rate of translation of the first 30 amino acids is slower by no more than 2.5 fold and no less than 1.3 fold than the average rate of translation of the remaining amino acids of the polypeptide in non-human cells, wherein said codon usage does not alter the predetermined amino acid sequence, wherein at least 60% of the codons for said first 30 amino acids correspond to low abundance tRNAs in said non-human cells.

2. The isolated polynucleotide of claim 1, wherein the 3' end of the polynucleotide is non-modified.

3. The isolated polynucleotide of claim 1, wherein the 3' end of the polynucleotide is modified.

4. The isolated polynucleotide of claim 1, wherein said non-human cells comprise cells of a species selected from the group consisting of a bacterial species, a fungal species, a plant species, an insect species and a mammalian species.

5. The isolated polynucleotide of claim 1, wherein said non-human cells are selected from the group consisting of *E. coli* cells, Chinese hamster ovary (CHO) cells and *S. cerevisiae* cells.

6. The isolated polynucleotide of claim 5, wherein said non-human cells comprise Chinese hamster ovary (CHO) cells.

7. The isolated polynucleotide of claim 1, wherein said polypeptide is selected from the group consisting of an antibody, insulin, interferon, growth hormone, erythropoietin, growth hormone, follicle stimulating hormone, factor VIII, low density lipoprotein receptor (LDLR) alpha galactosidase A and glucocerebrosidase.

8. The isolated polynucleotide of claim 5, wherein said polypeptide comprises a signal sequence.

9. The isolated polynucleotide of claim 6, comprising a sequence as set forth in SEQ ID NOs: 2-7.

10. An expression construct comprising the polynucleotide of claim 1 and a promoter suitable for expressing said polypeptide in said non-human species.

11. A method of generating a polypeptide, the method comprising:
 (a) inserting the isolated polynucleotide of claim 1 into a cell, said cell being of said another species; and
 (b) culturing the cell under conditions that allows expression of the polypeptide, thereby generating the polypeptide.

12. The method of claim 11, further comprising purifying the polypeptide following said culturing.

* * * * *

SEQUENCE LISTING

```
<160> NUMBER OF SEQ ID NOS: 20

<210> SEQ ID NO 1
<211> LENGTH: 63
<212> TYPE: DNA
<213> ORGANISM: Artificial sequence
<220> FEATURE:
<223> OTHER INFORMATION: A native signal peptide coding region

<400> SEQUENCE: 1
atggggccct ggggctggaa attgcgctgg accgtcgcct tgctcctcgc cgcggcgggg    60
act                                                                  63

<210> SEQ ID NO 2
<211> LENGTH: 63
<212> TYPE: DNA
<213> ORGANISM: Artificial sequence
<220> FEATURE:
<223> OTHER INFORMATION: An exemplary signal peptide coding sequence
      suitable for high expression of a polypeptide in Chinese Hampster
      Ovary cells

<400> SEQUENCE: 2
atgggcccat ggggctggaa gctgaggtgg actgtggctc tgctgctggc tgctgctggc    60
act                                                                  63

<210> SEQ ID NO 3
<211> LENGTH: 63
<212> TYPE: DNA
<213> ORGANISM: Artificial sequence
<220> FEATURE:
<223> OTHER INFORMATION: An exemplary signal peptide coding sequence
      suitable for high expression of a polypeptide in Chinese Hampster
      Ovary cells

<400> SEQUENCE: 3
atgggaccct ggggatggaa actacgctgg acagtagcac tactactagc agcagcagga    60
aca                                                                  63

<210> SEQ ID NO 4
<211> LENGTH: 63
<212> TYPE: DNA
```

-continued

<213> ORGANISM: Artificial sequence
<220> FEATURE:
<223> OTHER INFORMATION: An exemplary signal peptide coding sequence
      suitable for high expression of a polypeptide in Chinese Hampster
      Ovary cells

<400> SEQUENCE: 4
atggggccct ggggctggaa actacgctgg acagtagcac tactactagc agcagcagga    60
act                                                                  63

<210> SEQ ID NO 5
<211> LENGTH: 63
<212> TYPE: DNA
<213> ORGANISM: Artificial sequence
<220> FEATURE:
<223> OTHER INFORMATION: An exemplary signal peptide coding sequence
      suitable for high expression of a polypeptide in Chinese Hampster
      Ovary cells

<400> SEQUENCE: 5
atggggccct ggggctggaa attgcgatgg acagtcgcat tgttgttggc agcagcagga    60
act                                                                  63

<210> SEQ ID NO 6
<211> LENGTH: 63
<212> TYPE: DNA
<213> ORGANISM: Artificial sequence
<220> FEATURE:
<223> OTHER INFORMATION: An exemplary signal peptide coding sequence
      suitable for high expression of a polypeptide in Chinese Hampster
      Ovary cells

<400> SEQUENCE: 6
atggggccct ggggctggaa actccgttgg acggtcgcac tcctcctcgc agcagcagga    60
act                                                                  63

<210> SEQ ID NO 7
<211> LENGTH: 63
<212> TYPE: DNA
<213> ORGANISM: Artificial sequence
<220> FEATURE:
<223> OTHER INFORMATION: An exemplary signal peptide coding sequence
      suitable for high expression of a polypeptide in Chinese Hampster
      Ovary cells

<400> SEQUENCE: 7
atggggccct ggggctggaa gctgaggtgg actgtggctc tgctgctggc tgctgctggc    60
act                                                                  63

<210> SEQ ID NO 8
<211> LENGTH: 1074
<212> TYPE: DNA
<213> ORGANISM: Artificial sequence
<220> FEATURE:
<223> OTHER INFORMATION: human derived low density lipoprotein receptor
      (LDLR) coding sequence

<400> SEQUENCE: 8
atggggccct ggggctggaa attgcgctgg accgtcgcct tgctcctcgc cgcggcgggg    60
actgcagtgg gcgacagatg cgaaagaaac gagttccagt gccaagacgg gaaatgcatc   120
tcctacaagt gggtctgcga tgcagcgct gagtgccagg atggctctga tgagtcccag   180
gagacgtgct tgtctgtcac ctgcaaatcc ggggacttca gctgtgggg ccgtgtcaac   240

```
cgctgcattc ctcagttctg gaggtgcgat ggccaagtgg actgcgacaa cggctcagac    300
gagcaaggct gtcccccaa  gacgtgctcc caggacgagt tccgctgcca cgatgggaag    360
tgcatctctc ggcagttcgt ctgtgactca gaccgggact gcttggacgg ctcagacgag    420
gcctcctgcc cggtgctcac ctgtggtccc gccagcttcc agtgcaacag ctccacctgc    480 atccccagc  tgtgggcctg cgacaacgac cccgactgcg aagatggctc ggatgagtgg    540
ccgcagcgct gtaggggtct ttacgtgttc caaggggaca gtagccctg  ctcggccttc    600 gagttccact gcctaagtgg cgagtgcatc cactccagct ggcgctgtga tggtggcccc    660
gactgcaagg acaaatctga cgaggaaaac tgcgctgtgg ccacctgtcg ccctgacgaa    720
ttccagtgct ctgatggaaa ctgcatccat ggcagccggc agtgtgaccg ggaatatgac    780
tgcaaggaca tgagcgatga agttggctgc gttaatgtga cactctgcga gggacccaac    840
aagttcaagt gtcacagcgg cgaatgcatc accctggaca aagtctgcaa catggctaga    900
gactgccggg actggtcaga tgaacccatc aaagagtgcg gaccaacga  atgcttggac    960 aacaacggcg gctgttccca cgtctgcaat gaccttaaga tcggctacga gtgcctgtgc    1020
cccgacggct tccagctggt ggcccagcga agatgccacc accaccacca ccac          1074
```

<210> SEQ ID NO 9
<211> LENGTH: 1074
<212> TYPE: DNA
<213> ORGANISM: Artificial sequence
<220> FEATURE:
<223> OTHER INFORMATION: Max tAI adapted LDLR coding sequence

<400> SEQUENCE: 9

```
atgggcccat ggggctggaa gctgaggtgg actgtggctc tgctgctggc tgctgctggc    60
actgctgtgg gcgacaggtg cgagaggaac gagttccagt gccaggacgg caagtgcatt    120
tcttacaagt gggtgtgcga cggctctgct gagtgccagg acggctctga cgagtctcag    180
gagacttgcc tgtctgtgac ttgcaagtct ggcgacttct cttgcggcgg cagggtgaac    240
aggtgcattc cacagttctg gaggtgcgac ggccaggtgg actgcgacaa cggctctgac    300
gagcagggct gcccaccaaa gacttgctct caggacgagt tcaggtgcca cgacggcaag    360
tgcatttcta ggcagttcgt gtgcgactct gacagggact gcctggacgg ctctgacgag    420
gcttcttgcc cagtgctgac ttgcggccca gcttctttcc agtgcaactc ttctacttgc    480
attccacagc tgtgggcttg cgacaacgac ccagactgcg aggacggctc tgacgagtgg    540
ccacagaggt gcaggggcct gtacgtgttc caggctgact cttctccatg ctctgctttc    600
gagttccact gcctgtctgg cgagtgcatt cactcttctt ggaggtgcga cggcggccca    660
gactgcaagg acaagtctga cgaggagaac tgcgctgtgg ctacttgcag gccagacgag    720
ttccagtgct ctgacggcaa ctgcattcac ggctctaggc agtgcgacag ggagtacgac    780
tgcaaggaca tgtctgacga ggtgggctgc gtgaacgtga ctctgtgcga gggcccaaac    840
aagttcaagt gccactctgg cgagtgcatt actctggaca aggtgtgcaa catggctagg    900
gactgcaggg actggtctga cgagccaatt aaggagtgcg gcactaacga gtgcctggac    960
aacaacggcg gctgctctca cgtgtgcaac gacctgaaga ttggctacga gtgcctgtgc    1020
ccagacggct tccagctggt ggctcagagg aggtgccacc accaccacca ccac          1074
```

<210> SEQ ID NO 10
<211> LENGTH: 1074
<212> TYPE: DNA
<213> ORGANISM: Artificial sequence

```
<220> FEATURE:
<223> OTHER INFORMATION: tAI adapted LDLR coding sequence

<400> SEQUENCE: 10
atgggaccct ggggatggaa actacgctgg acagtagcac tactactagc agcagcagga      60
acagcagtag gagatcgctg tgaacgcaat gaatttcaat gtcaagatgg aaaatgtata     120
tcatataaat gggtatgtga tggatcagca gaatgtcaag atggatcaga tgaatcacaa     180
gaaacatgtc tatcagtaac atgtaaatca ggagattttt catgtggagg acgcgtaaat     240
cgctgtatac cccaattttg gcgctgtgat ggacaagtag attgtgataa tggatcagat     300
gaacaaggat gtcccccaa aacatgttca caagatgaat tcgctgtca tgatggaaaa       360
tgtatatcac gccaatttgt atgtgattca gatcgcgatt gtctagatgg atcagatgaa     420
gcatcatgtc ccgtactaac atgtggaccc gcatcatttc aatgtaattc atcaacatgt     480
atacccccaac tatgggcatg tgataatgat cccgattgtg aagatggatc agatgaatgg     540
ccccaacgct gtcgcggact atatgtattt caaggagatt catcaccctg ttcagcattt     600
gaatttcatt gtctatcagg agaatgtata cattcatcat ggcgctgtga tggaggaccc     660
gattgtaaag ataaatcaga tgaagaaaat tgtgcagtag caacatgtcg ccccgatgaa     720
tttcaatgtt cagatggaaa ttgtatacat ggatcacgcc aatgtgatcg gaatatgat     780
tgtaaagata tgtcagatga agtaggatgt gtaaatgtaa cactatgtga aggacccaat     840
aaatttaaat gtcattcagg agaatgtata acactagata aagtatgtaa tatggcacgc     900
gattgtcgcg attggtcaga tgaacccata aaagaatgtg aacaaatga atgtctagat     960
aataatggag gatgttcaca tgtatgtaat gatctaaaaa taggatatga atgtctatgt    1020
cccgatggat ttcaactagt agcacaacgc cgctgtcatc atcatcatca tcat          1074

<210> SEQ ID NO 11
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 11
atggggccct ggggctggaa actacgctgg acagtagcac tactactagc agcagcagga      60
actgcagtgg cgacagatg cgaaagaaac gagttccagt gccaagacgg aaatgcatc      120
tcctacaagt gggtctgcga tggcagcgct gagtgccagg atggctctga tgagtcccag     180
gagacgtgct tgtctgtcac ctgcaaatcc ggggacttca gctgtgggg ccgtgtcaac      240
cgctgcattc ctcagttctg gaggtgcgat ggccaagtgg actgcgacaa cggctcagac     300
gagcaaggct gtcccccaa gacgtgctcc caggacgagt tcgctgcca cgatgggaag      360
tgcatctctc ggcagttcgt ctgtgactca gaccgggact gcttggacgg ctcagacgag     420
gcctcctgcc cggtgctcac ctgtggtccc gccagcttcc agtgcaacag ctccacctgc     480
atccccagc tgtgggcctg cgacaacgac cccgactgcg aagatggctc ggatgagtgg     540
ccgcagcgct gtagggtct ttacgtgttc caagggaca gtagcccctg ctcggccttc      600
gagttccact gcctaagtgg cgagtgcatc cactccagct ggcgctgtga tggtggcccc     660
gactgcaagg acaaatctga cgaggaaaac tgcgctgtgg ccacctgtcg ccctgacgaa     720
ttccagtgct ctgatggaaa ctgcatccat ggcagccggc agtgtgaccg gaatatgac      780
tgcaaggaca tgagcgatga agttggctgc gttaatgtga cactctgcga gggacccaac     840
```

| | |
|---|---|
| aagttcaagt gtcacagcgg cgaatgcatc accctggaca aagtctgcaa catggctaga | 900 |
| gactgccggg actggtcaga tgaacccatc aaagagtgcg ggaccaacga atgcttggac | 960 |
| aacaacggcg gctgttccca cgtctgcaat gaccttaaga tcggctacga gtgcctgtgc | 1020 |
| cccgacggct tccagctggt ggcccagcga agatgccacc accaccacca ccac | 1074 |

<210> SEQ ID NO 12
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 12

| | |
|---|---|
| atggggccct ggggctggaa attgcgatgg acagtcgcat tgttgttggc agcagcagga | 60 |
| actgcagtgg gcgacagatg cgaaagaaac gagttccagt gccaagacgg gaaatgcatc | 120 |
| tcctacaagt gggtctgcga tggcagcgct gagtgccagg atggctctga tgagtcccag | 180 |
| gagacgtgct tgtctgtcac ctgcaaatcc ggggacttca gctgtggggg ccgtgtcaac | 240 |
| cgctgcattc ctcagttctg gaggtgcgat ggccaagtgg actgcgacaa cggctcagac | 300 |
| gagcaaggct gtcccccaa gacgtgctcc caggacgagt ttcgctgcca cgatgggaag | 360 |
| tgcatctctc ggcagttcgt ctgtgactca gaccgggact gcttggacgg ctcagacgag | 420 |
| gcctcctgcc cggtgctcac ctgtggtccc gccagcttcc agtgcaacag ctccacctgc | 480 |
| atccccage tgtgggcctg cacaacgac cccgactgcg aagatggctc ggatgagtgg | 540 |
| ccgcagcgct gtagggggtct ttacgtgttc caaggggaca gtagccctg ctcggccttc | 600 |
| gagttccact gcctaagtgg cgagtgcatc cactccagct ggcgctgtga tggtggcccc | 660 |
| gactgcaagg acaaatctga cgaggaaaac tgcgctgtgg ccacctgtcg ccctgacgaa | 720 |
| ttccagtgct ctgatggaaa ctgcatccat ggcagccggc agtgtgaccg ggaatatgac | 780 |
| tgcaaggaca tgagcgatga agttggctgc gttaatgtga cactctgcga gggacccaac | 840 |
| aagttcaagt gtcacagcgg cgaatgcatc accctggaca aagtctgcaa catggctaga | 900 |
| gactgccggg actggtcaga tgaacccatc aaagagtgcg ggaccaacga atgcttggac | 960 |
| aacaacggcg gctgttccca cgtctgcaat gaccttaaga tcggctacga gtgcctgtgc | 1020 |
| cccgacggct tccagctggt ggcccagcga agatgccacc accaccacca ccac | 1074 |

<210> SEQ ID NO 13
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 13

| | |
|---|---|
| atggggccct ggggctggaa actacgctgg acagtagcac tactactagc agcagcagga | 60 |
| actgctgtgg gcgacaggtg cgagaggaac gagttccagt gccaggacgg caagtgcatt | 120 |
| tcttacaagt gggtgtgcga cggctctgct gagtgccagg acggctctga cgagtctcag | 180 |
| gagacttgcc tgtctgtgac ttgcaagtct ggcgacttct cttgcggcgg cagggtgaac | 240 |
| aggtgcattc cacagttctg gaggtgcgac ggccaggtgg actgcgacaa cggctctgac | 300 |
| gagcagggct gcccaccaaa gacttgctct caggacgagt tcaggtgcca cgacggcaag | 360 |
| tgcatttcta ggcagttcgt gtgcgactct gacagggact gcctggacgg ctctgacgag | 420 |
| gcttcttgcc cagtgctgac ttgcggccca gcttcttttcc agtgcaactc ttctacttgc | 480 |

| | |
|---|---|
| attccacagc tgtgggcttg cgacaacgac ccagactgcg aggacggctc tgacgagtgg | 540 |
| ccacagaggt gcaggggcct gtacgtgttc cagggcgact cttctccatg ctctgctttc | 600 |
| gagttccact gcctgtctgg cgagtgcatt cactcttctt ggaggtgcga cggcggccca | 660 |
| gactgcaagg acaagtctga cgaggagaac tgcgctgtgg ctacttgcag gccagacgag | 720 |
| ttccagtgct ctgacggcaa ctgcattcac ggctctaggc agtgcgacag ggagtacgac | 780 |
| tgcaaggaca tgtctgacga ggtgggctgc gtgaacgtga ctctgtgcga gggcccaaac | 840 |
| aagttcaagt gccactctgg cgagtgcatt actctggaca aggtgtgcaa catggctagg | 900 |
| gactgcaggg actggtctga cgagccaatt aaggagtgcg gcactaacga gtgcctggac | 960 |
| aacaacggcg gctgctctca cgtgtgcaac gacctgaaga ttggctacga gtgcctgtgc | 1020 |
| ccagacggct tccagctggt ggctcagagg aggtgccacc accaccacca ccac | 1074 |

<210> SEQ ID NO 14
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 14

| | |
|---|---|
| atggggccct ggggctggaa actccgttgg acggtcgcac tcctcctcgc agcagcagga | 60 |
| actgctgtgg gcgacaggtg cgagaggaac gagttccagt gccaggacgg caagtgcatt | 120 |
| tcttacaagt gggtgtgcga cggctctgct gagtgccagg acggctctga cgagtctcag | 180 |
| gagacttgcc tgtctgtgac ttgcaagtct ggcgacttct cttgcggcgg cagggtgaac | 240 |
| aggtgcattc cacagttctg gaggtgcgac ggccaggtgg actgcgacaa cggctctgac | 300 |
| gagcagggct gcccaccaaa gacttgctct caggacgagt caggtgcca cgacggcaag | 360 |
| tgcatttcta ggcagttcgt gtgcgactct gacagggact gcctggacgg ctctgacgag | 420 |
| gcttcttgcc cagtgctgac ttgcggccca gcttcttcc agtgcaactc ttctacttgc | 480 |
| attccacagc tgtgggcttg cgacaacgac ccagactgcg aggacggctc tgacgagtgg | 540 |
| ccacagaggt gcaggggcct gtacgtgttc cagggcgact cttctccatg ctctgctttc | 600 |
| gagttccact gcctgtctgg cgagtgcatt cactcttctt ggaggtgcga cggcggccca | 660 |
| gactgcaagg acaagtctga cgaggagaac tgcgctgtgg ctacttgcag gccagacgag | 720 |
| ttccagtgct ctgacggcaa ctgcattcac ggctctaggc agtgcgacag ggagtacgac | 780 |
| tgcaaggaca tgtctgacga ggtgggctgc gtgaacgtga ctctgtgcga gggcccaaac | 840 |
| aagttcaagt gccactctgg cgagtgcatt actctggaca aggtgtgcaa catggctagg | 900 |
| gactgcaggg actggtctga cgagccaatt aaggagtgcg gcactaacga gtgcctggac | 960 |
| aacaacggcg gctgctctca cgtgtgcaac gacctgaaga ttggctacga gtgcctgtgc | 1020 |
| ccagacggct tccagctggt ggctcagagg aggtgccacc accaccacca ccac | 1074 |

<210> SEQ ID NO 15
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 15

| | |
|---|---|
| atggggccct ggggctggaa actacgctgg acagtagcac tactactagc agcagcagga | 60 |

| | |
|---|---|
| actgcagtgg gcgacagatg cgaaagaaac gagttccagt gccaagacgg gaaatgcatc | 120 |
| tcctacaagt gggtctgcga tggcagcgct gagtgccagg atggctctga tgagtcccag | 180 |
| gagacttgcc tgtctgtcac ctgcaaatcc ggggacttca gctgtggggg ccgtgtcaac | 240 |
| cgctgcattc ctcagttctg gaggtgcgat ggccaagtgg actgcgacaa cggctctgac | 300 |
| gagcaaggct gtcccccaa cgtgctcc caggacgagt ttcgctgcca cgatgggaag | 360 |
| tgcatttcta ggcagttcgt ctgtgactca gaccgggact gcttggacgg ctcagacgag | 420 |
| gcctcctgcc cggtgctcac ctgtggtccc gccagcttcc agtgcaacag ctccacctgc | 480 |
| atcccccagc tgtgggcctg cgacaacgac cccgactgcg aagacggctc tgacgagtgg | 540 |
| ccacagaggt gcaggggcct gtacgtgttc cagggcgact cttctccctg ctcggccttc | 600 |
| gagttccact gcctaagtgg cgagtgcatc cactccagct ggcgctgtga tggtggcccc | 660 |
| gactgcaagg acaaatctga cgaggaaaac tgcgctgtgg ccacctgtcg ccctgacgaa | 720 |
| ttccagtgct ctgatggaaa ctgcatccat ggcagccggc agtgtgaccg ggaatatgac | 780 |
| tgcaaggaca tgagcgatga agttggctgc gttaatgtga cactctgcga gggacccaac | 840 |
| aagttcaagt gtcacagcgg cgaatgcatc accctggaca aagtctgcaa catggctaga | 900 |
| gactgccggg actggtcaga tgaacccatc aaagagtgcg ggaccaacga atgcttggac | 960 |
| aacaacggcg gctgttccca cgtctgcaat gaccttaaga tcggctacga gtgcctgtgc | 1020 |
| cccgacggct tccagctggt ggcccagcga agatgccacc accaccacca ccac | 1074 |

<210> SEQ ID NO 16
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 16

| | |
|---|---|
| atggggcccct ggggctggaa actccgttgg acggtcgcac tcctcctcgc agcagcagga | 60 |
| actgcagtgg gcgacagatg cgaaagaaac gagttccagt gccaagacgg gaaatgcatc | 120 |
| tcctacaagt gggtctgcga tggcagcgct gagtgccagg atggctctga tgagtcccag | 180 |
| gagacttgcc tgtctgtcac ctgcaaatcc ggggacttca gctgtggggg ccgtgtcaac | 240 |
| cgctgcattc ctcagttctg gaggtgcgat ggccaagtgg actgcgacaa cggctctgac | 300 |
| gagcaaggct gtcccccaa cgtgctcc caggacgagt ttcgctgcca cgatgggaag | 360 |
| tgcatttcta ggcagttcgt ctgtgactca gaccgggact gcttggacgg ctcagacgag | 420 |
| gcctcctgcc cggtgctcac ctgtggtccc gccagcttcc agtgcaacag ctccacctgc | 480 |
| atcccccagc tgtgggcctg cgacaacgac cccgactgcg aagacggctc tgacgagtgg | 540 |
| ccacagaggt gcaggggcct gtacgtgttc cagggcgact cttctccctg ctcggccttc | 600 |
| gagttccact gcctaagtgg cgagtgcatc cactccagct ggcgctgtga tggtggcccc | 660 |
| gactgcaagg acaaatctga cgaggaaaac tgcgctgtgg ccacctgtcg ccctgacgaa | 720 |
| ttccagtgct ctgatggaaa ctgcatccat ggcagccggc agtgtgaccg ggaatatgac | 780 |
| tgcaaggaca tgagcgatga agttggctgc gttaatgtga cactctgcga gggacccaac | 840 |
| aagttcaagt gtcacagcgg cgaatgcatc accctggaca aagtctgcaa catggctaga | 900 |
| gactgccggg actggtcaga tgaacccatc aaagagtgcg ggaccaacga atgcttggac | 960 |
| aacaacggcg gctgttccca cgtctgcaat gaccttaaga tcggctacga gtgcctgtgc | 1020 |
| cccgacggct tccagctggt ggcccagcga agatgccacc accaccacca ccac | 1074 |

<210> SEQ ID NO 17
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 17

```
atgggcccat ggggctggaa gctgaggtgg actgtggctc tgctgctggc tgctgctggc      60
actgctgtgg gcgacaggtg cgagaggaac gagttccagt gccaggacgg caagtgcatt     120
tcttacaagt gggtgtgcga cggctctgct gagtgccagg acggctctga cgagtctcag     180
gagacttgcc tgtctgtgac ttgcaagtct ggcgacttct cttgcggcgg cagggtgaac     240
aggtgcattc cacagttctg gaggtgcgac ggccaggtgg actgcgacaa cggctctgac     300
gagcagggct gcccaccaaa gacttgctct caggacgagt tcaggtgcca cgacggcaag     360
tgcatttcta ggcagttcgt gtgcgactct gacaggact gcctggacgg ctctgacgag     420
gcttcttgcc cagtgctgac ttgcggccca gcttctttcc agtgcaactc ttctacttgc     480
attccacagc tgtgggcttg cgacaacgac ccagactgcg aggacggctc tgacgagtgg     540
ccacagaggt gcaggggcct gtacgtgttc cagggcgact cttctccatg ctctgctttc     600
gagttccact gcctgtctgg cgagtgcatt cactcttctt ggaggtgcga cggcggccca     660
gactgcaagg acaagtctga cgaggagaac tgcgctgtgg ctacttgcag gccagacgag     720
ttccagtgct ctgacggcaa ctgcattcac ggctctaggc agtgcgacag ggagtacgac     780
tgcaaggaca tgtctgacga ggtgggctgc gtgaacgtga ctctgtgcga gggcccaaac     840
aagttcaagt gccactctgg cgagtgcatt actctggaca aggtgtgcaa catggctagg     900
gactgcaggg actggtctga cgagccaatt aaggagtgcg gcactaacga gtgcctggac     960
aacaacggcg gctgctctca cgtgtgtaat gatctaaaaa taggatatga atgtctatgt    1020
cccgatggat ttcaactagt agcacaacgc cgctgtcatc atcatcatca tcat          1074
```

<210> SEQ ID NO 18
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 18

```
atgggcccat ggggctggaa gctgaggtgg actgtggctc tgctgctggc tgctgctggc      60
actgctgtgg gcgacaggtg cgagaggaac gagttccagt gccaggacgg caagtgcatt     120
tcttacaagt gggtgtgcga cggctctgct gagtgccagg acggctctga cgagtctcag     180
gagacttgcc tgtctgtgac ttgcaagtct ggcgacttct cttgcggcgg cagggtgaac     240
aggtgcattc cacagttctg gaggtgcgac ggccaggtgg actgcgacaa cggctctgac     300
gagcagggct gcccaccaaa gacttgctct caggacgagt tcaggtgcca cgacggcaag     360
tgcatttcta ggcagttcgt gtgcgactct gacaggact gcctggacgg ctctgacgag     420
gcttcttgcc cagtgctgac ttgcggccca gcttctttcc agtgcaactc ttctacttgc     480
attccacagc tgtgggcttg cgacaacgac ccagactgcg aggacggctc tgacgagtgg     540
ccacagaggt gcaggggcct gtacgtgttc cagggcgact cttctccatg ctctgctttc     600
gagttccact gcctgtctgg cgagtgcatt cactcttctt ggaggtgcga cggcggccca     660
```

```
gactgcaagg acaagtctga cgaggagaac tgcgctgtgg ctacttgcag gccagacgag    720
ttccagtgct ctgacggcaa ctgcattcac ggctctaggc agtgcgacag ggagtacgac    780
tgcaaggaca tgtctgacga ggtgggctgc gtgaacgtga ctctgtgcga gggcccaaac    840
aagttcaagt gccactctgg cgagtgcatt actctggaca aggtgtgcaa catggctagg    900
gactgcaggg actggtctga cgagccaatt aaggagtgcg gcactaacga gtgcctggac    960
aacaacggcg gctgctctca cgtgtgtaat gatctcaaaa taggatatga atgtctctgt   1020
ccggatggat tccaactcgt cgcacaacgt cgttgtcatc atcatcatca tcat          1074
```

<210> SEQ ID NO 19
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 19

```
atggggccct ggggctggaa gctgaggtgg actgtggctc tgctgctggc tgctgctggc     60
actgctgtgg gcgacaggtg cgagaggaac gagttccagt gccaggacgg caagtgcatt    120
tcttacaagt gggtgtgcga cggctctgct gagtgccagg atggatcaga tgaatcacaa    180
gaaacatgtc tatcagtaac atgtaaatca ggagattttt catgtggagg acgcgtgaac    240
aggtgcattc cacagttctg gaggtgcgac ggccaggtgg actgcgacaa cggctctgac    300
gagcagggct gcccaccaaa gacttgctct caggacgagt tcaggtgcca cgacggcaag    360
tgcatttcta ggcagttcgt gtgcgactct gacagggact gcctggacgg ctctgacgag    420
gcttcttgcc cagtgctgac ttgcggccca gcttcttttcc agtgcaactc ttctacttgc    480
attccacagc tgtgggcttg cgacaacgac ccagactgcg aggacggctc tgacgagtgg    540
ccacagaggt gcaggggcct gtacgtgttc cagggcgact cttctccatg ctctgctttc    600
gagttccact gcctgtctgg cgagtgcatt cactcttctt ggaggtgcga cggcggccca    660
gactgcaagg acaagtctga cgaggagaac tgcgctgtgg ctacttgcag gccagacgag    720
ttccagtgct ctgacggcaa ctgcattcac ggctctaggc agtgcgacag ggagtacgac    780
tgcaaggaca tgtctgacga ggtgggctgc gtgaacgtga ctctgtgcga gggcccaaac    840
aagttcaagt gccactctgg cgagtgcatt actctggaca aggtgtgcaa catggctagg    900
gactgcaggg actggtctga cgagccaatt aaggagtgcg gcactaacga gtgcctggac    960
aacaacggcg gctgctctca cgtgtgcaac gacctgaaga ttggctacga gtgcctgtgc   1020
ccagacggct tccagctggt ggctcagagg aggtgccacc accaccacca ccac          1074
```

<210> SEQ ID NO 20
<211> LENGTH: 1074
<212> TYPE: DNA
<213> ORGANISM: Artificial sequence
<220> FEATURE:
<223> OTHER INFORMATION: tAI adapted LDLR coding sequence

<400> SEQUENCE: 20

```
atggggccct ggggctggaa gctgaggtgg actgtggctc tgctgctggc tgctgctggc     60
actgctgtgg gcgacaggtg cgagaggaac gagttccagt gccaggacgg caagtgcatt    120
tcttacaagt gggtgtgcga cggctctgct gagtgccagg atggatccga tgaatcccaa    180
gaaacgtgtc tctccgtcac gtgtaaatcc ggagatttct cctgtggagg acgtgtgaac    240
aggtgcattc cacagttctg gaggtgcgac ggccaggtgg actgcgacaa cggctctgac    300
```

```
gagcagggct gcccaccaaa gacttgctct caggacgagt tcaggtgcca cgacggcaag    360
tgcatttcta ggcagttcgt gtgcgactct gacagggact gcctggacgg ctctgacgag    420
gcttcttgcc cagtgctgac ttgcggccca gcttctttcc agtgcaactc ttctacttgc    480
attccacagc tgtgggcttg cgacaacgac ccagactgcg aggacggctc tgacgagtgg    540
ccacagaggt gcaggggcct gtacgtgttc cagggcgact cttctccatg ctctgctttc    600
gagttccact gcctgtctgg cgagtgcatt cactcttctt ggaggtgcga cggcggccca    660
gactgcaagg acaagtctga cgaggagaac tgcgctgtgg ctacttgcag gccagacgag    720
ttccagtgct ctgacggcaa ctgcattcac ggctctaggc agtgcgacag ggagtacgac    780
tgcaaggaca tgtctgacga ggtgggctgc gtgaacgtga ctctgtgcga gggcccaaac    840
aagttcaagt gccactctgg cgagtgcatt actctggaca aggtgtgcaa catggctagg    900
gactgcaggg actggtctga cgagccaatt aaggagtgcg gcactaacga gtgcctggac    960
aacaacggcg gctgctctca cgtgtgcaac gacctgaaga ttggctacga gtgcctgtgc   1020
ccagacggct tccagctggt ggctcagagg aggtgccacc accaccacca ccac         1074
```